(12) United States Patent
Hansen et al.

(10) Patent No.: US 9,802,948 B2
(45) Date of Patent: *Oct. 31, 2017

(54) INHIBITORS OF LATE SV40 FACTOR (LSF) AS CANCER CHEMOTHERAPEUTICS

(71) Applicant: TRUSTEES OF BOSTON UNIVERSITY, Boston, MA (US)

(72) Inventors: Ulla Hansen, Bedford, MA (US); Scott Schaus, Boston, MA (US); Trevor Grant, Vernon, CT (US); Joshua Bishop, Belmont, MA (US); John Kavouris, Pittsburgh, PA (US); Lisa M. Christadore, Brighton, MA (US)

(73) Assignee: TRUSTEES OF BOSTON UNIVERISTY, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/389,564

(22) Filed: Dec. 23, 2016

(65) Prior Publication Data

US 2017/0107227 A1   Apr. 20, 2017

Related U.S. Application Data

(63) Continuation-in-part of application No. 15/337,584, filed on Oct. 28, 2016, which is a continuation-in-part of application No. 13/879,106, filed as application No. PCT/US2011/054305 on Sep. 30, 2011.

(60) Provisional application No. 61/392,607, filed on Oct. 13, 2010.

(51) Int. Cl.
*C07D 491/056* (2006.01)
*C07D 215/16* (2006.01)

(52) U.S. Cl.
CPC ....... *C07D 491/056* (2013.01); *C07D 215/16* (2013.01)

(58) Field of Classification Search
CPC .......................... C07D 491/056; C07D 215/16
See application file for complete search history.

(56) References Cited

U.S. PATENT DOCUMENTS

| | | | |
|---|---|---|---|
| 6,713,462 B2 | 3/2004 | Metcalf, III et al. | |
| 7,081,256 B2 | 7/2006 | Kubota et al. | |
| 2003/0130505 A1 | 7/2003 | Zhi et al. | |
| 2009/0081183 A1 | 3/2009 | Margolis et al. | |
| 2010/0004277 A1 | 1/2010 | Bulawa et al. | |

FOREIGN PATENT DOCUMENTS

| | | |
|---|---|---|
| CN | 101410384 A | 4/2009 |
| EP | 2433634 A2 | 3/2012 |
| WO | 98/36641 | 8/1998 |
| WO | 03/066630 | 8/2003 |
| WO | 2007/136592 | 11/2007 |
| WO | 2011/123427 | 10/2011 |

OTHER PUBLICATIONS

Chang et al., Journal of Medicinal Chemistry, 52(15):4883-4891 (2009). "Design and synthesis of 2-(3-Benzo[b] thienyl)-6,7-methylenedioxyquinolin-4-one analogues as potent antitumor agents that inhibit tubulin assembly."
Singh et al., Chemical & Pharmaceutical Bulletin, 58(2):242-246 (2010). "Design and synthesis of C-ring lactone- and actam-based podophyllotoxin analogues as anticancer agents."
Bing et al., J Biol Chem., 275:31616-31623 (2000). "Nfkappa B interacts with serum amyloid A3 enhancer factor to synergistically activate mouse serum amyloid A3 gene transcription."
Bovolenta et al., J. Immunol., 163:6892-6897 (1999). "In vivo administration of recombinant IL-2 to individuals infected by HIV down-modulates the binding and expression of the transcriptioni factors Ying-Yang-1 and leader binding protein-Mate simian virus 40 factor."
Bruni et al., J Biol Chem, 277:35481-35488 (2002). "Fe65, a ligand of the Alzheimer's beta-amyloid precursor protein, blocks cell cycle progression by down-regulating thymidylate synthase expression."
Drouin et al., J Immunol, 168:2847-2856 (2002). "The ubiquitously expressed DNA-binding protein Late SV40 Factor binds Ig switch regions and represses class switching to IgA."
Haigh et al., J. Chem. Inf. Model, 45:673-684 (2005). "Small molecule shape-fingerprints."
Hansen et al., Cell Cycle, 8:2146-2151 (2009). "Transcriptions factors LSF and E2Fs: Tandem cyclists driving G0 to S?".
Huang et al., Interferon Cytokine Res, 19:1403-1411 (1999). "Synergistic induction fo mouse serum amyloid A3 promoter by the inflammatory mediators IL-1 and IL-6."
Koehler et al., Curr. Opin. Chem. Biol., 14:331-340 (2010). "A complex task? Direct modulation of transcription factors with small molecules."
Li et al., J. Org. Chem., 70:2881-2883 (2005). "Trifluoroacetic acid-mediated hydroarylation: synthesis of dihydrocoumarins and dihydroquinolones."
Murata et al., Genes to Cells, 3:443-457 (1998). "Transcription factor CP2 is essential for lens-specific expression ofthe chicken alphaA-crystallin gene."
Porta-De-La-Riva et al., J. Biochem., 435:563-568 (2011). "TFCP2c/LSF/LBP-1c is required for Snail1-induced fibronectin gene expression".
Powell et al., EMBO J, 19:4665-4675 (2000). "Inhibition of the mammalian transcription factor LSF induces S-phase-dependent apoptosis by downregulating thymidylate synthase expression."
Saxena et al, Mol Cell Biol., 29:2335-2345 (2009). "Phosphorylation by cyclin C/cyclin-dependent kinase 2 following mitogenic stimulation of murine fibroblasts inhibits transcriptional activity of LSF during G1 progression."
Sharma et al., Biochem. Pharmacol, 80:666-673 (2010). "Exploiting the balance between life and death: targeted cancer therapy and 'oncogenic shock'."
Shirra et al., J Biol Chem., 273:19260-19268 (1998). "LSF and NTF-1 share a conserved DNA-recognition motif yet required different oligomerization states to form a stable protein-DNA complex."

(Continued)

*Primary Examiner* — Samira Jean-Louis
(74) *Attorney, Agent, or Firm* — Nixon Peabody LLP

(57) ABSTRACT

The present invention is directed to methods, compositions and kits for treatment of cancer, e.g. heptacellular carcinoma. In some embodiments, the present invention discloses the use of a small-molecule compound of formula (I)-(XXVI) and (III') as disclosed herein to inhibit transcription factor Late SV40 Factor (LSF) for treatment of cancer, e.g., HCC.

7 Claims, 62 Drawing Sheets

(56) References Cited

OTHER PUBLICATIONS

Swendeman et al., J Biol Chem, 269:11663-11671 (1994). "Characterization of the genomic structure chromosomal location, promoter and developmental expression fo the alpha-globin transcription factor CP2."
Traylor-Knowles et al., BMC Evolutionary Biology, 10:101 (2010). The evolutionary diversification of LSF and Grainyhead transcription factors preceded the radiation of basal animal lineages.
Veljkovic et al., Gene, 343:23-40 (2004). "Lineage-specific and ubiquitous biological roles of the mammalian transciption factor LSF."
Weinstein et al., Cancer Res, 68:3077-3080 (2008). "Oncogene Addiction."
Yoo et al., J Clin Invest, 119:465-477 (2009). "Astrocyte elevated gene-1 regulates hepatocellular carcinoma development and progression.".
Yoo et al., PNAS, 106:12938-12943 (2009). "Identification of genes conferring resistance to 5-fluorouracil."
Yoo et al., PNAS, 107:8357-8362 (2010). "Transcription factor late SV40 (LSF) functions as an oncogene in hepatocellular carcinoma."
Zhong et al., J Biol Chem, 269:21269-21276 (1994). "Evidence that levels of the dimeric cellular transcription factor CP2 play little role in the activation of the HIV-1 long terminal repeat in vivo or following superinfection with herpes simplex virus type 1. "
STN Registry Database, RN: 599151-35-6.
STN Registry Database, RN: 717828-57-4.
STN Registry Database, RN: 725687-12-7.
STN Registry Database, RN: 847462-19-5.
STN Registry Database, RN: 847482-88-6.
STN Registry Database, RN: 900129-51-3.

| ID | STRUCTURE | CELL LINE | IC50 (μM) | NOTES | | MAX % INHIB |
|---|---|---|---|---|---|---|
| C1 (FQI1) | Formula (IV) | HeLa<br>A549<br>NIH 3T3 | 0.768<br>5.57<br>3.41 | | | 99<br>99 |
| B1 | Formula (VIII) | HeLa<br>A549 | 0.958<br>7.24 | Insoluble<br>≥100uM | | 99<br>90 |
| C3 | Formula (IX) | HeLa<br>A549 | 1.30<br>21.0 | Insoluble><br>300uM | | 99<br>100 |
| E3 | Formula (X) | HeLa<br>A549 | 1.36<br>6.19 | | | |

*FIG. 1 (cont.)*

| ID | STRUCTURE | CELL LINE | IC50 (μM) | NOTES | MAX % INHIB |
|---|---|---|---|---|---|
| A1 | 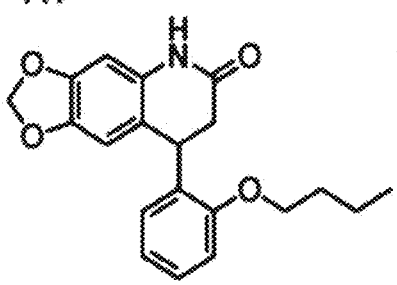 Formula (XII) | HeLa<br>A549<br>3T3 | 1.57<br>5.30<br>2.65 | Insoluble ≥100 uM | 100<br>96 |
| D1 | 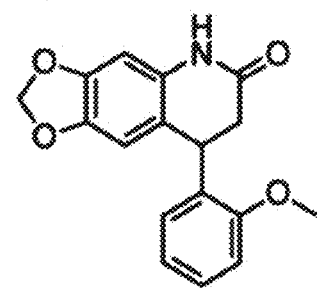 Formula (XIII) | HeLa<br>A549 | 1.41<br>13 | | 83<br>81 |
| A2 | 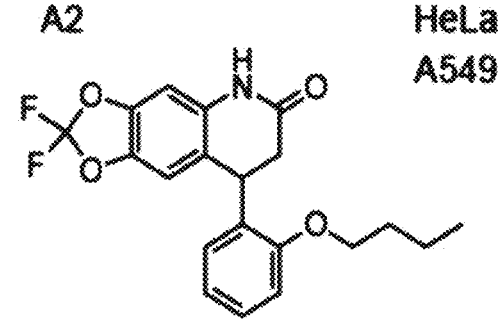 Formula (XIV) | HeLa<br>A549 | 2.93<br>21.9 | Insoluble ≥5 uM | 96<br>90 |
| E2 | 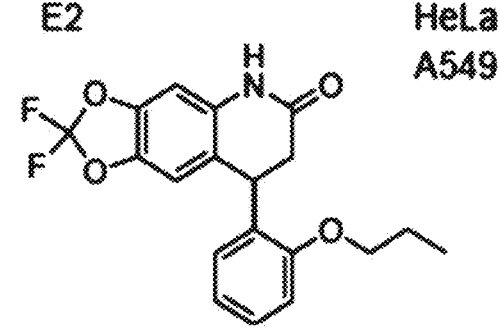 Formula (XV) | HeLa<br>A549 | 3.02<br>22.1 | Insoluble ≥5 uM | 91<br>94<br>99<br>99 |
*FIG. 1 (cont.)*

| ID | STRUCTURE | CELL LINE | IC50 (μM) | NOTES | MAX % INHIB |
|---|---|---|---|---|---|
| B3 | 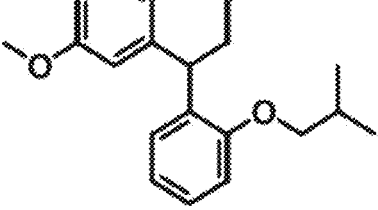 | A549<br>3T3 | 13.6<br>24.6 | ≥100 uM<br><br>Formula (XVI) | 96<br>63 |
| D3 | 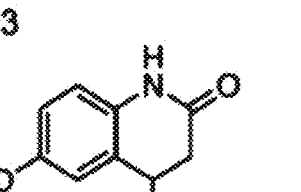 | HeLa<br>A549 | 3.95<br>105 | Insoluble><br>300uM<br><br>Formula (XI) | |
| C1-NCH3 | 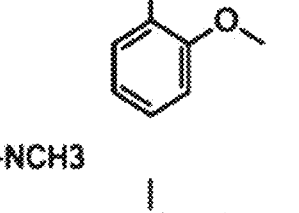 | HeLa | 4.71 | Formula (XXV) | 98<br>98 |
| S-(+)-FQI1 (C1-2) | 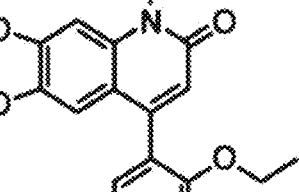 | HeLa<br>A549<br>NIH 3T3 | 8.22<br>17.9<br>46.2 | Formula (IV)<br>[R-configuration] | |
*FIG. 1 (cont.)*

| ID | STRUCTURE | CELL LINE | IC50 (μM) | NOTES | MAX % INHIB |
|---|---|---|---|---|---|
| B2 | 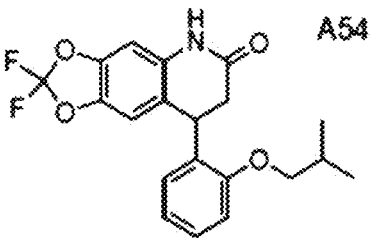 | HeLa<br>A549 | 11.1<br>44.3 | Insoluble ≥10 uM<br><br>Formula (XIX) | 92<br>86 |
| C2 | 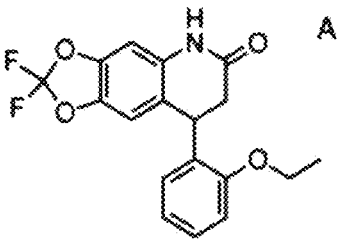 | HeLa<br>A549 | 6.67<br>>300 | (Max inhibition - 65%)<br>Insoluble ≥10 uM<br><br>Formula (XX) | 56<br>n/a |
| D2 | 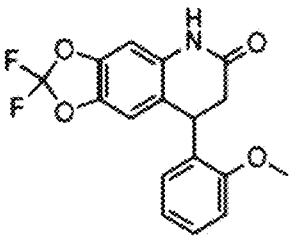 | HeLa<br>A549 | 9.25<br>>300 | (Max inhibition 55%)<br>Insoluble ≥5 uM<br><br>Formula (XXI) | 55<br>n/a |
| F2 | 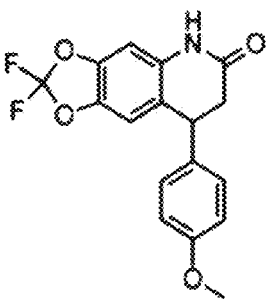 | HeLa<br>A549 | 29.9<br>48.5 | Insoluble ≥100 uM<br><br>Formula (XXII) | 99<br>99<br>93<br>69 |
*FIG. 1 (cont.)*

| ID | STRUCTURE | CELL LINE | IC50 (μM) | NOTES | MAX % INHIB |
|---|---|---|---|---|---|
| F3 | Formula (XVII) | HeLa<br>A549 | 69.3<br>>200 | | n/a<br>44 |
| F1 | Formula (XVIII) | HeLa<br>A549<br>3T3 | >200<br>>200<br>>200 | Insoluble>200uM | |

*FIG. 1 (cont.)*

| ID | STRUCTURE | CELL LINE | IC50 (μM) | NOTES | MAX % INHIB |
|---|---|---|---|---|---|
| C4 | (structure) | HeLa<br>A549 | >200<br>>200 | Insoluble<br>≥200 uM<br><br>Formula (XXIII) | n/a |
| D4 | (structure) | HeLa<br>A549 | >200<br>>100 | Insoluble<br>≥200 uM<br><br>Formula (XXIV) | n/a<br>16 |

*FIG. 1 (cont.)*

INHIBITORS OF LATE SV40 FACTOR (LSF) AS CANCER CHEMOTHERAPEUTICS

CROSS REFERENCE TO RELATED APPLICATIONS

This application is a continuation-in-part of and claims priority to U.S. patent application Ser. No. 15/337,584, filed Oct. 28, 2016, which is a continuation-in-part of and claims priority to U.S. patent application Ser. No. 13/879,106, filed Aug. 20, 2013, which is a 35 U.S.C. §371 National Phase Entry Application of International Application No. PCT/US2011/054305, filed Sep. 30, 2011, which designates the U.S., and which benefit under 35 U.S.C. 119(e) of U.S. Provisional Patent Application Ser. No. 61/392,607 filed on Oct. 13, 2010, the contents of all which are incorporated herein by reference in their entirety.

GOVERNMENT SUPPORT

This invention was made in part with U.S. Government support from the National Institutes of Health grant P50 GM067041 and the National Science Foundation HRD-0820175. The U.S. Government has certain rights in this application.

SEQUENCE LISTING

The instant application contains a Sequence Listing which has been submitted in ASCII format via EFS-Web and is hereby incorporated by reference in its entirety. Said ASCII copy, created on Oct. 28, 2016, is named 701586-068372_SequenceListing.txt and is 9,976 bytes in size.

FIELD OF THE INVENTION

The present invention relates generally to methods, compositions and kits for treatment of cancer, e.g. hepatocellular carcionoma (HCC). In some embodiments, the invention relates to the use of small-molecule compounds to inhibit expression of the transcription factor Late SV40 Factor (LSF) for treatment of cancer, e.g., HCC.

BACKGROUND OF THE INVENTION

Hepatocellular carcinoma (HCC) is a primary malignant tumor, which develops in the liver. HCC is one of the five most common cancers and the third leading cause of cancer deaths worldwide. The incidence of HCC is increasing despite a decrease in overall incidence of all cancers. In the United States, the estimated new cases of HCC for 2008 were 21,370, of which 18,410 were expected to die. There are multiple etiologies, with subcategories displaying distinct gene expression profiles. The prognosis of HCC remains poor. The mean 5-year survival rate is less than 10%. The mortality rate of HCC parallels that of its incidence because HCC is a tumor with rapid growth and early vascular invasion that is resistant to conventional chemotherapy, and only a single systemic therapy (sorafenib) is available for advanced disease, although the survival benefit averages only a few months.

Hepatocellular carcinoma (HCC) is characterized by late stage diagnosis and a poor prognosis for treatment, usually consisting of surgical resection of the tumor and chemotherapy[1-3]. Currently, the only approved treatment for primary malignancies is sorafenib, a receptor tyrosine kinase and Raf inhibitor originally developed for primary kidney cancer that is also marginally effective against HCC, increasing survival by 2-3 months as a single treatment.

The current treatment options for HCC are not optimal, especially following metastasis. Irradiation and chemotherapies have not so far proved to be satisfactory; surgery is the most effective treatment of HCC. However, surgery is only appropriate for patients with small resectable tumors. Only a single, molecularly based drug (Sorafenib), which targets tyrosine kinase receptors and the MEK/ERK pathway, has generated responses in patients as a single therapy. However, increased survival times with this drug are only a few months. As such, it is imperative to discover novel, effective, and targeted therapies for this highly aggressive cancer. In particular, there is a strong need in the art for improved methods for treatment of HCC with small-molecule drugs.

The transcription factor LSF, a member of a small family of transcription factors conserved throughout the animal kingdom[9], is ubiquitously expressed in mammalian tissues and cell lines[10]. LSF activity is tightly controlled as cells progress from quiescence into DNA replication (G0 to S)[11,12], and it is required for efficient progression of cells through the G1/S transition[4,5]. Regulation of LSF activity normally occurs via post-translational modifications, with LSF protein levels generally being low and constant. However, LSF protein levels were recently shown to be highly upregulated in tumor cells, particularly in HCC cell lines and HCC patient samples[6,13]. These elevated LSF levels were shown to promote oncogenesis in the HCC cells.

SUMMARY OF THE INVENTION

The present invention is generally directed to methods, compositions and kits to treat cancer, e.g. hepatocellular carcinoma (HCC), for example, by using inhibitors of late SV40 factor (LSF), such as a compound represented by formula (I) as disclosed herein. In some embodiments, an inhibitor of LSF is a compound of formula (IV). In some embodiments, an inhibitor of LSF is any one of compounds of formula (IV) to (XXVI). In some embodiments, the LSF inhibitor compounds, of formulas (I) to (XXVI) as disclosed herein can be used to treat other cancers, for example, cervical cancer, colon cancers, melanomas and the like.

Recently, the inventors were involved in demonstrating that the transcription factor LSF, which was previously reported to mediate G1/S progression in multiple cell types[4,5], can function as an oncogene for HCC[6]. Small molecule inhibitors of oncogenic kinases can provide tremendous therapeutic benefit, due to the phenomenon of oncogene addiction[7,8], in which primary cancers are uniquely dependent on an oncogene for continued cell growth and survival.

Previously, the inventors in collaboration with other scientists have reported that the expression of LSF is up-regulated in subjects, e.g. human subjects, with HCC (see Yoo et al., PNAS, 2010; 107; 8357-8362, which is incorporated herein in its entirety by reference). Herein, the inventors have discovered that small-molecule compounds disclosed herein that are specific inhibitors of LSF, and can cause cell death in HCC cell lines, as well as in primary cancer cells and cell lines derived from other cancer types. Previously, the inventors have demonstrated in collaboration with other scientists that the small molecules as disclosed herein decreases tumorigenesis and metastasis of HCC in an in vivo mouse model of HCC. Accordingly, the inventors have discovered a family of small molecule inhibitors LSF as disclosed herein, and can be used as chemotherapeutics agents for treatment of cancers, e.g., HCC in subjects, such as human subjects.

Accordingly, the inventors demonstrate herein that small molecules that specifically inhibit LSF could provide treatment for cancers, e.g., HCC. In particular, the inventors have identified a family of small molecules that specifically target the DNA-binding and corresponding transcriptional activities of LSF, and that inhibit proliferation of a number of cancer cell lines, e.g., cervical cancer cell lines, colon cancer cell lines, breast cancer cell lines, endometrium cell lines, kidney cell lines, melanoma cell lines, etc. The LSF inhibitors as disclosed herein rapidly induce apoptosis in an aggressive HCC cell line in vitro. Additionally, in collaboration with other scientists, the inventors have demonstrated that the small molecule inhibitors of LSF as disclosed herein significantly inhibits tumor growth in a mouse xenograft model, with no observable tissue toxicity (data not shown). In contrast, the inventors have demonstrated that the viability of primary cells is unaffected in vitro (data not shown). These data demonstrate oncogene addiction of HCC cells to LSF and support the feasibility of directly targeting this transcription factor for chemotherapeutic intervention.

One aspect of the present invention relates to a method to inhibit LSF in a subject, for example, using a compound of formula (I), or enantiomers, prodrugs, derivatives, or pharmaceutically acceptable salts thereof, wherein the formula (I) has the structure:

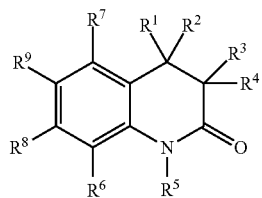

(I)

wherein:

$R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alky)amino, or $C_1$-$C_6$ alkoxy.

In some embodiments, $R^2$ and $R^3$ together form a second bond between the carbons to which they are attached.

$R^5$ is selected from the group of hydrogen, $C_1$-$C_6$ alkyl, $C_1$-$C_6$ haloalkyl, $C_1$-$C_6$ heteroalkyl, aryl, heteroaryl, F, Br, Cl, or I.

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl.

$R^8$ and $R^9$ are each independently selected from the group of hydrogen, $C_1$-$C_4$ alkyl, $C_1$-$C_4$ haloalkyl, $C_1$-$C_4$ heteroalky, $OR^{3A}$, $SR^{3A}$, $SO_2R^{3A}$, $NR^{3A}R^{4A}$, $PO_m(R^{3A})_n$, F, Br, Cl, I, heteroaryl or aryl, provided $R^9$ is not $NR^{3A}R^{4A}$.

In some embodiments, $R^8$ and $R^9$ together with the carbons to which they are attached form an optionally substituted 5-8 membered cycloalkyl or heterocycyl.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m is 1, 2, or 3; and n is 1, 2, or 3;

In one embodiment, the subject suffers from or is at risk of hepatocellular carcinoma.

Another aspect of the invention relates to methods and compositions to treat hepatocellular carcinoma in a subject. The methods of the invention as disclosed herein include administration to the subject a pharmaceutical composition comprising a compound of formula (I) as disclosed herein, or enantiomers, prodrugs, derivatives or pharmaceutically acceptable salts thereof.

In some embodiments, a compound of the invention as disclosed herein can be used in combination therapy.

In various embodiments, a compound of formula (I) can be represented by formula (II), wherein the formula (II) has the structure:

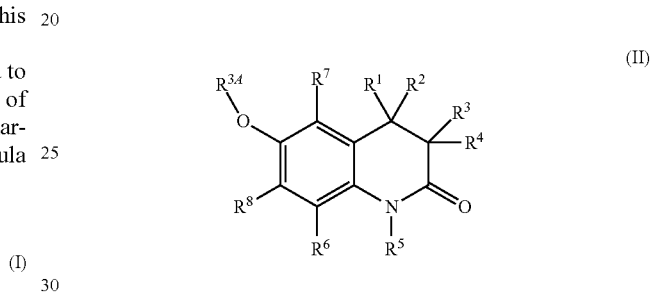

(II)

In formula (II), $R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalky, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy.

In some embodiments, $R^{3A}$ is $C_1$-$C_8$ alkyl. In some embodiments, $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

In some embodiments, $OR^{3A}$ is O—$C_1$-$C_8$ alkyl. In some embodiments, $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

$R^5$ is selected from the group of hydrogen, $C_1$-$C_6$ alkyl, $C_1$-$C_6$ haloalkyl, $C_1$-$C_6$ heteroalkyl, aryl, heteroaryl, F, Br, Cl, or I.

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl. In some embodiments, $R^7$ is $OR^{3A}$. In some embodiments, $OR^{3A}$ is O—$C_1$-$C_8$ alkyl. In some embodiments, $C_1$-$C_8$ alkyl is a branched chain alkyl. In some embodiments, $C_1$-$C_8$ alkyl is methyl, ethyl, n-propyl, propyl, n-butyl, i-butyl, or t-butyl.

$R^8$ is selected from the group of hydrogen, $C_1$-$C_4$ alkyl, $C_1$-$C_4$ haloalkyl, $C_1$-$C_4$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl or aryl. In some embodiments, $R^8$ is $OR^{3A}$. In some embodiments, $OR^{3A}$ is O—$C_1$-$C_8$ alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

In some embodiments, $R^2$ and $R^3$ together form a second bond between the carbons to which they are attached. In some embodiments, $R^2$ is a substituted aryl. In some embodiments, $R^2$ is a substituted phenyl. In some embodiments, the substituted phenyl is a $C_1$-$C_6$ alkoxy substituted phenyl. In certain embodiments, $C_1$-$C_6$ alkoxy is OMe, OEt, $O^nPr$, $O^iPr$, $O^nBu$, $O^iBu$, or $O^tBu$.

In some embodiments, $R^8$ and $OR^{3A}$ together with the carbons to which they are attached form an optionally substituted 5-8 membered cycloalkyl or heterocycyl.

m is 1, 2, or 3; and n is 1, 2, or 3;

In some embodiments, inhibitors of LSF with formula (I) can be represented by formula (III), wherein the formula (III) has the structure:

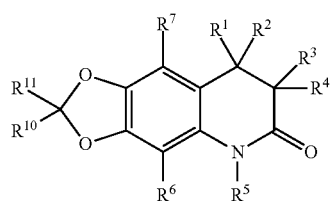

(III)

In formula (III), $R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy.

In some embodiments, $R^2$ and $R^3$ together form a second bond between the carbons to which they are attached.

$R^5$ is selected from the group of hydrogen, $C_1$-$C_6$ alkyl, $C_1$-$C_6$haloalkyl, $C_1$-$C_6$ heteroalkyl, aryl, heteroaryl, F, Br, Cl, or I;

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl;

$R^{10}$ and $R^{11}$ are each independently selected from the group of hydrogen, F, Br, Cl, or I.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m is 1, 2, or 3; and n is 1, 2, or 3;

In some embodiments, inhibitors of LSF with formula (III) can be represented by formula (XXVI), wherein the formula (XXVI) has the structure:

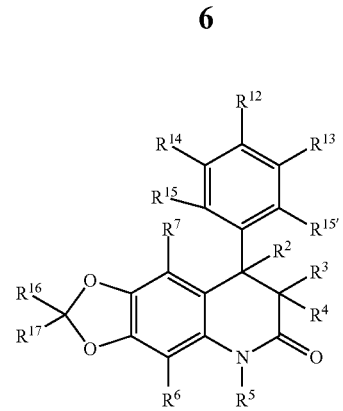

(XXVI)

In formula (XXVI), $R^2$, $R^3$ and $R^4$ are each independently selected from the group of hydrogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy. In various embodiments, $R^2$ and $R^3$ together can form a second bond between the carbons to which they are attached.

$R^5$ is selected from the group of hydrogen, $C_1$-$C_6$ alkyl, $C_1$-$C_6$haloalkyl, $C_1$-$C_6$ heteroalkyl, aryl, heteroaryl, F, Br, Cl, or I;

$R^6$, $R^7$, $R^{13}$, $R^{14}$, $R^{15}$ and $R^{15'}$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl;

each $R^{12}$ is independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl;

$R^{16}$ and $R^{17}$ are each independently selected from the group of hydrogen, F, Br, Cl, I, $C_1$-$C_4$ alkyl, or $OR^{3A}$;

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m is 1, 2, or 3; and n is 1, 2, or 3.

In some embodiments, at least two of $R^{12}$, $R^{13}$, $R^{14}$, $R^{15}$ and $R^{15'}$ are not hydrogen. In some embodiments, $R^{12}$ and at least one of $R^{15}$ and $R^{15'}$ are not hydrogen.

In some embodiments, at least one of $R^{12}$, $R^{13}$, $R^{14}$, $R^{15}$ and $R^{15'}$ is $OR^{3A}$ and at least one of $R^{12}$, $R^{13}$, $R^{14}$, $R^{15}$ and $R^{15'}$ is F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl.

In some embodiments, at least one of $R^{12}$, $R^{13}$, $R^{14}$, $R^{15}$ and $R^{15'}$ is $OR^{3A}$ and at least one of $R^{12}$, $R^{13}$, $R^{14}$, $R^{15}$ and $R^{15'}$ is F, Br, Cl, I, $NR^{3A}R^{4A}$, $SO_2R^{3A}$, $PO_m(R^{3A})_n$, $C_2$-$C_8$ alkenyl, $C_1$-$C_6$ haloalkyl or $C_1$-$C_6$ heteroalkyl.

In some embodiments, at least one of $R^{12}$, $R^{13}$, $R^{14}$, $R^{15}$ and $R^{15'}$ is $OR^{3A}$ and at least one of $R^{12}$, $R^{13}$, $R^{14}$, $R^{15}$ and $R^{15'}$ is F, Br, Cl, $NR^{3A}R^{4A}$ or $C_2$-$C_8$ alkenyl.

In some embodiments, at least one of $R^{12}$, $R^{15}$ and $R^{15'}$ is $OR^{3A}$ and at least one of $R^{12}$, $R^{15}$ and $R^{15'}$ is F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl.

In some embodiments, at least one of $R^{12}$, $R^{15}$ and $R^{15'}$ is $OR^{3A}$ and at least one of $R^{12}$, $R^{15}$ and $R^{15'}$ is F, Br, Cl, I, $NR^{3A}R^{4A}$, $SO_2R^{3A}$, $PO_m(R^{3A})_n$, $C_2$-$C_8$ alkenyl, $C_1$-$C_6$ haloalkyl or $C_1$-$C_6$ heteroalkyl.

In some embodiments, at least one of $R^{12}$, $R^{15}$ and $R^{15'}$ is $OR^{3A}$ and at least one of $R^{12}$, $R^{15}$ and $R^{15'}$ is F, Br, Cl, $NR^{3A}R^{4A}$ or $C_2$-$C_8$ alkenyl.

In some embodiments, at least one of $R^{15}$ and $R^{15'}$ is $OR^{3A}$ and $R^{12}$ is F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl.

In some embodiments, at least one of $R^{15}$ and $R^{15'}$ is $OR^{3A}$ and $R^{12}$ is F, Br, Cl, I, $NR^{3A}R^{4A}$, $SO_2R^{3A}$, $PO_m(R^{3A})_n$, $C_2$-$C_8$ alkenyl, $C_1$-$C_6$ haloalkyl or $C_1$-$C_6$ heteroalkyl.

In some embodiments, at least one of $R^{15}$ and $R^{15'}$ is $OR^{3A}$ and $R^{12}$ is F, Br, Cl, I, $OR^{3A}$, $NR^{3A}R^{4A}$ or $C_2$-$C_8$ alkenyl.

In some embodiments, $R^{15}$ or $R^{15'}$ is $OR^{3A}$ and $R^{12}$ is F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl.

In some embodiments, $R^{15}$ or $R^{15'}$ is $OR^{3A}$ and $R^{12}$ is F, Br, Cl, I, $NR^{3A}R^{4A}$, $SO_2R^{3A}$, $PO_m(R^{3A})_n$, $C_2$-$C_8$ alkenyl, $C_1$-$C_6$ haloalkyl or $C_1$-$C_6$ heteroalkyl.

In some embodiments, $R^{15}$ or $R^{15'}$ is $OR^{3A}$ and $R^{12}$ is F, Br, Cl, $NR^{3A}R^{4A}$ or $C_2$-$C_8$ alkenyl.

In some embodiments, one of $R^{15}$ and $R^{15'}$ is hydrogen and the other is $OR^{3A}$.

In some embodiments, one of $R^{15}$ and $R^{15'}$ is hydrogen and the other is $OR^{3A}$, and $R^{12}$ is F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl.

In some embodiments, one of $R^{15}$ and $R^{15'}$ is hydrogen and the other is $OR^{3A}$, and $R^{12}$ is F, Br, Cl, I, $NR^{3A}R^{4A}$, $SO_2R^{3A}$, $PO_m(R^{3A})_n$, $C_2$-$C_8$ alkenyl, $C_1$-$C_6$ haloalkyl or $C_1$-$C_6$ heteroalkyl.

In some embodiments, one of $R^{15}$ and $R^{15'}$ is hydrogen and the other is $OR^{3A}$, and $R^{12}$ is F, Br, Cl, $NR^{3A}R^{4A}$ or $C_2$-$C_8$ alkenyl.

In some embodiments, $R^{13}$, $R^{14}$ and one of $R^{15}$ and $R^{15'}$ is hydrogen.

In some embodiments, $R^2$, $R^3$ and $R^4$ are hydrogen or $R^4$ is hydrogen and $R^2$ and $R^3$ together form a second bond between the carbons to which they are attached.

In some embodiments, $R^5$ is hydrogen or $C_1$-$C_6$alkyl. Exemplary alkyls for $R^5$ include, but are not limited to methyl, ethyl, propyl, isopropyl, 1-butyl, 2-butyl, 2-methylpropyl, pentyl, t-butyl, and hexyl. In some embodiments, $R^5$ is ethyl.

In some embodiments, $R^6$ and $R^7$ both are hydrogen.

In some embodiments, $R^{16}$ and $R^{17}$ are independently hydrogen, F, Br, Cl or I. In some embodiments $R^{16}$ and $R^{17}$ both are hydrogen, F, Br or Cl.

In some embodiments, the inhibitor of LSF is a compound of Formula (III'):

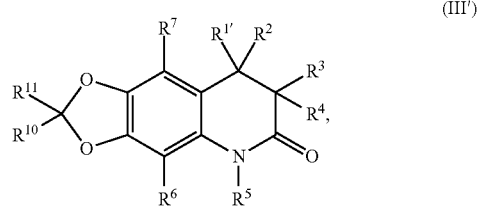

(III')

or enantiomers, prodrugs, derivatives, and pharmaceutically acceptable salts thereof.

In compounds of Formula (III'), $R^{1'}$ is an aryl substituted with at least one $C_1$-$C_6$ alkoxyl and at least one di($C_1$-$C_{24}$alkyl)amino, halogen, $C_1$-$C_6$alkyl, $C_2$-$C_8$alkenyl, polyethylene glycol, polyethyleneglycol substituted $C_1$-$C_6$alkenyl, wherein the substituted aryl can be optionally further substituted with halogen, $C_1$-$C_4$ alkyl, $C_1$-$C_4$haloalkyl, $C_1$-$C_4$ heteroalkyl, di($C_1$-$C_{24}$alkyl)amino or combinations thereof; $R^2$ and $R^3$ are hydrogen or $R^2$ and $R^3$ together form a second bond between the carbons to which they are attached; $R^4$ is hydrogen; $R^5$ is selected from the group consisting of hydrogen and $C_1$-$C_6$ alkyl; $R^6$ and $R^7$ are each independently selected from the group consisting of hydrogen, F, Br, Cl and I; and $R^{10}$ and $R^{11}$ are each independently selected from the group consisting of hydrogen, F, Br, Cl, and I.

In some embodiments of Formula (III'), $R^{1'}$ is an aryl substituted with at least one $C_1$-$C_6$ alkoxyl and at least one di($C_1$-$C_{24}$alkyl)amino, halogen, $C_2$-$C_8$alkenyl, or polyethyleneglycol substituted $C_1$-$C_6$alkenyl, wherein the substituted aryl can be optionally further substituted with halogen, $C_1$-$C_4$ alkyl, $C_1$-$C_4$haloalkyl, $C_1$-$C_4$ heteroalkyl, di($C_1$-$C_{24}$alkyl)amino or combinations thereof, $R^2$ and $R^3$ are hydrogen or $R^2$ and $R^3$ together form a second bond between the carbons to which they are attached; $R^4$ is hydrogen; $R^5$ is selected from the group consisting of hydrogen and $C_1$-$C_6$ alkyl; $R^6$ and $R^7$ are each independently selected from the group consisting of hydrogen, F, Br, Cl and I; and $R^{10}$ and $R^{11}$ are each independently selected from the group consisting of hydrogen, F, Br, Cl, and I.

In some embodiments, a compound of Formula (III') is 8-(4-(dimethylamino)-2-ethoxyphenyl)-7,8-dihydro-[1,3]dioxolo[4,5-g]quinolin-6(5H)-one (FQI-34), having the structure:

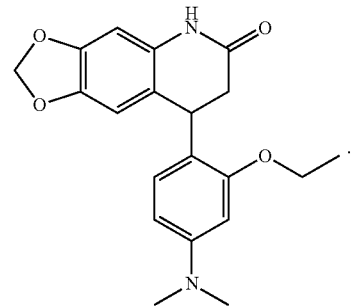 [SMILES: CCOc1cc(N(C)C)ccc1C1CC(=O)Nc2cc3c(cc21)OCO3]

In some embodiments, a compound of Formula (III') is selected from the group consisting of:

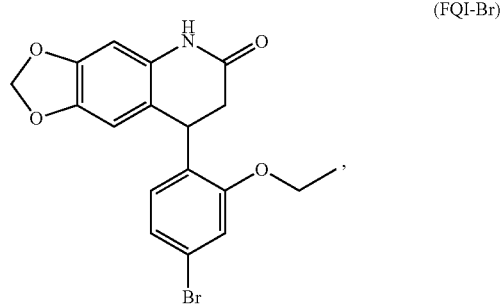

(FQI-Br)

-continued
(FQI-Cl)
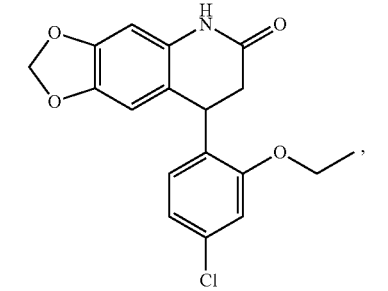
(FQI-F)
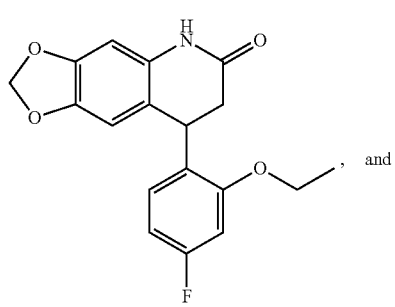
, and
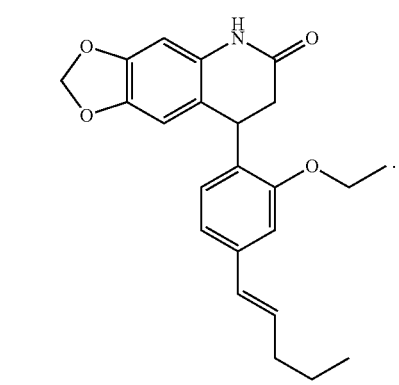
In one embodiment, an inhibitor of LSF of formula (I), (II), (III) or (XXVI) is a compound of formula (IV), wherein the formula (IV) has the structure:
(IV)
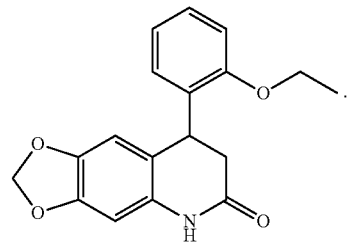
In further embodiments, inhibitors of LSF of formula (I), (II), (III) or (XXVI) can be a compound selected from the group consisting of compounds of formula (V) to (XXV):
(IV)
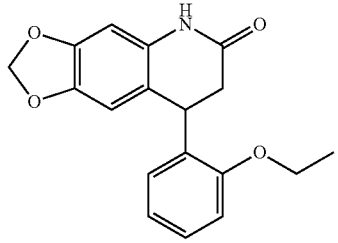
C1 (FQI1)
(S)-(IV)
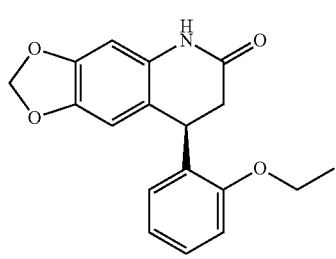
C1-2 ((S)-FQI1)
(R)-(IV)
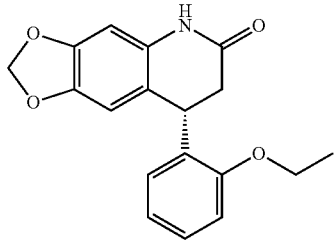
C1-1 ((R)-FQI1)
(V)
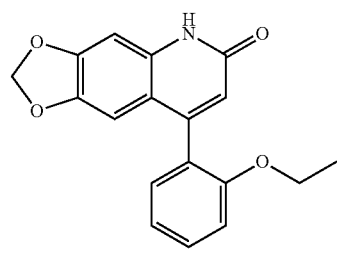
C1-U (FQI2)
(VI)
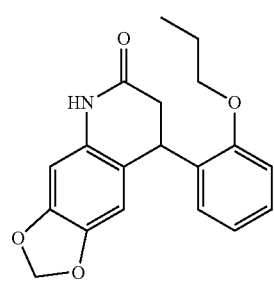
E1 (FQI16)

(VII)
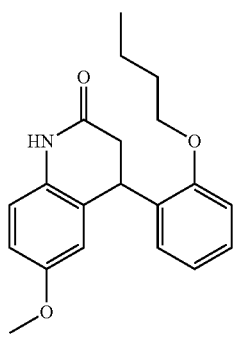
A3 (FQI5)
(VIII)
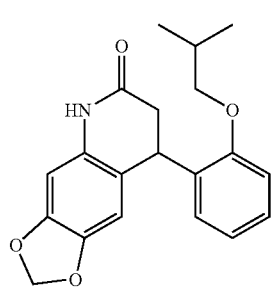
B1 (FQI6)
(IX)
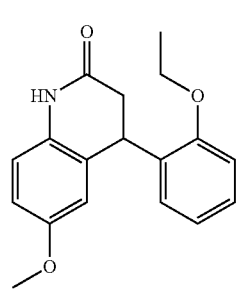
C3 (FQI10)
(X)
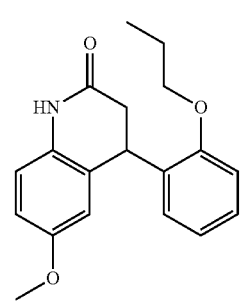
E3 (FQI18)
(XI)
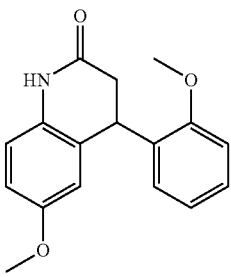
D3 (FQI14)
(XII)
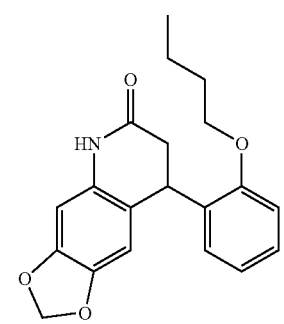
A1 (FQI3)
(XIII)
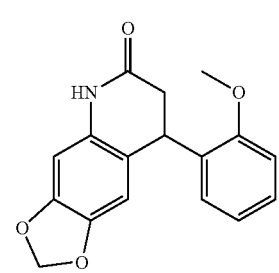
D1 (FQI12)
(XIV)
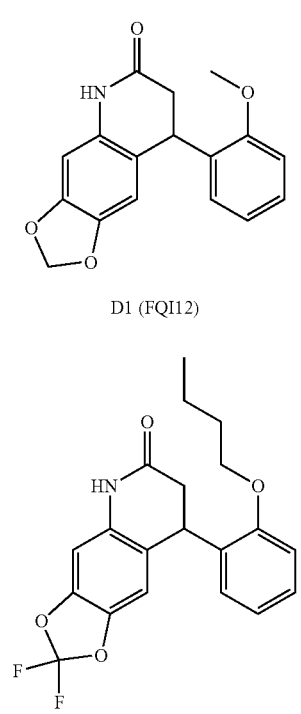
A2 (FQI4)

(XV)

E2 (FQI17)

(XVI)

B3 (FQI8)

(XVII)

F3 (FQI21)

(XVIII)

F1 (FQI19)

(XIX)

B2 (FQI7)

(XX)

C2 (FQI9)

(XXI)

D2 (FQI13)

(XXII)

F2 (FQI20)

-continued

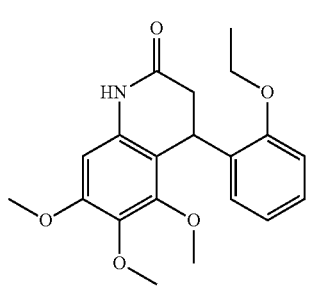

C4 (FQI11) (XXIII)

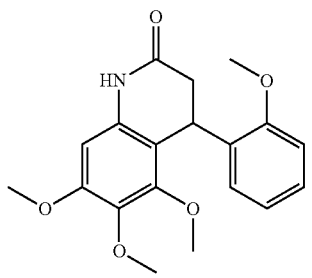

D4 (FQI15) (XXIV)

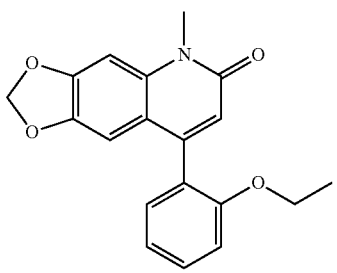

C1-NCH3 (XXV)

As noted above, compounds any of formula (I) to (XXVI) can inhibit LSF. Without limitations, inhibition of LSF can be determined using any method available, including, but not limited to in vitro assays. For example, inhibition of LSF can be determined using the methods described in the Examples section.

In various embodiments, enantiomers, prodrugs, derivatives and pharmaceutically acceptable salts of a compound of any of formula (I) to (XXVI) and (III') also fall within the scope of the invention.

Yet another aspect of the present invention is directed to the use of pharmaceutical composition comprising a compound of formula (I) or (III') as disclosed herein for the manufacturer of a medicament for treatment of hepatocellular carcinoma. In some embodiments, a compound of formula (I) can be a compound of any of formula (II) to (XXVI) and (III'). In one embodiment, a compound of formula (IV) is used in pharmaceutical compositions of the invention as disclosed herein. In additional embodiments, enantiomers, prodrugs, derivatives and pharmaceutically acceptable salts of a compound of any of formula (III') or (I) to (XXVI) are also included in the invention.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 2A shows Factor quinolinone inhibitor 1 (FQI1) was initially identified as the racemate. The more active (S)-enantiomer, (S)-FQI1, and the achiral quinolinone inhibitor FQI2 possess similar chemical properties and biological activities. FIG. 2B shows a computationally generated overlay of (S)-FQI1 (cpk) and FQI2 (red) using the OpenEye Scientific Software shape similarity comparison program ROCS. Although achiral, FQI2 is capable of adopting similar conformations as (S)-FQI1.

FIG. 3A shows LSF-dependent firefly luciferase reporter assays, which were normalized to activity in the absence of FQIs. USF-dependent reporter assays were performed with FQI1 only. Averages with standard deviation (SD) derive from 3-4 independent experiments. FIG. 3B shows a representative electrophoretic mobility shift assay (EMSA) of LSF/DNA complexes from in vitro translated LSF incubated with FQI1. "-LSF": translation extract with no programmed LSF. FIG. 3C shows the fraction of radiolabeled DNA bound to LSF, normalized to bound levels in absence of FQI1; values were averaged (with standard error of the mean (SEM)) from 3 EMSAs. FIG. 3D shows a representative chromatin immunoprecipitation assay (ChIP) of myc-LSF-HA binding to the endogenous POLA1 promoter in a human cell line. Myc-LSF-HA expression was induced with the small molecule inducer RSL1. In induced cells, FQI1 or vehicle was added for the final 12 h of myc-LSF-HA induction.

FIG. 4A shows viability of QGY-7703 HCC cells, treated with FQI1 (top) or FQI2 (bottom), as assayed by the MTT (3-(4,5-dimethylthiazol-2-yl)-2,5-diphenyltetrazolium bromide) cell viability assay. Averages with SEM of three experiments are shown. *P<0.05, by one-tailed t-test. FIG. 4B shows apoptosis in QGY-7703 cells treated with FQI1, but not with vehicle. The cells were imaged separately for TUNEL-positivity and DNA at the top. Below: Merged images; green for TUNEL (Terminal deoxynucleotidyl transferase dUTP nick end labeling) staining, blue for DAPI (4',6-diamidino-2-phenylindole) staining. FIG. 4C shows newly plated primary mouse hepatocytes, treated as indicated, were stained for DNA (blue) and F-actin (green). Binucleate cells are common for adult hepatocytes.

FIG. 5A shows the average cell viability (measured by the MTT assay in three independent experiments) of HepG3 and QGY-7703 HCC cells treated with increasing concentrations of FQI1 over a two-day timecourse. Error bars represent standard error of the mean. The symbol "*" indicates P<0.05, measured by t-test. FIG. 5B is representative flow cytometric data demonstrating induction of apoptosis in QGY-7703 cells after FQI1 treatment. Cells were treated with either vehicle (DMSO) or FQI1 (10 μM) for 48 h; TUNEL assays were performed, followed by flow cytometric analyses.

FIG. 9A shows effect of inhibition of increasing doses of FQI1 on kidney primary cancer cells (RCC10RGB cell line). FIG. 9B shows effect of inhibition of increasing doses of FQI1 on 5 different Hematopoietic cell lines (AMO1, EJM, KMS11, LP1, OCILY10 cell lines). FIG. 9C shows effect of increasing doses of FQI1 on inhibition of an Endometrium cancer cell line (HEC151 cell line). FIG. 9D shows effect of increasing doses of FQI1 on inhibition of a Breast cancer cell line (MCF7). FIG. 9E shows effect of increasing doses of FQI1 on inhibition of an upper digestive tract cancer (SCC9) cell line. FIG. 9F shows effect of increasing doses of FQI1 on inhibition of a stomach cancer (AGS) cell line. FIG. 9G shows effect of increasing doses of FQI1 on inhibition of ovary cancer cell lines (A2780, COV362, COV434, EFO27, IGROV1, JHOC5, JHOM1, OAW42, OVCAR4, OVCAR8, OVKATE, RKN, and RMGI cell lines). FIG. 9H shows effect of increasing doses of FQI1 on inhibition of lung cancer primary cell lines (CORL23, NCIH1836, NCIH2073, NCIH2110, NCIH3255, CAL12T, COLO699, CORL51, HCC1171, HCC1195, HCC1359, HCC1833, HCC2108, HCC2935, HCC4006, HCC827, NCUH105, HCIH1694, NCIH1876, NCIH1963, NCIH2023, NCIH2030, NCIH2081, NCIH2141, NCIH2172, NCIH2342, NCIH841, SCLC21H and SQ1 cell lines). FIG. 9I shows effect of increasing doses of FQI1 on inhibition on liver cancer cell lines (HEPG2, SNU398 cell lines). FIG. 9J shows effect of increasing doses of FQI1 on inhibition of large intestine primary cancer cell lines (COLO320, CW2, HCT116, KM12, SNU1033, SNU175, SNU61, SNU81, SNUC5, SW948 cell lines). FIG. 9K shows the effect of increasing doses of FQI1 on inhibition all cancer cell lines tested and shown in FIGS. 9A-9J.

FIG. 10A shows effect of increasing doses of FQI2 on inhibition of an upper digestive tract cancer (SCC9) cell line. FIG. 10B shows effect of increasing doses of FQI2 on inhibition of a stomach cancer (AGS) cell line. FIG. 10C shows effect of increasing doses of FQI2 on inhibition of ovary cancer cell lines (A2780, COV362, COV434, EFO27, IGROV1, JHOC5, JHOM1, OAW42, OVCAR4, OVCAR8, OVKATE, RKN, and RMGI cell lines). FIG. 10D shows effect of increasing doses of FQI2 on inhibition on liver cancer cell lines (HEPG2, SNU398 cell lines). FIG. 10E shows effect of increasing doses of FQI2 on inhibition of lung cancer primary cell lines (CORL23, NCIH1836, NCIH2073, NCIH2110, NCIH3255, CAL12T, COLO699, CORL51, HCC1171, HCC1195, HCC1359, HCC1833, HCC2108, HCC2935, HCC4006, HCC827, NCUH105, HCIH1694, NCIH1876, NCIH1963, NCIH2023, NCIH2030, NCIH2081, NCIH2141, NCIH2172, NCIH2342, NCIH841, SCLC21H and SQ1 cell lines). FIG. 10F shows effect of increasing doses of FQI2 on inhibition of large intestine primary cancer cell lines (COLO320, CW2, HCT116, KM12, SNU1033, SNU175, SNU61, SNU81, SNUC5, SW948 cell lines). FIG. 10G shows effect of inhibition of increasing doses of FQI2 on kidney primary cancer cells (RCC10RGB cell line). FIG. 10H shows effect of inhibition of increasing doses of FQI2 on 5 different Hematopoietic cell lines (AMO1, EJM, KMS11, LP1, OCILY10 cell lines). FIG. 10I shows effect of increasing doses of FQI2 on inhibition of an Endometrium cancer cell line (HEC151 cell line). FIG. 10J shows effect of increasing doses of FQI2 on inhibition of a Breast cancer cell line (MCF7). FIG. 10K shows the effect of increasing doses of FQI2 on inhibition of all cancer cell lines tested and shown in FIGS. 10A-10J.

FIG. 13A shows representative western blot for CETSA analysis. FIG. 13B shows quantification of CETSA western blots (N≥3), mean±S.E.M. Mean AUC for each graph is shown. *p<0.001, p<0.01, NS p>0.05.

FIG. 16A shows representative western blots against LSF (N≥3). FIG. 16B shows quantification of anti-LSF western blots (N≥3). Area-under-the-curve (AUC) was calculated. Mean AUC+SEM is plotted, with mean DMSO AUC indicated as dashed line. Significance determined using GraphPad PRISM unpaired, parametric t test. *<0.05 <0.01 *<0.001 ****<0.0001.

DETAILED DESCRIPTION OF THE INVENTION

Figure 1:
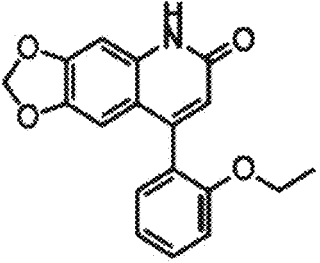
FIG. 1 shows exemplary compounds that inhibit cell proliferation in tissue culture cells along with the values of $IC_{50}$ and maximum percent of cell growth inhibition for indicated cell lines. Compounds C1-1 and C1-2 are enantiomers (S- or R-configuration) of compound C1 (Formula IV), while other compounds are examples of compounds derived from formula (I), (II) or (III). The designations "R" and "S" as shown in compounds C1-1 and C1-2, respectively, are used to denote the absolute configuration of the molecule about its chiral center. The designations "(+)" and "(−)" as shown in compounds C1-1 and C1-2 are employed to designate the sign of rotation of plane-polarized light by the compound.

In some embodiments, the present invention is based upon the discovery that expression of LSF is increased in subjects, e.g. human subjects with HCC. The inventors have also discovered small-molecule compounds that inhibit LSF.

The inventors have discovered that the small molecule inhibitors of LSF as disclosed herein can cause cell death of cancer cell lines and primary cancer cells in an in vitro assay, e.g., HCC cancer cell lines, breast cancer cell lines, colon cancer cell lines, ovarian cancer cell lines etc., Studies performed by the inventors in collaboration with other scientists revealed that the small molecule inhibitors as disclosed herein can decrease tumorigenesis and metastasis of HCC in an in vivo mouse model of HCC. Therefore, the small-molecule inhibitors of LSF disclosed herein can be used in a method for treatment of cancers in subjects, e.g. HCC and other cancers human subjects.

Accordingly, in some embodiments, the present invention provides methods and compositions for inhibition of LSF and can be used for treatment of hepatocellular carcinoma in a subject. In some embodiments, the present invention relates in part to the use of small-molecule compounds to inhibit LSF for treatment of cancer, e.g. hepatocellular carcinoma (HCC), liver cancers, breast cancers, ovarian cancers, colon cancers, cervical cancers, melanomas etc.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions for Chemical Functional Groups

The structure definitions such as "alkyl" are provided below for nomenclature purposes. They do not exclude the meaning as those acquired in the art to which this invention pertains. The term "alkyl" as used herein refers to a linear, branched, or cyclic saturated hydrocarbon group typically although not necessarily containing 1 to about 24 carbon atoms, preferably 1 to about 12 carbon atoms, more preferably 1 to about 6 carbon atoms, such as methyl, ethyl, n-propyl, isopropyl, n-butyl, isobutyl, sec-butyl, tert-butyl, pentyl, hexyl, and the like, as well as cycloalkyl groups such as cyclopentyl, cyclohexyl and the like. The term "cycloalkyl" intends a cyclic alkyl group, typically having 4 to 10, preferably 5 to 8, carbon atoms. The term "substituted alkyl" refers to alkyl substituted with one or more substituent groups, and the terms "heteroalkyl" and "heteroatom-containing alkyl" refer to alkyl in which at least one carbon atom is replaced with a heteroatom. The term "haloalkyl" as used herein refers to an alkyl structure with at least one substituent of fluorine, chorine, bromine or iodine, or with combinations thereof. If not otherwise indicated, the term "alkyl" includes linear, branched, cyclic, unsubstituted, substituted, and/or heteroatom-containing alkyl, respectively.

The term "alkenyl" as used herein refers to a linear, branched, or cyclic hydrocarbon group of 2 to about 16 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl, respectively.

The term "alkynyl" as used herein refers to a linear or branched-chain hydrocarbon group having one or more carbon-carbon triple-bonds and having from 2 to about 8 carbon atoms. Examples of alkynyl groups include ethynyl, propynyl, butynyl and the like.

The term "alkoxy" as used herein intends an alkyl group bound through a single, terminal ether linkage; that is, an "alkoxy" group may be represented as —O-alkyl where alkyl is as defined herein.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom such as oxygen, nitrogen and sulfur. The term "heteroaryl" includes ring systems such as pyridine, quinoline, furan, thiophene, pyrrole, imidazole and pyrazole.

The term "heterocycyl" as used herein refers to a single ring or multiple rings that are fused together, directly linked, or indirectly inked (such that the different rings are bound to a common group such as a methylene or ethylene moiety), in which at least one carbon atom is replaced with a heteroatom such as oxygen, nitrogen and sulfur. Preferred heterocycyl groups contain 5 to 24 carbon atoms, and particularly preferred heterocycyl groups contain 5 to 14 carbon atoms. For example, a heterocycyl group can be a five-membered ring with at least one carbon replaced by oxygen or nitrogen.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. In one embodiment, the bicyclic or polycyclic ring may be fused ring. The fusion of the ring may be across a bond between two atoms, i.e. two cyclic rings share one bond or two atoms, for example, a decalin; the fusion of the ring may be across a sequence of atoms, i.e. two cyclic rings share three or more atoms, for example a norbornane.

By "substituted" as in "substituted alkyl," "substituted aryl," and the like, as alluded to in some of the definitions as described herein, is meant that in the alkyl, aryl, or other moiety, at least one hydrogen atom bound to a carbon (or other) atom is replaced with one or more non-hydrogen substituents. Examples of such substituents include, without limitation: halogen, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aryl alkoxy, $C_6$-$C_{24}$ alkyl aryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_1$-$C_{24}$ aryl)-substituted carbamoyl (—(CO)—N($C_5$-$C_{24}$ aryl)$_2$), alkyl), N—($C_1$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR═NH where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R═hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—$PO_2$), phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), and $C_5$-$C_{24}$ aryl (preferably $C_5$-$C_{14}$ aryl). In preferred embodiments, the substituents as used herein are halogen, $C_1$-$C_4$ alkyl, $C_1$-$C_4$ haloalkyl, $C_1$-$C_4$ heteroalkyl or $C_1$-$C_6$ alkoxy.

In addition, the functional groups as described herein may, if a particular group permits, be further substituted with one or more additional functional groups or with one or more hydrocarbyl moieties such as those specifically enumerated herein. Analogously, the hydrocarbyl moieties described herein may be further substituted with one or more functional groups or additional hydrocarbyl moieties such as those specifically enumerated.

Other Definitions

The term "inhibit LSF" as used herein refers to inhibiting expression (level) of LSF and/or biological activity of LSF. In some embodiments, the term "inhibit LSF" refers to a decrease in the protein level of LSF and/or gene transcript level of LSF. For example, inhibition of LSF can result in a reduction in the gene expression of TFCP2 encoding LSF. The term "inhibit LSF" also refers to a down-regulation or an inhibition of biological activity of LSF, e.g. the function of LSF to modulate expression of LSF-regulated downstream genes such as; thymidylate synthetase (TYMS), secreted phosphoprotein 1 (SPP1), complement factor H (CFH) and fibronectin 1 (FN1) (see Porta-de-la-Riva M, et al (2011) J. Biochem. 435:563-8, which is incorporated herein in its entirety by reference).

The terms "cellular LSF activity" and "biological activity of LSF" are used herein interchangeably. Both terms refer to the ability of LSF to regulate cellular processes downstream of LSF, for example, to modulate the expression of genes that are downstream of LSF. In some embodiments, the biological activity of LSF can elicit a stimulatory effect on expression of LSF-downstream genes. In other embodiments, the biological activity of LSF can induce an inhibitory effect on expression of LSF-downstream genes. In yet other embodiments, the biological activity of LSF may be due to interactions with other cellular proteins.

The phrase "level of LSF" as used herein encompasses the expression and/or biological activity of LSF. As described herein, the term "expression" refers to the amount of the protein obtained by translation of RNA transcribed from a gene, and/or the amount of RNA transcribed from a gene.

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The terms "inhibitors of LSF" and "LSF inhibitors" used interchangeably herein, generally refers to agents that inhibit LSF. They can be of synthetic or biological origins. They can be organic, or inorganic molecules, or peptides, antibodies or antisense RNA that inhibit LSF. Inhibitors of LSF of the invention are chemical entities or molecules that can inhibit expression of LSF and/or biological activity of LSF, as disclosed herein, for example, compounds of any of formula (I) to (XXVI), and enantiomers, prodrugs, derivatives and pharmaceutically acceptable salts thereof, which are discussed further in the section Inhibitors of LSF.

The ability of a compound to inhibit LSF can be assessed by measuring a decrease in expression of LSF as compared to the level of LSF in the absence of inhibitors of LSF. In some embodiments, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor as disclosed herein can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor as disclosed herein can inhibit biological activity of LSF, such as a decrease in expression of SPP1 that encodes OPN (also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor. In some embodiments, ability of a compound to inhibit LSF is assessed by inhibition of LSF-induced tumorigenesis and metastasis of cancer cells, e.g. hepatocellular carcinoma cells in vitro or in an in vivo animal model as demonstrated in the Examples herein, as compared to a reference condition without treatment with such a LSF inhibitor. In such embodiments, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

The term 'disorder' or 'disease' used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In one embodiment, the disorder or disease is cancer. In one embodiment, the disease or disorder is liver cancer, e.g., hepatocellular carcinoma. In one embodiment, the disease or disorder is a cancer selected from the group selected from: colon cancer, breast cancer, ovarian cancer, melanomia, endometrium cancer, pancreatic cancer, prostate cancer, bone cancer, kidney cancer, leukemia, large intestine cancer, lung cancer, small cell lung carcinoma (SSLC), stomach cancer and other cancers.

The term 'cancer' and 'malignancy' are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations. A small molecule LSF inhibitor as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see also Freshney, Culture of Animal Cells: A Manual of Basic Technique (3rd ed. 1994)).

A "tumorigenic cell," as used herein, is a cell that, when introduced into a suitable site in a subject, can form a tumor. The cell may be non-metastatic or metastatic. A variety of types of tumorigenic and/or metastatic cells can be used in a method of the invention, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, liver, uterus, ovary, nasopharynges, prostate, bone or bone marrow, brain, skin or other suitable tissues or organs. In a preferred embodiment, the cancer cells are of human origin.

The term "tumor" or "tumor cell" are used interchangeably herein, refers to the tissue mass or tissue type of cell that is undergoing abnormal proliferation.

A "metastatic" cell, as used herein, refers to a cell that has a potential for metastasis and, when used in a method of the invention, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, as described herein, can be considered to be highly metastatic cells. Metastatic cells can be generated in a variety of ways, which are discussed further below.

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. The term "subject" and "individual" are used interchangeably herein, and refer to an animal, for example a human, to whom treatment, including prophylactic treatment, with the cells according to the present invention, is provided. The "non-human animals" of the invention include mammals such as rats, mice, rabbits, sheep, cats, dogs, cows, pigs, and non-human primates.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The term "tissue" is intended to include intact cells, blood, blood preparations such as plasma and serum, bones, joints, muscles, smooth muscles, and organs. In one embodiment, the tissue is liver tissue.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer. As used herein with respect to cancer, the term treating is used to refer to the reduction of a symptom and/or a biochemical marker of in appropriate proliferation, for example a reduction in at least one biochemical marker of cancer by at least 10%. For example but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as an effective treatments by the methods as disclosed herein. In other embodiments, treatment can be therapeutic in terms of eliminating or reducing at least one symptom of the condition or disease. For example, in the case of HCC, therapeutic treatment refers to inhibiting or delaying the progression of HCC in a subject that is already inflicted with HCC. Measurable lessening includes any statistically significant decline in a measurable marker or symptom, such as measuring a tumor size or level of a biomarker.

As used herein, the term "treating" includes preventing the progression and/or reducing or reversing at least one adverse effect or symptom of a condition, disease or disorder associated with inappropriate proliferation, for example cancer. Accordingly, in some embodiments, treatment can be prophylactic in terms of completely or partially preventing a disease or sign or symptom of cancer. For example, subjects at high risk of cancer, e.g., HCC, such as HBV or HCV, can be subjected to prophylactic treatment to prevent the onset of HCC. In some embodiments, prophylactic treatment can be administered to subjects who had prior treatment of a disease and the disease is in remission. For example, for subjects who have their HCC tumors removed or stabilized by previous therapeutic methods can be prophylactically treated (e.g. with a LSF inhibitor as disclosed herein) to prevent the recurrence and metastasis of HCC.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. LSF, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, the small-molecule LSF inhibitors as disclosed herein decrease the activity or expression of LSF. Preferably, this decrease is at least about 5%, at least about 10%, at least about 25%, at least about 50%, at least about 75%, at least about 80%, or even at least about 90% of the level of expression or activity under control conditions. The term "level" as used herein in reference to LSF refers to expression or activity of LSF.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" as used herein refers to the amount of at least one agent of pharmaceutical composition to reduce or stop at least one symptom of the abnormal proliferation, for example a symptom of a cancer or malignancy. For example, an effective amount using the methods as disclosed herein would be considered as the amount sufficient to reduce a symptom of the abnormal proliferation, for example at least one symptom of a cancer or malignancy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. at least one small molecule inhibitor of LSF of Formula (I) to (XXVI) as disclosed herein) of pharmaceutical composition to alleviate at least some of the symptoms of cancer e.g. HCC. Stated another way, "therapeutically effective amount" of a small molecule LSF inhibitor as disclosed herein is the amount of a LSF inhibitor which exerts a beneficial effect on, for example, cancer, e.g., HCC. Beneficial effects include inhibition or delay of cancer, e.g., HCC progression. The dosage administered, as single or multiple doses, to an individual will vary depending upon a variety of factors, including pharmacokinetic properties of a LSF inhibitor, the route of administration, conditions and characteristics (sex, age, body weight, health, size) of subjects, extent of symptoms, concurrent treatments, frequency of treatment and the effect desired.

An "agent" is a chemical molecule of synthetic or biological origin. In the context of the present invention, an agent is generally a molecule that can be used in a pharmaceutical composition. In some embodiments, the agent is chemotherapeutic agents. In some embodiments, the agent is small-molecule LSF inhibitors as disclosed herein. In some embodiments, the agent can provide a therapeutic value. In some embodiments, the small molecule LSF inhibitors as disclosed herein can be used as a preventative or prophylactic treatment for prevention of cancer, e.g., where a subject is at risk or is likely to develop cancer. In other embodiments, the agent is used solely to implement the invention, e.g. pharmaceutically acceptable carriers as disclosed herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a LSF inhibitor of the invention by methods of administration such as parenteral or systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least an inhibitor of LSF as disclosed herein such that it enters the animal's system and, thus, is subject to metabolism and other like processes, for example, subcutaneous administration.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

Latent SV40 Factor (LSF)

LSF is short for late SV40 factor or late Simian Virus 40 factor, and is also known as aliases LBP-1 (leader binding protein-1), LBP-1c, LBP-1d, UBP-1 (upstream binding protein-1), SEF (SAA3 enhancer factor), TFCP2 (transcription factor CP2) and CP2. LSF regulates diverse cellular and viral promoters (7, 8).

For the purposes of this disclosure, the term "LSF" refers to a transcription factor encoded by the gene TFCP2. The sequences of nucleic acid and amino acid of LSF are known and have been assigned NCBI accession numbers for different species such as human, mouse and rat. In particular, the NCBI accession numbers for the nucleic acid and amino acid sequence of LSF for human are NM_005653 (SEQ ID NO: 1) and NP_005644 (SEQ ID NO: 2), respectively.

LSF is a DNA-binding transcription factor that is required in multiple cell types for cell cycle progression. It binds to the alpha-globin promoter and activates transcription of the alpha-globin gene. It has been reported that LSF facilitates entry into G1/S phase of the cell cycle, promotes DNA synthesis, and functions as an antiapoptotic factor (9).

LSF also regulates erythroid gene expression, plays a role in the transcriptional switch of globin gene promoters, and it activates many other cellular and viral gene promoters. The gene product interacts with certain inflammatory response factors, and polymorphisms of this gene can be involved in the pathogenesis of Alzheimer's disease.

A major cellular target of LSF is the thymidylate synthase (TS) gene (TYMS), which encodes the rate-limiting enzyme in the production of dTTP, required for DNA synthesis (9). TS has been a long-standing chemotherapeutic target for cancer treatments, and recently it was discussed that elevated levels of LSF in hepatocellular carcinoma cell lines can contribute to chemoresistance to one commonly utilized thymidylate synthetase inhibitor, 5-fluorouracil. Inhibition of LSF abrogates TS induction, induces either arrest at the G1/S transition, or in apoptosis after entry into S phase. Thus, LSF plays an important role in DNA synthesis and cell survival.

In the liver, LSF is activated by inflammatory cytokines and regulates the expression of acute phase proteins (10, 11).

Inhibitors of LSF

The present invention relates in part to methods and compositions to inhibit LSF, more specifically, with small-molecule LSF inhibitors. In some embodiments, inhibitors of LSF as disclosed herein can be used to inhibit the cellular LSF activity. In some embodiments, LSF inhibitors as disclosed herein can decrease expression (level) of LSF.

One of the major targets of LSF is thymidylate synthase (TS) gene (TYMS), which encodes the rate-limiting enzyme in the production of dTTP, required for DNA synthesis (9). Additional examples of LSF-downstream genes are disclosed in Yoo et al, PNAS, 2010, 107; 8357-8362, and include without limitation SPP1 (encoding osetopontin), complement factor H (CFH), TSPAN8, S100A10, CDH17, EFNB2, ZEB1, REG1A, REG3A, SAA4, TAGLN, FGFR2, EGFR, CYP2B7P1, CYP2B6, GPX2, DPYD, PKLR, LEF1, ICAM2 and IGFBP7.

In some embodiments, the genes downstream of LSF are tumor-associated genes, such as relating to invasion and metastasis, angiogenesis, epithelial-mesenchymal transition (EMT), cell growth, drug metabolism, senescence, cell adhesion, glycolysis, Wnt signaling, growth and regeneration, inflammatory response, e.g. acute phase proteins, and modulators of matrix-degrading enzymes e.g. MMP9. In various embodiments, LSF is a transcription factor encoded by TFCP2. Thus, inhibiting LSF can disrupt or inhibit LSF binding to DNA and/or interaction of LSF with other proteins to form a complex.

Accordingly, in some embodiments, inhibition of cellular LSF activity can be determined by measuring the level of downstream genes regulated by the transcription factor LSF. The effect of LSF on expression (level) of LSF-targeted or LSF-downstream genes can be stimulatory or inhibitory. For example, one gene induced by LSF is SPP1 encoding OPN. Thus, an inhibition of biological activity of LSF results in a decrease in level of SPP1 mRNA and/or a decrease in the amount of the respective encoded protein, OPN. In another embodiment, one gene inhibited by LSF is TAGLN. Thus, an inhibition of biological activity of LSF leads to an increase in level of TAGLN mRNA. In some embodiments, the cellular activity of LSF can be measured by a reduction in the level of TS.

In further embodiments, inhibition of LSF can decrease expression of LSF, for example, a reduction in protein level, and/or a decrease in gene transcript level (e.g. mRNA) of LSF.

One aspect of the present invention provides methods of identifying inhibitors of LSF, for example, by the method comprising measuring the LSF activity in a LSF-dependent luciferase reporter assay as described in Example 1. As disclosed herein, inhibitors of LSF can decrease functional transcriptional activity or the expression of LSF (e.g., such as protein level of LSF, and/or gene transcript level of LSF), by at least about 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. The expression of LSF can be measured by standard methods known to an skilled artisan such as western blot, ELISA, and quantitative PCR as well as the methods provided in Examples section.

In some embodiments, inhibitors of LSF as disclosed herein can inhibit or decrease cellular LSF activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%. In certain embodiments, inhibitors of LSF as disclosed herein can decrease expression of downstream genes up-regulated by LSF, e.g. SPP1 encoding OPN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. In alternative embodiments, inhibitors of LSF can increase expression of downstream genes down-regulated by LSF, e.g. TAGLN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF.

As disclosed herein, the inventors have identified compounds that can inhibit LSF, such compounds being represented by formula (I), wherein formula (I) has the structure:

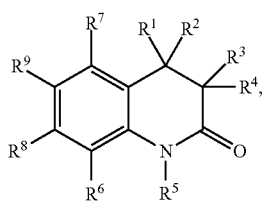

(I)

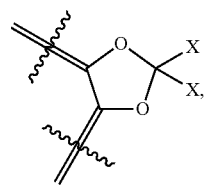

wherein X is hydrogen or halogen such as fluorine. In various embodiments, $R^9$ is not $NR^{3A}R^{4A}$. In various embodiments, $R^9$ is not an aryl, heterocycyl or halogen.

In some embodiments, inhibitors of LSF with formula (I) can be represented by formula (II), wherein the formula (II) has the structure:

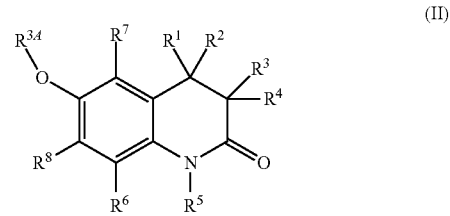

(II)

In formula (I), $R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalky, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy. In various embodiments, $R^2$ and $R^3$ together can form a second bond between the carbons to which they are attached.

$R^5$ is selected from the group of hydrogen, $C_1$-$C_6$ alkyl, $C_1$-$C_6$ haloalkyl, $C_1$-$C_6$ heteroalkyl, aryl, heteroaryl, F, Br, Cl, or I.

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl.

$R^8$ and $R^9$ are each independently selected from the group of hydrogen, $C_1$-$C_4$ alkyl, $C_1$-$C_4$ haloalkyl, $C_1$-$C_4$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl or aryl.

In various embodiments, $R^9$ is not $NR^{3A}R^{4A}$. In various embodiments, $R^9$ is not an aryl, heterocycyl or halogen.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m and n are each independently selected from 1, 2, or 3.

In certain embodiments of formula (I), $R^1$, $R^3$ and $R^4$ are hydrogen. $R^2$ is an optionally substituted aryl, for example,

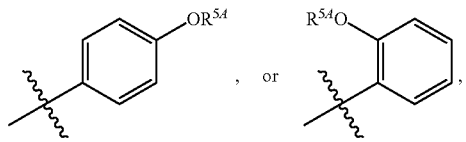

wherein $R^{5A}$ is $C_1$-$C_6$ alkyl. $R^5$ can be hydrogen or $C_1$-$C_6$ alkyl, such as —$CH_3$. $R^6$ is hydrogen. $R^7$ can be hydrogen or —$OR^{5A}$, wherein $R^{5A}$ is $C_1$-$C_6$ alkyl, e.g. $CH_3$. $R^8$ can be hydrogen or —$OR^{5A}$, and $R^9$ is —$OR^{5A}$, wherein $R^{5A}$ is $C_1$-$C_6$ alkyl, e.g. $CH_3$. In some embodiments, $R^8$ and $R^9$ together with the carbons to which they are attached form an optionally substituted 5-membered heterocycyl, such as In formula (II), $R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy. In various embodiments, $R^2$ and $R^3$ together can form a second bond between the carbons to which they are attached. In some embodiments, $R^2$ is a substituted aryl. In some embodiments, $R^2$ is a substituted phenyl. In some embodiments, a substituted phenyl is a $C_1$-$C_6$ alkoxy substituted phenyl. In certain embodiments, a $C_1$-$C_6$ alkoxy substituted phenyl, or OMe, OEt, O$^n$Pr, O$^i$Pr, O$^n$Bu, O$^i$Bu or O$^t$Bu.

$R^5$ is selected from the group of hydrogen, $C_1$-$C_6$ alkyl, $C_1$-$C_6$ haloalkyl, $C_1$-$C_6$ heteroalkyl, aryl, heteroaryl, F, Br, Cl, or I.

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl. In some embodiments, $R^7$ is $OR^{3A}$. In some embodiments, $OR^{3A}$ is O—$C_1$-$C_8$ alkyl.

$R^8$ is selected from the group of hydrogen, $C_1$-$C_4$ alkyl, $C_1$-$C_4$ haloalkyl, $C_1$-$C_4$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl or aryl. In some embodiments, $OR^{3A}$ is O—$C_1$-$C_8$ alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

In some embodiments, $R^{3A}$ is $C_1$-$C_8$ alkyl. In some embodiments, $R^{3A}$ is $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

In some embodiments, $OR^{3A}$ is $O$—$C_1$-$C_4$ alkyl. In some embodiments, $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

m is 1, 2, or 3; and n is 1, 2, or 3;

In some embodiments of formula (II), $R^1$, $R^3$ and $R^4$ are hydrogen. $R^2$ is an optionally substituted aryl, for example,

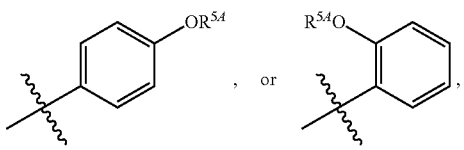

wherein $R^{5A}$ is $C_1$-$C_6$ alkyl. $R^5$ can be hydrogen or $C_1$-$C_6$ alkyl, such as —$CH_3$. $R^6$ is hydrogen. $R^7$ can be hydrogen or —$OR^{5A}$, wherein $R^{5A}$ is $C_1$-$C_6$ alkyl, e.g. $CH_3$. $R^8$ can be hydrogen or —$OR^{5A}$, wherein $R^{5A}$ is $C_1$-$C_6$ alkyl, e.g. $CH_3$, and $R^{3A}$ is $C_1$-$C_6$ alkyl, e.g. $CH_3$. In some embodiments, $R^8$ and $OR^{3A}$ together with the carbons to which they are attached form an optionally substituted 5-membered heterocycyl, such as

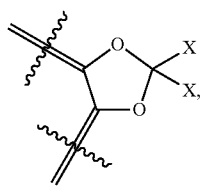

wherein X is hydrogen or halogen such as fluorine.

In some embodiments, inhibitors of LSF with formula (I) can be represented by formula (III), wherein the formula (III) has the structure:

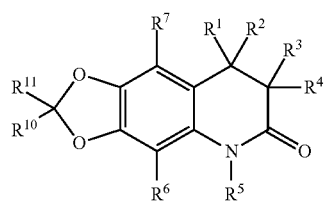

(III)

In formula (III), $R^1$, $R^2$, $R^3$ and $R^4$ are each independently selected from the group of hydrogen, $C_1$-$C_6$ alkyl, $C_1$-$C_6$ haloalkyl, $C_1$-$C_6$ heteroalky, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl, di($C_1$-$C_{24}$alkyl)amino, or $C_1$-$C_6$ alkoxy. In various embodiments, $R^2$ and $R^3$ together can form a second bond between the carbons to which they are attached.

$R^5$ is selected from the group of hydrogen, $C_1$-$C_6$ alkyl, $C_1$-$C_6$haloalkyl, $C_1$-$C_6$ heteroalkyl, aryl, heteroaryl, F, Br, Cl, or I;

$R^6$ and $R^7$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_1$-$C_6$ haloalkyl, $C_1$-$C_6$ heteroalkyl, aryl or heteroaryl;

$R^{10}$ and $R^{11}$ are each independently selected from the group of hydrogen, F, Br, Cl, or I.

$R^{3A}$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m is 1, 2, or 3; and n is 1, 2, or 3;

In some embodiments of formula (III), $R^1$, $R^3$ and $R^4$ are hydrogen. $R^2$ is an optionally substituted aryl, for example,

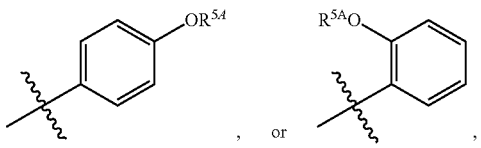

wherein $R^{5A}$ is $C_1$-$C_6$ alkyl. $R^5$ can be hydrogen or $C_1$-$C_6$ alkyl, such as —$CH_3$. $R^6$ is hydrogen. $R^7$ can be hydrogen or —$OR^{5A}$, wherein $R^{5A}$ is $C_1$-$C_6$ alkyl, e.g. $CH_3$. $R^{10}$ and $R^{11}$ are each independently selected from either hydrogen or halogen such as fluorine.

In some embodiments, inhibitors of LSF with formula (III) can be represented by formula (XXVI), wherein the formula (XXVI) has the structure:

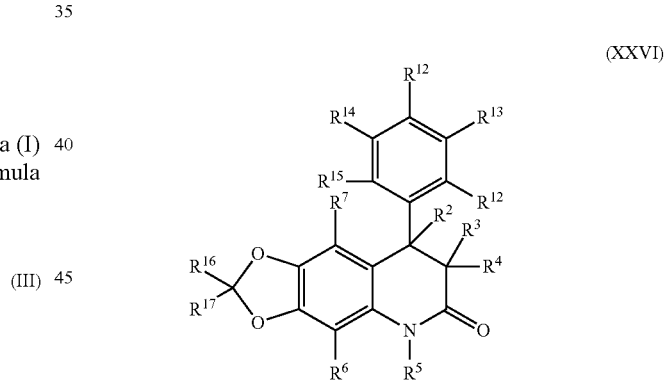

(XXVI)

In formula (XXVI), $R^2$, $R^3$ and $R^4$ are each independently selected from the group of hydrogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, $PO_m(R^{3A})_n$, F, Br, Cl, I, heteroaryl, or aryl, wherein the alkyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy. In various embodiments, $R^2$ and $R^3$ together can form a second bond between the carbons to which they are attached.

$R^5$ is selected from the group of hydrogen, $C_1$-$C_6$ alkyl, $C_1$-$C_6$haloalkyl, $C_1$-$C_6$ heteroalkyl, aryl, heteroaryl, F, Br, Cl, or I;

$R^6$, $R^7$, $R^{13}$, $R^{14}$, $R^{15}$ and $R^{15'}$ are each independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl;

each $R^{12}$ is independently selected from the group of hydrogen, F, Br, Cl, I, $OR^{3A}$, $NR^{3A}R^{4A}$, $SR^{3A}$, $SO_2R^{3A}$, $PO_m(R^{3A})_n$, $C_1$-$C_6$ alkyl, $C_2$-$C_8$ alkenyl, $C_1$-$C_6$ haloalkyl, $C_1$-$C_6$ heteroalkyl, aryl or heteroaryl;

$R^{16}$ and $R^{17}$ are each independently selected from the group of hydrogen, F, Br, Cl, I, $C_1$-$C_4$ alkyl, or $OR^{3A}$;

$R^4$ and $R^{4A}$ are each independently selected from the group of hydrogen, $C_1$-$C_8$ alkyl, $C_2$-$C_8$ alkenyl, $C_2$-$C_8$ alkynyl, $C_1$-$C_8$ haloalkyl, $C_1$-$C_8$ heteroalkyl, heteroaryl, or aryl, wherein the alkyl, alkenyl, alkynyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

m is 1, 2, or 3; and n is 1, 2, or 3;

In certain embodiments of formula (XXVI), $R^2$, $R^3$ and $R^4$ can be hydrogen, $-CH_3$, $-CH_2CH_3$ or $R^4$ is hydrogen or $-CH_3$ and $R^2$ and $R^3$ together can form a second bond between the carbons to which they are attached. $R^5$ can be hydrogen, $-CH_3$ or $-CH_2CH_3$. $R^6$, $R^{13}$, $R^{14}$ and $R^{15'}$ each independently can be hydrogen, F, Cl, Br, I, $-CH_3$ or $-CH_2CH_3$. $R^7$ can be hydrogen, F, Cl, Br, I, $-CH_3$, $-CH_2CH_3$ or $-OR^{5A}$, wherein $R^{5A}$ is $-CH_3$ or $-CH_2CH_3$. $R^{12}$ can be hydrogen, F, Br, Cl, $-CH=CH-(CH_2)_{0-5}CH_3$, $NR^{3A}R^{4A}$ or $-OR^{5A}$, wherein $R^{3A}$, $R^{4A}$ and $R^{5A}$ are independently a $C_1$-$C_6$ alkyl such as methyl, ethyl, n-propyl, isopropyl, n-butyl, iso-butyl or sec-butyl. $R^{15}$ can be $OR^{3A}$, where $R^{3A}$ is a $C_1$-$C_6$ alkyl such as methyl, ethyl, n-propyl, isopropyl, n-butyl, iso-butyl or sec-butyl. $R^{16}$ and $R^{17}$ are each independently selected from either hydrogen or halogen such as fluorine.

In some embodiments, $R^{3A}$ is $OR^{3A}$. In some embodiments, $OR^{3A}$ is $C_1$-$C_8$ alkyl. In some embodiments, $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

In some embodiments, $R^{16}$ and $R^{17}$ are different. In some embodiments, $R^{16}$ and $R^{17}$ are the same. In some embodiments, at least one of $R^{16}$ or $R^{17}$ is F. In some embodiments both $R^{16}$ and $R^{17}$ is F.

In some embodiments, $R^{15}$ is $OR^{3A}$. In some embodiments, $R^{3A}$ is $C_1$-$C_8$ alkyl. In some embodiments, $C_1$-$C_8$ alkyl is a straight chain alkyl. In some embodiments, $C_1$-$C_8$ alkyl is a branched chain alkyl. In some embodiments, $C_1$-$C_8$ alkyl is methyl, ethyl, n-propyl, i-propyl, n-butyl, i-butyl, or t-butyl.

In some embodiments, the $R^1$ group in Formulas (I), (II), (III) or (XXVI) is a phenyl substituted with at least one $C_1$-$C_6$ alkoxyl and at least one di($C_1$-$C_{24}$alkyl)amino. In some embodiments, $R^1$ is

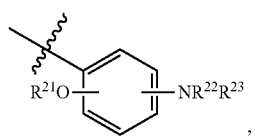

wherein $R^{21}$ is $C_1$-$C_6$alkyl and $R^{22}$ and $R^{23}$ are independently selected $C_1$-$C_{24}$alkyl. In some embodiments, $R^{1'}$ is

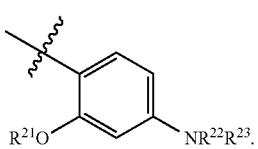

In some preferred embodiments, $R^1$ is

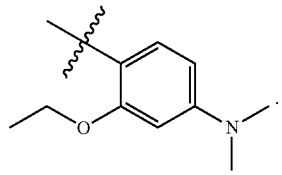 [SMILES: *c1ccc(N(C)C)cc1OCC]

In some embodiments, the $R^1$ group in Formulas (I), (II), (III) or (XXVI) is a phenyl substituted with at least one $C_1$-$C_6$ alkoxyl and at least one halogen. In some embodiments, $R^{1'}$ is

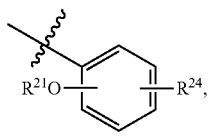

wherein $R^{21}$ is $C_1$-$C_6$alkyl and $R^{24}$ is halogen. In some embodiments, $R^{1'}$ is

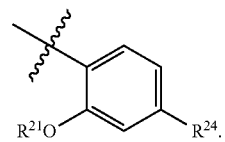

In some preferred embodiments, $R^{1'}$ is

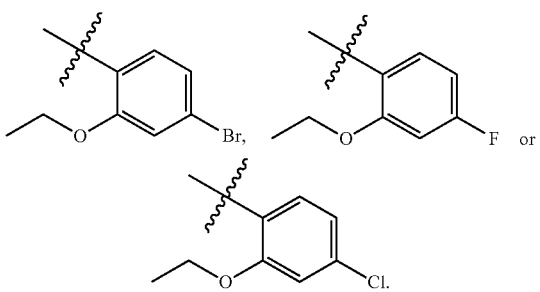

In some embodiments, the $R^1$ group in Formulas (I), (II), (III) or (XXVI) is a phenyl substituted with at least one $C_1$-$C_6$ alkoxyl and at least one $C_2$-$C_6$alkenyl. In some embodiments, $R^{1'}$ is

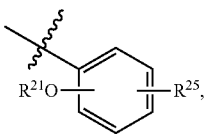

wherein $R^{21}$ is $C_1$-$C_6$alkyl and $R^{25}$ is $C_2$-$C_8$alkenyl. In some embodiments, $R^{1'}$ is

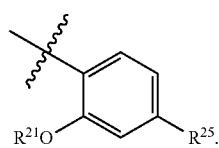

In some preferred embodiments, $R^{1'}$ is

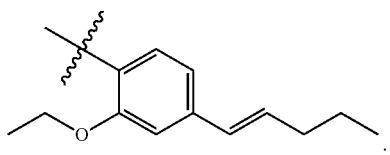 [SMILES: *c1ccc(/C=C/CCC)cc1OCC]

In one embodiment, an inhibitor of LSF of formula (I), (II), (III) or (XXVI) is a compound of formula (IV), wherein the formula (IV) has the structure:

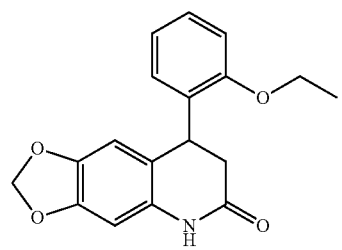
(IV)

An inhibitor of LSF with the formula (IV) is known in the art under a chemical name, 8-(2-ethoxyphenyl)-7,8-dihydro-[1,3]dioxolo[4,5-g]quinolin-6(5H)-one. It is also known in the art under an alternative name, 8-(2ethoxyphenyl)-2H,5H,6H,7H,8H-[1,3]dioxolo[4,5-g]quinolin-6-one. The simplified molecular input line entry specification (SMILES) of the compound of formula (IV) is known in the art as CCOC(C=CC=C1)=C1C(C2=CC(OCO3)=C3C=C2N4)CC4=O. The IUPAC International Chemical Identifier (InChI) of the compound of formula (IV) known to an skilled artisan is 1S/C18H17NO4/c1-2-21-15-6-4-3-5-11(15)12-8-18(20)19-14-9-17-16(7-13(12)14)22-10-23-17/h3-7,9,12H,2,8,10H2,1H3,(H,19,20).

In some embodiments, inhibitors of LSF of formula (I), (II), (III) or (XXVI) can be a compound selected from the group consisting of compounds of formula (V) to (XXV):

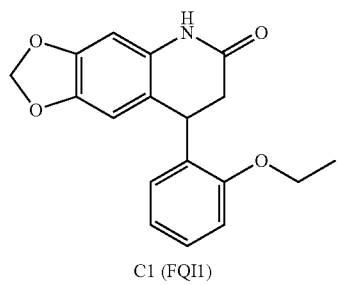
C1 (FQI1)
(IV)

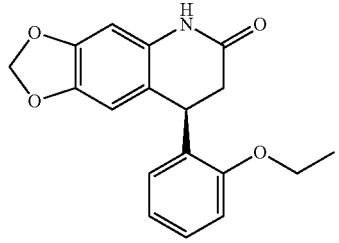
C1-2 ((S)-FQI1)
(S)-(IV)

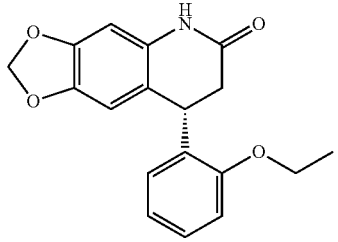
C1-1 ((R)-FQI1)
(R)-(IV)

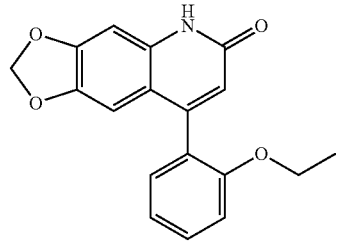
C1-U (FQI2)
(V)

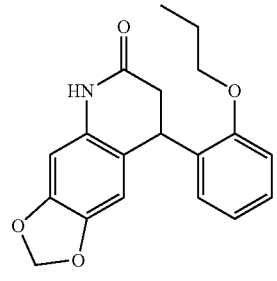
E1 (FQI16)
(VI)

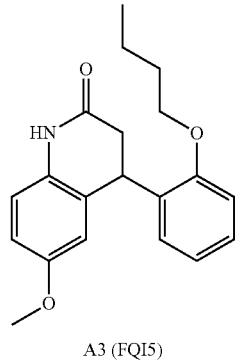
A3 (FQI5)
(VII)

-continued
(VIII)
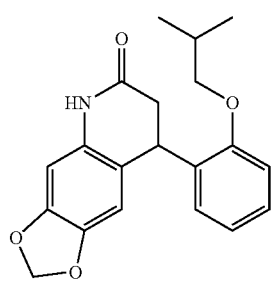
B1 (FQI6)
(IX)
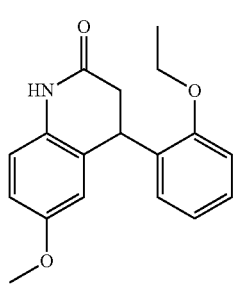
C3 (FQI10)
(X)
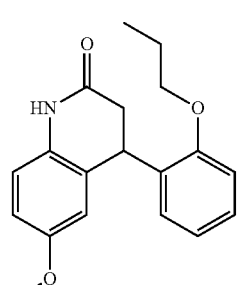
E3 (FQI18)
(XI)
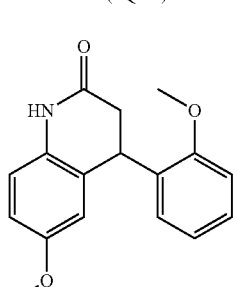
D3 (FQI14)
(XII)
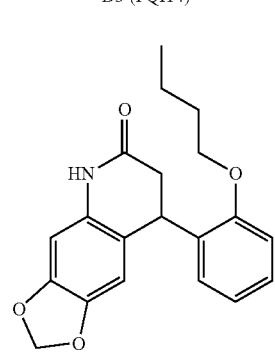
A1 (FQI3)
-continued
(XIII)
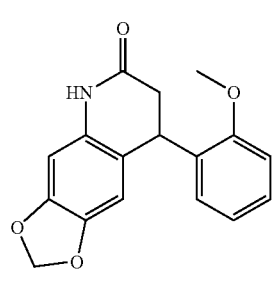
D1 (FQI12)
(XIV)
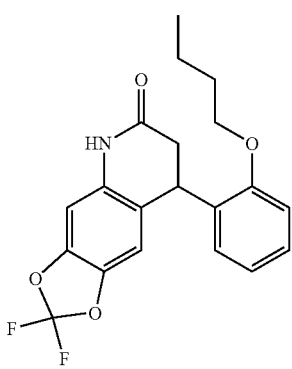
A2 (FQI4)
(XV)
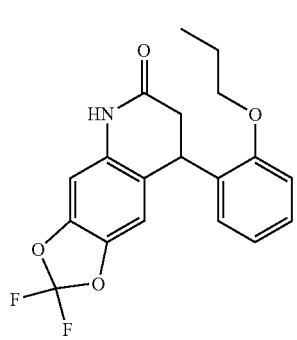
E2 (FQI17)
(XVI)
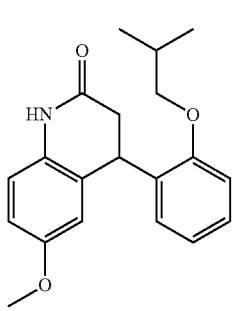
B3 (FQI8)

-continued
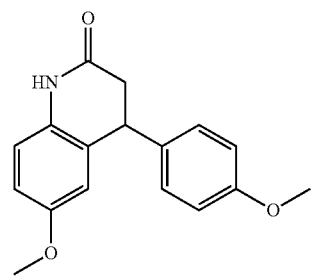
F3 (FQI21) (XVII)
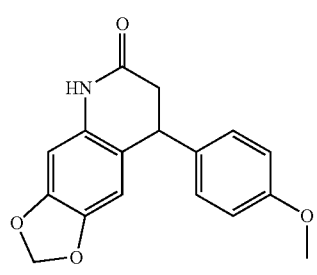
F1 (FQI19) (XVIII)
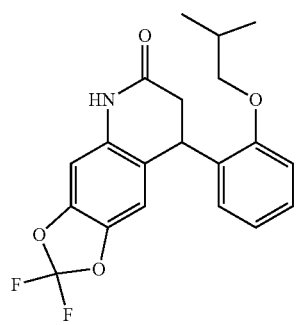
B2 (FQI7) (XIX)
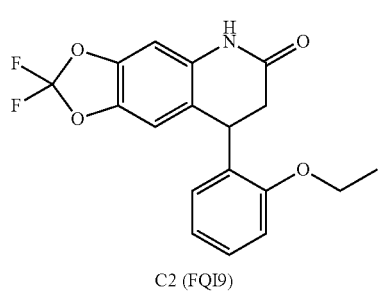
C2 (FQI9) (XX)
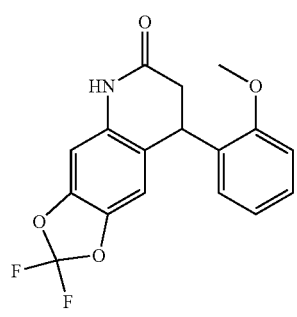
D2 (FQI13) (XXI)
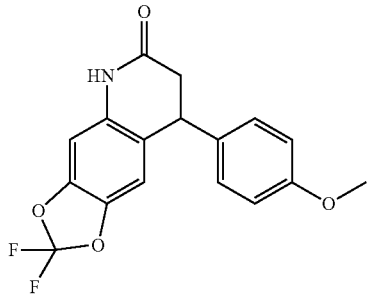
F2 (FQI20) (XXII)
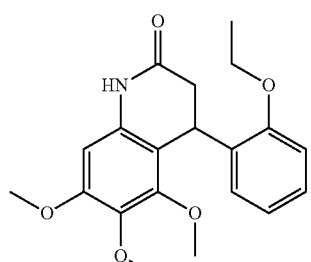
C4 (FQI11) (XXIII)
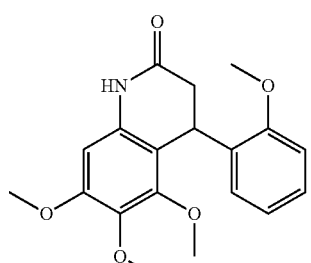
D4 (FQI15) (XXIV)
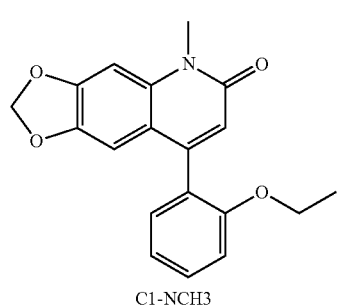
C1-NCH3 (XXV)
As disclosed herein, the inventors have identified compounds that can inhibit LSF. In some embodiments, such compounds being represented by formula (III'):
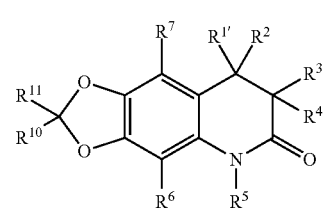
(III')

or enantiomers, prodrugs, derivatives, and pharmaceutically acceptable salts thereof.

In compounds of Formula (III'), $R^{1'}$ is an aryl substituted with at least one $C_1$-$C_6$alkoxyl and at least one di($C_1$-$C_{24}$alkyl)amino, halogen, $C_1$-$C_6$alkyl, $C_2$-$C_6$alkenyl, polytheylene glycol or polyethylene glycol substituted $C_1$-$C_6$alkyl, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one di($C_1$-$C_{24}$alkyl)amino, halogen, or $C_2$-$C_6$alkenyl, polytheylene glycol or polyethylene glycol substituted $C_1$-$C_6$alkyl, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one di($C_1$-$C_{24}$alkyl)amino, halogen or $C_2$-$C_6$alkenyl, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one di($C_1$-$C_{24}$alkyl)amino, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one halogen, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one $C_2$-$C_6$alkenyl, wherein the substituted aryl can be optionally further substituted with halogen, $C_1$-$C_4$alkyl, $C_1$-$C_4$haloalkyl, $C_1$-$C_4$ heteroalkyl, di($C_1$-$C_{24}$alkyl)amino or combinations thereof.

In some compounds of Formula (III'), $R^{1'}$ is an aryl substituted with at least one $C_1$-$C_6$ alkoxyl and at least one of halogen, $C_1$-$C_6$alkyl, $C_2$-$C_8$alkenyl, $C_1$-$C_4$haloalkyl, $C_1$-$C_4$ heteroalkyl, di($C_1$-$C_{24}$alkyl)amino, polyethylene glycol, or combinations thereof.

In some embodiments, the aryl of the $R^1$ group is substituted with the $C_1$-$C_6$alkoxyl at the ortho position.

In compounds of Formula (III'), where the aryl of $R^1$ group is substituted with a $C_1$-$C_6$alkoxyl and a second substituent. Without limitations the second substituent can be present at the meta, ortho or para position. In some embodiments, the $C_1$-$C_6$alkoxyl is at the ortho position and the second substituent is at the para position.

In some embodiments, $R^{1'}$ is a phenyl substituted with at least one $C_1$-$C_6$ alkoxyl and at least one di($C_1$-$C_{24}$alkyl) amino. In some embodiments, $R^{1'}$ is

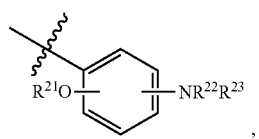

, wherein $R^{21}$ is $C_1$-$C_6$alkyl and $R^{22}$ and $R^{23}$ are independently selected $C_1$-$C_{24}$alkyl. Exemplary alkyls for the $R^{21}$ group include, but are not limited to, methyl, ethyl, propyl, isopropyl, 1-butyl, 2-butyl, 2-methylpropyl, pentyl, t-butyl, and hexyl. In some embodiments, $R^{21}$ is ethyl.

Without limitations, $R^{22}$ and $R^{23}$ can be same or different. Moreover, they can comprise the same number of carbons or different number of carbons. In some embodiments, $R^{22}$ and $R^{23}$ are selected independently from $C_1$-$C_6$ alkyl groups. Exemplary alkyls for the $R^{22}$ and $R^{23}$ group include, but are not limited to, methyl, ethyl, propyl, isopropyl, 1-butyl, 2-butyl, 2-methylpropyl, pentyl, t-butyl, and hexyl. In some embodiments, $R^{22}$ and $R^{23}$ are methyl.

In some embodiments, $R^{1'}$ is

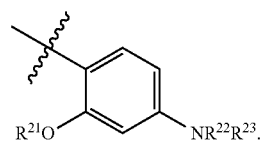

In some embodiments, $R^{1'}$ is

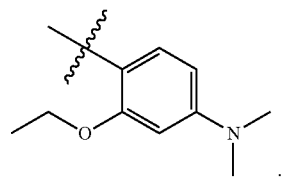 [SMILES: *c1ccc(N(C)C)cc1OCC]

In some embodiments, $R^{1'}$ is a phenyl substituted with at least one $C_1$-$C_6$ alkoxyl and at least one halogen. In some embodiments, $R^{1'}$ is

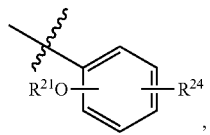

, wherein $R^{21}$ is $C_1$-$C_6$alkyl and $R^{24}$ is halogen. Exemplary alkyls for the $R^{21}$ group include, but are not limited to, methyl, ethyl, propyl, isopropyl, 1-butyl, 2-butyl, 2-methylpropyl, pentyl, t-butyl, and hexyl. In some embodiments, $R^{21}$ is ethyl. In some embodiments, $R^{24}$ is selected from the group consisting of Br, F, and Cl.

In some embodiments, $R^{1'}$ is

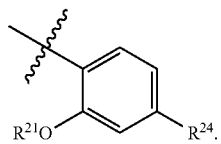

.

In some embodiments, $R^{1'}$ is

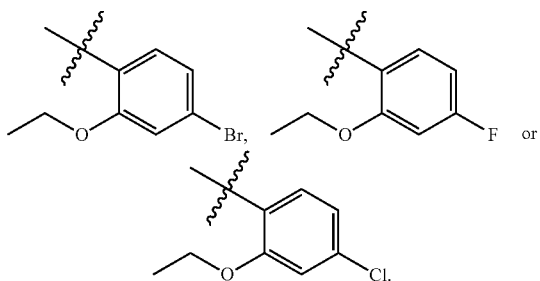

In some embodiments, $R^{1'}$ is a phenyl substituted with at least one $C_1$-$C_6$ alkoxyl and at least one $C_2$-$C_6$ alkenyl. In some embodiments, $R^{1'}$ is

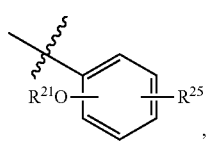

wherein $R^{21}$ is $C_1$-$C_6$ alkyl and $R^{25}$ is $C_2$-$C_6$ alkenyl. Exemplary alkyls for the $R^{21}$ group include, but are not limited to, methyl, ethyl, propyl, isopropyl, 1-butyl, 2-butyl, 2-methylpropyl, pentyl, t-butyl, and hexyl. In some embodiments, $R^{21}$ is ethyl. In some embodiments, $R^{25}$ is selected from the group consisting of ethylenyl, propylenyl, butylenyl, isobutylenyl, and pentylenyl. In some embodiments, $R^{25}$ is pentylenyl.

In some embodiments, $R^{1'}$ is

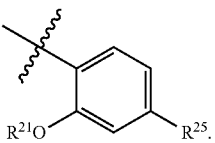

In some embodiments, $R^{1'}$ is

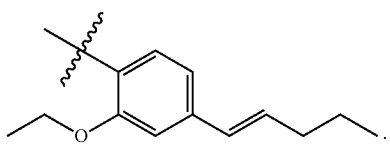 [SMILES: *c1ccc(/C=C/CCC)cc1OCC]

In compounds of Formula (III'), $R^2$ and $R^3$ are hydrogen or $R^2$ and $R^3$ together form a second bond between the carbons to which they are attached. In some embodiments, $R^2$ and $R^3$ are hydrogen.

In compounds of Formula (III') $R^4$ is hydrogen and $R^5$ is selected from the group consisting of hydrogen and $C_1$-$C_6$ alkyl. Exemplary alkyls for the $R^5$ group include, but are not limited to, methyl, ethyl, propyl, isopropyl, 1-butyl, 2-butyl, 2-methylpropyl, pentyl, t-butyl, and hexyl. In some embodiments, $R^5$ is hydrogen or methyl. In some further embodiments, $R^5$ is hydrogen.

In compounds of Formula (III'), $R^6$ and $R^7$ are each independently selected from the group consisting of hydrogen, F, Br, Cl, and I. Without limitations, $R^6$ and $R^7$ can be the same or different. In some embodiments, $R^6$ and $R^7$ are hydrogen.

In compounds of Formula (III'), $R^{10}$ and $R^{11}$ are each independently selected from the group consisting of hydrogen, F, Br, Cl, and I. Without limitations, $R^{10}$ and $R^{11}$ can be the same or different. In some embodiments, $R^6$ and $R^7$ are hydrogen of fluorine. In some embodiments $R^{10}$ and $R^{11}$ are hydrogen. In some other embodiments, $R^{10}$ and $R^{11}$ are fluorine.

An exemplary compound of Formula (III') is the compound FQI-34 represented having the structure:

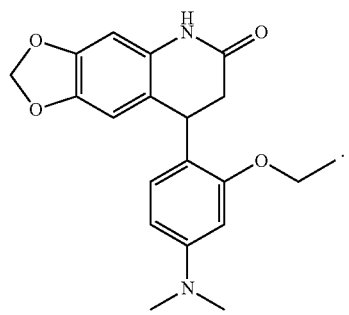

In some embodiments, a compound of Formula (III') can be selected from the group consisting of (FQI-Br)

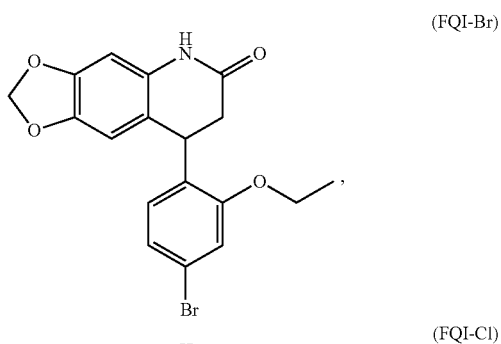

(FQI-Cl)

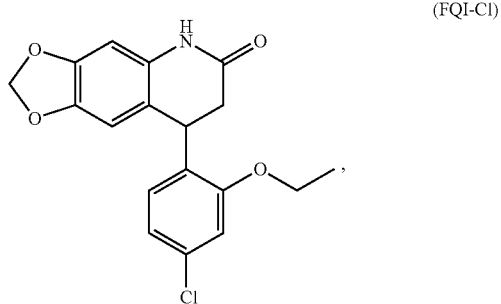

(FQI-F)

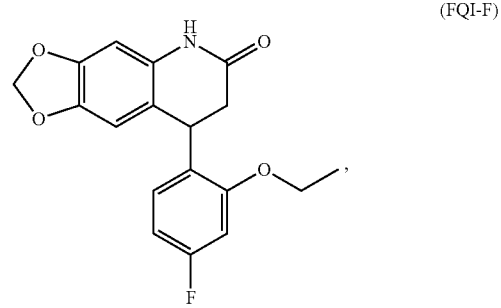

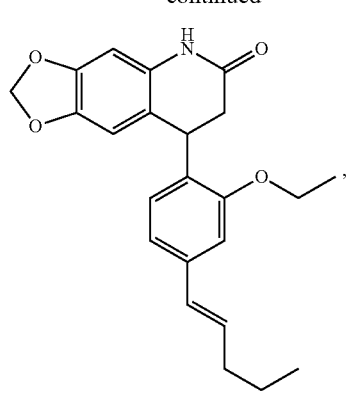
(FQI32)

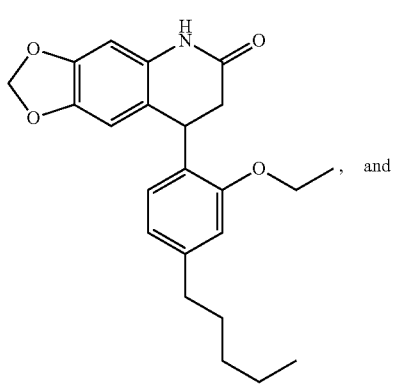
(FQI33), and

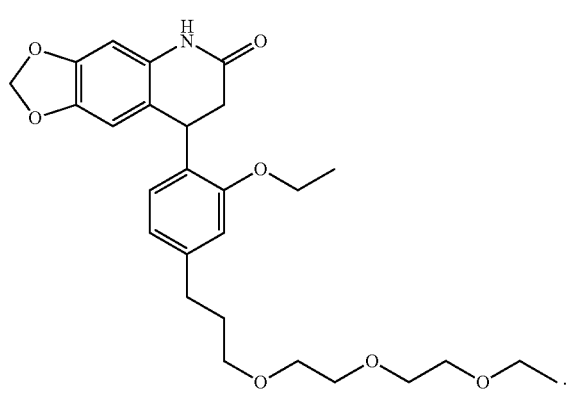
(PEG-FQI).

In some embodiments, a LSF inhibitor is not FQI-F, FQI32, FQI33 or PEG-FQI.

A compound of Formula (III') can be formulated in a pharmaceutical composition described herein. Further, a compound of Formula (III') can be used in the methods, e.g., a method for inhibiting LSF or treating cancer disclosed herein.

All structures of any of formula (I) to (XXVI) and (III') are provided herein for illustrative purpose and disclose a particular isomer. However, one of ordinary skill in the art will recognize all possible isomers of the structures of any of formula (I) to (XXVI) and (III'). Therefore, other isomers such as enantiomers of any of formula (I) to (XXVI) and (III') are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. For example, as disclosed herein, compounds C1-1 and C1-2 as shown in FIG. 1 are enantiomers of compounds of formula (IV). The designations "R" and "S" of compounds C1-1 and C1-2 in FIG. 1, respectively, are used to denote the absolute configuration of the molecule about its chiral center. The designations may appear as a prefix or as a suffix; they may or may not be separated from the isomer by a hyphen; they may or may not be hyphenated; and they may or may not be surrounded by parentheses. The designations "(+)" and "(−)" of compounds C1-1 and C1-2 in FIG. 1 are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

In various embodiments, inhibitors of LSF of any of formula (I) to (XXVI) and (III') include enantiomers, derivatives, prodrugs, and pharmaceutically acceptable salts thereof.

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

In some embodiments, prodrugs of LSF inhibitors selected from any of formula (I) to (XXVI) also fall within the scope of the invention. As used herein, a "prodrug" refers to a compound that can be converted via some chemical or physiological process (e.g., enzymatic processes and metabolic hydrolysis) to a LSF inhibitor selected from the group consisting of compounds of formula (I) to (XXVI) and (III').

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), content of all of which is herein incorporated by reference in its entirety.

Inhibitors of LSF of formula (I) to (XXVI) and (III') also include pharmaceutically acceptable salts thereof. As used herein, the term "pharmaceutically-acceptable salts" refers to the conventional nontoxic salts or quaternary ammonium salts of LSF inhibitors as disclosed herein, e.g., from non-toxic organic or inorganic acids. These salts can be prepared in situ in the administration vehicle or the dosage form manufacturing process, or by separately reacting a LSF inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Inhibition of LSF has been previously discussed as a potential treatment of latent HIV infection or cancer in general, or as a therapeutic regulator of immune function, specifically when there is a need thereof to decrease inflammatory response (U.S. Patent Application No.: US 2009/0081183 and International Patent Application No.: WO1998/36641, which are incorporated herein in their entirety by reference). However, these patent applications do not teach or describe any small-molecule LSF inhibitors of the invention as disclosed herein, or the use thereof for treatment of hepatocellular carcinoma (HCC).

Use of the LSF Inhibitors of any of Formula (I) to (XXVI) and (III) to Treat Cancers and Hepatocellular Carcinoma In some embodiments, a LSF inhibitor compound of any of formulas (I) to (XXVI) and (III') as disclosed herein can be used to treat various cancers, such as liver cancer (hepatocellular carcinoma), brain cancer, breast cancer, colon cancer, head and neck squamous cell carcinoma, lung cancer, pancreatic cancer, ovarian cancer, and thyroid cancer; HIV; inflammation-related diseases such as hepatitis B virus (HBV), hepatitis C (HCV), cirrhosis and Alzheimer's disease. In some embodiments, the liver diseases can be any selected from, but not limited to, HBV, HCV, cirrhosis, hepatic adenoma, hepatic angiosarcoma and hepatic angiosarcomas; emphysema; and hereditary hemochromatosis.

In some embodiments, a LSF inhibitor compound of any of formulas (I) to (XXVI) and (III') as disclosed herein can be used to treat other cancers, for example, cervical cancer, colon cancers, melanomas and the like. Other cancers which can be treated include any cancer with overexpression of LSF in the tumor, for example, but not limited to, oligodendroglioma, meningioma, GBM, breast cancer, colon cancer, Non-Hodgkin's small cell carcinoma (HNSCC), lung cancer (adrenocarcinomas), lung cancer (small cell carcinoma), pancreatic cancer, ovarian cancer, thyroid cancer and undifferentiated cancer.

In some embodiments, a LSF inhibitor of any of formulas (I) to (XXVI) and (III') as disclosed herein can be used to treat any cancer cell type. Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In one embodiment, compositions and methods of the invention as disclosed herein is used to treat a subject with hepatocellular carcinoma (HCC).

In another embodiment, a subject at high risk of developing HCC is suitable for treatment with the compositions of the invention comprising at least a LSF inhibitor as disclosed herein.

Hepatocellular carcinoma (HCC) is one of the five most common cancers worldwide (1). The incidence of HCC is increasing despite a decrease in overall incidence of all cancers (2, 3). In the United States, the estimated new cases of HCC for 2008 were 21,370, of which 18,410 were expected to die (2). The mean 5-year survival rate is less than 10%. The mortality rate of HCC parallels that of its incidence because HCC is a tumor with rapid growth and early vascular invasion that is resistant to conventional chemotherapy, and no systemic therapy is available for the advanced disease (4).

To date, other than curative resection, treatments for HCC have had minimal impact on survival. Unfortunately, approximately 90% of HCC patients have unresectable HCC. Moreover, even after potentially curative hepatectomy in patients with resectable HCC, new HCC arises in the cirrhotic remnants in 70% of these patients, and frequently arises in the grafted liver following orthotopic liver transplantation. Other approaches to treating HCC, such as intralesional ethanol injection, chemoembolization, radiofrequency ablation, cryosurgery and radiation therapy have demonstrated some success in selected patient populations; however, the efficacies of these approaches have not been definitely established. Both percutaneous intralesional ethanol injection and transarterial chemoembolization have shown limited success, but not without risks of serious side effects. Radiotherapy is not usually an option because liver is very radiosensitive. Systemic chemotherapy for HCC has had uniformly poor response rates, and therefore it is generally reserved for patients ineligible for curative resection.

All systemic therapies for HCC to date are associated with uniformly poor outcomes, and only one chemotherapeutic agent (sorafenib), alone or in combination with other treatments, has been associated with any improvement in survival rates (Fuchs et al., 94 Cancer 3186 (2002)). In addition, most patients with HCC have underlying liver disease so their ability to tolerate to undergo surgery is compromised. Therefore, there is a strong need in the art to provide improved methods for treatment of HCC.

One aspect of the invention provides methods for therapeutic and prophylactic treatment of cancers, e.g., HCC by administering to a subject a pharmaceutical composition comprising an effective amount of a LSF inhibitor. In preferred embodiments, a LSF inhibitor is a small molecule selected from the group consisting of compounds of formulae (I) to (XXVI) and (III'), and enantiomers, prodrugs, derivatives, and pharmaceutically acceptable salts thereof. In one embodiment, a LSF inhibitor is a compound of formula (IV) or enantiomers, prodrugs, derivatives or pharmaceutically acceptable salts thereof. In other embodiments, a LSF inhibitor is a compound with any of formula (V) to (XXVI) or enantiomers, prodrugs, derivatives or pharmaceutically acceptable salts thereof. In some embodiments, a LSF inhibitor is the compound FQI-34 or enantiomers, prodrugs, derivatives or pharmaceutically acceptable salts thereof. In some embodiments, a LSF inhibitor is the compound FQI-Br, FQI-F, FQI-Cl, FQI32 or enantiomers, prodrugs, derivatives or pharmaceutically acceptable salts thereof.

The inventors in collaboration with other scientists have revealed that administration of of a LSF inhibitor formula (IV) or (III") at about 1.0-2.0 mg/kg once every 3 days, can suppress the growth of HCC tumor size by 65-80% in an in vivo mouse model, as compared to the mice without treatment of an LSF inhibitor (data not shown). Accordingly, in some embodiments, individuals with heptocellular carcinoma can be treated with a LSF inhibitor of any of compounds of formula (I) to (XXVI) and (III') as disclosed herein and a pharmaceutical composition thereof.

In some embodiments, a LSF inhibitor or a pharmaceutical composition thereof as disclosed herein can be used in conjunction with other therapeutic treatment of HCC such as hepatointralesional ethanol injection, chemoembolization, radiofrequency ablation, cryosurgery, radiation therapy, percutaneous intralesional ethanol injection, transarterial chemoembolization, and radiotherapy.

In some embodiments, a LSF inhibitor or a pharmaceutical composition thereof can be used to treat HCC subjects who are not responsive to any prior treatment of HCC, or show little/no improvement from any prior treatment of HCC, e.g. continued progression or worsening of HCC. In such embodiments, the HCC subjects can be treated again with the previous therapeutic method in combination with an inhibitor of LSF. In alternative embodiments, they can be administered with a LSF inhibitor or a pharmaceutical composition thereof alone, or concurrently with alternative therapeutic methods.

It has been previously reported that LSF is a downstream gene of astrocyte elevated gene-1 (AEG-1), which is overexpressed in >90% of human HCC patients and induces chemoresistance of HCC to an chemotherapeutic agent, such as 5-fluorouracil (5-FU) (5, 6). Accordingly, in some embodiments, an inhibitor of LSF described herein can be administered prior to, or concurrently with at least one chemotherapeutic agent such as 5-FU. Other exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In one embodiment, a LSF inhibitor or a pharmaceutical composition thereof as disclosed herein can be combined with Sorafenib for treatment of HCC.

As a prophylactic measure against HCC recurrence or metastasis, an inhibitor of LSF or a pharmaceutical composition thereof can be administered after surgery or after aforementioned treatments for HCC where solid tumors have been removed or eliminated. In some embodiments, subjects with resectable HCC can be treated with an inhibitor of LSF or a pharmaceutical composition thereof after hepatectomy or liver transplantation to prevent the recurrence of HCC.

Most cases of HCC are developed from either chronic infection with hepatitis B or hepatitis C virus (HBV or HCV, respectively), or hepatic cirrhosis due to alcoholism. Chronic hepatitis can progress into cirrhosis (a noncancerous liver disease associated with fibrosis and abnormal nodules), which increases the risk of developing HCC. Subjects with chronic hepatitis and/or cirrhosis, therefore form a high risk population. Accordingly, in some embodiments, a LSF inhibitor can be used in conjunction with other therapeutic treatment for liver diseases such as infection with HBV, HCV or cirrhosis, as a preventive measure against the onset of HCC.

In some embodiments, a LSF inhibitor of any of compounds of formula (I) to (XXVI) and (III') as disclosed herein can be administered to a subject with a high risk of developing hepatocellular carcinoma. For example, subjects amenable to treatment by methods and compositions as disclosed herein, e.g. using an inhibitor of LSF, are subjects having a risk factor for HCC. Examples of risk factors for HCC include, but not limited to, HBV, HCV, chronic alcohol consumption, exposure to aflatoxin B1 in food (which is a liver carcinogenic chemical produced by a mold called *Aspergillus flavus* after exposure of food to a hot and humid environment), hepatic adenoma resulted from the use of female hormones (estrogens) and protein-building (anabolic) steroids, exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia. In some embodiments, a LSF inhibitor can be used alone or combined with other therapeutic treatment of the aforementioned diseases or disorders. In further embodiments, subjects who have been previously subjected to high risk of developing HCC can be continually treated with an inhibitor of LSF or a pharmaceutical composition thereof, even after they have discontinued treatment of liver diseases such as HBV, HCV or cirrhosis.

Other indications that can be contemplated for the use of LSF inhibitors of the invention as disclosed herein include diseases or disorders, in which expression and/or biological activity of LSF is up-regulated, e.g. by inflammatory cytokines (10, 11), or in which it is desirable to decrease or inhibit LSF. Non-limiting examples of such diseases or disorders include HIV and inflammation-associated diseases including Alzheimer's disease.

It has been previously reported that LSF activates cell survival-regulating pathways, such as MEK/ERK and NF-κB pathways, and is up-regulated in various cancers (see Yoo et al., PNAS, 2010, 107; 8357-8362). Accordingly, in some embodiments, a LSF inhibitor disclosed herein can be used alone or in combination with chemotherapeutic agents for treatment of other various cancers such as brain cancer, breast cancer, colon cancer, head and neck squamous cell carcinoma, lung cancer, pancreatic cancer, ovarian cancer, and thyroid cancer. Exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib), In some embodiments, diseases or disorders associated with LSF-induced MEK/ERK activation can be contemplated for treatment with a LSF inhibitor as disclosed herein alone or in combination with inhibitors of MEK/ERK pathway such as PD98059 and U0126.

Selection of Subjects for Administration with a Pharmaceutical Composition Comprising a LSF Inhibitor of any of Compounds (I) to (XXVI) and (III')

In some embodiments, a subject amenable or suitable for treatment with a composition comprising a LSF inhibitor of any of compounds of formula (I) to (XXVI) and (III') as disclosed herein can be selected based on an increased level of LSF expression in a biological sample, or tumor or cancer sample as compared to a control reference LSF expression level, e.g., in a normal non-cancerous sample. In some embodiments, a subject is at risk of having a cancer if the level of LSF expression in the biological sample from the subject is above a pre-determined reference LSF expression threshold level. In some embodiments, the reference LSF expression threshold level the based on the level of LSF expression a non-cancer cell or non-tumor tissue, or a control cell line, or cells from a normal tissue sample, where in the tissue sample is a biological tissue sample from a tissue matched, and species matched and age matched biological sample. In some embodiments, the reference level is based on a reference sample is from a non-cancer matched tissue sample.

In some embodiments, the level of LSF expression is measured in a biological sample comprising a tumor sample. In some embodiments, a biological sample obtained from the subject comprises cancer cells, and can be a biological sample which is serum plasma, blood or tissue sample. In some embodiments, a biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample or primary ascite sample. In alternative embodiments, the biological sample includes, for example blood, plasma, serum, urine, spinal fluid, plural fluid, nipple aspirates, lymph fluid, external secretions of the skin, respiratory, internal and genitoururinary tracts, bile, tears, sweat, saliva, organs, milk cells and primary ascite cells, biopsy tissue sample, a cancer biopsy tissue sample, an in vitro or ex vivo cultivated biopsy tissue sample.

Screening for HCC:

In some embodiments, a subject amenable to treatment according to the methods as disclosed herein is screened for HCC. A convention biomarker for HCC is alpha-fetoproteins (AFP). Yang et al., 123 J. Cancer Res Clin Oncol. 357

(1997). Individuals with elevated serum levels of AFP can be an indication of hepatocellular carcinoma. Other biomarkers for HCC include, but not limited to, the ones disclosed in the U.S. Patent Application Nos.: US2009/0317844, US2010/0015605, US 2010/0120631, and International Patent Application Nos.: WO 2010/048304, WO 2005/0233392, and WO2008/056854, which are incorporated herein in their entirety by reference. One of the skill in the art can easily perform the measurement of mRNA or protein level of these biomarkers in a biological sample e.g. blood from a subject such as human, using the standard methods in the art. In some embodiments, a subject identified with HCC is administered a LSF inhibitor according to the methods as disclosed herein.

As disclosed herein, a subject with HCC can also be selected by detecting a high level of LSF expression in a biological sample such as a liver sample from the subject as compared to a reference level. In one embodiment, the reference level is the level of LSF in a normal healthy subject.

In addition, a biopsy can be used to diagnose HCC. (Walter et al., 24 Curr Opin Gastroenterol. 312 (2008)). Other diagnostic methods for HCC known to one of the skill in the art include imaging methods such as ultrasound, computed tomography (CT) scan and MRI (Scholmerich et al., 52 Gut. 1224 (2004)). In various embodiments, a pharmaceutical composition comprising a LSF inhibitor as disclosed herein can be administered to a subject diagnosed with HCC or HCC susceptibility.

In some embodiments, a subject undergoing treatment of HCC, e.g. chemotherapy, can be treated alone or in combination with the methods and compositions of the invention as disclosed herein. For example, the inventors have previously reported in collaboration with other scientists that inhibition of LSF can increase sensitivity of HCC cells to chemotherapeutic agents, such as, but not limited to 5-fluorouracil (5-FU) (see Yoo et al., PNAS, 2010; 107; 8357-8362). Accordingly, in some embodiments, subjects with no response to current HCC therapeutic treatment, e.g. HCC subjects who have shown chemoresistance to chemotherapeutic agents such as 5-FU, can be administered with a LSF small molecule inhibitor as disclosed herein using the methods and compositions of the invention, prior to or concurrently with chemotherapy.

Detection of hepatocellular carcinoma can be difficult as most of the patients who develop this tumor have no symptoms other than those inflicted with their longstanding liver disease. The onset of abdominal pain, weight loss, early satiety, jaundice and a palpable mass in the upper abdomen usually indicate an advanced cancer. Accordingly, in some embodiments, subjects at high risk for HCC can be administered an inhibitor of LSF as disclosed herein in the methods and compositions for prevention of the development of HCC (e.g. prophylactic treatment). For example, subjects highly susceptible to HCC are subjects with HBV, HCV, chronic alcohol consumption, an exposure to aflatoxin B1 in food (which is a liver carcinogenic chemical produced by a mold called *Aspergillus flavus* after food has been stored in a hot and humid environment), hepatic adenoma resulted from the use of female hormones (estrogens) and protein-building (anabolic) steroids, an exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia.

In additional embodiments, for prophylactic treatment (e.g. to prevent reoccurrence of HCC), subjects who was diagnosed with HCC before and HCC is in remission can be selected for treatment with a LSF inhibitor as disclosed herein using the methods and compositions of the invention. For example, subjects who had their HCC tumor removed by hepatectomy and/or liver transplantation, or who had their HCC tumor reduced or stabilized by other therapeutic methods are amenable to administration of a LSF inhibitor or a pharmaceutical composition thereof as disclosed herein.

In yet other embodiments, subjects amenable to therapeutic treatment with methods and compositions of the invention, e.g. using a LSF inhibitor as disclosed herein, include subjects in need of inhibition of LSF. For example, it has been reported that HIV patients, or individuals in need for a decrease in inflammatory response or immune function can be treated by inhibiting LSF (Bovolenta et al, 163 J. Immuno. 6892, (1999), U.S. Patent Application No.: US2009/0081183 and International Application No.: WO1998/36641, which are incorporated herein in their entirety by reference). Accordingly, a LSF inhibitor of the invention as disclosed herein can be administered alone, or concurrently with other LSF inhibitors such as IL2, or peptides, antibodies or antisense RNA against LSF, to subjects in which inhibition of LSF is desirable, such as HIV.

In still another embodiment, a subject who has other cancers such as breast cancer but has an up-regulated expression of LSF as compared to a reference level can be selected for therapeutic treatment with methods and compositions of the invention using a LSF inhibitor as disclosed herein. In some embodiments, a reference level is the expression of LSF in a normal healthy subject. In other embodiments, a reference level is the expression of LSF in the same subject measured at the previous time point of the treatment regime. Other cancer indications that can be used for the purposes of the invention include brain cancer, colon cancer, head and neck squamous cell carcinoma, lung cancer, pancreatic cancer, ovarian cancer, and thyroid cancer.

Pharmaceutical Compositions Comprising a LSF Inhibitor of any of Compounds (I) to (XXVI) and (III')

Another aspect of the present invention relates to pharmaceutical compositions for treatment of diseases or disorders where it is therapeutically beneficial to inhibit LSF, e.g hepatocellular carcinoma. In some embodiments, a pharmaceutical composition of the invention comprises a therapeutically effective amount of at least one LSF inhibitor selected from any of the compounds represented by formula (I) to (XXVI) and (III') disclosed herein. In one embodiment, a LSF inhibitor is a compound of formula (IV). In some embodiments, a LSF inhibitor is a compound selected from the group consisting of compounds of formulae (V) to (XXVI). In some embodiments, a LSF inhibitor is the compound FQI-34. In some embodiments, a LSF inhibitor is the compound FQI-Br, FQI-F, FQI-Cl or FQI32. In various embodiments, a LSF inhibitor is an enantiomer, a prodrug, a derivative, or a pharmaceutically acceptable salt of a compound of any of formula (I) to (XXVI) and (III').

A LSF inhibitor as disclosed herein selected from any of formula (I) to (XXVI) and (III') can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an inhibitor of LSF can be used in an amount of about 0.1 to 1000 µg/kg of body weight or about 1 to 100 µg/kg of body weight or about 10 to 50 µg/kg of body weight. In some embodiments, a LSF inhibitor as disclosed herein selected from any of formula (I) to (XXVI) and (III') can be used at a concentration of about 0.001 mg/ml or 0.1 mg/ml or a higher concentration of 0.1 mg/ml. In some embodiments, a pharmaceutical composition comprises at least one LSF inhibitor at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized.

Collaborative data from animal studies using an in vivo mouse model where a LSF inhibitor (e.g. formula IV) is injected intraperitoneally once every 3 days at an effective amount of about 1.0-2.0 mg/kg of body weight revealed that the LSF small molecule inhibitor was effective at abrogating the growth of hepatocellular carcinoma in vivo. Depending on routes of administration, one of skill in the art can determine and adjust an effective dosage of a LSF inhibitor disclosed herein to a subject such as a human subject accordingly, by determining pharmacokinetics and bioavailability of a LSF inhibitor and analyzing dose-response relationship specific to a LSF inhibitor in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. A dose can be formulated in animal models to achieve a circulating plasma concentration range that includes the IC50 (i.e., the concentration of the therapeutic which achieves a half-maximal inhibition of symptoms) as determined in cell culture by methods disclosed in Examples 8. An effective dose of a LSF inhibitor can be determined in an animal model by measuring the tumor weight and tumor volume over the course of treatment with a LSF inhibitor as compared to no treatment. In some embodiments, a dosage comprising a LSF inhibitor is considered to be effective if the dosage inhibits or decreases the growth of tumor weight and/or tumor volume by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a LSF inhibitor), In some embodiments, a therapeutically effective amount of a LSF inhibitor administered to a subject is dependent upon factors known to a person of ordinary skill, including bioactivity and bioavailability of a LSF inhibitor (e.g. half-life and stability of a LSF inhibitor in the body), chemical properties of a LSF inhibitor (e.g molecular weight, hydrophobicity and solubility); route and frequency of administration, time of administration (e.g. before or after a meal), and the like. Further, it will be understood that the specific dose of the pharmaceutical composition comprising a LSF inhibitor as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a LSF inhibitor can be determined by methods known to a skilled artisan such as pharmacologists and physicians.

According to the invention, a LSF inhibitor as disclosed herein selected from any of formula (I) to (XXVI) can be administered prophylactically or therapeutically to a subject prior to, simultaneously or sequentially with other therapeutic regimens or agents (e. g. multiple drug regimens), in a therapeutically effective amount. In some embodiments, a LSF inhibitor administered concurrently with other therapeutic agents can be administered in the same or different compositions.

The active ingredients (e.g. a LSF inhibitor selected from any of formula (I) to (XXVI) and (III') of the pharmaceutical composition according to the invention can be administered to an individual by any route known to persons skilled in the art. The routes of administration include intradermal, transdermal (e.g. in slow release formulations), intramuscular, intraperitoneal, intravenous, subcutaneous, oral, buccal, nasal, rectal, epidural, topical, intrathecal, rectal, intracranial, intratracheal and intrathecal and intranasal routes. Any other therapeutically efficacious route of administration can be used, for example absorption through epithelial or endothelial tissues or systemic administration. In addition, a LSF inhibitor according to the invention can be administered together with other components of biologically active agents such as pharmaceutically acceptable surfactants, excipients, carriers, diluents and vehicles.

For parenteral (e.g. intravenous, subcutaneous, intramuscular) administration, a LSF inhibitor can be formulated as a solution, suspension, emulsion or lyophilized powder in association with a pharmaceutically acceptable parenteral vehicle (e.g. water, saline, dextrose solution) and additives that maintain isotonicity (e g. mannitol) or chemical stability (e.g. preservatives and buffers). The formulation is sterilized by commonly used techniques.

In some embodiments, the route of administration is administration by subcutaneous route. Intramuscular administration is another alternative route of administration. In some embodiments, a pharmaceutical composition comprising a LSF inhibitor selected from any of formula (I) to (XXVI) and (III') can be administered as a formulation adapted for systemic delivery. In some embodiments, the compositions can be administered as a formulation adapted for delivery to specific organs, for example but not limited to the liver. In some embodiments, a pharmaceutical composition comprising a LSF inhibitor selected from any of formula (I) to (XXVI) and (III') as disclosed herein can be administered as a formulation adapted for passage through the blood-brain barrier.

Alternatively, in some embodiments, a pharmaceutical composition can be incorporated in a gel, sponge, or other permeable matrix (e.g., formed as pellets or a disk) and placed in proximity to the liver endothelium for sustained, local release. The composition comprising a LSF inhibitor can be administered in a single dose or in multiple doses, which are administered at different times.

The exact route of administration as well as the optimal dosages can be determined by standard clinical techniques for each specific case, mainly based on the nature of the disease or disorder and on the stage of this disease. Preferably, the medicament according to the present invention is applied locally or systemically, in particular, orally, intravenously, parenterally, epicutaneously, subcutaneously, intrapulmonarily by inhalation or bronchoalveolar lavage, intramuscularily, intracranially, locally into intervertebral discs or other connective tissues.

As disclosed herein, a pharmaceutical composition comprising an effective amount of at least one LSF inhibitor selected from any of formula (I) to (XXVI) and (III') can be administered to a subject for the therapeutic treatment or prevention (e.g. prophylactic treatment) for diseases and disorders mediated by level of LSF.

In some embodiments, a composition of the invention comprising an inhibitor of LSF of any of formula (I) to (XXVI) and (III') as disclosed herein is formulated for treatment of cancer, e.g. hepatocellular carcinoma. In one embodiment, an inhibitor of LSF in compositions of the invention as disclosed herein is a compound of formula (IV), or enantiomers (compound C1-1 or C1-2 in FIG. 1), prodrugs, derivatives or pharmaceutically acceptable salts thereof. In various embodiments, pharmaceutical compositions of the invention used for inhibition of LSF in diseases or disorders, e.g. HCC, comprises a racemic mixture of a LSF inhibitor of any of formula (I) to (XXVI) and (III').

The phrase "racemic mixture" refers to a mixture of the two enantiomers of one compound. An ideal racemic mixture is one wherein there is a 50:50 mixture of both enantiomers of a compound such that the optical rotation of the (+) enantiomers cancels out the optical rotation of the (-) enantiomers. For example, in one embodiment, a pharmaceutical composition for treatment of cancer, e.g., HCC as disclosed herein comprises compounds C1-1 and C1-2 (shown in FIG. 1), which are enantiomers of a compound of formula (IV). In some embodiments, a pharmaceutical composition for treatment of cancer, e.g., HCC as disclosed herein comprises a compound of FQI2 (Formula (V)). In some embodiments, a pharmaceutical composition for treatment of cancer, e.g., HCC as disclosed herein comprises the compound FQI-34. In some embodiments, a pharmaceutical composition for treatment of cancer, e.g., HCC as disclosed herein comprises the compound FQI-Br, FQI-F, FQI-Cl or FQI32.

In some embodiments, a pharmaceutical composition comprising at least one LSF inhibitor further comprises a second therapeutic agent. In one embodiment, the second therapeutic agent is a chemotherapeutic agent such as Sorafenib or 5-FU. In some embodiments, the second therapeutic agent is a second LSF inhibitor, e.g. a compound selected from any of formula (I) to (XXVI) and (III'). In some embodiments, a second LSF inhibitor is an enantiomer of a first LSF inhibitor as disclosed herein. In other embodiments, the second therapeutic agent is a therapeutic for liver diseases such as HBV, HCV and cirrhosis.

In prophylactic applications, pharmaceutical compositions (or medicaments) comprising a LSF inhibitor can be administered to a subject susceptible to, or otherwise at risk of, a disease or disorder mediated by level of LSF in an amount sufficient to eliminate or reduce the risk or delay the onset of the disease. In one embodiment, the disease or disorder to be prevented is hepatocellular carcinoma (HCC). As most HCCs are generated from the background of hepatitis B virus (HBV) or hepatitis C virus (HCV), a subject with HBV or HCV can be subjected to an effective amount or dose of a pharmaceutical composition comprising a LSF inhibitor described herein. In one embodiment, a pharmaceutical composition of the invention disclosed herein comprises a LSF inhibitor of formula (IV), or enantiomers, prodrugs, derivatives or pharmaceutically acceptable salts thereof. In some embodiments, an effective amount or dose of a pharmaceutical composition comprising a LSF inhibitor disclosed herein can be administered to a subject at high risk of HCC. In additional embodiments, a pharmaceutical composition further comprises a second therapeutic agent, e.g. therapeutics to treat high-risk factors such as liver diseases (e.g HBV). Representative high-risk factors of HCC include hepatic cirrhosis, chronic alcohol consumption, (prolonged) exposure to liver carcinogenic chemicals such as aflatoxin B1 in food, thorotrast in diagnostic contrast agent and vinyl chloride, hepatic adenoma, hepatic angiosarcoma, hepatic angiosarcomas, hereditary hemochromatosis, emphysema and cirrhosis resulted from alpha 1 anti-trypsin deficiency, and hereditary tyrosinemia. In various embodiments, individuals that have discontinued treatment for high-risk factors of HCC can still be subjected to a pharmaceutical composition comprising an effective dose of LSF inhibitor selected from any of formula (I) to (XXVI) and (III') as disclosed herein for prevention of development of HCC. For such embodiments, an effective dose of a LSF inhibitor can be higher or lower than the previous dosage.

In therapeutic applications, according to the invention provided herein, when an effective amount or effective dose of a pharmaceutical composition comprising a LSF inhibitor selected from any of formula (I) to (XXI) and (III') of the present invention is administered to the subject with cancer, e.g. hepatocellular carcinoma, progression of cancer, e.g. HCC, can be delayed or inhibited. In some embodiments, administration of an effective amount or effective dose of a pharmaceutical composition comprising a LSF inhibitor selected from any of formula (I) to (XXVI) and (III') to a subject with hepatocellular carcinoma can inhibit or delay progression of HCC. In further embodiments, treating subjects with an effective dose of a pharmaceutical composition comprising a LSF inhibitor can prevent or delay metastasis of HCC in the subject. In various embodiments, a LSF inhibitor used for therapeutic treatment of various diseases, e.g. HCC, using the methods and compositions disclosed herein is a compound of formula (IV), or enantiomers thereof or a mixture thereof. In some embodiments, a LSF inhibitor used for therapeutic treatment of various diseases, e.g. HCC, using the methods and compositions disclosed herein is the compound FQI-34. In some embodiments, a LSF inhibitor used for therapeutic treatment of various diseases, e.g. HCC, using the methods and compositions disclosed herein is the compound FQI-BR, FQI-F, FQI-Cl or FQI32. In further embodiments, a LSF inhibitor useful for such treatment is a compound of any of formula (I) to (XXVI) and (III'), or enantiomers, prodrugs, pharmaceutically acceptable salts thereof. Other diseases or disorders that can be treated by compositions of the present invention disclosed herein include other various cancers such as brain cancer, breast cancer, colon cancer, head and neck squamous cell carcinoma, lung cancer, pancreatic cancer, ovarian cancer, and thyroid cancer; HIV and inflammation-associated diseases.

In various embodiments, a pharmaceutical composition comprising a LSF inhibitor of the invention further comprises a second therapeutic agent. In some embodiments, a second therapeutic agent is a chemotherapeutic agent for treatment of cancer, e.g. Sorafenib. Other chemotherapeutic agents include, but not limited to, Doxorubicin, 5-FU, Paclitaxel, Irinotecan, Patupilone, Everolimus, multikinase inhibitors (e.g. Sorafenib and Sunitinib), and EGFR inhibitors (e.g. Cetuximab, Erlotinib, Gefitinib, Brivanib, Lapatinib).

In further embodiments, a second therapeutic agent is a second inhibitor of LSF. In one embodiment, the second inhibitor of LSF is a different LSF inhibitor (e.g. IL2 or a different compound selected from formula (I) to (XXVI) and (III'). In one embodiment, the second inhibitor of LSF is an enantiomer of a first LSF inhibitor. For example, compounds C1-1 and C1-2 (shown in FIG. 1) are enantiomers of the same compound of formula (IV). In such embodiments, pharmaceutical compositions of the invention comprise a racemic mixture of the same compound. Enantiomers of the same compound can have different biological activity. Accordingly, different effective doses can be applied to enantiomers of the same compound in a pharmaceutical composition of the invention. For example, in one embodiment, a pharmaceutical composition as disclosed herein can comprise compounds C1-1 and C1-2 (enantiomers of Formula IV) at different effective amounts or doses. In alternative embodiments, an inhibitor of LSF can be formulated in a separate pharmaceutical composition and administered to a subject separately or concurrently with a second therapeutic agent.

In some embodiments, the present invention also provides compositions useful for practicing the therapeutic and prophylactic methods described herein. In some embodiments, combinations of a LSF inhibitor and another therapeutics can be tailored to be combined in a pharmaceutical composition, where each therapeutics can target a different symptom, a different disease or a different disorder. In further embodiments, a LSF inhibitor and another therapeutics can be mixed together in a pharmaceutical composition as disclosed herein. In other embodiments, a LSF inhibitor and another therapeutics can be present in a different formulation when combined in a pharmaceutical composition. For example, in one embodiment, a LSF inhibitor can be present in a liquid formulation, while another therapeutics is lypholized into powder. The formulations of different active ingredients in a pharmaceutical compositions as disclosed herein (e.g. a LSF inhibitor and/or another therapeutics) can be optimized accordingly by various factors such as physical and chemical properties of a drug, bioavailability, route of administration, and whether it is a sustained or a burst release for the drug. Therapeutic and prophylactic compositions of the present invention can further comprise a physiologically tolerable carrier together with a LSF inhibitor as disclosed herein, or derivatives, enantiomers, prodrugs or pharmaceutically acceptable salts thereof. In additional embodiments, a LSF inhibitor and another therapeutics can employ different physiologically tolerable carriers when combined in a pharmaceutical composition of the invention as disclosed herein.

In some embodiments, a pharmaceutical composition as disclosed herein comprises a LSF inhibitor together with other therapeutics and a pharmaceutically acceptable excipient. Suitable carriers for a LSF inhibitor of the invention, and their formulations, are described in Remington's Pharmaceutical Sciences, 16th ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of a LSF inhibitor being administered.

In some embodiments, bioavailability of a LSF inhibitor according to the invention can also be improved by using conjugation procedures which increase the half-life of a LSF inhibitor in a subject, for example linking a LSF inhibitor to polyethylene glycol, as described in WO 92/13095, which is incorporated herein in its entirety by reference.

In some embodiments, bioavailability of a LSF inhibitor according to the invention can be also enhanced by encapsulating a LSF inhibitor in biocompatible delivery vehicles which increase the half-life of a LSF inhibitor in a human body. Exemplary biocompatible delivery vehicles include polymeric vehicles such as PEG-based vehicles, or liposome-based vehicles.

In some embodiments, a LSF inhibitor can be dissolved or dispersed as an active ingredient in the physiologically tolerable carrier to increase the half-life of a LSF inhibitor in a subject.

The preparation of a pharmacological composition that contains active ingredients (e.g. a LSF inhibitor) dissolved or dispersed therein is well understood in the art and need not be limited based on formulation. Typically such compositions are prepared as injectable either as liquid solutions or suspensions, however, solid forms suitable for solution or suspension in liquid prior to use can also be prepared. The preparation can also be emulsified or presented as a liposome composition. In some embodiments, a LSF inhibitor can be mixed with excipients which are pharmaceutically acceptable and compatible with the active ingredient and in amounts suitable for use in the therapeutic methods described herein. In addition, if desired, the composition comprising a LSF inhibitor can contain minor amounts of auxiliary substances such as wetting or emulsifying agents, pH buffering agents and the like which enhance the effectiveness of the active ingredient.

Physiologically tolerable carriers (i.e. physiologically acceptable carriers) are well known in the art. Selection of pharmaceutically acceptable carriers can be accomplished by means of administration by a skilled artisan. For example, if the composition is orally administered, it can be formulated in coated tablets, liquids, caplets and so forth. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. For topical application, the carrier may be in the form of, for example, and not by way of limitation, an ointment, cream, gel, paste, foam, aerosol, suppository, pad or gelled stick. In some embodiments, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). An inhibitor of LSF of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

A skilled artisan will be able to determine the appropriate way of administering pharmaceutical compositions comprising at least one LSF inhibitor as disclosed herein in view of the general knowledge and skill in the art.

Treatment Regimes

Another aspect of the present invention relates to methods for therapeutic and prophylactic treatment of diseases or disorders, where inhibition of LSF is desirable. The methods comprise administering to a subject in need thereof a pharmaceutical composition comprising a therapeutically effective amount of at least one LSF inhibitor selected from any of compounds represented by formula (I) to (XXVI) and (III') as disclosed herein.

In some embodiments, such diseases or disorders that can be treated or prevented by methods and compositions of the invention as disclosed herein include but not limited to, various cancers such as liver cancer (e.g. hepatocellular carcinoma (HCC), hepatoblastoma, cholangiocarcinoma (cancer of the bile duct), angiosarcoma), brain cancer, breast cancer, colon cancer, head and neck squamous cell carcinoma, lung cancer, pancreatic cancer, ovarian cancer, cervical cancer, melanoma and thyroid cancer; HIV; inflammation-related diseases such as hepatitis B virus (HBV), hepatitis C (HCV), cirrhosis and Alzheimer's disease; liver diseases such as HBV, HCV, cirrhosis, hepatic adenoma, hepatic angiosarcoma and hepatic angiosarcomas; emphysema; and hereditary hemochromatosis.

In one embodiment, hepatocellular carcinoma is treated or prevented by the methods and compositions of the present invention with a LSF inhibitor as disclosed herein. In some embodiments, a LSF inhibitor present in pharmaceutical compositions of the invention is the compound FQI-34. In some embodiments, a LSF inhibitor present in pharmaceutical compositions of the invention is the compound FQI-Br, FQI-F or FQI-Cl. In some embodiments, a LSF inhibitor present in pharmaceutical compositions of the invention is the compound FQI32. In one embodiment, a LSF inhibitor present in pharmaceutical compositions of the invention is a compound of formula (IV), or enantiomers, prodrugs, derivatives and pharmaceutically acceptable salts thereof. In some embodiments, a LSF inhibitor is a compound selected from the group consisting of compounds of formula (V) to (XXVI) and (III').

Effective doses of the pharmaceutical composition comprising a LSF inhibitor as disclosed herein, for the treatment of the above described examples of diseases or disorders mediated by level of LSF vary depending upon many different factors, including means of administration, target site, physiological state of the subject, whether the subject is human or an animal, other medications administered, and whether treatment is prophylactic or therapeutic. In one embodiment, the disease or disorder to be treated or prevented is hepatocellular carcinoma.

The dosage and frequency of administration can vary depending on whether the treatment is prophylactic or therapeutic. In prophylactic applications, a relatively low dosage is administered at relatively infrequent intervals over a long period of time. For example, subjects at high risk of HCC, e.g. individuals with hepatitis B virus or hepatitis C virus can be treated with a LSF inhibitor as disclosed herein in a prophylactic regime to prevent the onset of HCC. Some subjects continue to receive treatment for the rest of their lives. In some embodiments, individuals with HCC in remission after HCC treatment (e.g. hepatectomy, liver transplantation or other therapeutic treatment such as chemotherapy) can be subjected to a pharmaceutical composition comprising a LSF inhibitor as disclosed herein, as a preventive measure against recurrence of HCC. Depending on the clinical condition of a subject, dosage and frequency of pharmaceutical compositions of the present invention can be adjusted accordingly over time by one of the skill in the art, e.g physicians.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with HCC can be treated with a LSF inhibitor as disclosed herein at an effective dose in a therapeutic regimen accordingly to prevent or delay the progression of HCC or metastasis. In other embodiments, a LSF inhibitor can be administered using the methods and compositions as disclosed herein to chemotherapy subjects in order to increase sensitivity to chemotherapy. In some embodiments, an inhibitor of LSF as disclosed herein can be administered to subjects prior to, concurrently with, or sequentially to treatment with chemotherapeutic drugs, e.g. Sorafenib. In further embodiments, HCC subjects selected for other therapeutic procedures or surgeries, such as hepatectomy, intralesional ethanol injection, or chemoembolization, can be subjected to a treatment with a LSF inhibitor as disclosed herein. For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of a LSF inhibitor depends on the stage of the disease, e.g. HCC as well as whether a second therapeutic agent is also administered. The second therapeutic agent can be an agent to treat a different disease or disorder. In some embodiments, the second therapeutic agent can be a chemotherapeutic agent such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In alternative embodiments, the second therapeutic agent can be a second LSF inhibitor. In some embodiments, a second LSF inhibitor can be selected from the group consisting of compounds of formulae (V) to (XXVI) and (III'), and enantiomers, prodrugs and pharmaceutically acceptable salts thereof. In one embodiment, a second LSF inhibitor can be an enantiomer of a first LSF inhibitor. In further embodiments, a second therapeutic agent is another therapeutics to target another disease, or another disorder, or a different symptom. In combination with other therapeutics, the dosage of a LSF inhibitor can be reduced, compared to the standard dosage of a LSF inhibitor when administered alone.

In some embodiments, a LSF inhibitor can be administered to a subject in a pharmaceutical composition comprising an amount of a LSF inhibitor of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, a LSF inhibitor can be used in an amount of about 0.1 to 1000 µg/kg of body weight or about 1 to 100 µg/kg of body weight or about 10 to 50 m/kg of body weight. In some embodiments, a LSF inhibitor can be administered at a concentration of about 0.001 mg/ml or 0.1 mg/ml or a higher concentration of 0.1 mg/ml. In alternative embodiments, a pharmaceutical composition comprises at least one LSF inhibitor at a concentration of about 0.01 µM to 300 µM, or about 0.1 µM to 150 µM, or about 1 µM to 50 µM, or about 1 µM to 25 µM.

The inventors in collaboration with other scientists have demonstrated that a LSF inhibitor (e.g., a compound of formula IV or III') reduces HCC tumor volume in vivo in a mouse model by about 80% (data not shown). Accordingly, in some embodiments, a LSF inhibitor selected from any of formula (I) to (XXVI) and (III') can be administered to a subject (e.g. a HCC subject) according to the methods as disclosed herein in an effective dose to reduce tumor volume by at least about 15%, at least about 20%, at least about 30%, at least about 40%, at least about 50%, at least about 60%, at least about 70%, at least about 80%, at least about 90%, at least about 98%, about 99%, or about 100%. Tumor volume and tumor weight in a subject can be determined by one of ordinary skill in the art, e.g. using imaging techniques such as MRI, CAT scan, and the like.

In collaboration with other scientists, the inventors have discovered that in an in vivo mouse model of HCC, the administration of a small molecule inhibitor of LSF a compound of formula (IV) as disclosed herein injected intraperitoneally once every 3 days at an effective amount of about 1.0-2.0 mg/kg prevented or delayed the growth of hepatocellular carcinoma (HCC) (data not shown). Accordingly in some embodiments, the frequency of administration can vary significantly from once a day, once every other day, once every 3 days, once weekly, once monthly to once a year, depending on the disease of cancer (e.g., stage of cancer) such as HCC stage, and/or mode of administration.

Generally, effective dosages and dosing schedules can be adjusted based on, for example, the outcome of the treatment such as whether the progression rate of HCC is slower or terminated, or whether at least one of the symptoms associated with HCC is reduced. In accordance with the teachings provided herein, the effectiveness of the treatment can be monitored by obtaining a biological sample from a subject, e.g. a blood serum sample, and determining the level of biomarkers for HCC, such as AFP in the serum sample, using methods well known in the art and the diagnostic methods as disclosed later herein. The efficacy of the treatment can also be monitored by imaging modalities such as CT scan, MRI, ultrasound, and the like that are known to a skilled artisan.

In some embodiments, the daily dose administered to a subject in a form of a bolus composition comprising a LSF inhibitor can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

The pharmaceutical compositions comprising at least one LSF inhibitor selected from any of formula (I) to (XXVI) and (III') as disclosed herein can be administered by parenteral, topical, intravenous, oral, subcutaneous, intraperitoneal, intranasal or intramuscular means for prophylactic and/or therapeutic treatment. For example, for treatment of cancer, e.g., HCC, a pharmaceutical composition comprising at least one LSF inhibitor can be injected systemically such as by intravenous injection, or by injection or application to the relevant site, such as by direct injection into a tumor, or direct application to the site when the site is exposed in surgery. Other routes of administration of a LSF inhibitor as disclosed herein are intramuscular (i.m.), intravenous (i.v.), subcutaneous (s.c.), or orally, although other routes can be equally effective. Intramuscular injection is most typically performed in the arm or leg muscles. In some embodiments, pharmaceutical compositions as disclosed herein for the treatment of inflammation-associated disease of the brain such as Alzheimer's disease can be administered directly to the head or brain via injection directly into the cranium. In some methods, a LSF inhibitor as disclosed herein can be administered as a sustained release composition or device, such as a Medipad™ device. In some methods, the sustained release composition or device is implanted directly close to or at the site of the HCC tumor.

In some embodiments, a LSF inhibitor selected from any of formula (I) to (XXVI) and (III') as disclosed herein can optionally be administered in combination with other agents that are at least partly effective in treatment of LSF-mediated diseases or disorders such as cancers (e.g. HCC), HIV, and inflammation-related diseases. In other embodiments, a LSF inhibitor of the invention can be administered prior to, concurrently, or after administration of another therapeutics that targets another disease or disorder, or a different symptom. In one embodiment, a pharmaceutical composition comprising a LSF inhibitor can be administered alone or in combination with other therapeutic agents to treat liver diseases such as hepatitis B virus and hepatitis C virus for the prevention of HCC development.

In some embodiments, a LSF inhibitor selected from any of formula (I) to (XXVI) and (III') as disclosed herein can be used alone to treat cancer, e.g. hepatocellular carcinoma. In some embodiments, a LSF inhibitor can also be administered in combination with other therapeutic procedures or surgeries for HCC treatment such as curative hepatectomy, intralesional ethanol injection, chemoembolization, radiofrequency ablation, cryosurgery, radiation therapy, percutaneous intralesional ethanol injection, transarterial chemoembolization, radiotherapy, systemic chemotherapy and surgery. In further embodiments, a chemotherapy subject can be subjected to an inhibitor of LSF using the compositions and methods of the invention prior to, simultaneously with, or subsequently after treatment with other chemotherapeutic agents, such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). An inhibitor of LSF selected from any of formula (I) to (XXVI) and (III') can also be administered after surgery or after the other aforementioned treatments of cancer, e.g., where solid tumors have been removed to prevent cancer recurrence or metastasis.

In various embodiments, a LSF inhibitor selected from any of formula (I) to (XXVI) and (III') can be a pro-drug, where it is activated by a second agent. Accordingly, in such embodiments, administration of such the second agent which activates the pro-drug into its active form can be administered the same time, concurrent with, or prior to, or after the administration of the pharmaceutical composition comprising a LSF inhibitor as disclosed herein.

In some embodiments, a LSF inhibitor selected from any of formula (I) to (XXVI) and (III') as disclosed herein is often administered as pharmaceutical compositions comprising an active therapeutic agent, i.e. a LSF inhibitor, and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

For parenteral administration, a LSF inhibitor selected from any of formula (I) to (XXVI) and (III') as disclosed herein can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Other mode of administration includes systemic delivery. In some embodiments, for treatment of cancer, e.g., HCC, a pharmaceutical composition comprising at least one LSF inhibitor selected from any of formula (I) to (XXVI) as disclosed herein can be injected systemically such as by intravenous injection, or by injection or application to the relevant site, such as by direct injection into a tumor, or direct application to the site when the site is exposed in surgery. In some embodiments, a pharmaceutical composition of the invention can be formulated in a tablet and used orally for systemic administration. In various embodiments, pharmaceutical compositions of the invention can further comprises non-active ingredients (i.e. ingredients that have no therapeutic values for treatment of diseases, disorders or symptoms), such as physiologically acceptable carriers.

In various embodiments, modification of a LSF inhibitor selected from any of formula (I) to (XXVI) and (III') specifically contemplated is attachment, e.g., covalent attachment, to a polymer. In other embodiments, a LSF inhibitor selected from any of formula (I) to (XXVI) and (III') can be mixed with or encapsulated in a biocompatible polymer.

In another aspect, biodegradable or absorbable polymers can provide extended, often localized, release of a LSF inhibitor selected from any of formula (I) to (XXVI) and (III') as disclosed herein. The potential benefits of an increased half-life or extended release for a therapeutic agent are clear. A potential benefit of localized release is the ability to achieve much higher localized dosages or concentrations, for greater lengths of time, relative to broader systemic administration, with the potential to avoid possible undesirable side effects that may occur with systemic administration.

Bioabsorbable polymeric matrix suitable for delivery of a LSF inhibitor as disclosed herein, or variants or fragments or derivatives thereof can be selected from a variety of synthetic bioabsorbable polymers, which are described extensively in the literature. Such synthetic bioabsorbable, biocompatible polymers, which may release proteins over several weeks or months can include, for example, polyhydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563 (which are incorporated herein in their entirety by reference), among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

It was previously reported in Yoo et al., (PNAS, 2010; 107; 8357-8362) that the level of LSF expression is useful to identify a subject with HCC. Accordingly, a subject amenable to treatment using the methods and compositions as disclosed herein can be identified by measuring the level of LSF in a biological sample obtained from the subject and if the level of LSF in the biological sample from the subject is higher by a statistically significant amount relative to a reference level of LSF, the subject likely is at risk of having HCC, and accordingly, can be administered a composition comprising at least one small molecule inhibitor of LSF selected from any of formula (I) to (XXVI) and (III') as disclosed herein.

A subject is identified as suffering from HCC or having a disordered characterized by increased LSF expression, when the expression level of LSF in a biological sample obtained from the subject is higher relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. The extent of increase in LSF expression can indicate the grades and stages of HCC (See Yoo et al., PNAS, 2010; 107; 8357-8362). Accordingly, subjects identified with HCC or having a disorder characterized by increased LSF expression can be treated with an effective dose of a pharmaceutical composition as disclosed herein comprising a LSF inhibitor selected from any of formula (I) to (XXVI) and (III') as disclosed herein to inhibit or delay progression of HCC.

In some embodiments, a biological sample is a tissue sample, e.g. a liver sample.

In some embodiments, the level of LSF in a biological sample is compared to a reference level, or a reference biological sample, such as biological sample obtained from an age-matched normal control (e.g. an age-matched subject not having HCC or an age-matched normal healthy subject).

In other embodiments, in order to determine the therapeutic efficacy of the treatment (e.g. treatment of HCC), a reference level can be the level of LSF expression can be measured at a previous time point from the same subject on a treatment regimen.

The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of LSF in a biological sample obtained from the subject is decreased relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. In such embodiments, the reference level is the measurement of LSF at a previous time point from the same subject who has been administered to the treatment regimen. Based on the outcome of treatment, the dosage and frequency of administration using the methods and compositions as disclosed herein can be adjusted accordingly by one of skill in the art.

In one embodiment, the biological sample for analysis is a liver sample, wherein the sample comprises at least one cell. One can use any immunoassay to determine the level of LSF in a biological sample, such as ELISA or immunohistochemical methods of detecting LSF which are commonly known in the art and are encompassed for use in the present invention.

In some embodiments, a method of determining the presence and/or level of LSF in a biological sample from a subject comprises performing a binding assay. Any reasonably specific binding partner can be used. For example, the binding partner is labeled. For example, the assay is an immunoassay, especially between LSF and an antibody that recognizes LSF, especially a labeled antibody. It can be an antibody raised against part or all of it, such as a monoclonal antibody or a polyclonal antiserum of high specificity for LSF. In some embodiments, the antibodies is specific to mammalian LSF, such as human LSF.

Thus, any anti-LSF antibody can be used in the method to determine the presence and/or level of LSF in a biological sample, which can be used to detect the increased or decreased level of LSF present in a diagnostic sample. Such antibodies can be raised by any of the methods well known in the immunodiagnostics field.

In some embodiments, an immunoassay is carried out by measuring the extent of the protein/antibody interaction of the LSF/antibody interaction. Any known method of immunoassay may be used. A sandwich assay or ELISA is preferred. In this method, a first antibody to the marker protein is bound to the solid phase such as a well of a plastics microtitre plate, and incubated with the sample and with a labeled second antibody specific to the protein to be assayed. Alternatively, an antibody capture assay could be used. In some embodiments, a biological test sample is allowed to bind to a solid phase, and the anti-LSF protein antibody is then added and allowed to bind. After washing away unbound material, the amount of antibody bound to the solid phase is determined using a labeled second antibody against the first.

In some embodiments, a label is preferably an enzyme. The substrate for the enzyme may be, for example, color-forming, fluorescent or chemiluminescent.

In some embodiments, a binding partner, e.g. an antibody or a ligand binding to LSF in the binding assay is preferably a labeled specific binding partner, but not necessarily an antibody. The binding partner will usually be labeled itself, but alternatively it may be detected by a secondary reaction in which a signal is generated, e.g. from another labeled substance.

In some embodiments, one can use an amplified form of assay, whereby an enhanced "signal" is produced from a relatively low level of protein to be detected. One particular form of amplified immunoassay is enhanced chemiluminescent assay. Conveniently, the antibody is labeled with horseradish peroxidase, which participates in a chemiluminescent reaction with luminol, a peroxide substrate and a compound which enhances the intensity and duration of the emitted light, typically 4-iodophenol or 4-hydroxycinnamic acid.

In another embodiment, an amplified immunoassay can be used which is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, in some embodiments, one method to determine the level of LSF in a biological sample is to use a two dimensional gel electrophoresis to yield a stained gel and the increased or decreased level of the protein detected by an increased an increased or decreased intensity of a protein-containing spot on the stained gel, compared with a corresponding control or comparative gel.

In some embodiments, methods to determine the amount of LSF in a biological sample does not necessarily require a step of comparison of the level of LSF with a control sample (e.g. from a normal healthy subject), but it can be carried out with reference either to a control or a comparative sample. Thus, in relation to HCC, measuring the amount of LSF in a biological sample can be used to determine the stage of progression, if desired with reference to results obtained earlier from the same subject or by reference to standard values that are considered typical of the stage of the disease. In this way, the invention can be used to determine whether, for example after treatment of the subject with a LSF inhibitor, the disease has progressed or not. The result can lead to a prognosis of the outcome of the disease.

In some embodiments, one method to detect the presence and/or the level of LSF in a biological sample is to perform immunohistochemical assay on a biopsy sample, such as a liver sample. The methods for detecting the presence and/or a level of protein on a biopsy sample are well within the level of skill in the art. In alternative embodiments, the mRNA level of LSF in a biological sample is determined by quantitative PCR with primers designed according to the nucleotide sequence of LSF. The design for primers of LSF can be performed easily by one of the skill in the art.

In various embodiments, the level of LSF can be measured and used in combination with other biomarkers for HCC such as AFP to diagnose HCC in a subject. Other biomarkers for HCC include, but not limited to, U.S. Patent No: US 2009/0317844, US Patent No.: 2010/0015605, US 2010/0120631, WO 2010/048304, WO 2005/0233392, and WO2008/056854, which are incorporated herein in their entirety by reference.

Kits

Another aspect of the present invention relates to a kit comprising one or more LSF inhibitor of formula (I) to (XXVI) and (III') as disclosed herein, and instructions for carrying out a method as disclosed herein.

In some embodiments, a kit can optionally additionally comprise reagents or agents for measuring the level of LSF expression in a tumor sample from the subject, for example to identify a subject amenable to treatment with the methods and compositions as disclosed herein. Such agents are well known in the art, and include without limitation, labeled antibodies that specifically bind to LSF protein and/or mRNA and the like. In some embodiments, the labeled antibodies are fluorescently labeled, or labeled with magnetic beads and the like. In some embodiments, a kit as disclosed herein can further comprise at least one or more reagents for profiling and annotating a biological sample from the subject in high throughput assay.

In some embodiments, the kit can further comprise instructions for administering a composition comprising a LSF inhibitor of formula (I) to (XXVI) and (III') to a subject in need thereof, e.g., with cancer, e.g., HCC and instructions for doses and the like.

In addition to the above mentioned component(s), the kit can also include informational material. The informational material can be descriptive, instructional, marketing or other material that relates to the methods described herein and/or the use of the components for the assays, methods and systems described herein. For example, the informational material may describe methods for enriching the metastatic cancer cell population, for characterizing a plurality of properties of a metastatic cancer cell population.

In some embodiments, the methods and kits comprising a LSF inhibitor of any of formula (I) to (XXVI) and (III') as disclosed herein can be performed by a service provider, for example, where an investigator or physician can send the biological sample to a diagnostic laboratory service provider to measure the level of LSF in the biological subject from the subject. In such an embodiment, after performing the measurement of the LSF expression, the service provider can provide the investigator or physician a report of the characteristics of the level of LSF expression and if report that the subject is a suitable or amenable to be treated with a LSF inhibitor of any of compounds of formula (I) to (XXVI) and (III') according to the methods and composition as disclosed herein.

In alternative embodiments, a service provider can provide the investigator with the raw data of the level of LSF expression (protein and/or mRNA) and leave the analysis to be performed by the investigator or physician. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays to measure the level of LSF in the subject as disclosed herein in the investigators laboratories, and analyses the result and provides a report to the investigator of the level of LSF expression for each subject, and leaves the physician to make appropriate recommendations of treatment of the subject with a composition comprising a LSF inhibitor of any formula (I) to (XXVI) and (III') according to the methods as disclosed herein.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Although any known methods, devices, and materials may be used in the practice or testing of the invention, the methods, devices, and materials in this regard are described herein.

The examples presented herein relate to methods and compositions comprising at least one LSF inhibitor selected from any of formula (I) to (XXVI) and (III') as disclosed herein to inhibit LSF for treatment of cancers, for example, but not limited to HCC. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials And Methods (for Examples 1 to 3)

Synthesis of FQI1 (8-(2-ethoxyphenyl)-7,8-dihydro-[1,3]dioxolo[4,5-g]quinolin-6(5H)-one)

To a flame-dried 250 mL round bottom flask equipped with a stir bar was added 5 mmol (960 mg) (E)-2-ethoxy cinnamic acid, 100 mL toluene, and 7.5 mmol (1.5 mL) thionyl chloride. The reaction was heated to 85° C. and allowed to stir at this temp for 12 h and then cooled to room temperature. The solvent was removed under reduced pressure and the resulting crude material was then azeotroped (2×25 mL toluene) to remove excess thionyl chloride. The resulting material was dried under high vacuum for 2 hours and made into a 1.0 M solution in $CH_2Cl_2$. To a 25 mL round bottom flask fitted with stir bar and flame dried under vacuum was added 5 mL $CH_2Cl_2$, 1.0 mmol (1 mL, 1.0 M solution in $CH_2Cl_2$) acyl chloride and 1.1 mmol (151 mg) benzo[d][1,3]dioxol-5-amine. Reaction was brought to 50° C. and stirred at this temperature for 15 h. Reaction was cooled to room temperature, quenched by addition of 10 mL saturated sodium bicarbonate, extracted with EtOAc (2×10 mL), dried over sodium sulfate, filtered and concentrated in vacuo. The crude material was then dissolved in minimal $CH_2Cl_2$ (8 mL) and poured into 20 mL ice cold hexane. (E)-N-(Benzo[d][1,3]dioxol-5-yl)-3-(2-ethoxyphenyl) acrylamide precipitated from solution and was isolated via filtration, washed with ice cold diethyl ether (10 mL) and dried under high vacuum for 2 h to yield 215 mg of the desired acrylamide. The resulting material was used without further purification. To an 8 mL microwave reaction tube was added 250 µmol acrylamide (80 mg) and 4 mL trifluoroacetic acid. The reaction was heated in a CEM microwave at 85° C. and 200 W power for 30 minutes. The vessel was removed from microwave reactor and allowed to cool to room temperature. The crude reaction mixture was then transferred to a 50 mL round bottom flask and to it was added 2 mL $CH_2Cl_2$ and 15 mL saturated sodium bicarbonate with stirring (portion wise, 3×5 mL), followed by extraction with $CH_2Cl_2$ (2×10 mL). Organic layers were separated and combined then dried over sodium sulfate. The $CH_2Cl_2$ separated by filtration and concentrated under reduced pressure using a rotary evaporator onto silica gel. The crude material was then purified via flash column chromatography over silica gel with 6:4 hexanes:EtOAc as the eluent to yield 8-(2-ethoxyphenyl)-7,8-dihydro-[1,3]dioxolo[4,5-g]quinolin-6(5H)-one (54 mg, 172 µmol). The material was determined to be >95% pure by $^1$H NMR, $^{13}$C NMR, and HPLC-MS analysis.

LSF-Dependent Reporter Assays.

NIH 3T3 cells were transfected with the expression construct pEF1α-LSF, a LSF expression vector[6,20]; the reporter construct pGL3B-WT4E1b, a firefly luciferase reporter vector driven by LSF[12]; phRL-TK, a control *renilla* luciferase reporter vector; and pEFGP, essentially as previously described[12]. Five hours after transfection, either vehicle (DMSO) or FQI compound was added, keeping DMSO at 0.5%. Cell extracts were harvested 36 hours post-transfection and firefly and *renilla* luciferase activities measured via a dual luciferase assay (Promega). Five µl of extract was mixed with 30 µl of luciferase assay reagent (Promega), and luminescence measured for 10 seconds using a 20/20n luminometer (Turner Biosystems). Subsequently, 30 µl of Stop & Glo reagent (Promega) was added, and luminescence also measured for 10 seconds. LSF transactivation activity is given as relative luciferase activity, the ratio of firefly to *renilla* activities.

Electrophoretic Mobility Shift Assays.

LSF was translated in vitro as previously described[16] for use in EMSAs. Protein was preincubated with inhibitor or DMSO and then incubated with 0.5 µg poly d(I-C) for 15 min at 4° C. in 40 mM KCl, 15 mM HEPES pH 7.9, 1 mM EDTA, 0.5 mM DTT, 5% glycerol. Finally, radiolabelled double-stranded DNA (TGGCTGGTTATGGCTGGTCAGACTAG—SEQ ID NO: 5—and its complement) were added for a 30-min incubation at 30° C. Results were visualized using a Phosphodmager and quantified using ImageQuant software.

Cell Proliferation Assays.

Cells were plated at 3×10$^4$ cells/mL, A549 and HeLa, and 1×10$^4$ cells/mL, NIH/3T3, in 96-well plates and incubated for 24 h to allow for cell adhesion. LSF-library compounds were dissolved in DMSO, serial diluted in appropriate medium and added to cells in triplicate (2 plates). DMSO was added to control wells at a final concentration of 1%. After 72 h incubation in the presence of compound, confluent cells were assayed for growth proliferation with CellTiter 96® AQueous One Solution Cell Proliferation Assay (MTS) (Promega) according to the manufacturer's protocol. Plates were read at 490 nm on a microplate reader, and IC$_{50}$ values were determined as the percentage of compound-treated cell growth to control cell growth. HCC cells—one hour after plating HCC cells onto 96-well plates, compound or vehicle (DMSO) was added to the desired concentrations, keeping DMSO at 0.5%. At indicated time points, cell viability was assayed using the CellTiter 96® Non-Radioactive Cell Proliferation Assay (MTT) (Promega).

TUNEL Assays.

HCC cells were plated 24 h prior to incubation with FQI1. At the indicated time points, cells were analyzed using the FragEL™ DNA fragmentation kit (Calbiochem) according to the manufacturer's protocol. Flow cytometry was performed using a FACS caliber (Becton Dickinson) and analyzed with Cell Quest software.

Materials And Methods (for Examples 4 and 5)

All $^1$H NMR, and $^{13}$C NMR spectra were recorded using Varian 400 (93.94 kG, 1H 400 MHz) or Varian 500 (70.5 kG, $^{13}$C 196 MHz) spectrometers at ambient temperature in CDCl$_3$. Chemical shifts are reported in parts per million as follows: chemical shift, multiplicity (s=singlet, d=doublet, t=triplet, q=quartet, m=multiplet, br=broad), coupling constant, and integration. Infrared spectra were recorded on a Nicolet Nexus 670 FT-IR ESP spectrophotometer. Optical rotations were recorded on a Rudolph Autopol II Polarimeterand were reported as [α]D (concentration). Analytical thin layer chromatography was performed using EMD 0.25 mm silica gel 60-F plates. Flash column chromatography was performed on Sorbent Technologies 60 Å silica gel. Chiral HPLC analysis was performed using an Agilent 1100 series HPLC with a diode array detector. Chiralcel®OD (Chiral Technologies Inc., 24 cm×4.6 mm I.D.) column was used. UPLC/MS analysis was done on a Waters Acquity UPLC/MS with ELS Detection. Acrylic acids and amines were purchased from Alfa Aesar or Sigma Aldrich. Non-commercially available acrylic acids were synthesized through saponification of respective methyl esters following known literature procedure[1].

Example 1

Identification of Small-Molecule LSF Inhibitors.

The role of LSF in HCC (which is reported in Yoo et al., PNAS, 2010; 107; 8357-8362, which is incorporated herein in its entirety by reference) clearly demonstrates that LSF inhibitors are prime candidates for the treatment of hepatocellular carcinoma. Subsequent data suggest utility in other cancer indications, including but not limited to oligodendroglioma, meningioma, GBM, breast cancer, colon cancer, HNSCC, lung cancer (adrenocarcinomas and Small cell carcinomas), pancreas, ovary, thyroid, and undifferenated cells. In particular, the inventors demonstrate using an in vitro cell assay that the FQI1 and FQI2 compounds of Formulas (IV) and (V) respectively as disclosed herein can be used to inhibit the growth of a variety of cancers, as demonstrated from the Examples (see FIGS. 9 and 10). Accordingly, in some embodiments, a composition comprising any compound of formula (I) to (XXVI) can be used to inhibit the growth of a variety of cancers in a subject, for example, a cancer selected from one or more of kidney cancer, cancers of the hematopoietic system (e.g., blood cancers such as leukemia etc.), cancers of the endometrium (e.g., cervical cancer), breast cancer, cancers of the upper digestive tract, stomach cancer, ovarian cancer, lung cancers, liver cancers (e.g., HCC), and cancers of the small intestine.

Without wishing to be bound by theory, the transcription factor LSF, a member of a small family of transcription factors conserved throughout the animal kingdom[9], is ubiquitously expressed in mammalian tissues and cell lines[10]. LSF activity is tightly controlled as cells progress from the quiescent state into DNA replication (G0 to S)[11,12], and it is required for efficient progression of cells through the G1/S transition[6,7]. Although LSF protein levels are usually constant, with its activity modified instead by post-translational control, LSF protein levels were previously discussed to be highly upregulated in tumor cells, particularly in HCC cell lines[8,13]. These elevated LSF levels were shown to promote oncogenesis in the HCC cells, leading to the search for specific small molecule inhibitors of this transcription factor.

Until recently, transcription factors, were generally considered to be un-druggable, in particular their specific DNA-binding activities. However, such inhibitors are now being identified for an increasing number of transcription factors[14], with some targeting oligomerization domains, and others directly targeting specific DNA-interaction surfaces. LSF is predominantly dimeric in solution, but tetrameric upon interacting specifically with DNA sites[15-17], potentially permitting inhibition by either mode.

Herein, the inventors were provided with the results of a screen of 110,000 commercially available compounds using a fluorescence polarization assay to identify compounds that inhibit LSF-binding to DNA in vitro. Small-molecule compounds that inhibit LSF transcriptional activity in tissue culture cells were identified, including multiple quinolinones. This led to the inventors synthesizing quinolinones, of which examples are shown in FIG. 1. The initial set of inhibitors were additionally screened for specificity using an electrophoretic mobility shift assay (EMSA), testing the ability to prevent specific DNA-binding of LSF, but not of three other transcription factors (Sp1, Oct, and E2F1). Positive compounds from the screen (personal communication of B. Andrews and L. Briggs, Sierra Sciences, Inc.) included 4-aryl-3,4-dihydroquinolin-2(1H)-ones as competent LSF inhibitors.

Figure 3A:
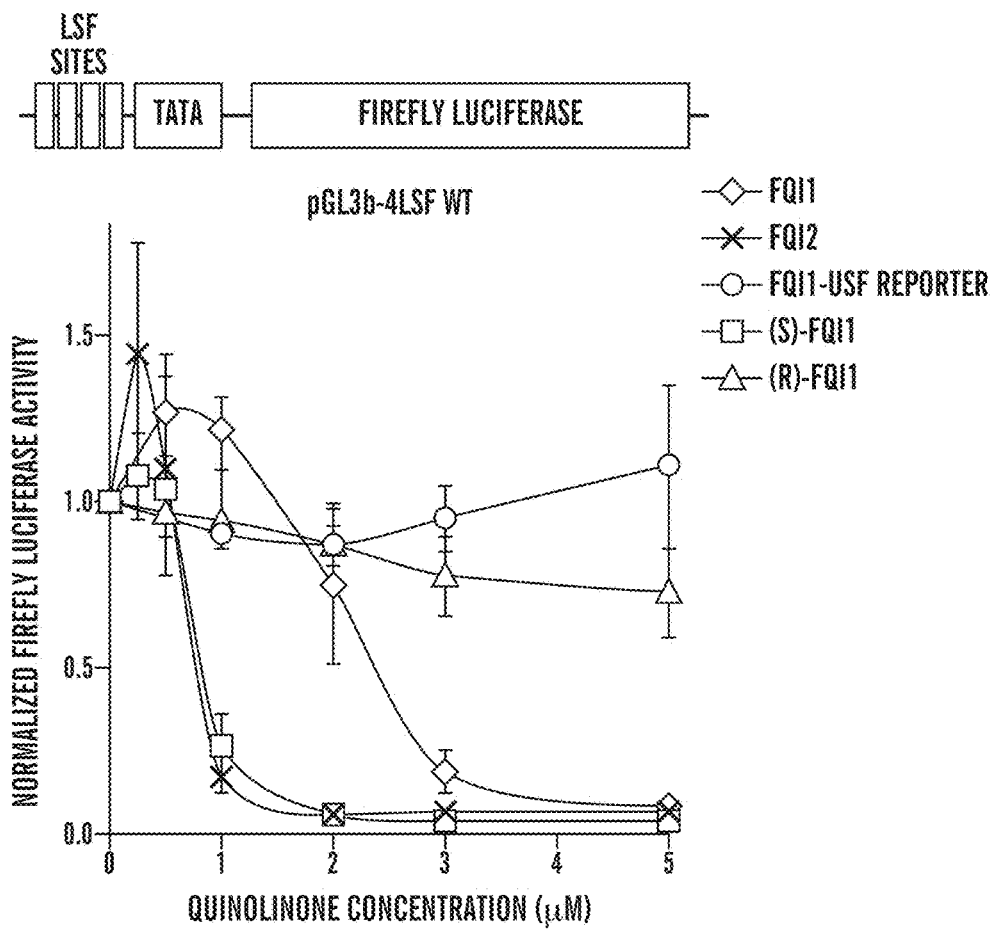
FIGS. 3A-3D show that FQI compounds inhibit LSF transcriptional activation and DNA-binding.
Figure 6:
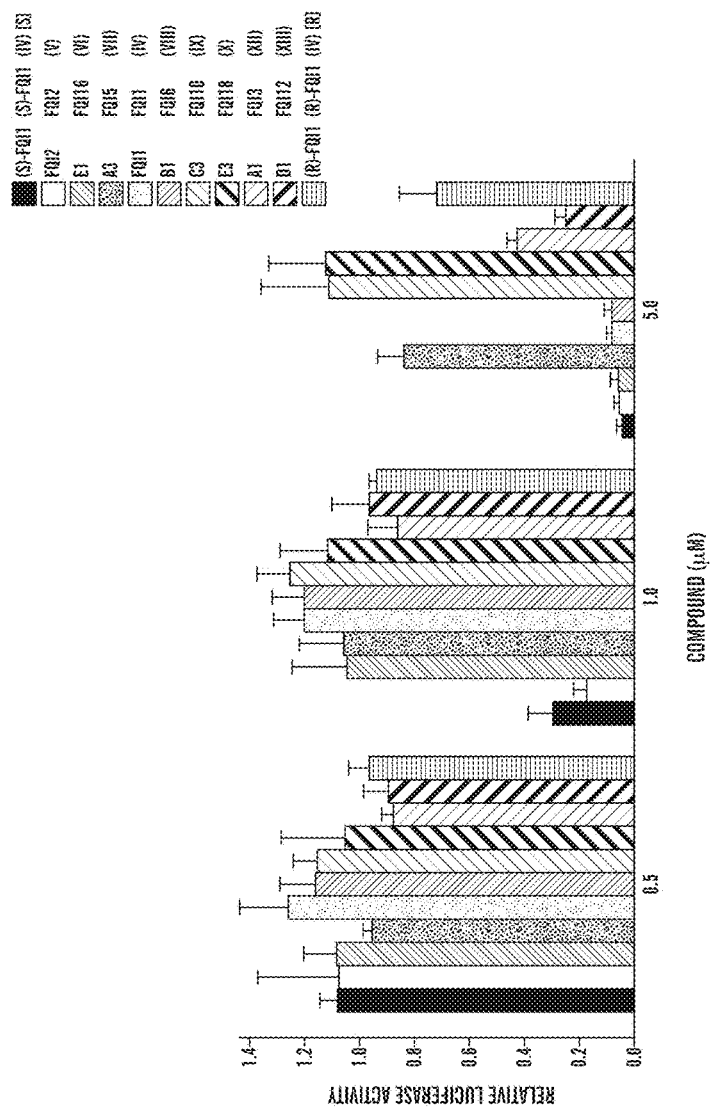
FIG. 6 shows that the potent antiproliferative FQIs in NIH 3T3 cells also inhibit LSF transcriptional activity. Dual luciferase reporter assays demonstrate the relative degrees of inhibition of LSF transactivation in NIH 3T3 cells. Compounds were assayed for 0.5, 1.0 and 5.0 μM to facilitate comparisons. Shown are averages of three independent experiments. Error bars represent SEM.

A LSF-dependent luciferase reporter assay was used to confirm whether these compounds would inhibit LSF activity in a cellular context, and identified that all hits in the initial screen were also positive. Thus, a collection of compounds based on this structure was prepared[18] (FIG. 1) and a subset of the compounds (Formula IV to X, and XII to XIII) were evaluated using the luciferase reporter assay in NIH 3T3 cells (FIG. 6). The factor quinolinone inhibitor 1 (FQI1, (Formula IV), FIG. 1) was identified as the most active compound from this initial collection, which has a chemical name is 8-(2-ethoxyphenyl)-7,8-dihydro-[1,3]dioxolo[4,5-g]quinolin-6(5H)-one. The concentration at which LSF transactivation was inhibited 50% was approximately 2.4 µM (FIG. 3A) Inhibition of transcriptional activation was specific to LSF, for example, transactivation of a USF-dependent reporter by USF was unaffected by addition of FQI1 (Formula IV) (FIG. 3A).

Figure 2A:
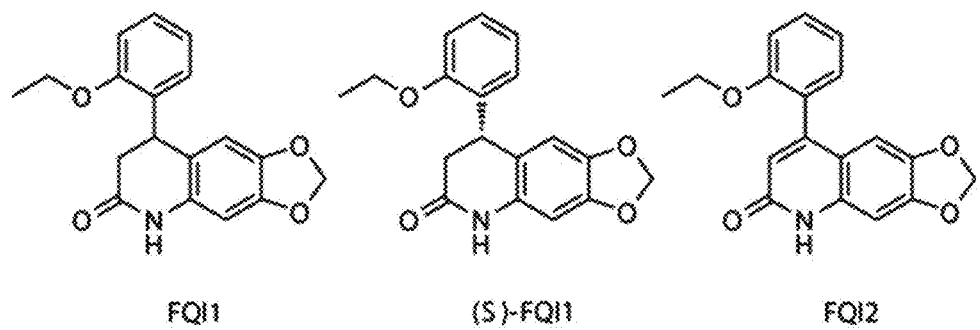
FIGS. 2A-2B shows the structures of LSF inhibitors of structures of FQI1 (Formula IV) and FQI2 (Formula V).
Figure 2B:
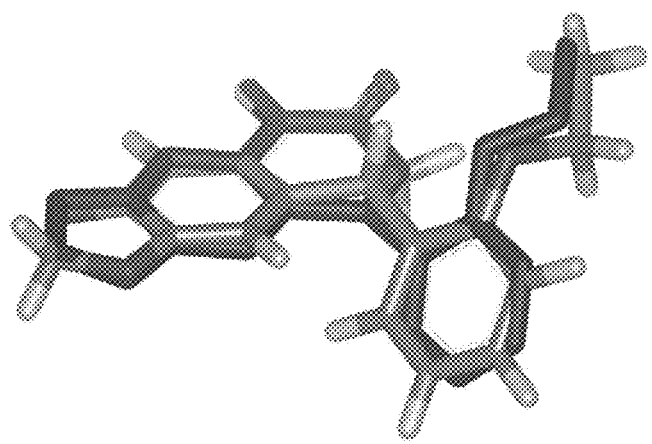

Using FQI1's structure as a starting framework, it was sought to determine whether inhibition of LSF was unique to the racemate or if an achiral quinolinone could function as a competent inhibitor, or if restricting the movement of the aryl substitution altered the molecules potency against LSF. First, FQI1 [Formula (IV)] was separated by chiral chromatography to the corresponding (R)- and (S)-enantiomers (Formula (S)-IV); and Formula (R)-IV) (FIG. 1). Assessment in the luciferase reporter assay demonstrated that the (R)-FQI1 (Formula (R)-IV) was much less active than the racemate while (S)-FQI1 (Formula (S)-IV) was approximately 3-fold more active (FIG. 3A, Table 3). Without wishing to be bound by the theory, it was reasoned that the achiral quinolin-2(1H)-one FQI2 (Formula V) can adopt similar conformations as the chiral counterparts[19] (FIG. 2B), thereby being a competent inhibitor. Indeed the activity of FQI2 (Formula V) against LSF in the transactivation assay proved to be as effective as the (S)-enantiomer.

Figure 3B:
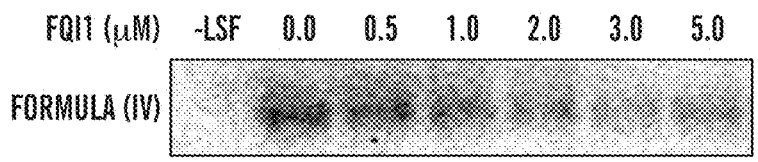
Figure 3C:
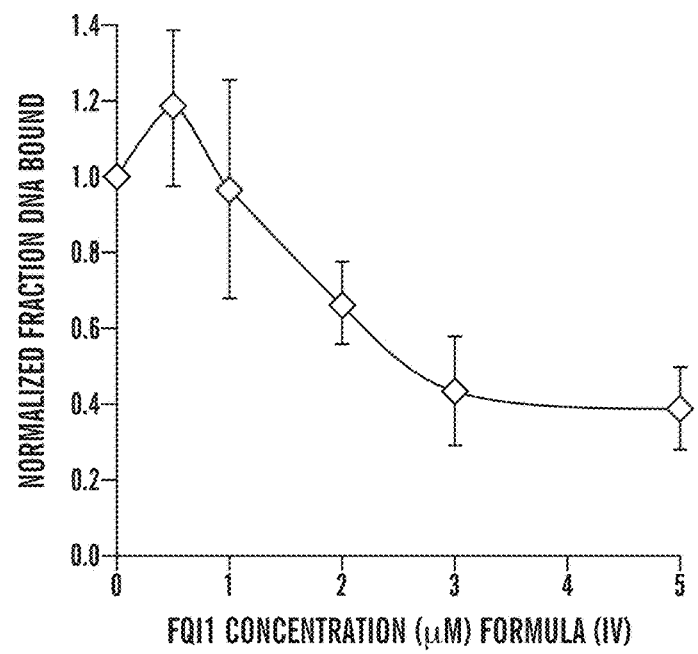
Figure 3D:
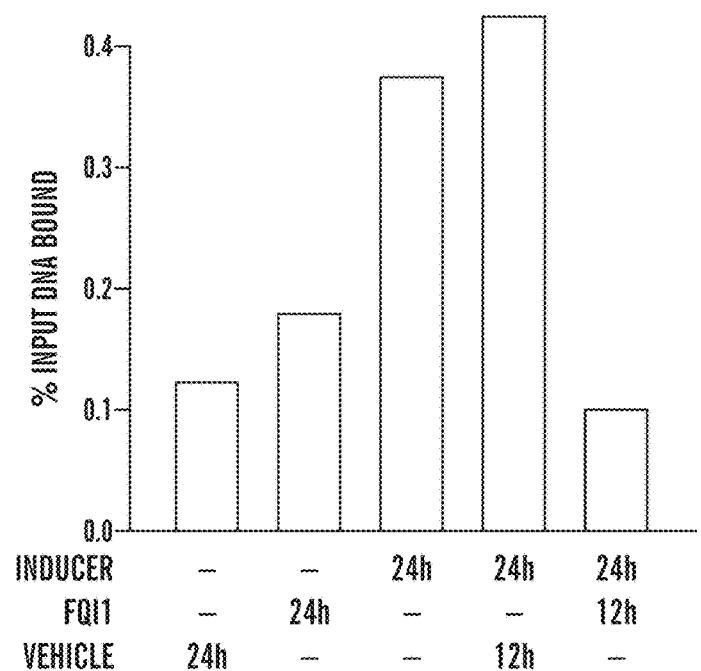

An unanticipated result from the LSF-dependent reporter assays was that the potent FQIs reproducibly stimulated LSF transcriptional activity at low concentrations, followed by sharp inhibition. Since the DNA-binding moiety of LSF is tetrameric, the inventors assessed if starting at sub-saturating levels, binding of FQIs to LSF monomers results in conformational changes that enhance LSF activity. Only at saturating levels of FQIs is LSF activity then ablated. Modulation of LSF DNA-binding by FQI1 (Formula IV) was also observed in electrophoretic mobility shift assays in vitro (FIG. 3B, 3C). Both initial enhancement at low concentrations and inhibition at higher concentrations were observed. These results mirrored the concentration-dependent effects of FQI1 (Formula IV) on LSF transactivation, although the extent of inhibition of DNA-binding in vitro was not as pronounced as inhibition of activity in the cell-based reporter assay. Thus, we tested effects of FQI1 (Formula IV) on binding of LSF to an endogenous cellular target promoter by chromatin immunoprecipitation. Binding of an inducible HA-tagged LSF to the promoter of POLA1, encoding the catalytic subunit of DNA polymerase α, was efficiently blocked by FQI1 (FIG. 3D).

TABLE 3

Comparison of inhibitor concentrations for cell proliferation and LSF-dependent reporter assays for FQI compounds with $GI_{50}$ <50 µM.

| Compound | $IC_{50}$ (µM) LSF-dependent reporter assat NIH 3T3 | $GI_{50}$ (µM) NIH 3T3 |
| --- | --- | --- |
| FQI2 (Formula V) | 0.8 | 0.71 ± 0.13 |
| (S)-FQI1 (Formula (S)-IV) | 0.8 | 1.1 ± 0.4 |
| FQI16 (Formula VIII) | 2-4* | 2.3 ± 0.5 |
| FQI3 (Formula XII) | 3-5* | 2.6 ± 0.5 |
| FQI1 (Formula IV) | 2.4 | 3.0 ± 0.9 |
| FQI12 (Formula XIII) | 3-4* | 4.0 ± 0.8 |

*represents values given as a range, due to the limited number of concenrations tested (see FIG. 6).

Example 2

Antiproliferative Activities of Inhibiting LSF with FQI1 and FQI2.

Given previous discussions that LSF activity is essential for G1/S progression[6,7], cell proliferation assays were conducted to characterize the antiproliferative properties of inhibiting LSF with the identified quinolinone inhibitors. The lead compound, FQI1 (formula IV), inhibited NIH 3T3 fibroblasts, HeLa S3 cells, and A549 cells at 50% inhibitory concentrations of 3.0, 0.79, and 6.3 µM ($GI_{50}$'s) respectively (Table 4).

TABLE 4

Growth-inhibitory activities of FQI compounds in different cell lines

| Compound | GI$_{50}$ (μM) | | |
|---|---|---|---|
| | NIH/3T3 | HeLa | A549 |
| FQI1 (Formula IV) | 3.0 ± 0.85 | 0.79 ± 0.04 | 6.3 ± 1.1 |
| (R)-FQI1 (Formula (R)-IV) | 45 ± 7 | 8.0 ± 1.0 | 18 ± 3.2 |
| (S)-FQI1 (Formula (S)-IV) | 1.1 ± 0.41 | 0.30 ± 0.03 | 3.0 ± 1.3 |
| FQI2 (Formula V) | 0.71 ± 0.13 | 0.40 ± 0.04 | 1.9 ± 0.9 |

Consistent with the observations in the luciferase reporter assay, the (R)-enantiomer was almost 10 times less active, whereas the (S)-enantiomer was determined to be at least twice as active against each cell line. Similarly, the achiral quinolinone inhibitor FQI2 (Formula V) was determined to be as active as (S)-FQI1 (Formula (S)-IV) at inhibiting cell growth. Strikingly, the half maximal concentrations for growth inhibition of NIH 3T3 cells matched, within experimental error, the half maximal concentrations for inhibition of LSF transcriptional activity (2.4 μM, 0.8 μM, and 0.8 μM), measured by the luciferase reporter assay also in NIH 3T3 cells (Table 4 and FIG. 3A). The structure activity relationships determined by the luciferase reporter assay and antiproliferative activities are consistent with these observations. This concordance demonstrates that the antiproliferative properties of these compounds are due directly to inhibition of LSF.

To test whether the antiproliferative effects resulted from specific or broad target specificity, GI$_{50}$ values from all the FQI analogs, containing combinations of peripheral structural variations, were compared Changes resulting from each modification were consistent overall, in multiple cell lines. The high degree of specificity inferred from the remarkably concordant structure activity relationships suggested that the FQI antiproliferative phenotypes were a consequence of targeting a single, or highly related, molecular target(s). Furthermore, the strong correlation between concentrations that inhibit cell proliferation and LSF transactivation indicated that the biological target is almost certainly the LSF family of transcription factors.

FQI1 (Formula IV) was evaluated as a part of the NIH Molecular Libraries Initiative as a member of the Small Molecule Repository screened in the Probe Production Network. A search in PubChem (CID 656346) indicated that as of 22 Sep. 2010, FQI1 (Formula IV) had been assayed in 465 assays and determined to be active in 19 of those assays. Three of these 19 assays were confirmed activities in antiproliferative assays performed at the Burnham Center for Chemical Genomics (AID's 430, 431, 620). Although these activities were confirmed, no inhibitory concentrations were reported, nor did FQI1 (Formula IV) lead to a probe series. Further, these NIH studies do not teach or describe FQI1 (Formula IV) or FQI2 (Formula V) as a LSF inhibitor, or can be used to inhibit cancer cell growth.

Example 3

Effect of FQI1 on Inhibition of HCC Cell Proliferation.

Figure 4A:
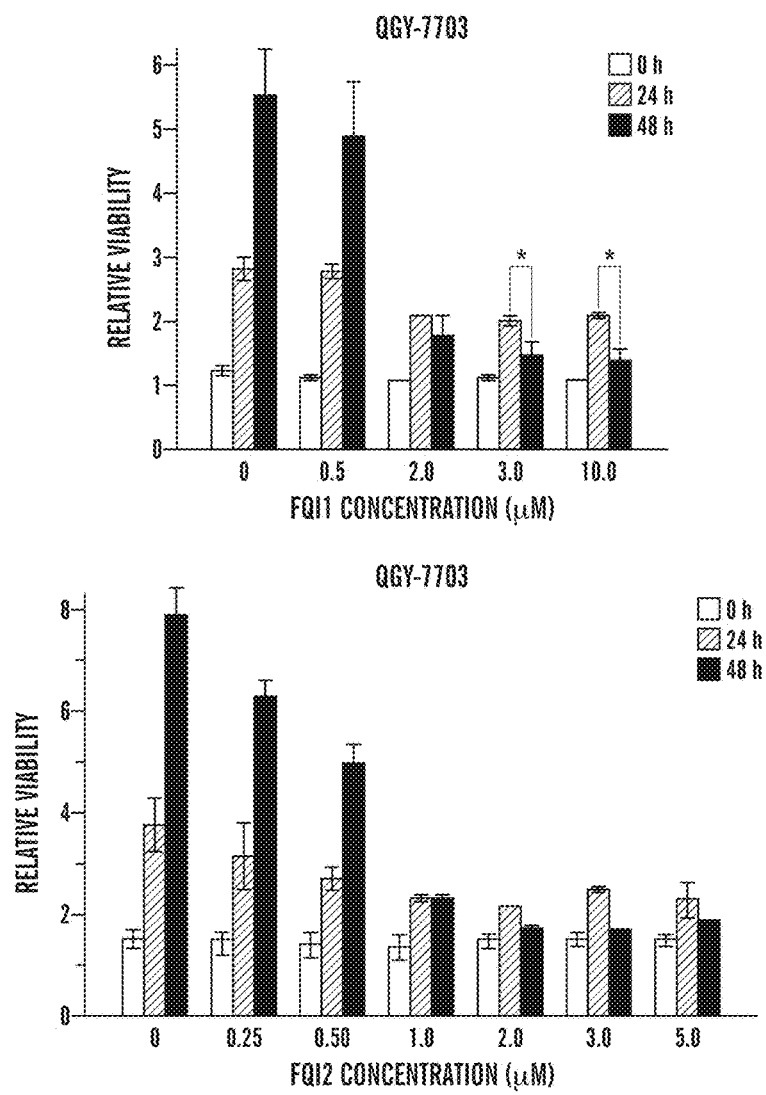
FIGS. 4A-4C shows in vitro growth inhibition and induction of apoptosis in HCC cells, but not hepatocytes, by FQI compounds.
Figure 4B:
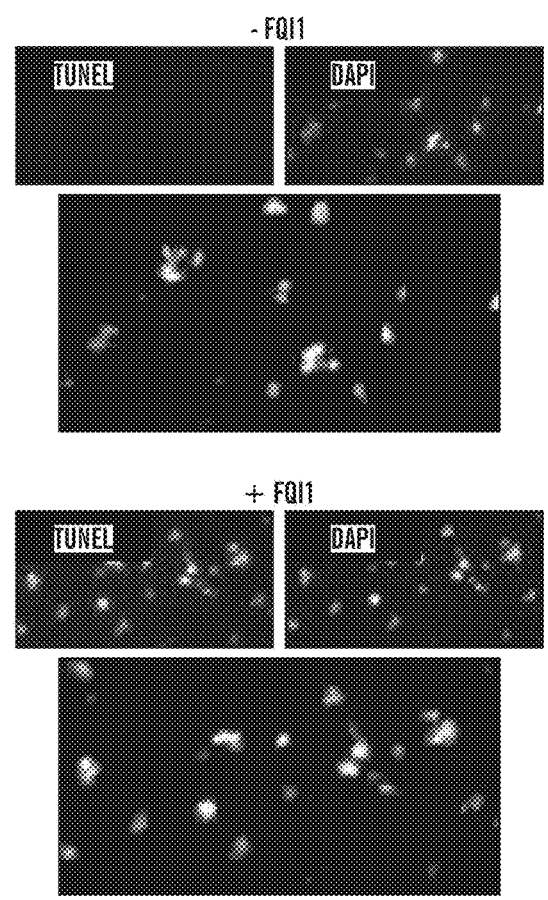
Figure 4C:
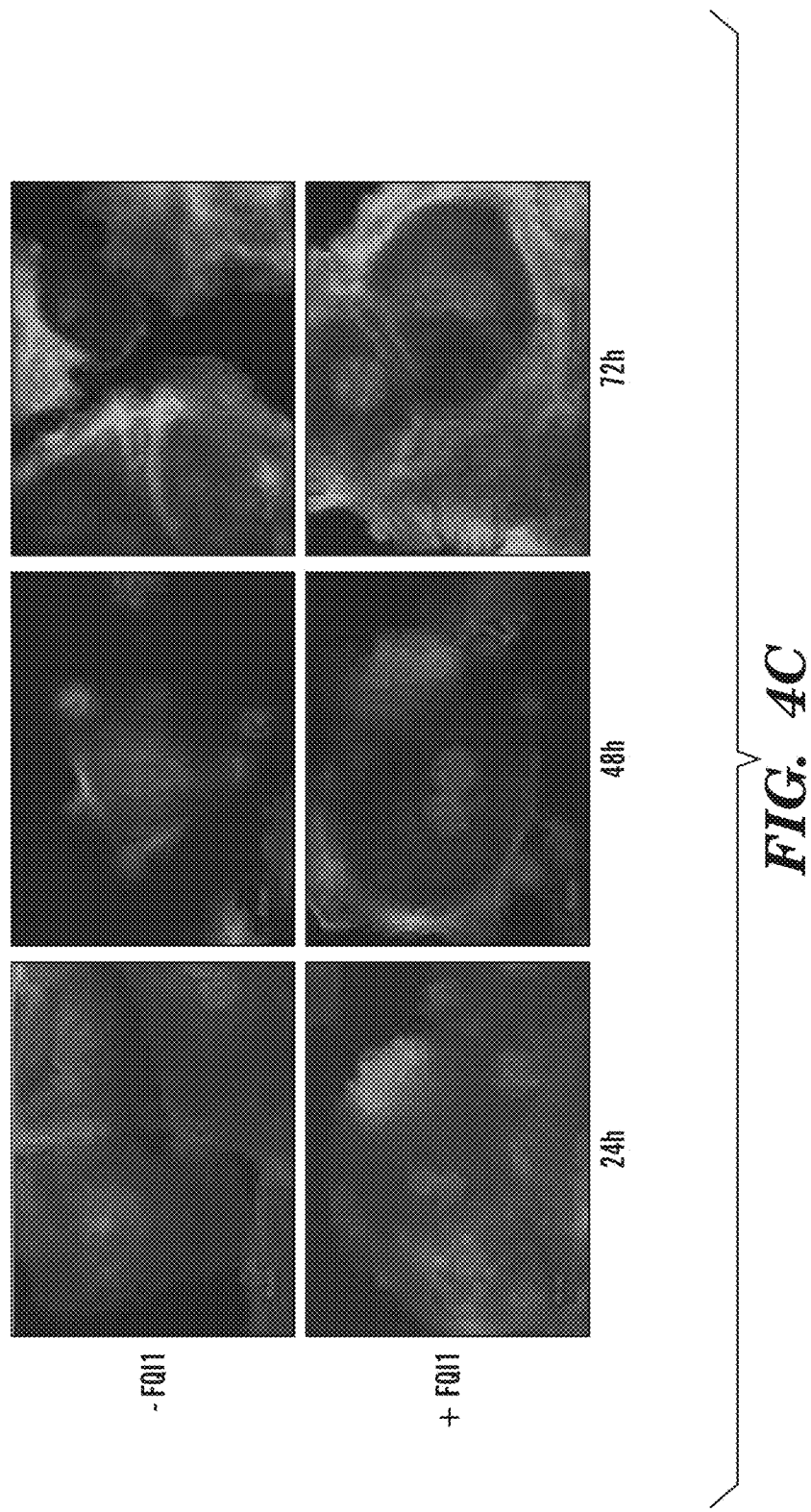
Figure 5A:
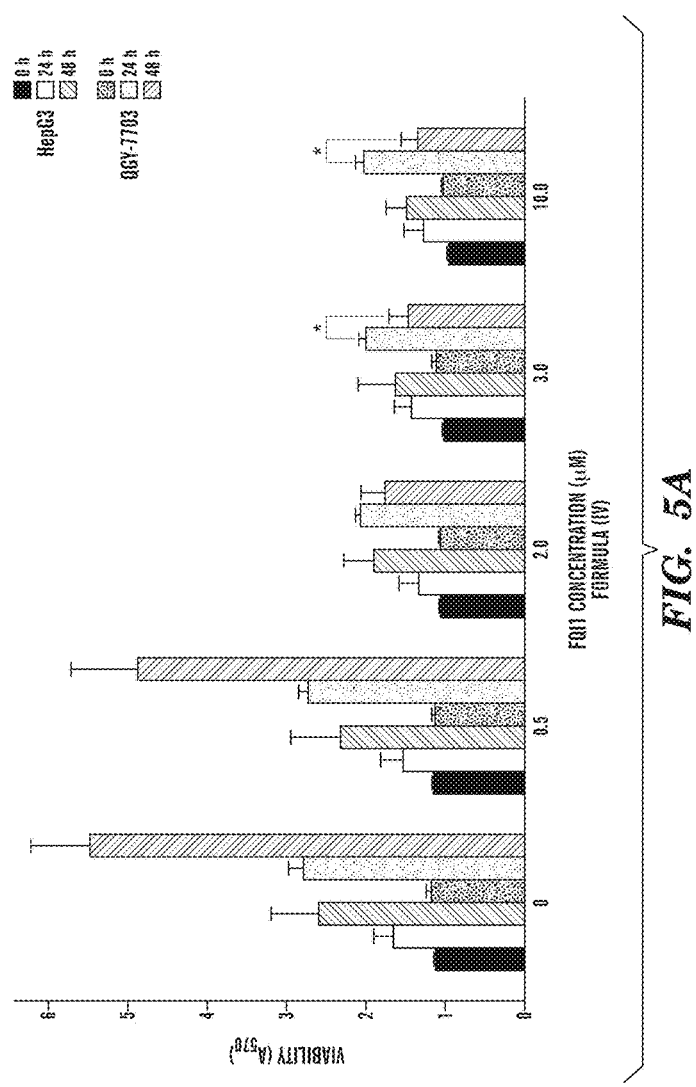
FIGS. 5A-5B shows induction of apoptosis in vitro in aggressive HCC cells (QGY-7703), but not in HepG3 cells, by LSF inhibitors.
Figure 5B:
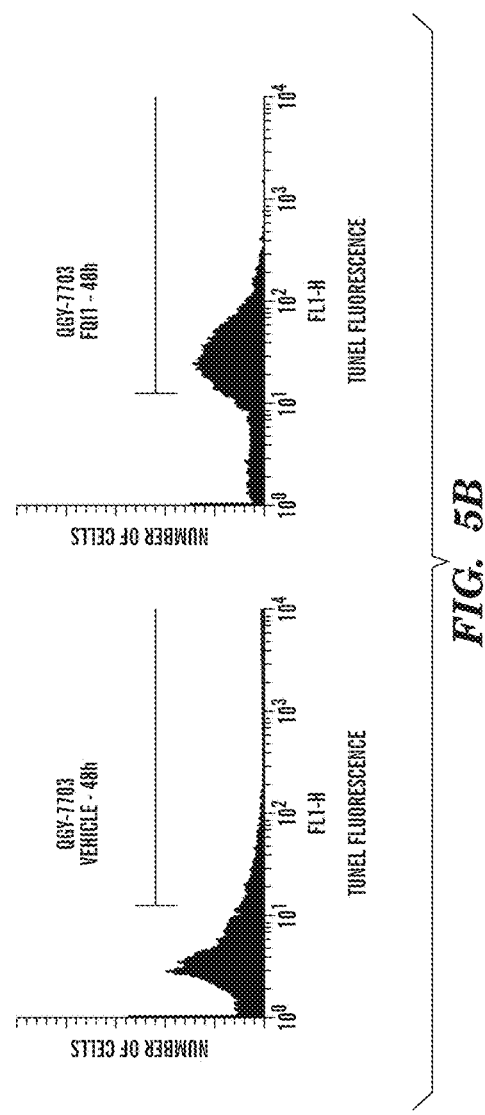
Figure 7:
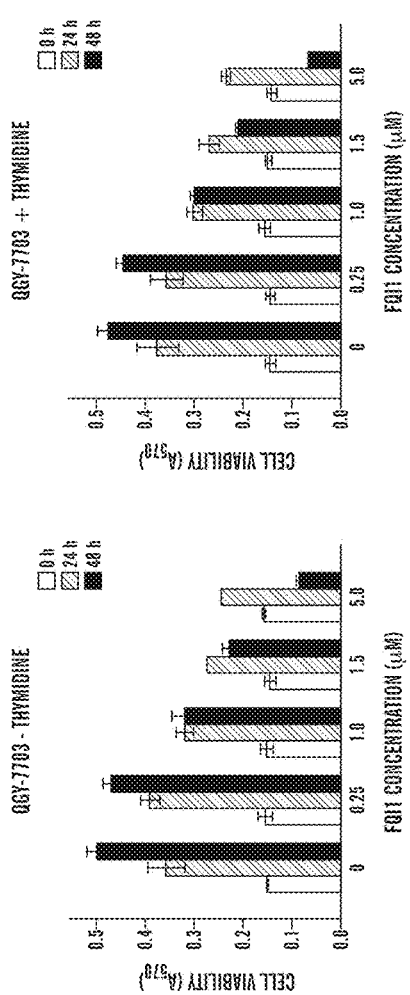
FIG. 7 shows FQI1-treated cell viability profiles are not affected by exogenous thymidine. QGY-7703 cells were treated with increasing concentrations of FQI1 over a two-day timecourse, in the presence or absence of 20 μM thymidine. Shown is a single experiment, performed in triplicate. Error bars represent standard deviation of the replicates.

The effect of LSF small molecule inhibitors on growth properties of HCC cells, in which LSF overexpression is oncogenic[8], was assessed. Two cell lines were assayed: QGY-7703, an aggressive HCC cell line that expresses LSF at highly elevated levels, and HepG3, a non-tumorigenic cell line that expresses LSF only at moderate levels[8]. These cells were used in earlier Examples in demonstrating the oncogenic properties of LSF: expression of a dominant negative mutant of LSF in QGY-7703 cells is sufficient to reduce cell growth in vitro and in xenograft models, and expression of LSF in HepG3 cells is sufficient to enhance cell growth and induce tumorigenic ability in xenografts. In cell viability (MTT) assays, both FQI1 (Formula IV) and FQI2 (Formula V) decreased overall cellular proliferation of QGY-7703 cells (FIG. 4A). Subsequent studies performed by the inventors in collaboration with other scientists demonstrated similar growth inhibition for other HCC lines with elevated levels of LSF (e.g., Huh7, data not shown). These data are consistant with growth inhibition observed by the inventors in NIH 3T3, HeLa and A549 cells in Example 2 and 7. It was discovered that specifically in the QGY-7703 cells, cell viability dropped between 24 and 48 hours of incubation after treatment with FQI1 (Formula IV) (FIG. 4A). This decrease in HCC cell viability was observable at 2 μM FQI1, and was statistically significant at higher concentrations of inhibitor (3 and 10 μM; P<0.05). In contrast, although HepG3 cell proliferation was also inhibited by FQI compounds, cell viability never decreased over time. These discoveries demonstrated that the QGY-7703 cells can be "addicted" to the elevated activity of LSF, therefore leading to cell death upon LSF inhibition, and this was verified by a flow cytometric TUNEL assay, in which massive apoptosis (averaging 90%) was observed at 10 μM FQI1 (Formula IV), with lower extents of DNA nicks observed per cell at 2 μM (FIG. 4B). In contrast to the aggressive QGY-7703 cells, HepG3 cells were not TUNEL-positive under these conditions, consistent with their non-tumorigenic properties and lower expression levels of LSF. It was previously discussed that inhibition of LSF by high expression of dominant negative LSF in murine fibroblasts or human prostate cancer cells can cause apoptosis in S phase, due substantially to blocking expression of thymidylate synthase. However, in the QGY-7703 cells, incubation with thymidine to overcome cellular dependence on thymidylate synthase did not affect the decreased viability upon FQI treatment (FIG. 7, indicating that blockage of additional LSF target genes or regulated pathways can contribute to the cell death. Finally, the inventors assessed whether FQI1 (Formula IV) affected normal hepatocytes. No growth consequences or toxicity were observed in primary non-dividing mouse hepatocytes (FIG. 4D), demonstrating specificity of FQI1 growth consequences to oncogenic cells. In particular, the inventors studies with compounds of Formula (I) to (XXVI) in cell assays in vitro revealed that there are very low or no toxic side effects of these compositions in primary cells, in contrast to effects on multiple immortalized or tumorigenic cell lines. (data not shown).

Example 4

Use of the FQI1 Compound for Treatment of HCC in a Mouse In Vivo Model.

The inventors, in collaboration with other scientists performed in vivo experiments in a subcutaneous xenograft model, where mice with small QGY-7703-derived tumors were given multiple, spaced intraperitoneal injections of FQI1 (Formula IV) over a 2 week period, followed by an additional 2-weeks prior to analysis. These collaborative data revealed that there was a remarkable decrease in tumor growth, as measured by the endpoint tumor volumes and weights, and of vascularity, in the mice injected with FQI1 (Formula IV), as measured by endpoint tumor volumes (data not shown; ~9 fold), and tumor weights, and by the degrees of vascularity (data not shown). Further, these collaborative data revealed that the general toxicity of the FQI1 (Formula IV) compound was not evident in the inhibitor-treated animals, as assayed by lack of changes in body weight, feeding, grooming, posture, and general behavior, as well as hematoxylin and eosin staining of liver, lung, heart, intestine, kidney, spleen and stomach tissue. When the endpoint tumors were analyzed by immunofluorescence, tumors from the FQI1-treated mice expressed LSF at similar levels to those of control mice. However, expression of osteopontin, whose gene is activated directly by LSF[8], was abolished by FQI1 treatment, as was expression of Ki-67, indicative of the replicative capacity of the tumors (data not shown). These collaborative results demonstrate the in vivo inactivation or inhibition of LSF by FQI1 (Formula IV) treatment, of LSF activities as both a transcription factor and a proliferation driver. In contrast to the dramatic effects on tumor growth, no general toxicity was evident in the inhibitor-treated animals, as assayed by lack of changes in body weight, feeding, grooming, posture, and general behavior, as well as hematoxylin and eosin staining of multiple tissues (data not shown), and levels of liver enzymes and protein in the blood (data not shown).

Hepatocellular carcinoma (HCC) is characterized by late stage diagnosis and a poor prognosis for treatment, usually consisting of surgical resection of the tumor and chemotherapy[1-3]. Currently, the only approved treatment for primary malignancies is sorafenib, a receptor tyrosine kinase and Raf inhibitor originally developed for primary kidney cancer that is also marginally effective for HCC, increasing survival by 2-3 months as a single treatment. Inhibition of oncogenic kinases using small molecules has underscored the therapeutic benefit of oncogene addiction[4,5], in which primary cancers are uniquely dependent on an oncogene for continued cell survival. It was previously discussed that the transcription factor LSF, that mediates G1/S progression in multiple cell types[6,7], can function as an oncogene for HCC[8]. However, it does not teach or describe inhibition of the transcriptional activity of LSF with small-molecule inhibitors for treatment of cancer, e.g., HCC. The invention herein has demonstrated that a family of small molecules that inhibit proliferation of a number of cancer cell lines specifically target the DNA-binding and corresponding transcriptional activities of LSF. The LSF inhibitors rapidly induce apoptosis in an aggressive HCC cell line in vitro and significantly inhibit tumor growth in a mouse xenograft model, with no observable general toxicity.

In one embodiment, the FQI family of quinolones was identified herein as therapeutic compounds of formulas (I) to (XXVI) for inhibition of the ubiquitously expressed transcription factor LSF, leading to their antiproliferative consequences. In addition, the inventors discoveries of the ability of these LSF inhibitors of formulas (I) to (XXVI) to cause apoptosis in aggressive HCC cells demonstrate that the exciting therapeutic possibility of oncogene addiction to LSF in cancers, e.g., hepatocellular carcinoma. It was previously discussed, in mouse xenograft assays, that LSF was both sufficient (in HepG3 cells) and necessary (in QGY-7703 cells) for aggressive tumor growth. In addition, in human patient HCC samples expression levels of LSF correlate with increased stage and decreased differentiation state of disease[8]. While the current therapeutic treatment options for HCC are limited, the invention disclosed herein teaches that the FQI compounds described herein are promising candidates for chemotherapeutic intervention and pharmaceutical development for HCC treatment. Further, the discovery of overexpression of LSF in cancer indications other than HCC demonstrates an oncogenic function of LSF in diverse other cancers (data not shown) Thus, without wishing to be bound by the theory, it is reasoned that the small-molecule LSF inhibitors disclosed herein can also be an effective therapeutic for treatment of various cancers.

Example 5

General Procedure for Synthesis of Isoquinolinones.

Synthesis of FQI1 (8-(2-ethoxyphenyl)-7, 8-dihydro-[1,3]dioxolo[4,5-g]quinolin-6(5H)-one) (Formula IV)

To a flame-dried 25 mL round bottom flask equipped with stir bar and back filled with argon was added 7.5 mL dimethyl formamide, 134 mg (0.7 mmol) 2-ethoxycinnamic acid, and 306 mg HATU (0.81 mmol, 1.15 equiv). Reaction was allowed to stir at room temperature for 1 hour and then to it was added 244 μL DIPEA (1.4 mmol, 2.0 equiv) and 112 mg methylenedioxle aniline (0.735 mmol, 1.05 equiv). Reaction was allowed to stir at room temperature for 3 hours and then to it was added 25 mL EtOAc and 25 mL water. Organic layer was then separated and aqueous layer was washed with EtOAc (2×25 mL). Organic layers were combined and washed with brine, dried over sodium sulfate and collected via filtration. Ethyl acetate solution was then concentrated onto silica gel and purified via column chromatography with eluant 50:50 hexane:EtOAc. Fractions with desired material present as seen by UV were collected and concentrated to give 230 mg desired acrylamide (84% yield). Material was then used without further purification. To an 8 mL microwave reaction tube was added 230 μmol acrylamide (70 mg) and 4 mL trifluoroacetic acid. The reaction was run under microwave conditions at 70° C. and 200 W power for 30 minutes. Vessel was removed from microwave reactor and allowed to cool to room temperature. The crude reaction mixture was then transferred to a 50 mL round bottom flask and placed in an icebath. To it was added 2 mL $CH_2Cl_2$ and 15 mL saturated sodium bicarbonate with stirring (portion wise, 3×5 mL), followed by extraction with EtOAc (2×10 mL). Organic layers were separated and combined then dried over sodium sulfate. The EtOAc was separated by filtration and concentrated under reduced pressure using a rotary evaporator onto silica gel. The crude material was then purified via flash column chromatography over silica gel with 6:4 hexanes:EtOAc as the eluent to yield 8-(2-ethoxyphenyl)-7,8-dihydro-[1,3]dioxolo[4,5-g]quinolin-6(5H)-one (60 mg, 193 μmol).

Spectral Data of Isoquinolinones

FQI1: 8-(2-ethoxyphenyl)-7,8-dihydro-[1,3]dioxolo[4,5-g]quinolin-6(5H)-one (Formula IV)

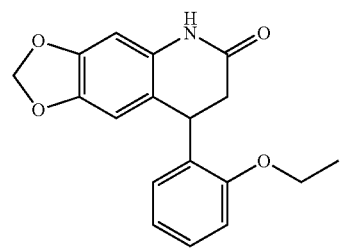 [SMILES: CCOc1ccccc1C1CC(=O)Nc2cc3c(cc21)OCO3]

$^1$H NMR (400 MHz, CHLOROFORM-d) δ ppm 1.34 (t, J=7.03 Hz, 3H), 2.72-2.92 (m, 2H), 3.95-4.04 (m, 2H), 4.53 (t, J=6.64 Hz, 1H), 5.84 (s, 2H), 6.32 (s, 1H), 6.40 (s, 1H), 6.73-6.78 (m, 2H), 6.81 (d, J=8.60 Hz, 1H), 7.13 (m, 1H), 8.03 (br. s., 1H). $^{13}$C NMR (126 MHz, CHLOROFORM-d) δ ppm 14.88 (s) 35.69 (s) 36.72 (s) 63.51 (s) 97.80 (s) 101.15 (s) 111.40 (s) 118.68 (s) 120.57 (s) 128.19 (s) 128.29 (s) 129.74 (s) 131.80 (s) 143.57 (s) 146.98 (s) 156.16 (s) 171.72 (s) FTIR CM$^{-1}$3208, 2982, 2895, 1677, 1482, 1233, 1039. Low Res MS: Calculated Formula Weight $(C_{18}H_{17}NO_4)$=311.3. Observed M+1 ion=312.

FQI3: 8-(2-Butoxyphenyl)-7,8-dihydro-[1,3]dioxolo[4,5-g]quinolin-6(5H)-one (Formula XII)

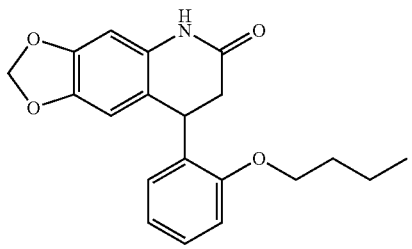 [SMILES: CCCCOc1ccccc1C1CC(=O)Nc2cc3c(cc21)OCO3]

Compound was synthesized as described for FQI1 to give 44 mg desired isoquinolinone after flash column chromatography. $^1$H NMR (400 MHz, CHLOROFORM-d) δ ppm 0.95 (t, J=7.62 Hz, 3H) 1.43 (m, 2H) 1.75 (m, 2H) 2.82 (dd, J=16.26, 6.89 Hz, 1H) 2.95 (dd, J=16.26, 6.89 Hz, 1H) 3.91-4.07 (m, 2H) 4.57 (t, J=6.74 Hz, 1H) 5.90 (s, 2H) 6.44 (s, 1H) 6.77-6.91 (m, 2H) 7.14-7.23 (m, 1H) 7.72 (br. s., 1H). $^{13}$C NMR (126 MHz, CHLOROFORM-d) δ ppm 13.84 (s) 19.34 (s) 31.35 (s) 35.98 (s) 36.70 (s) 67.56 (s) 97.49 (s) 101.18 (s) 108.45 (s) 111.34 (s) 118.84 (s) 120.50 (s) 128.24 (s) 129.51 (s) 131.60 (s) 143.59 (s) 146.97 (s) 156.29 (s) 170.96 (s). FTIR CM$^{-1}$3213, 3065, 2958, 2930, 1676, 1483, 1386, 1242, 1038. Low Res MS. Calculated formula weight $(C_{20}H_{21}NO_4)$=339.1, Observed M+1 ion=340.

FQI4: 8-(2-butoxyphenyl)-2,2-difluoro-7,8-dihydro-[1,3]dioxolo[4,5-g]quinolin-6(5H)-one (Formula XIV)

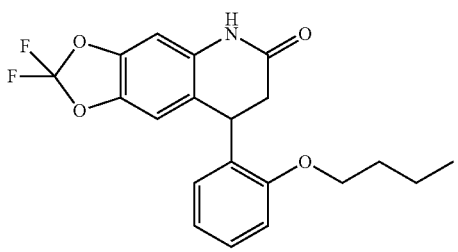 [SMILES: CCCCOc1ccccc1C1CC(=O)Nc2cc3c(cc21)OC(F)(F)O3]

Compound was synthesized as described for FQI1 to give 41 mg desired isoquinolinone after flash column chromatography. $^1$H NMR (500 MHz, CHLOROFORM-d) δ ppm 0.86 (d, J=14.92 Hz, 3H) 1.26-1.38 (m, 2H) 1.59-1.71 (m, 2H) 2.72-3.00 (m, 2H) 3.85-3.99 (m, 2H) 4.56 (t, J=7.34 Hz, 1H) 6.58 (s, 2H) 6.75-6.86 (m, 3H) 7.14-7.19 (m, 1H) 8.90 (br. s., 1H) $^{13}$C NMR (126 MHz, CHLOROFORM-d) δ ppm 13.74 (s) 19.27 (s) 31.27 (s) 36.23 (s) 36.36 (s) 67.58 (s) 97.98 (s) 109.38 (s) 111.55 (s) 120.67 (s) 121.68 (s) 128.40 (s) 128.71 (s) 131.71 (s) 133.31 (s) 133.75 (s) 139.71 (s) 142.97 (s) 156.28 (s) FTIR CM$^{-1}$3226, 3131, 2961, 2933, 1687, 1491, 1245, 121167. Low Res MS: Calculated Formula Weight $(C_{20}H_{19}F_2NO_4)$=375.4. Observed M+1 ion=376.

FQI5: 4-(2-butoxyphenyl)-6-methoxy-3,4-dihydro-quinolin-2(1H)-one (Formula VII)

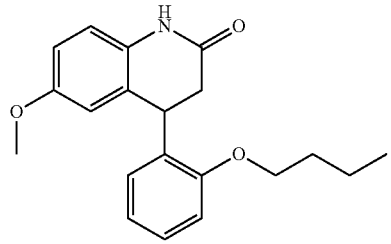 [SMILES: CCCCOc1ccccc1C1CC(=O)Nc2ccc(OC)cc21]

Compound was synthesized as described for FQI1 to give 33 mg desired isoquinolinone after flash column chromatography. $^1$H NMR: (500 MHz, CHLOROFORM-d) ppm 0.87 (t, J=7.46 Hz, 3H) 1.36 (m, 2H) 1.68 (m, 2H) 2.83 (m, 2H) 3.62 (s, 3H) 3.92 (m, 2H) 4.59 (t, J=6.97 Hz, 1H) 6.46 (d, J=2.20 Hz, 1H) 6.68 (m, 2H) 6.77 (m, 2H) 6.82 (d, J=8.07 Hz, 1H) 7.13 (m, J=8.30, 6.30, 2.80 Hz, 1H) 8.15 (br. s., 1H). $^{13}$C NMR (126 MHz, CHLOROFORM-d) δ ppm 13.84 (s) 19.33 (s) 31.35 (s) 36.44 (s) 36.66 (s) 55.51 (s) 67.58 (s) 111.36 (s) 112.83 (s) 114.14 (s) 116.12 (s) 120.53 (s) 127.79 (s) 128.26 (s) 128.49 (s) 129.32 (s) 131.01 (s) 155.81 (s) 156.33 (s). FTIR CM$^{-1}$3201, 3062, 2958, 2872, 1677, 1503, 1385, 1245. Low Res MS: Calculated Formula Weight $(C_{20}H_{23}NO_3)$=325.4. Observed M+1 ion=326.

FQI6: 8-(2-isobutoxyphenyl)-7,8-dihydro-[1,3]dioxolo[4,5-g]quinolin-6(5H)-one (Formula VIII)

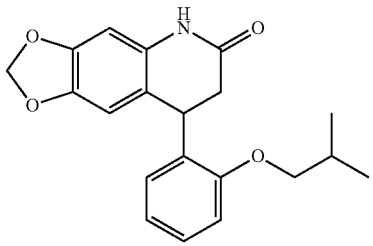

Compound was synthesized as described for FQI1 to give 45 mg desired isoquinolinone after flash column chromatography. $^1$H NMR 500 MHz, CHLOROFORM-d) δ ppm 0.93 (dd, J=6.72, 2.08 Hz, 6H), 2.01 (m, 1H), 2.72-2.94 (m, 2H), 3.62-3.75 (m, 2H), 4.51 (t, J=6.97 Hz, 1H), 5.82-5.85 (m, 2H), 6.31 (s, 1H), 6.37 (s, 1H), 6.74-6.78 (m, 2H), 6.80 (d, J=8.31 Hz, 1H), 7.11-7.16 (m, 1H), 7.84 (s, 1H) $^{13}$C NMR (126 MHz, CHLOROFORM-d) δ ppm 18.34 (s) 18.39 (s) 27.36 (s) 35.11 (s) 35.68 (s) 73.21 (s) 96.57 (s) 100.14 (s) 107.39 (s) 110.27 (s) 117.76 (s) 119.47 (s) 127.24 (s) 127.41 (s) 128.41 (s) 130.61 (s) 142.59 (s) 145.96 (s) 155.26 (s) 170.11 (s) FTIR CM$^{-1}$3213, 3118, 2961, 2910, 1679, 1483, 1240, 1037. Low Res MS: Calculated Formula Weight $(C_{20}H_{21}NO_4)$=339.4. Observed M+1 ion=340.

83

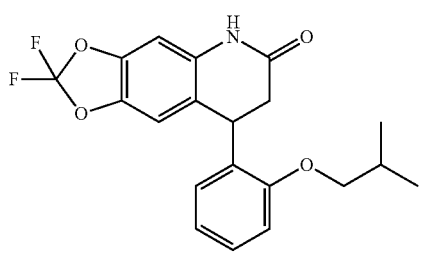 [SMILES: CC(C)COc1ccccc1C1CC(=O)Nc2cc3c(cc21)OC(F)(F)O3]

FQI7: 2,2-difluoro-8-(2-isobutoxyphenyl)-7,8-dihydro-[1,3]dioxolo[4,5-g]quinolin-6(5H)-one (Formula XIX)

Compound was synthesized as described for FQI1 to give 32 mg desired isoquinolinone after flash column chromatography. $^1$H NMR (500 MHz, CHLOROFORM-d) δ ppm 0.89 (dd, J=6.72, 4.77 Hz, 6H), 1.98 (m, 1H), 2.87 (m, 2H), 3.69 (m, 2H), 4.56 (m, 1H), 6.57 (m, 2H), 6.80 (m, 2H), 6.83 (d, J=8.07 Hz, 1H), 7.17 (m, 1H), 8.65 (s, 1H) $^{13}$C NMR (126 MHz, CHLOROFORM-d) δ ppm 18.26 (s) 18.31 (s) 27.30 (s) 35.23 (s) 35.47 (s) 73.27 (s) 97.13 (s) 108.30 (s) 110.49 (s) 119.65 (s) 120.58 (s) 127.42 (s) 127.46 (s) 127.70 (s) 128.66 (s) 130.69 (s) 132.36 (s) 132.73 (s) 138.72 (s) 141.97 (s) 155.25 (s) 170.55 (s) FTIR CM$^{-1}$ 3226, 3132, 2963, 2916, 1687, 1491, 1245, 1167, 1037. Low Res MS: Calculated Formula Weight $(C_{20}H_{19}F_2NO_4)$=375.4. Observed M+1 ion=376.

FQI8: 4-(2-isobutoxyphenyl)-6-methoxy-3,4-dihydroquinolin-2(1H)-one (Formula XVI)

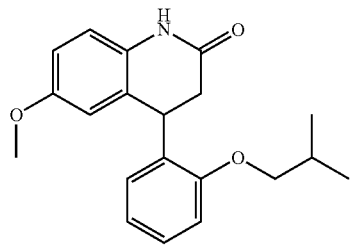 [SMILES: COc1ccc2c(c1)C(c1ccccc1OCC(C)C)CC(=O)N2]

Compound was synthesized as described for FQI1 to give 45 mg desired isoquinolinone after flash column chromatography. $^1$H NMR (400 MHz, CHLOROFORM-d) δ ppm 0.86-0.96 (m, 6H), 2.00 (m, 1H), 2.72-2.97 (m, 2H), 3.62 (d, J=1.17 Hz, 3H), 3.63-3.75 (m, 2H), 4.59 (t, J=7.03 Hz, 1H), 6.46 (s, 1H), 6.68 (s, 2H), 6.76 (d, J=4.69 Hz, 2H), 6.81 (d, J=8.21 Hz, 1H), 7.10-7.17 (m, 1H), 7.77 (br. s., 1H). $^{13}$C NMR (126 MHz, CHLOROFORM-d) δ ppm 18.33 (s) 18.37 (s) 27.35 (s) 35.62 (s) 54.51 (s) 73.24 (s) 110.28 (s) 111.87 (s) 113.07 (s) 115.20 (s) 119.51 (s) 126.69 (s) 127.27 (s) 127.56 (s) 128.22 (s) 130.01 (s) 154.81 (s) 155.30 (s) 169.77 (s) FTIR CM$^{-1}$ 3050, 2957, 1682, 1504, 1246, 1031. Low Res MS: Calculated Formula Weight $(C_{20}H_{23}NO_3)$=325.4. Observed M+1 ion=326.

84

FQI9: 8-(2-ethoxyphenyl)-2,2-difluoro-7,8-dihydro-[1,3]dioxolo[4,5-g]quinolin-6(5H)-one (Formula XX)

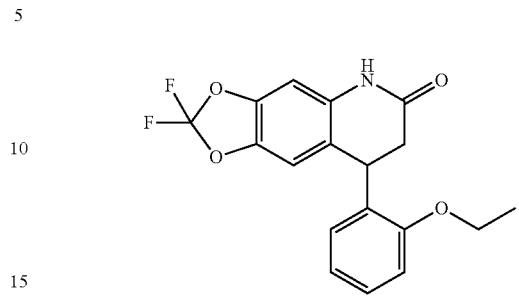

Compound was synthesized as described for FQI1 to give 55 mg desired isoquinolinone after flash column chromatography. $^1$H NMR (400 MHz, CHLOROFORM-d) δ ppm 1.39 (t, J=6.89 Hz, 3 H) 2.84 (dd, J=16.41, 6.45 Hz, 1H) 2.99 (dd, J=16.41, 7.62 Hz, 1H) 4.07 (m, 2H) 4.66 (t, J=6.89 Hz, 1H) 6.62 (s, 1H) 6.68 (s, 1H) 6.88 (m, 2H) 7.23 (m, 2H) 8.50 (br. s., 1H) $^{13}$C NMR (126 MHz, CHLOROFORM-d) δ ppm 14.81 (s) 35.94 (s) 36.28 (s) 63.56 (s) 97.99 (s) 109.46 (s) 111.59 (s) 120.71 (s) 121.64 (s) 128.20 (s) 128.66 (s) 128.68 (s) 133.37 (s) 139.68 (s) 142.98 (s) 156.13 (s) 171.16 (s) FTIR CM$^{-1}$3215, 3062, 2922, 1684, 1490, 1243, 1044. Low Res MS. Calculated Formula Weight $(C_{18}H_{15}F_2NO_4)$=347. Observed M+1 ion=348.

FQI10: 4-(2-ethoxyphenyl)-6-methoxy-3,4-dihydroquinolin-2(1H)-one (Formula IX)

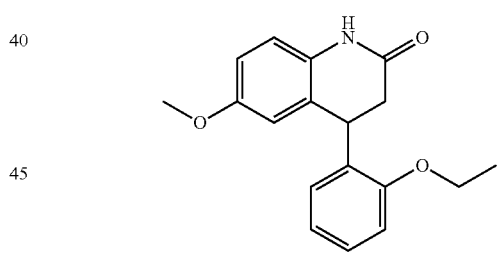

Compound was synthesized as described for FQI1 to give 59 mg desired isoquinolinone after flash column chromatography. $^1$H NMR (400 MHz, CHLOROFORM-d) δ ppm 1.40 (t, J=7.03 Hz, 3H) 2.84 (dd, J=16.70, 6.45 Hz, 1H) 2.96 (dd, J=16.41, 7.03 Hz, 1H) 3.70 (s, 3H) 4.08 (m, 2H) 4.68 (t, J=6.74 Hz, 1H) 6.56 (s, 1H) 6.74 (s, 2H) 6.83 (d, J=4.10 Hz, 2H) 6.88 (d, J=8.21 Hz, 1H) 7.20 (dt, J=8.42, 4.43 Hz, 1H) 7.73 (br. s., 1H). $^{13}$C NMR (126 MHz, CHLOROFORM-d) □ ppm 13.84 (s) 35.15 (s) 35.67 (s) 54.50 (s) 62.51 (s) 110.43 (s) 111.81 (s) 113.23 (s) 114.98 (s) 119.57 (s) 126.86 (s) 127.34 (s) 128.35 (s) 129.95 (s) 154.78 (s) 155.19 (s) 169.34 (s). FTIR CM$^{-1}$3198, 3062, 2976, 1674, 1505, 1243, 1039. Low Res MS. Calculated Formula Weight $(C_{18}H_{19}NO_3)$=297.3. Observed M+1 Ion=298.

FQI11: 4-(2-ethoxyphenyl)-5,6,7-trimethoxy-3,4-dihydroquinolin-2(1H)-one (Formula XXIII)

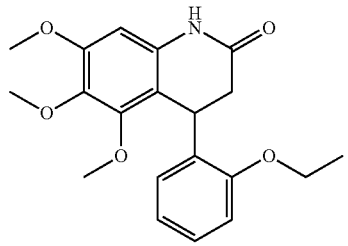 [SMILES: CCOc1ccccc1C1CC(=O)Nc2cc(OC)c(OC)c(OC)c21]

Compound was synthesized as described for FQI1 to give 40 mg desired isoquinolinone after flash column chromatography. $^1$H NMR (400 MHz, CHLOROFORM-d) δ ppm 1.47 (t, J=6.89 Hz, 3H) 2.86 (m, 2H) 3.56 (s, 3H) 3.80 (s, 3H) 3.87 (s, 3H) 4.10 (q, J=7.03 Hz, 2H) 4.91 (d, J=7.33 Hz, 1H) 6.17 (s, 1H) 6.56 (d, J=8.20 Hz, 1H) 6.70 (t, J=7.62 Hz, 1H) 6.83 (d, J=7.91 Hz, 1H) 7.12 (m, 1H) 7.72 (br. s., 1H) $^{13}$C NMR (126 MHz, CHLOROFORM-d) ppm 14.90 (s) 30.15 (s) 36.56 (s) 56.15 (s) 60.86 (s) 63.44 (s) 95.47 (s) 111.25 (s) 111.55 (s) 120.16 (s) 127.59 (s) 127.89 (s) 130.26 (s) 134.08 (s) 138.27 (s) 151.42 (s) 153.31 (s) 155.96 (s) 170.94 (s). FTIR CM$^{-1}$ 3058, 2975, 2935, 1684, 1490, 1244, 1116. Low Res MS. Calculated Formula Weight ($C_{20}H_{23}NO_5$)=357.4. Observed M+1 Ion=358.

FQI12: 8-(2-methoxyphenyl)-7,8-dihydro-[1,3]dioxolo[4,5-g]quinolin-6(5H)-one (Formula XIII)

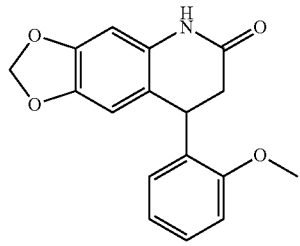 [SMILES: COc1ccccc1C1CC(=O)Nc2cc3c(cc21)OCO3]

Compound was synthesized as described for FQI1 to give 32 mg desired isoquinolinone after flash column chromatography. $^1$H NMR (400 MHz, CHLOROFORM-d) δ ppm 2.82 (dd, J=16.12, 6.74 Hz, 1H) 2.91 (dd, J=16.26, 6.59 Hz, 1H) 3.85 (s, 3H) 4.58 (t, J=6.59 Hz, 1H) 5.90 (s, 2H) 6.36 (s, 1H) 6.44 (s, 1H) 6.87 (m, 3H) 7.23 (m, 1H) 7.70 (br. s., 1H) $^{13}$C NMR (126 MHz, CHLOROFORM-d) δ ppm 34.61 (s) 35.70 (s) 54.26 (s) 96.63 (s) 100.17 (s) 107.37 (s) 109.59 (s) 117.67 (s) 119.74 (s) 127.20 (s) 128.55 (s) 130.69 (s) 142.58 (s) 146.00 (s) 155.77 (s) 170.19 (s). FTIR CM$^{-1}$ 3213, 2977, 2930, 1684, 1506, 1242, 1036. Low Res MS. Calculated Formula Weight ($C_{17}H_{15}NO_4$)=297.3. Observed M+1 Ion=298.

FQI13: 2,2-difluoro-8-(2-methoxyphenyl)-7,8-dihydro-[1,3]dioxolo[4,5-g]quinolin-6(5H)-one (Formula XXI)

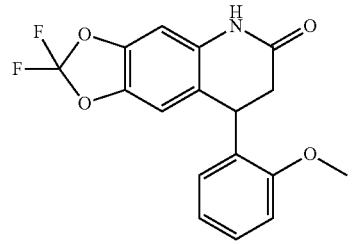 [SMILES: COc1ccccc1C1CC(=O)Nc2cc3c(cc21)OC(F)(F)O3]

Compound was synthesized as described for FQI1 to give 41 mg desired isoquinolinone after flash column chromatography. $^1$H NMR (400 MHz, CHLOROFORM-d) δ ppm 2.83 (dd, J=16.41, 6.15 Hz, 1H) 2.93 (dd, J=16.26, 7.18 Hz, 1H) 3.70 (s, 3H) 3.85 (s, 3H) 4.67 (t, J=6.59 Hz, 1H) 6.54 (s, 1H) 6.74 (s, 1H) 6.84 (m, 2H) 6.90 (d, J=8.20 Hz, 1H) 7.22 (dt, J=5.27, 2.93 Hz, 1H) 7.76 (br. s., 1H). $^{13}$C NMR (126 MHz, CHLOROFORM-d) ppm 35.87 (s) 36.28 (s) 55.31 (s) 98.02 (s) 109.40 (s) 110.82 (s) 120.92 (s) 121.56 (s) 128.16 (s) 128.73 (s) 131.71 (s) 133.40 (s) 139.70 (s) 143.01 (s) 156.77 (s) 171.11 (s). FTIR CM$^{-1}$ 3235, 3025, 2982, 2922, 1684, 1489, 1244, 1166. Low Res MS. Calculated Formula Weight ($C_{17}H_{13}F_2NO_4$)=333. Observed M+1 Ion=334.

FQI14: 6-methoxy-4-(2-methoxyphenyl)-3,4-dihydroquinolin-2(1H)-one (Formula XI)

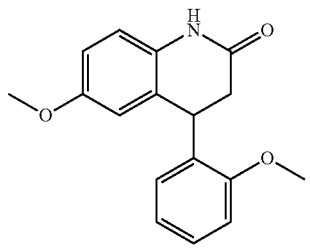

Compound was synthesized as described for FQI1 to give 48 mg desired isoquinolinone after flash column chromatography. $^1$H NMR (400 MHz, CHLOROFORM-d) δ ppm 2.85 (d, J=4.69 Hz, 2H) 3.57 (s, 3H) 3.80 (s, 3H) 4.89 (t, J=4.69 Hz, 1H) 6.56 (s, 1H) 6.74 (s, 2H) 6.83 (d, J=4.10 Hz, 2H) 6.88 (d, J=8.21 Hz, 1H) 7.20 (dt, J=8.42, 4.43 Hz, 1H) 7.73 (br. s., 1H). $^{13}$C NMR (126 MHz, CHLOROFORM-d) δ ppm 35.15 (s) 35.67 (s) 54.50 (s) 62.51 (s) 110.43 (s) 111.81 (s) 113.23 (s) 114.98 (s) 119.57 (s) 126.86 (s) 127.34 (s) 128.35 (s) 129.95 (s) 154.78 (s) 155.19 (s) 169.34 (s). FTIR CM$^{-1}$ 3255, 3044, 2934, 2915, 1683, 1506, 1242, 1110. Low Res MS. Calculated Formula Weight ($C_{17}H_{17}NO_3$) 283.3. Observed M+1 Ion=284.

FQI15: 5,6,7-trimethoxy-4-(2-methoxyphenyl)-3,4-dihydroquinolin-2(1H)-one (Formula XXIV)

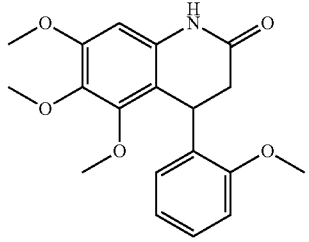

Compound was synthesized as described for FQI1 to give 35 mg desired isoquinolinone after flash column chromatography. $^1$H NMR (400 MHz, CHLOROFORM-d) δ ppm 2.85 (d, J=4.69 Hz, 2H), 3.57 (s, 3H), 3.80 (s, 3H), 3.87 (s, 3H), 3.89 (s, 3H), 4.89 (t, J=4.69 Hz, 1H), 6.18 (s, 1H), 6.58 (d, J=7.62 Hz, 1H), 6.72 (t, J=7.62 Hz, 1H), 6.86 (d, J=7.91 Hz, 1H), 7.15 (t, J=7.62 Hz, 1H), 7.98 (br. s., 1H) $^{13}$C NMR (126 MHz, CHLOROFORM-d) δ ppm 30.08 (s), 36.61 (s), 55.27 (s), 56.15 (s), 60.84 (s), 60.95 (s), 95.53 (s), 110.43 (s), 111.39 (s), 120.37 (s), 127.63 (s), 127.95 (s), 130.30 (s), 134.10 (s), 138.24 (s), 151.39 (s), 153.34 (s), 156.59 (s), 171.04 (s). FTIR CM$^{-1}$ 3058, 2975, 2935, 1684, 1490, 1244, 1116 Low Res MS. Calculated Formula Weight ($C_{19}H_{21}NO_5$)=343.4. Observed M+1 ion=344.

FQI16: 8-(2-propoxyphenyl)-7,8-dihydro-[1,3]dioxolo[4,5-g]quinolin-6(5H)-one (Formula VI)

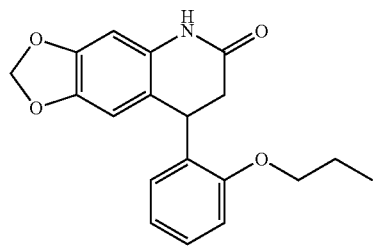 [SMILES: CCCOc1ccccc1C1CC(=O)Nc2cc3c(cc21)OCO3]

Compound was synthesized as described for FQI1 to give 41 mg desired isoquinolinone after flash column chromatography. $^1$H NMR (400 MHz, CHLOROFORM-d) δ ppm 0.94 (t, J=7.42 Hz, 3H), 1.74 (sxt, J=6.96 Hz, 2H), 2.72-2.93 (m, 2H), 3.80-3.96 (m, 2H), 4.53 (t, J=6.64 Hz, 1H), 5.84 (s, 2H), 6.31 (d, J=2.34 Hz, 1H), 6.39 (d, J=1.56 Hz, 1H), 6.73-6.79 (m, 2H), 6.81 (d, J=8.60 Hz, 1H), 7.08-7.17 (m, 1H), 7.83 (br. s., 1H). $^{13}$C NMR (126 MHz, CHLOROFORM-d) δ ppm 9.70 (s), 21.63 (s), 34.91 (s), 35.69 (s), 68.40 (s), 96.55 (s), 100.15 (s), 107.41 (s), 110.33 (s), 117.78 (s), 119.49 (s), 127.22 (s), 127.32 (s), 128.53 (s), 130.62 (s), 142.57 (s), 145.96 (s), 155.25 (s), 170.12 (s). FTIR CM$^{-1}$ 3211, 3116, 2966, 2878, 1678, 1483, 1239, 1038. Low Res MS. Calculated Formula Weight (C19H19NO4)=325.4. Observed M+1 ion=326.

FQI17: 2,2-difluoro-8-(2-propoxyphenyl)-7,8-dihydro-[1,3]dioxolo[4,5-g]quinolin-6(5H)-one (Formula XV)

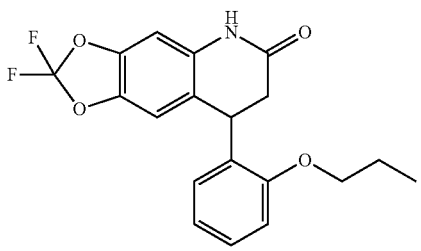 [SMILES: CCCOc1ccccc1C1CC(=O)Nc2cc3c(cc21)OC(F)(F)O3]

Compound was synthesized as described for FQI1 to give 45 mg desired isoquinolinone after flash column chromatography. $^1$H NMR (500 MHz, CHLOROFORM-d) δ ppm 0.91 (t, J=7.34 Hz, 3H), 1.67-1.76 (m, 2H), 2.74-2.98 (m, 1H), 3.82-3.96 (m, 2H), 4.58 (t, J=7.09 Hz, 1H), 6.54 (s, 1H), 6.60 (s, 1H), 6.78-6.82 (m, 2H), 6.84 (d, J=8.07 Hz, 1H), 7.15-7.19 (m, 1H), 8.27 (s, 1H). $^{13}$C NMR (126 MHz, CHLOROFORM-d) δ ppm 10.64 (s) 22.59 (s) 36.22 (s) 36.26 (s) 69.48 (s) 98.11 (s) 109.37 (s) 111.56 (s) 120.68 (s) 121.61 (s) 128.34 (s) 128.58 (s) 128.68 (s) 131.71 (s) 133.39 (s) 133.75 (s) 139.70 (s) 142.98 (s) 156.24 (s) 171.48 (s). FTIR CM$^{-1}$ 3226, 3131, 2969, 2934, 1688, 1491, 1246, 1167. Low Res MS: Calculated Formula Weight ($C_{19}H_{17}F_2NO_4$)=361.3. Observed M+1 ion=362.

FQI18: 6-methoxy-4-(2-propoxyphenyl)-3,4-dihydroquinolin-2(1H)-one (Formula X)

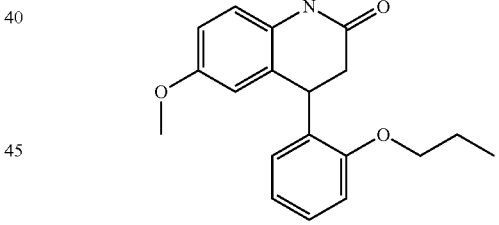

Compound was synthesized as described for FQI1 to give 43 mg desired isoquinolinone after flash column chromatography. $^1$H NMR (500 MHz, CHLOROFORM-d) δ ppm 0.92 (t, J=7.46 Hz, 3H), 1.73 (m, J=7.00, 7.00, 7.00, 7.00 Hz, 2H), 2.73-2.97 (m, 2H), 3.62 (s, 3H), 3.82-3.95 (m, 2H), 4.60 (t, J=6.85 Hz, 1H), 6.47 (d, J=1.96 Hz, 1H), 6.63-6.72 (m, 2H), 6.74-6.79 (m, 2H), 6.82 (d, J=8.07 Hz, 1H), 7.10-7.16 (m, 1H), 8.08 (br. s., 1H). $^{13}$C NMR (126 MHz, CHLOROFORM-d) δ ppm 10.70 (s), 22.65 (s), 36.40 (s), 36.66 (s), 55.52 (s), 69.44 (s), 111.38 (s), 112.86 (s), 114.15 (s), 116.13 (s), 120.54 (s), 127.78 (s), 128.26 (s), 128.47 (s), 129.33 (s), 131.01 (s), 155.81 (s), 156.31 (s). FTIR CM$^{-1}$ 3197, 3061, 2965, 2934, 1675, 1503, 1245, 1043. Low Res MS: Calculated Formula Weight ($C_{19}H_{21}NO_3$)=311.4.

FQI19: 8-(4-methoxyphenyl)-7,8-dihydro-[1,3]dioxolo[4,5-g]quinolin-6(5H)-one (Formula XVIII)

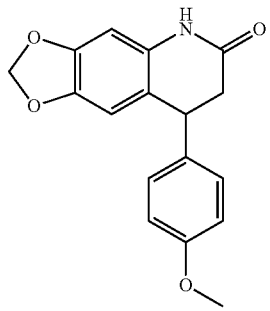 [SMILES: COc1ccc(C2CC(=O)Nc3cc4c(cc32)OCO4)cc1]

Compound was synthesized as described for FQI1 to give 53 mg desired isoquinolinone after flash column chromatography. $^1$H NMR (400 MHz, CHLOROFORM-d) δ ppm 2.76-2.90 (m, 13H), 3.79 (s, 3H), 4.09-4.16 (m, 1H), 5.90 (s, 2H), 6.37 (d, J=7.91 Hz, 2H), 6.86 (d, J=8.50 Hz, 2H), 7.09 (d, J=8.50 Hz, 2H), 7.86 (s, 1H). $^{13}$C NMR (126 MHz, CHLOROFORM-d) δ ppm 38.64 (s), 41.18 (s), 55.29 (s), 97.67 (s), 101.26 (s), 108.42 (s), 114.30 (s), 119.68 (s), 128.70 (s), 131.14 (s), 133.51 (s), 143.59 (s), 147.09 (s), 158.72 (s), 170.53 (s) FTIR CM$^{-1}$ 2918, 1638, 1481, 1252, 1036. Low Res MS: Calculated Formula Weight ($C_{17}H_{15}NO_4$)=297.3. Observed M+1 ion=298.

FQI20: 2,2-difluoro-8-(4-methoxyphenyl)-7,8-dihydro-[1,3]dioxolo[4,5-g]quinolin-6(5H)-one (Formula XXII)

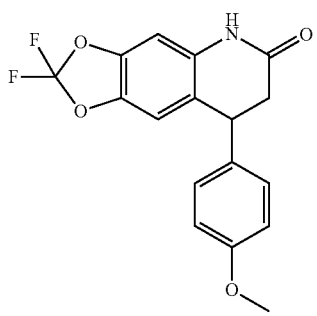 [SMILES: COc1ccc(C2CC(=O)Nc3cc4c(cc32)OC(F)(F)O4)cc1]

Compound was synthesized as described for FQI1 to give 41 mg desired isoquinolinone after flash column chromatography. $^1$H NMR (400 MHz, CHLOROFORM-d) δ ppm 2.78-2.93 (m, 2H), 3.80 (s, 3H), 4.19 (t, J=7.77 Hz, 1H), 6.59 (s, 1H), 6.66 (s, 1H), 6.88 (d, J=8.50 Hz, 2H), 7.09 (d, J=8.79 Hz, 2H), 9.02 (br. s., 1H). $^{13}$C NMR (126 MHz, CHLOROFORM-d) δ ppm 37.21 (s), 40.15 (s), 54.27 (s), 97.38 (s), 108.36 (s), 113.50 (s), 121.36 (s), 127.70 (s), 128.66 (s), 130.69 (s), 131.54 (s), 132.13 (s), 132.73 (s), 138.67 (s), 142.08 (s), 157.97 (s), 170.38 (s). FTIR CM$^{-1}$ 3228, 3002, 2911, 1685, 1490, 1251, 1168. Low Res MS: Calculated Formula Weight ($C_{17}H_{13}F_2NO_4$)=333.3. Observed M+1 ion=334.

FQI21: 6-methoxy-4-(4-methoxyphenyl)-3,4-dihydroquinolin-2(1H)-one (Formula XVII)

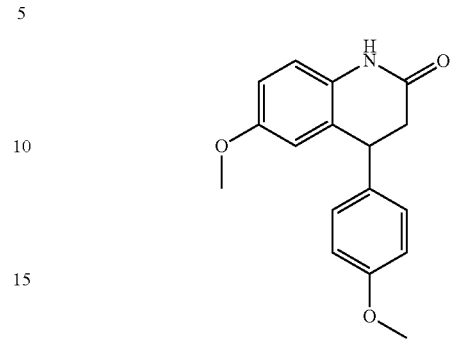

Compound was synthesized as described for FQI1 to give 41 mg desired isoquinolinone after flash column chromatography. $^1$H NMR (400 MHz, CHLOROFORM-d) δ ppm 2.83-2.91 (m, 2H), 3.69 (s, 3H), 3.79 (s, 3H), 4.20 (t, J=7.47 Hz, 1H), 6.47 (s, 1H), 6.69-6.79 (m, 2H), 6.86 (d, J=8.50 Hz, 2H), 7.10 (d, J=8.50 Hz, 2H), 8.30 (br. s., 1H). $^{13}$C NMR (126 MHz, CHLOROFORM-d) δ ppm 37.36 (s), 40.37 (s), 54.13 (s), 54.38 (s), 111.57 (s), 113.15 (s), 115.42 (s), 127.39 (s), 127.67 (s), 129.45 (s), 132.12 (s), 154.64 (s), 157.56 (s), 169.70 (s). FTIR CM$^{-1}$ 3204, 3063, 2957, 2835, 1678, 1505, 1248, 1036. Low Res MS: Calculated Formula Weight ($C_{17}H_{17}NO_3$)=283.3. Observed M+1 ion=284.

Example 6

Synthesis of FQI2 (Formula V).

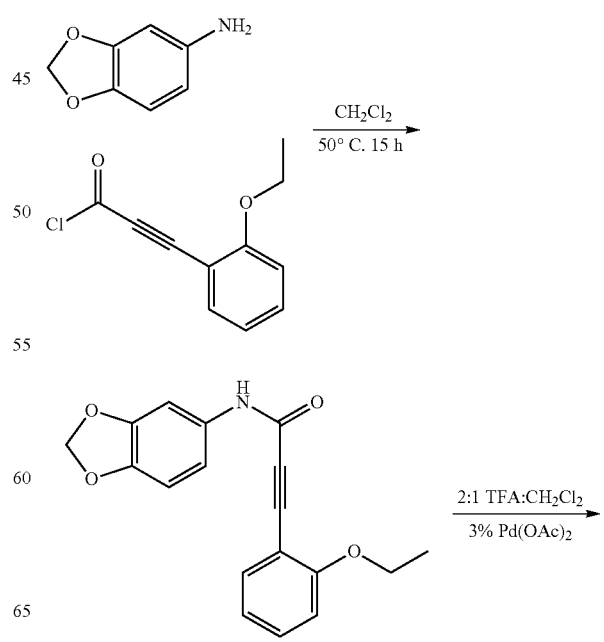

-continued

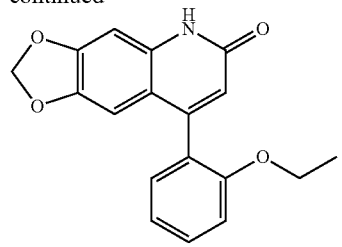

FQI2: 8-(2-ethoxyphenyl)-[1,3]dioxolo[4,5-g]quinolin-6(5H)-one (Formula V)

To a flame-dried 250 mL round bottom flask equipped with a stir bar was added 5 mmol (950 mg) 3-(2-ethoxyphenyl)propiolic acid, 100 mL toluene, and 7.5 mmol (1.5 mL) thionyl chloride. The reaction was heated to 85° C. and allowed to stir at this temp for 12 h and then cooled to room temperature. The solvent was removed under reduced pressure and the resulting crude material was then azeotroped (2×25 mL toluene) to remove excess thionyl chloride. The resulting material was dried under high vacuum for 2 hours and made into a 1.0 M solution in $CH_2Cl_2$. To a 25 mL round bottom flask fitted with stir bar and flame dried under vacuum was added 5 mL $CH_2Cl_2$, 1.0 mmol (1 mL, 1.0 M solution in $CH_2Cl_2$) acyl chloride and 1.1 mmol (151 mg) benzo[d][1,3]dioxol-5-amine. Reaction was brought to 50° C. and stirred at this temperature for 15 h. Reaction was cooled to room temperature, quenched by addition of 10 mL saturated sodium bicarbonate, extracted with EtOAc (2×10 mL), dried over sodium sulfate, filtered and concentrated in vaccuo. Crude material was then dissolved in minimal $CH_2Cl_2$ (5 mL) and poured into 20 mL ice cold hexane. N-(benzo[d][1,3]dioxol-5-yl)-3-(2-ethoxyphenyl)propiolamide precipitated from solution and was isolated via filtration, washed with ice cold diethyl ether (10 mL) and dried under high vacuum for 2 h to yield 309 mg of the desired propargyl amide. The resulting material was used without further purification. To a flame dried 10 mL round bottom flask fitted with stir bar was added 84 mg propargyl amide (0.270 mmol, 1 equiv), 500 uL $CH_2Cl_2$, 1 mL trifluoroacetic acid, and 3 mg $Pd(OAc)_2$ (0.01 mmol, 0.05 equiv). Reaction was allowed to stir at room temperature 2 hours and then quenched by addition of 10 mL saturated ammonium chloride, extracted with $CH_2Cl_2$ (3×10 mL), dried over sodium sulfate, $CH_2Cl_2$ isolated via filtration, concentrated onto silica gel and isolated via flash column chromatography over silica gel with 7:3 hexanes:EtOAc as the eluent to yield 8-(2-ethoxyphenyl)-[1,3]dioxolo[4,5-g]quinolin-6(5H)-one. Residual Pd was then scavenged by treating with MP-TMT resin (15 mg) in 5 mL THF for 24 hours at room temperature. Material was then filtered through a pad of celite, and celite washed with $CH_2Cl_2$ (2×10 mL). $CH_2Cl_2$ solution was then concentrated onto silica gel and purified via a second silica gel column with eluent 7:3 hexanes:EtOAc to give purified 8-(2-ethoxyphenyl)-[1,3]dioxolo[4,5-g]quinolin-6(5H)-one (65 mg, 232 μmol). The material was determined to be >95% pure by $^1$H NMR, $^{13}$C NMR, and HPLC-MS.

FQI2: 8-(2-ethoxyphenyl)-[1,3]dioxolo[4,5-g]quinolin-6(5H)-one (Formula V)

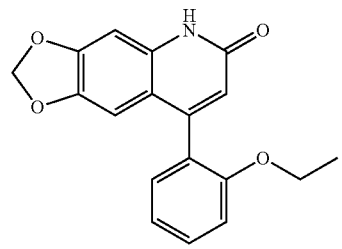

1H NMR (500 MHz, CHLOROFORM-d) δ ppm 1.12 (t, J=6.97 Hz, 3H), 3.95 (m, 2H), 5.91 (d, J=1.22 Hz, 2H), 6.47 (s, 1H), 6.55 (s, 1H), 6.90 (s, 1H), 6.95 (d, J=8.56 Hz, 1H), 6.99 (m, 1H), 7.15 (d, J=7.34 Hz, 1H), 7.35 (m, 1H), 12.98 (br. s., 1H). $^{13}$C NMR (126 MHz, CHLOROFORM-d) δ ppm 14.60 (s), 63.96 (s), 96.33 (s), 101.62 (s), 104.48 (s), 112.29 (s), 114.87 (s), 118.72 (s), 120.69 (s), 126.86 (s), 130.08 (s), 130.48 (s), 135.55 (s), 144.13 (s), 150.43 (s), 150.99 (s), 155.71 (s), 164.40 (s). FTIR $CM^{-1}$ 2978, 2886, 1653, 1487, 1251, 1037. Low Res MS: Calculated Formula Weight $(C_{18}H_{15}NO_4)$=309.3. Observed M+1 ion=310.

Prior to running in assays, material was digested in 10 mL of a 4.5% $HNO_3$ and 0.5% HF aqueous solution then analyzed via ICP-MS for Pd concentration (6.8 ppm observed).

Chiral HPLC Separation of FQI1 to (R)-FQI1 and (S)-FQI1

To a 1.5 mL HPLC vial was added 10 mg of FQI1 and 1 mL of an 8:1:1 mixture of Hexane:Isopropanol:Chloroform. Solution was sonicated for 30 minutes to ensure complete dissolution. An Agilent 1100 Series HPLC fitted with analytical ChiralCel OD column (10μ particle size, 4.6 mm ID, 250 mm length) was primed for 30 minutes with a 20% isopropanol in Hexane mixture at a flow rate of 1 mL/min. After priming, 100 μL of the FQI1 solution was injected onto the column and allowed to separate. Starting from the 9 minute mark, a number of collections were made from the end of the column into a series of 1.5 mL HPLC vials every 15 seconds (24 vials in all with ~250 μL collected in each vial). After the 15 minute mark, the vials were diluted to 750 μL with a 20% isopropanol in hexane mixture and analyzed for enantiopurity. All vials containing material with an er of >95:5 were collected and combined. This procedure was repeated 20 times and produced 7 mg of (S)-FQI1 (retention time of 9.6 minutes, $[α]_D^{23}$=−8.5° (c=0.47, $CHCl_3$) er>99:1) and 10 mg of (R)-FQI1 (retention time of 10.6 minutes, $[α]_D^{23}$=+10.5 (c=0.67, $CHCl_3$) er>99:1).

(S)-FQI1. Retention time 9.6 minutes. (R)-FQI1. Retention time 10.6 minutes.

Optical Rotation and Determination of Absolute Stereochemistry of (S)-FQI1 and (R)-FQI1

(S)-FQI1 (Formula (S)-IV)

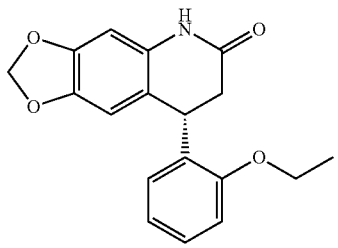

(-)-(S)-FQI1 [α]$_D^{23}$ = -8.5° (c = 0.47, CHCl$_3$, er = 99 :1)

Compounds known in the literature and used for comparative analysis of optical rotation. (Paquin, J. F., Stephenson, C. R., Defieber, C. & Carreira, E. M. Catalytic asymmetric synthesis with Rh-diene complexes: 1,4-addition of arylboronic acids to unsaturated esters. Org. Lett. 7, 3821-3824 (2005); Chen, G., Tokunaga, N. & Hayashi, T. Rhodium-catalyzed asymmetric 1,4-addition of arylboronic acids to coumarins: asymmetric synthesis of (R)-tolterodine. Org. Lett. 7, 2285-2288 (2005)

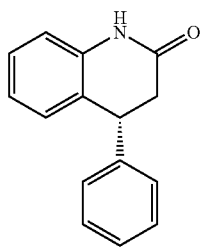

a

[α]$_D^{23}$ = -53.4°

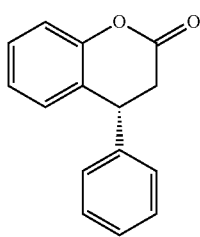

b

[α]$_D^{23}$ = -45.2°

(R)-FQI1 (Formula (R)-IV)

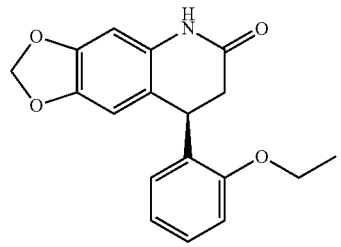

(+)-(R)-FQI1 [α]$_D^{23}$ = +10.5 (c = 0.67, CHCl$_3$, er = 99 :1)

Compounds known from the literature and used for comparative analysis of optical rotation. (Defieber, C., Paquin, J. F., Serna, S. & Carreira, E. M. Chiral [2.2.2] dienes as ligands for Rh(I) in conjugate additions of boronic acids to a wide range of acceptors. Org. Lett. 6, 3873-3876 (2004); Alper, H. & Dong, C. Enantioselective cyclocarbonylation of 2-vinylanilines to six-membered lactams. Tetrahedron: Asymmetry 15, 35-40 (2004).)

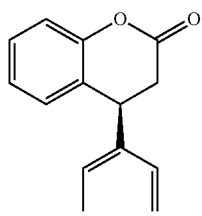

c

[α]$_D^{23}$ = +37.4

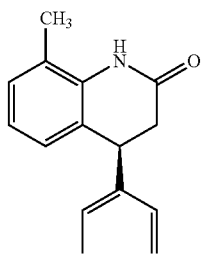

d

[α]$_D^{23}$ = +21.6

Example 7

Cell Growth Inhibition Assays.

Figure 8A:
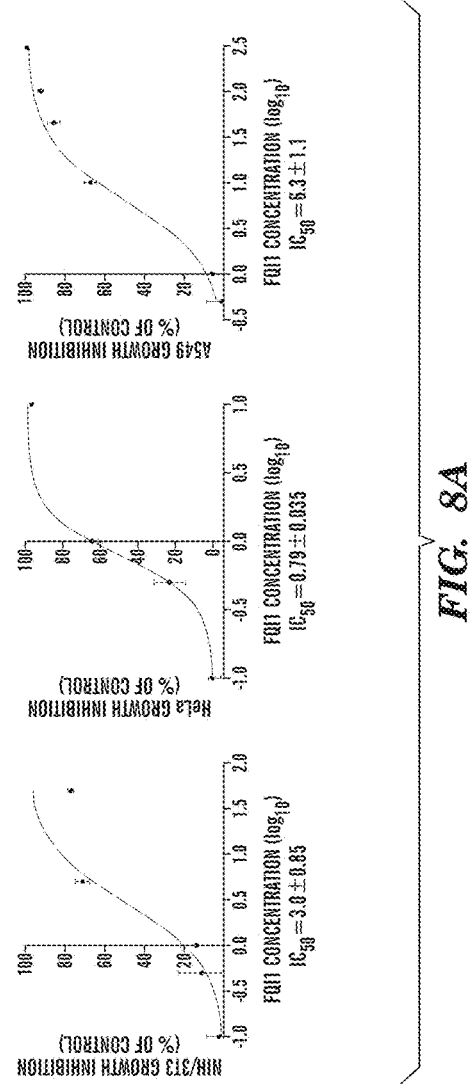
FIG. 8A-8Q show graphs of the growth inhibition (as % control) versus concentrations of different FQI ($log_{10}$) in three different cell lines (NIH 3T3, HeLa, A549) to determine $GI_{50}(IC_{50})$ values of inhibitors. All data are reported in micromolar (μM) concentrations.
Figure 8B:
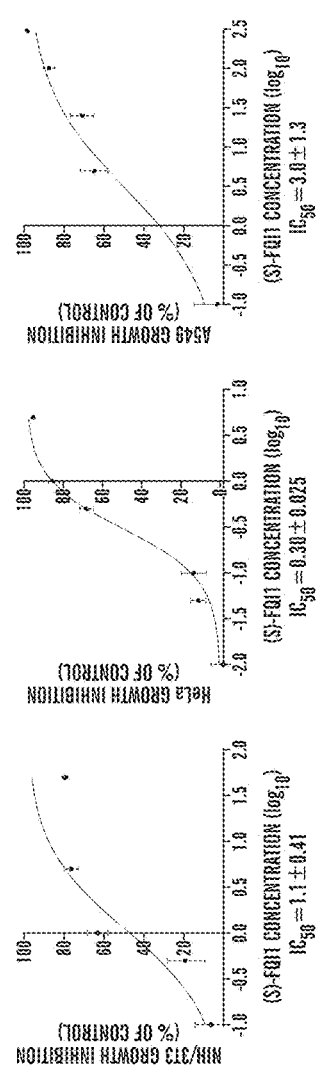
Figure 8C:
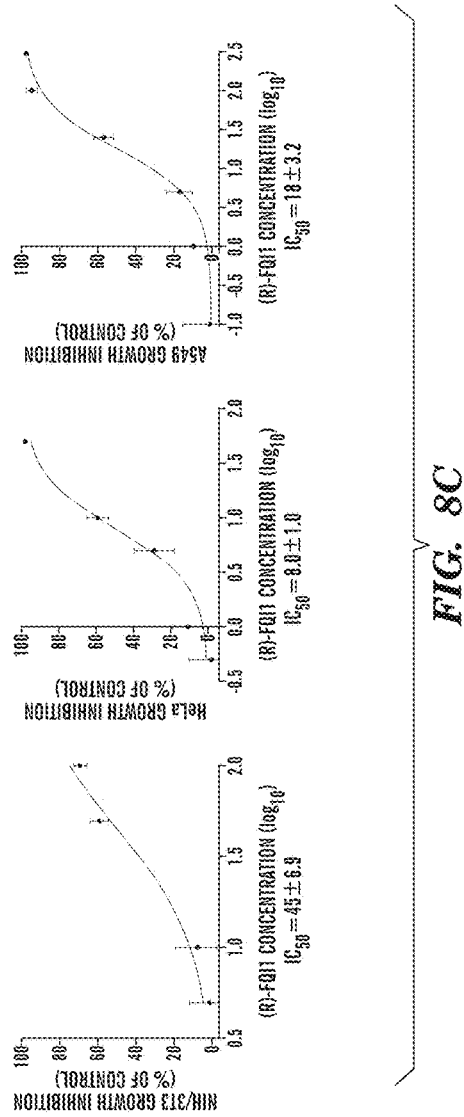
Figure 8D:
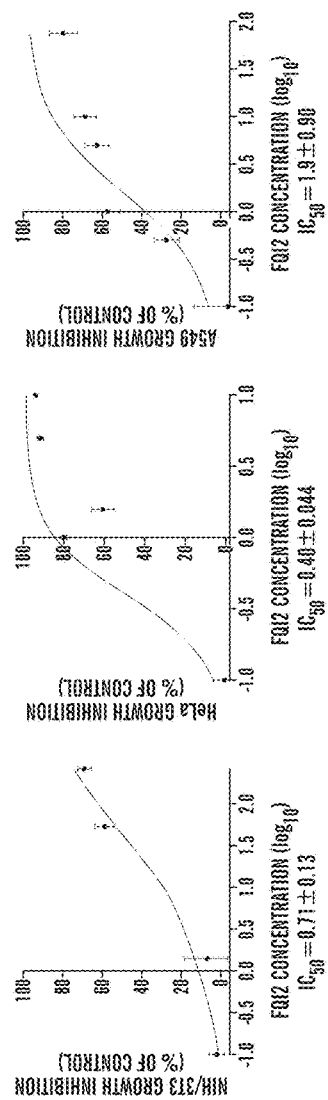
Figure 8E:
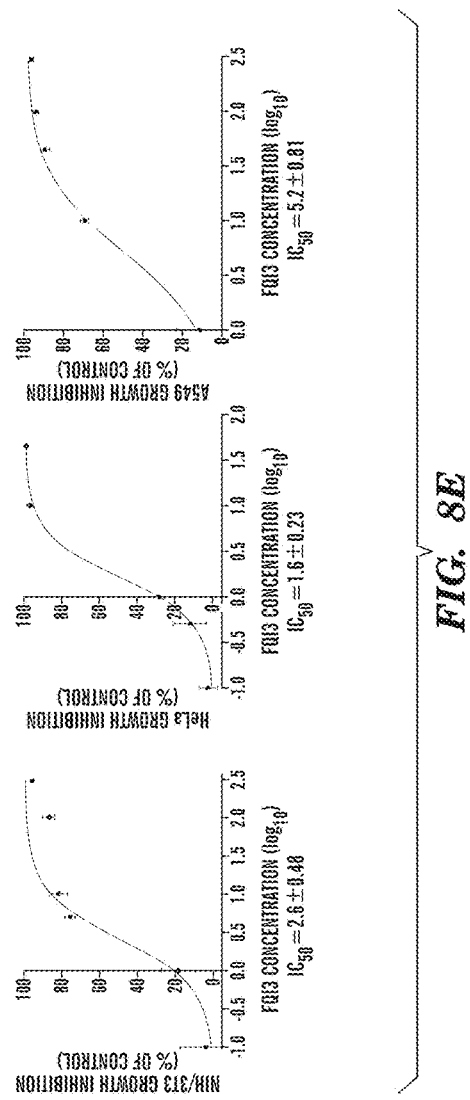
Figure 8F:
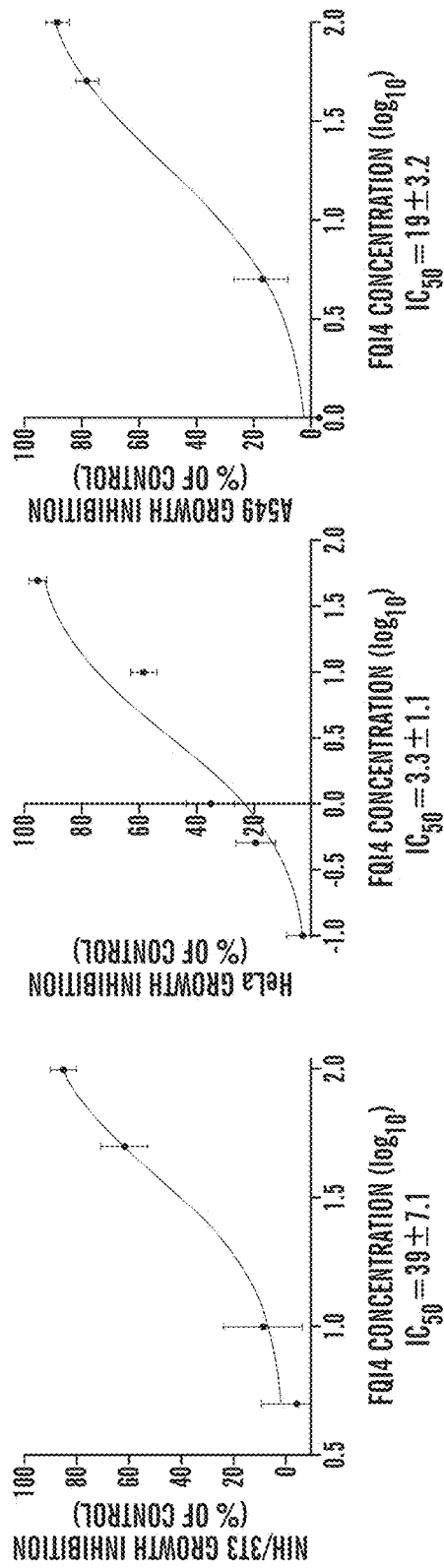
Figure 8G:
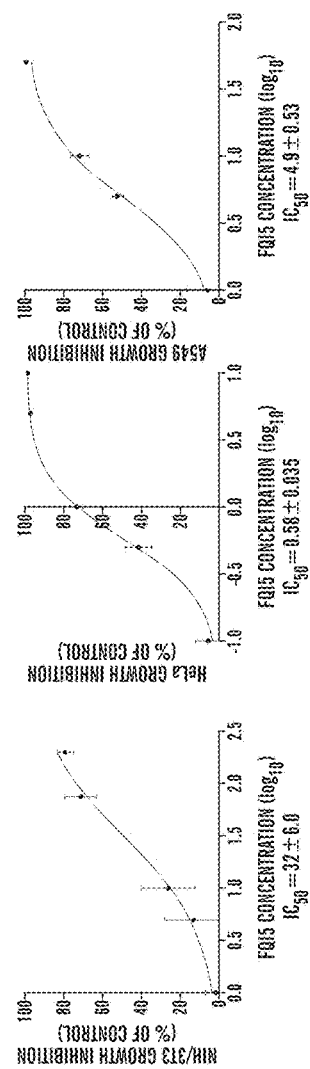
Figure 8H:
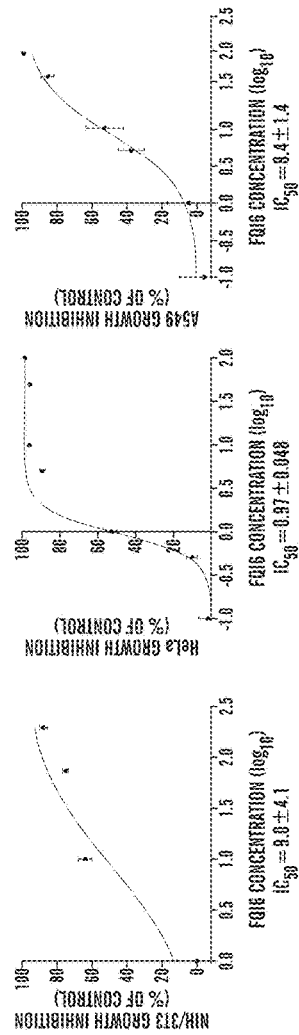
Figure 8I:
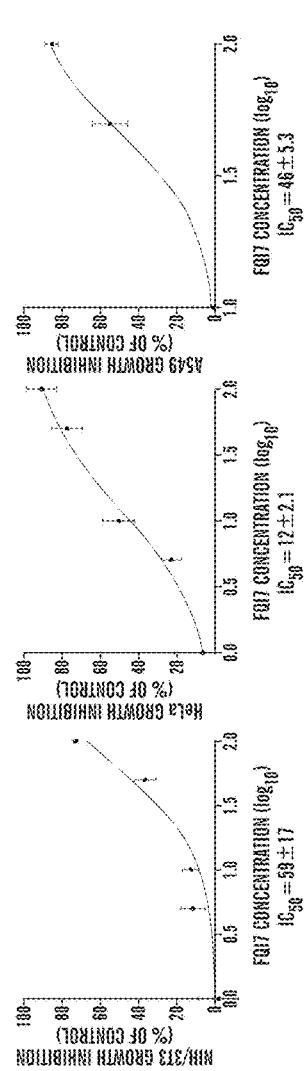
Figure 8J:
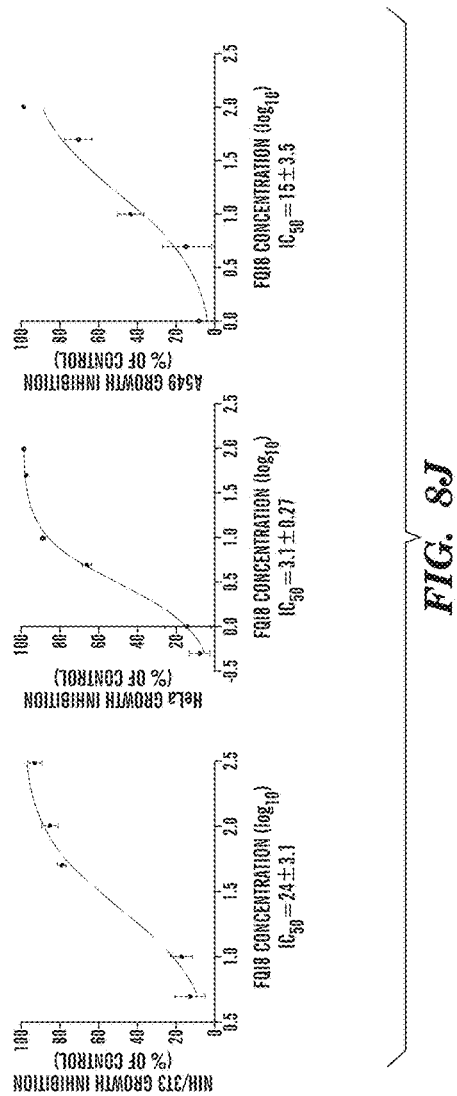
Figure 8K:
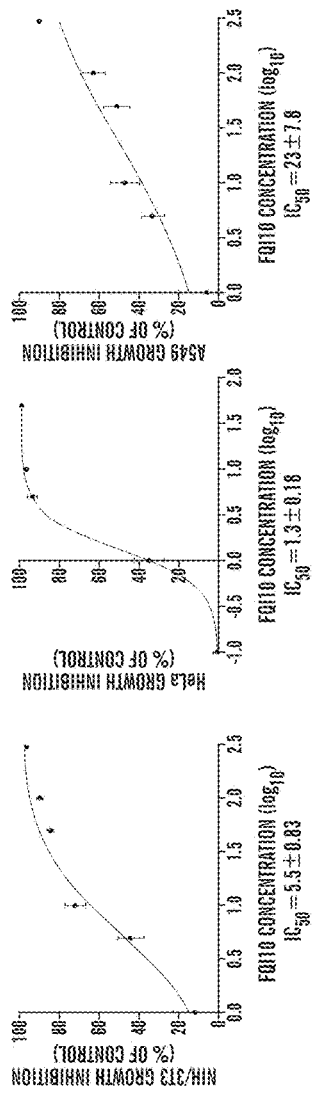
Figure 8L:
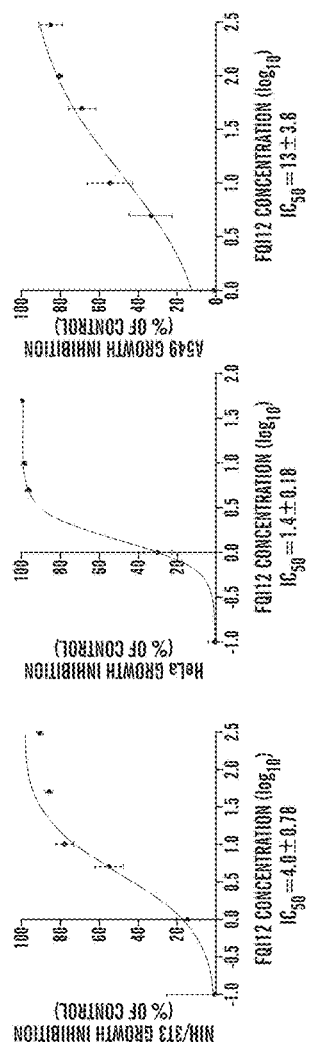
Figure 8M:
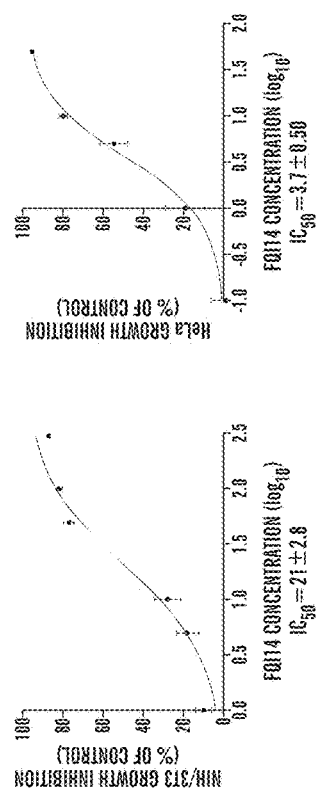
Figure 8N:
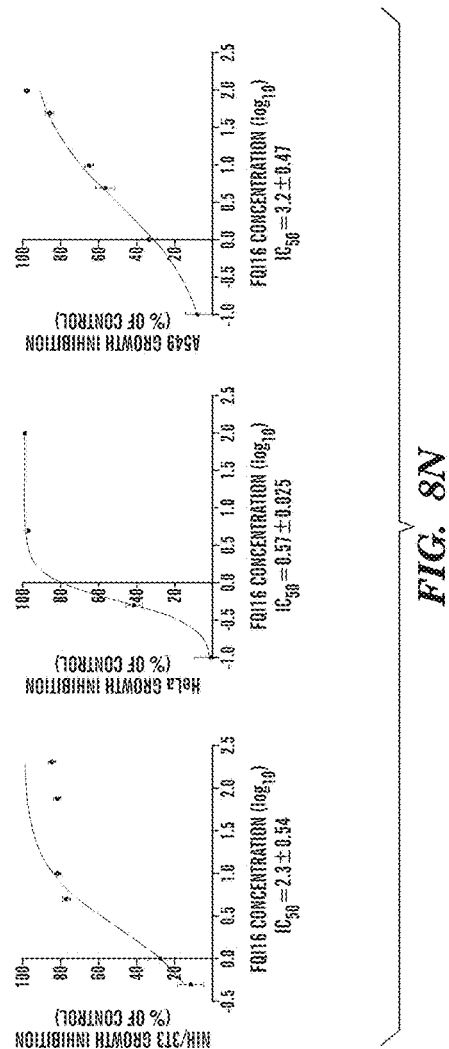
Figure 80:
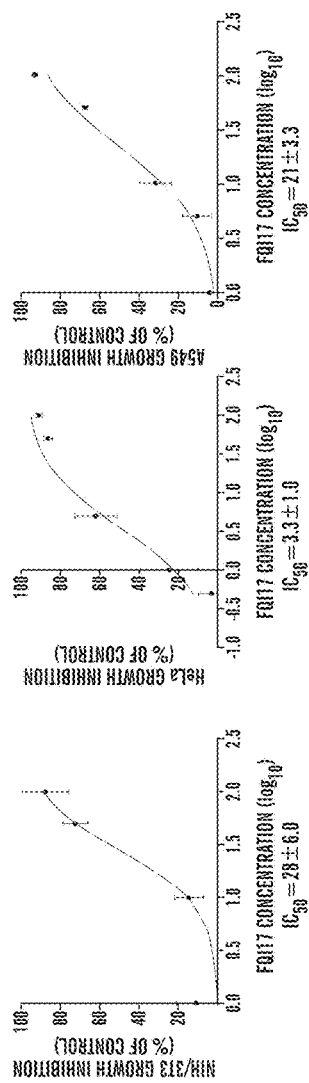
Figure 8P:
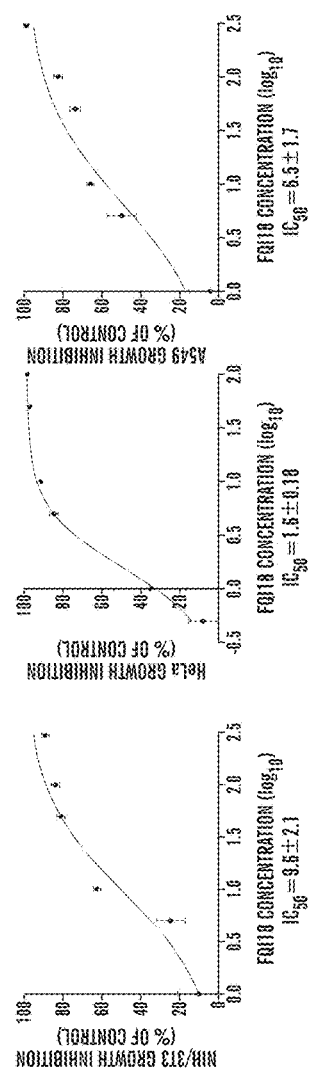
Figure 8Q:
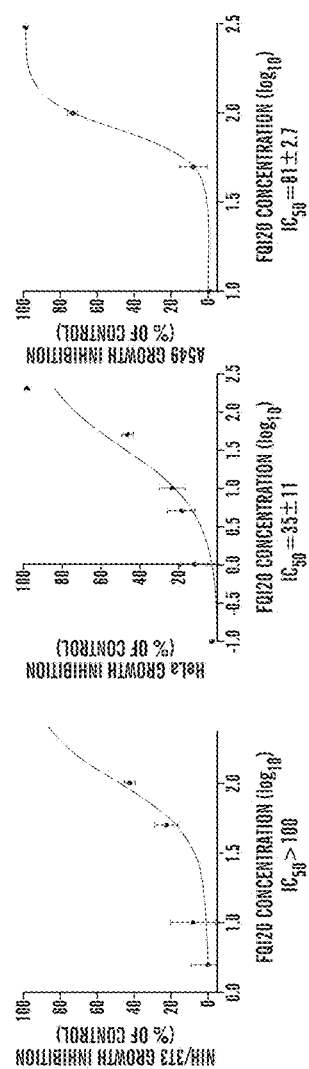
Figure 9A:
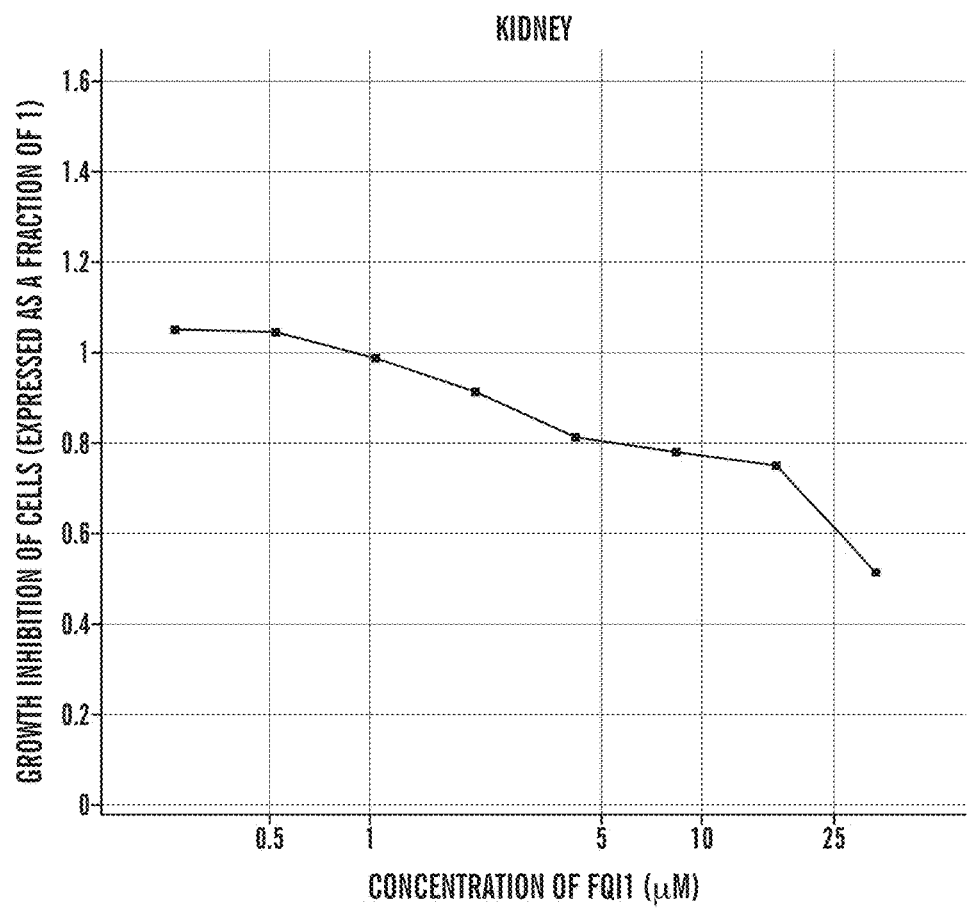
FIG. 9A-9K show the results of inhibition of growth of cancer cell lines in vitro by FQI1 (Formula (IV)). The effect of inhibition of cell growth (represented as a fraction of 1) of increasing concentrations of FQI1 between 0.2-33 μM is shown.
Figure 9B:
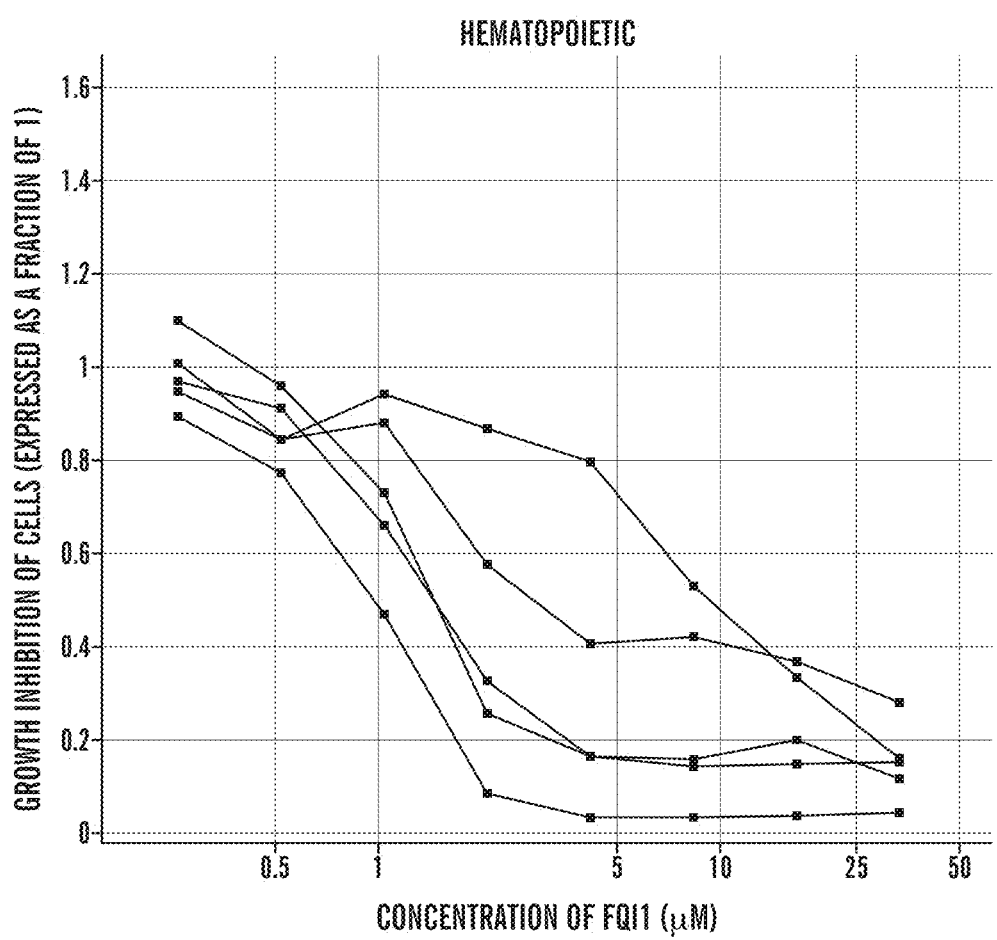
Figure 9C:
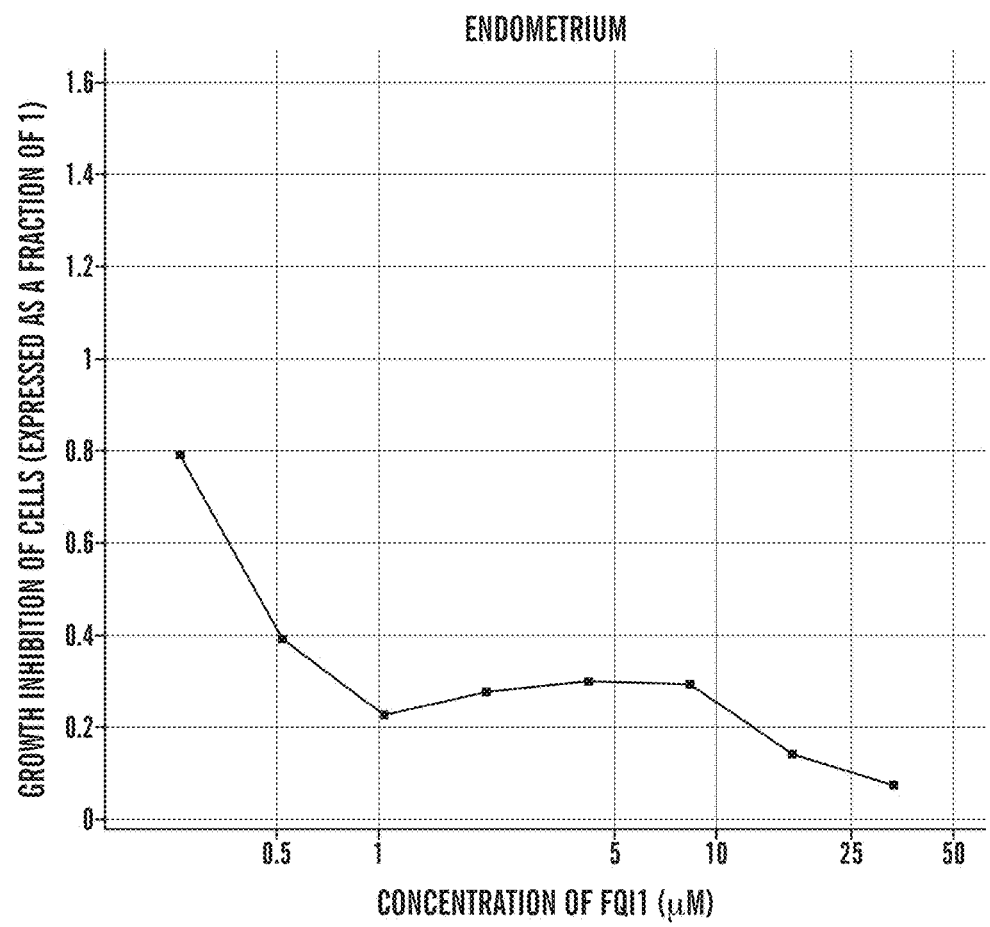
Figure 9D:
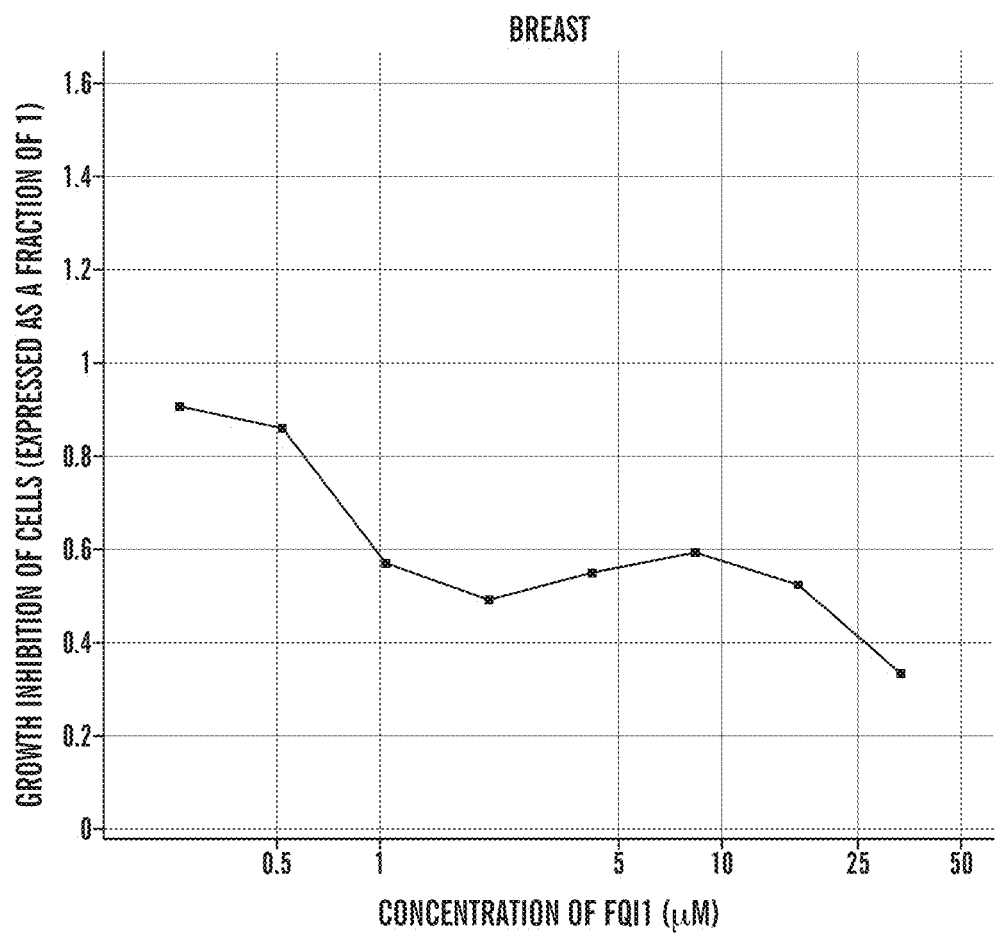
Figure 9E:
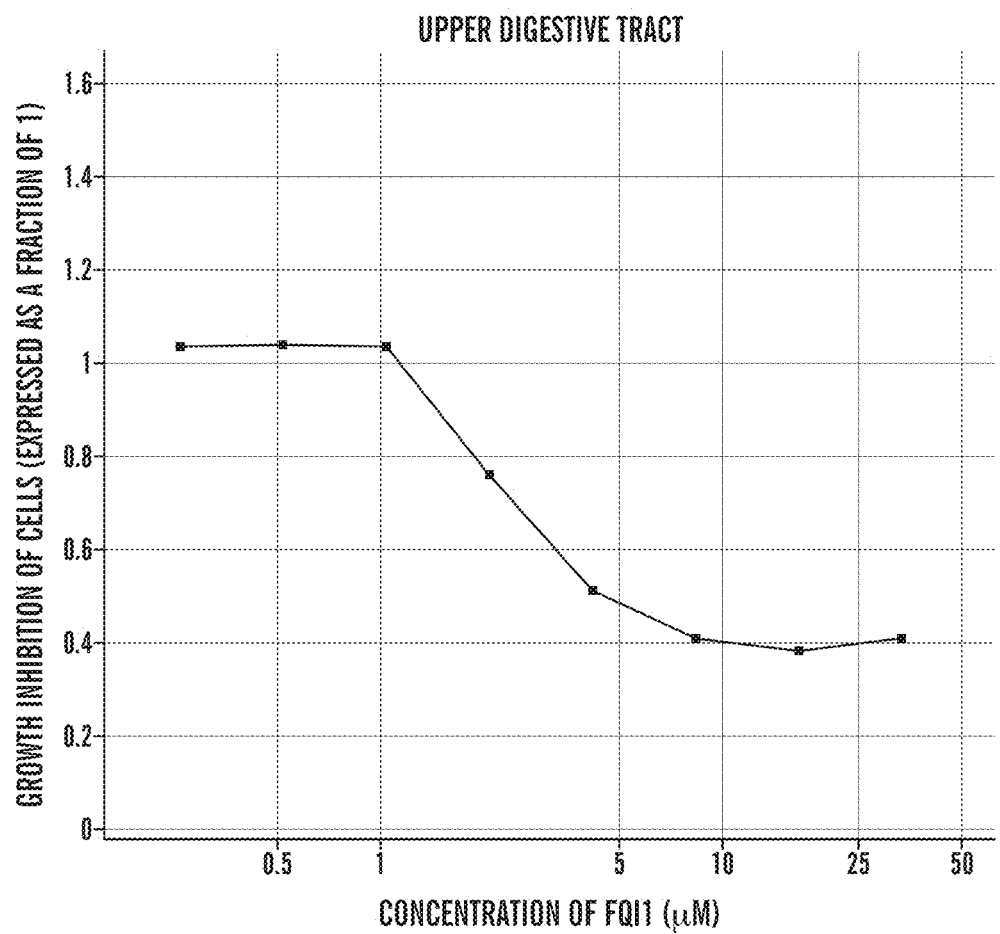
Figure 9F:
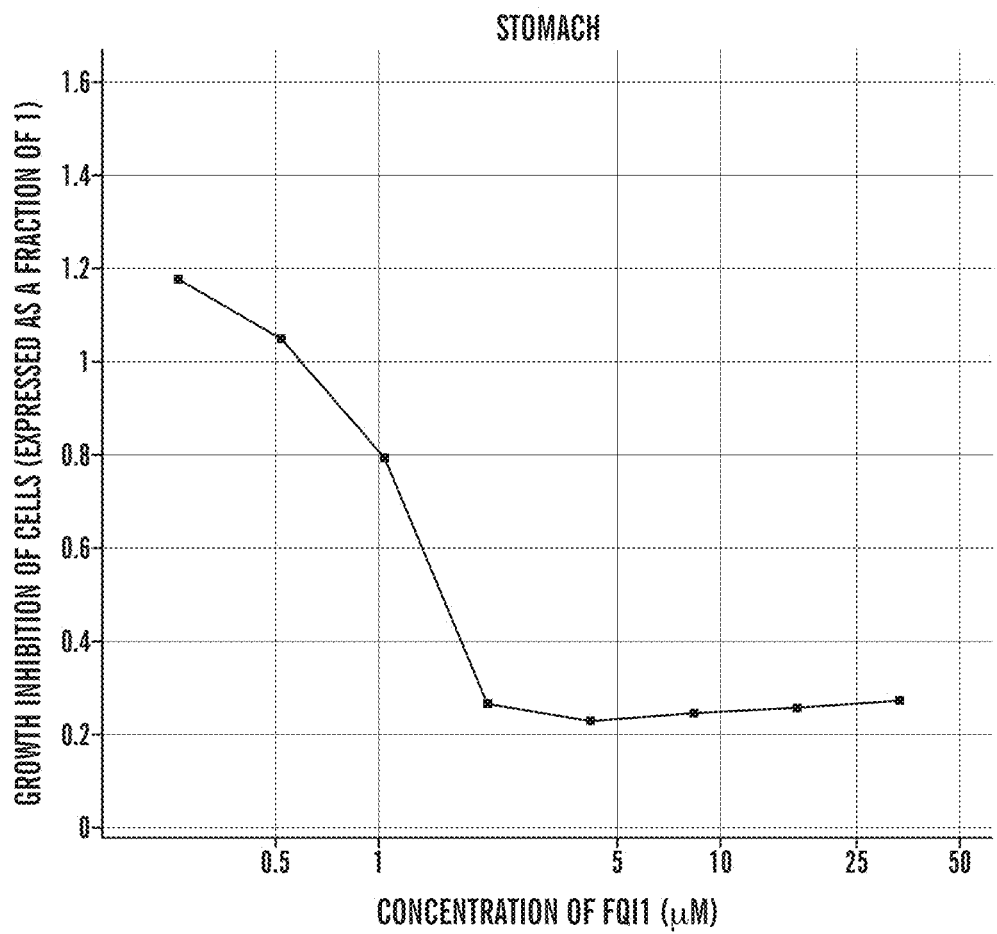
Figure 9G:
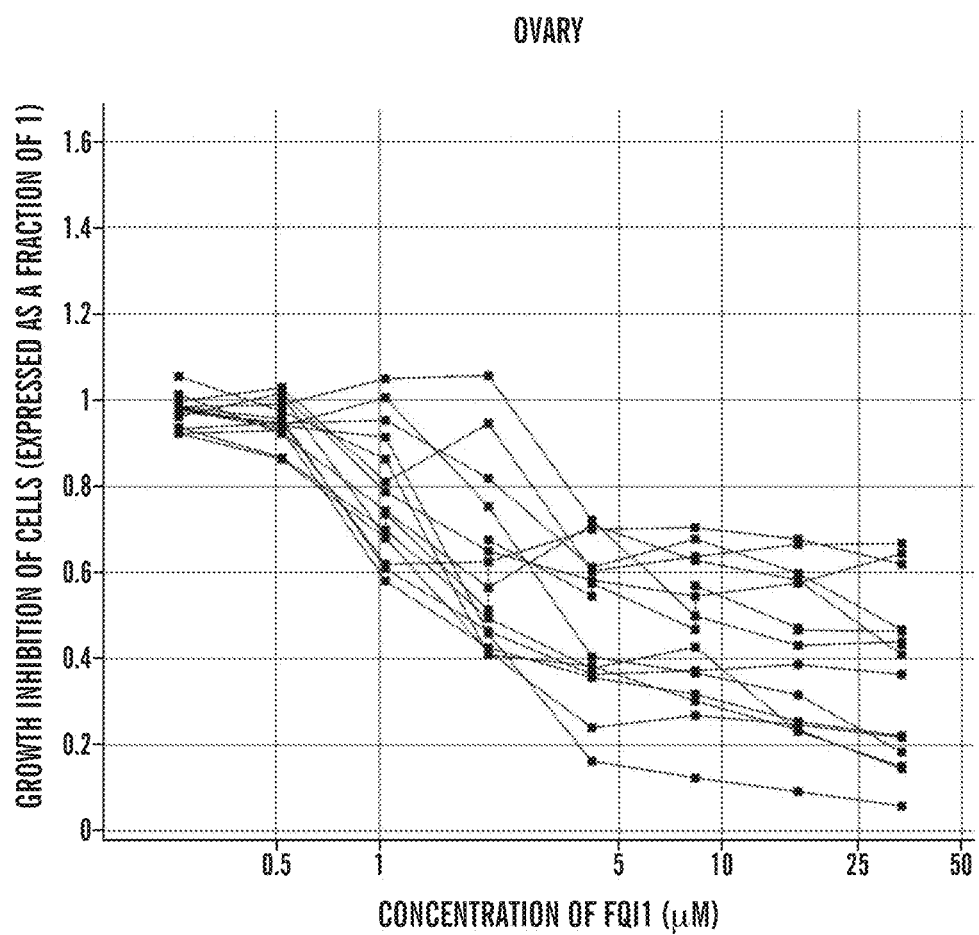
Figure 9H:
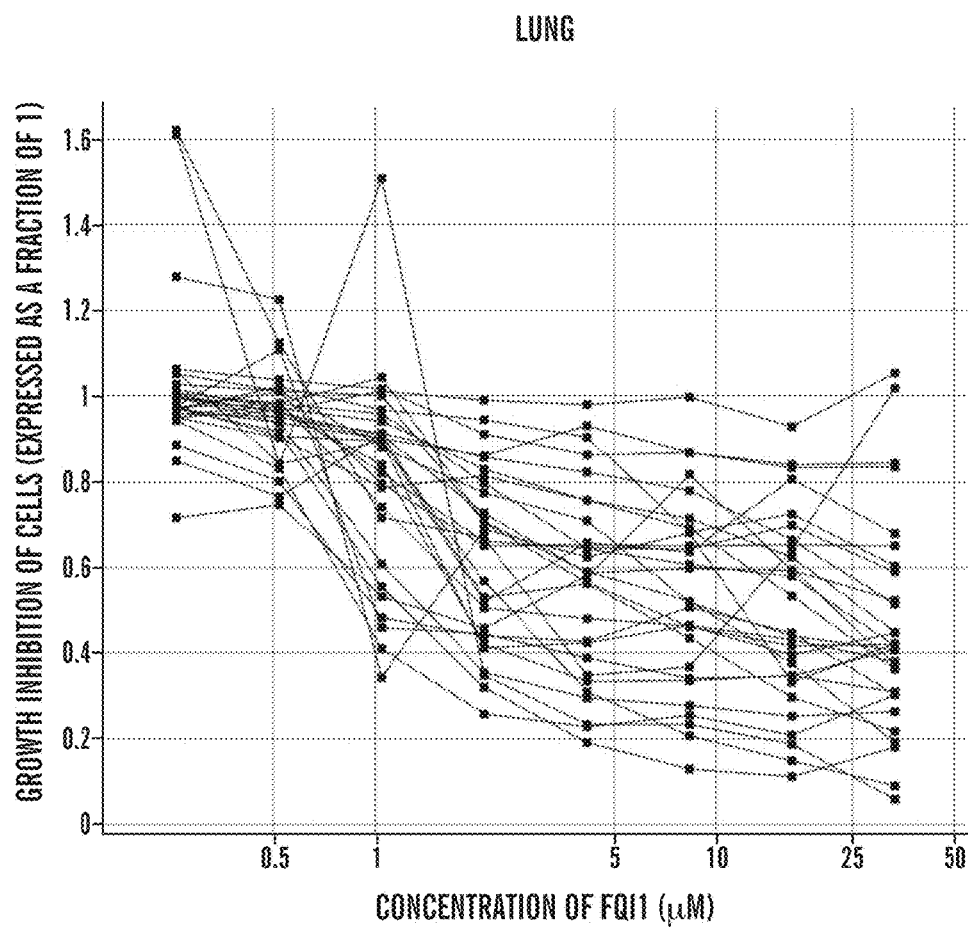
Figure 9I:
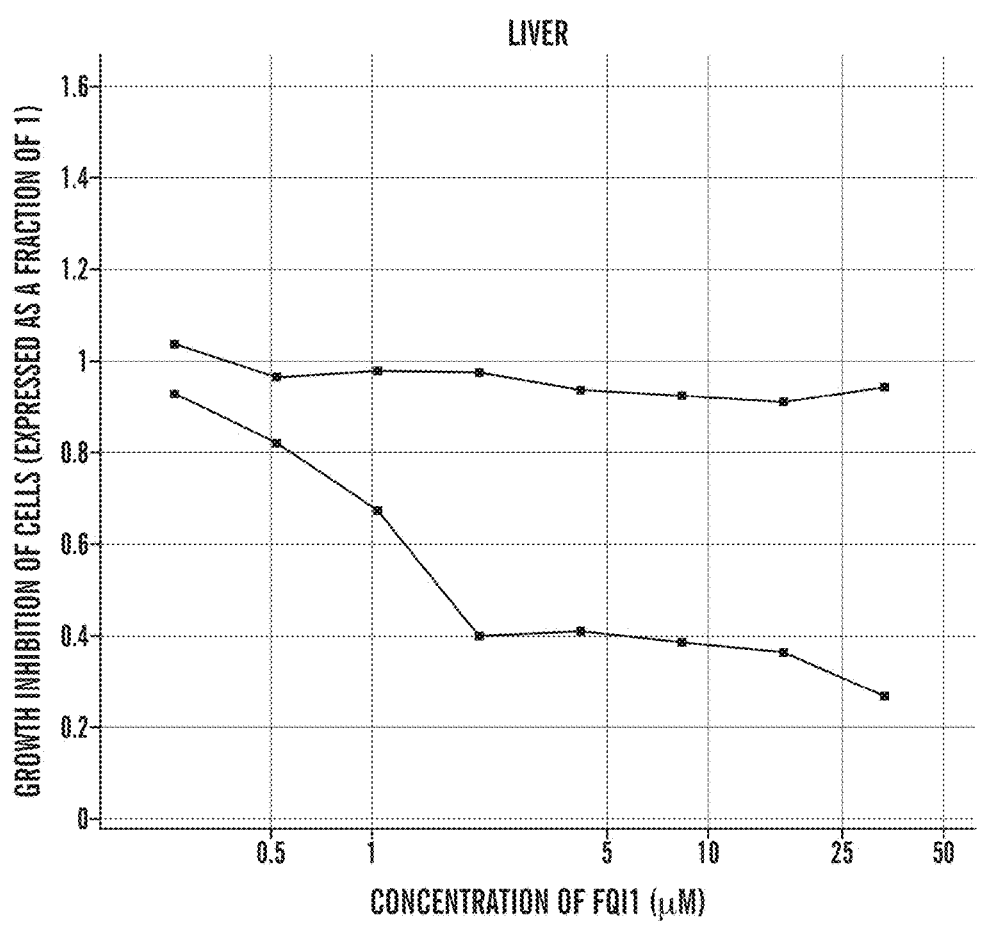
Figure 9J:
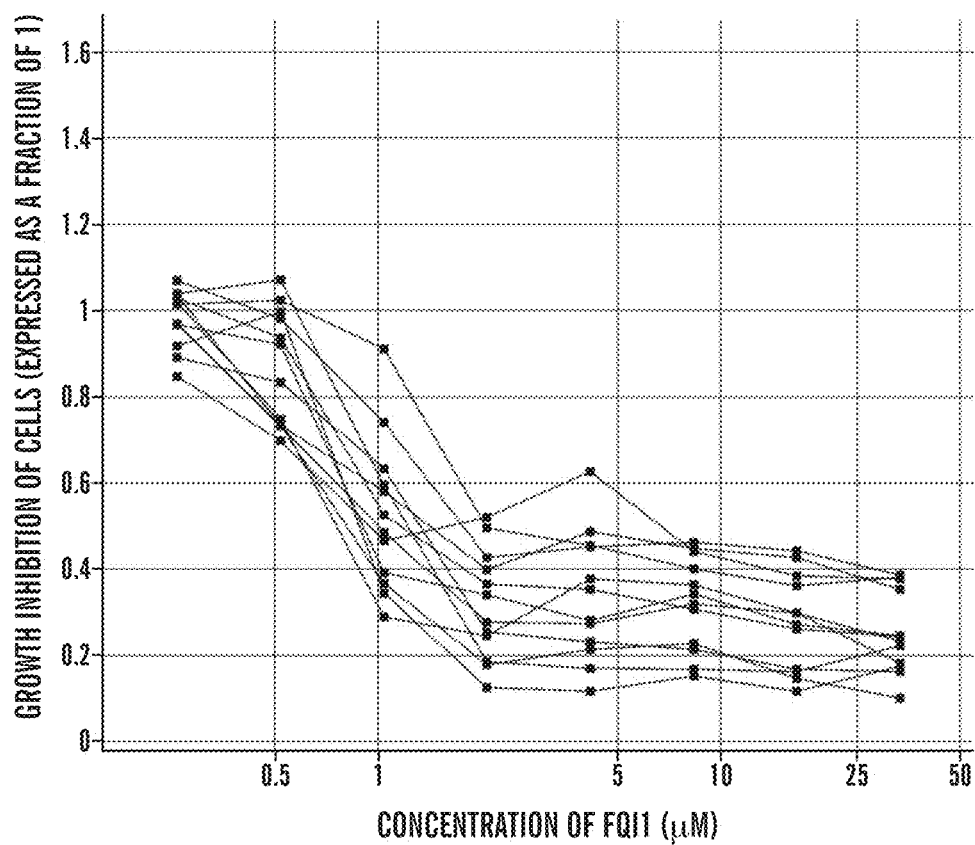
Figure 9K:
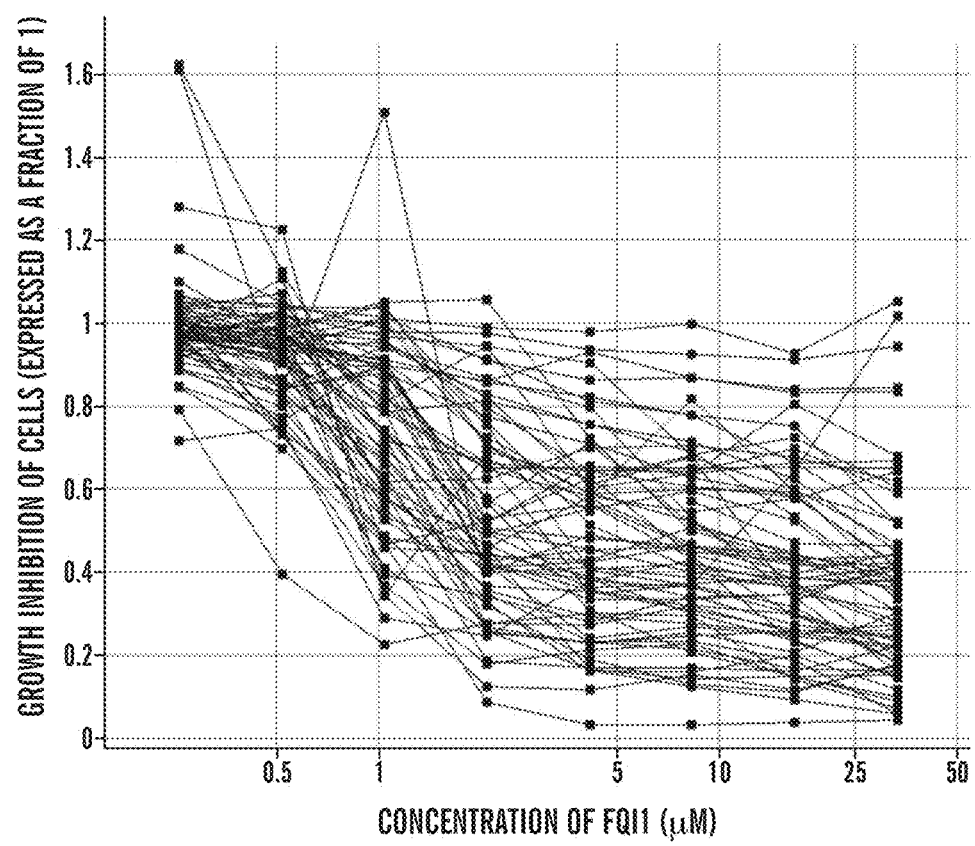
Figure 10A:
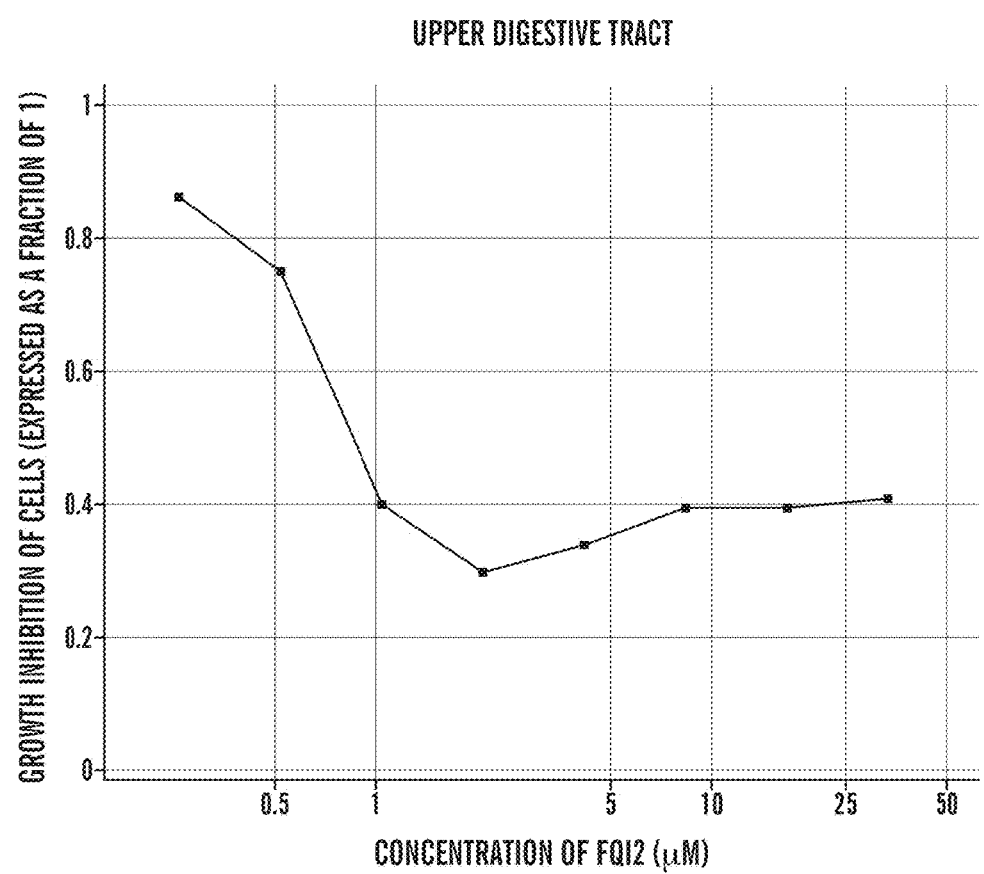
FIGS. 10A-10K shows the results of inhibition of growth of cancer cell lines in vitro by FQI2 (Formula (V)). The effect of inhibition of cell growth (represented as a fraction of 1) of increasing concentrations of FQI2 between 0.2-33 μM is shown.
Figure 10B:
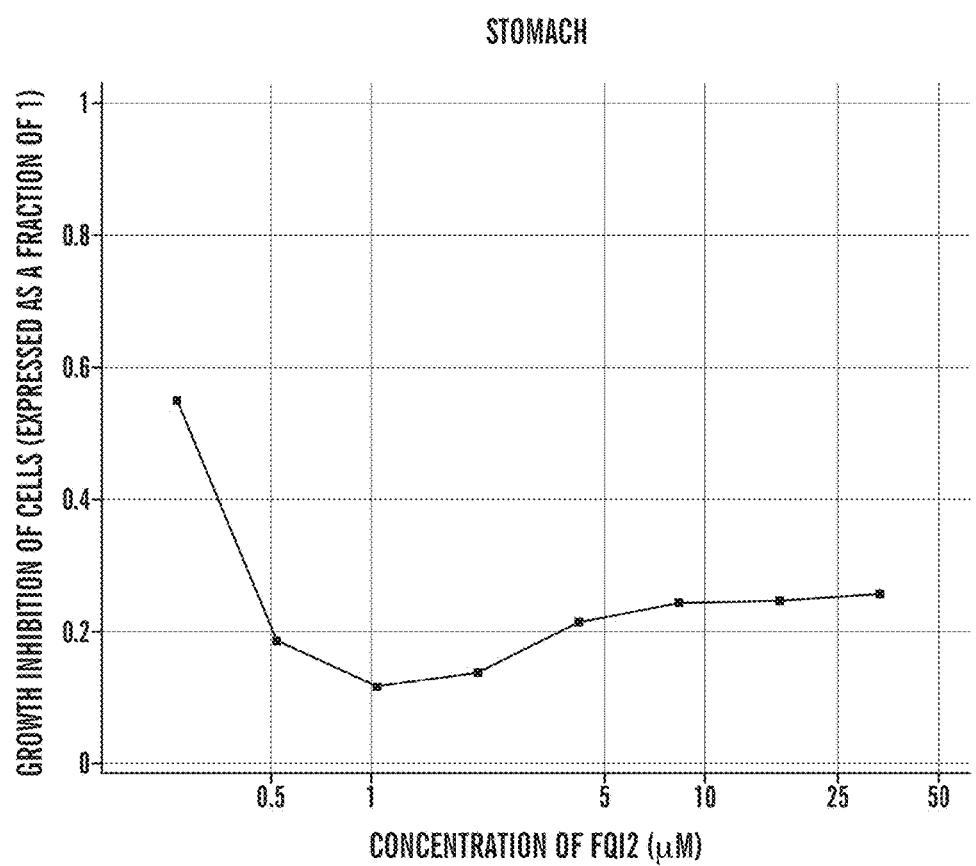
Figure 10C:
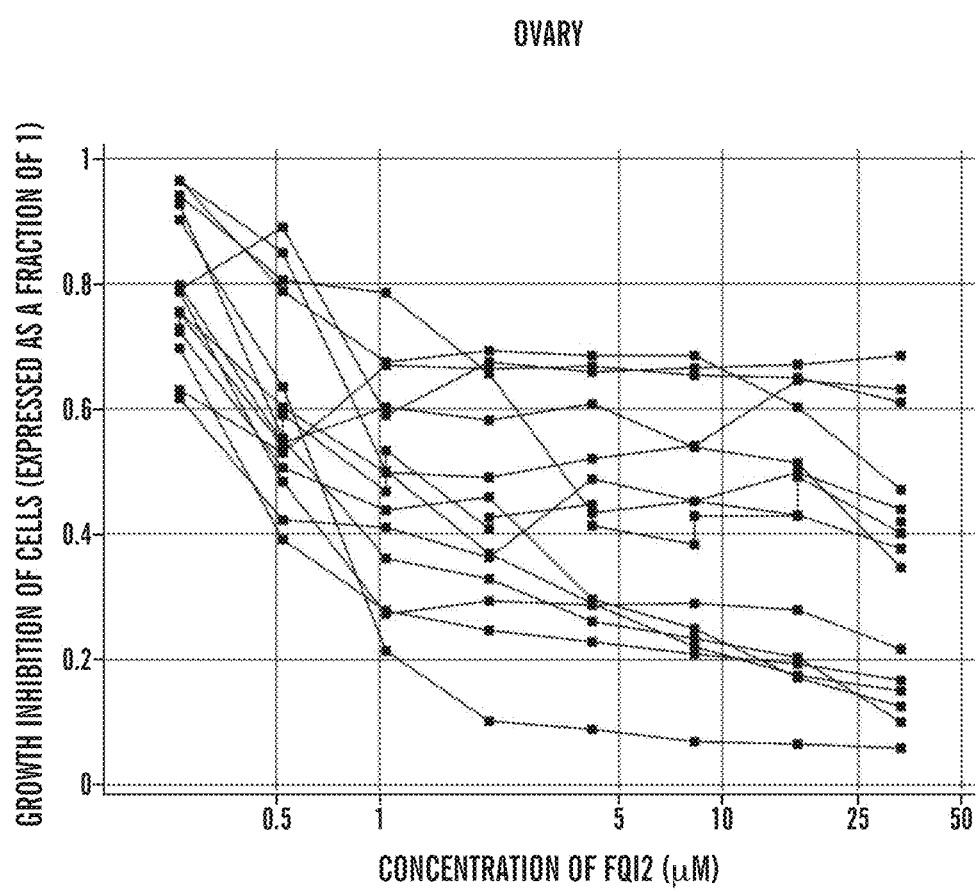
Figure 10D:
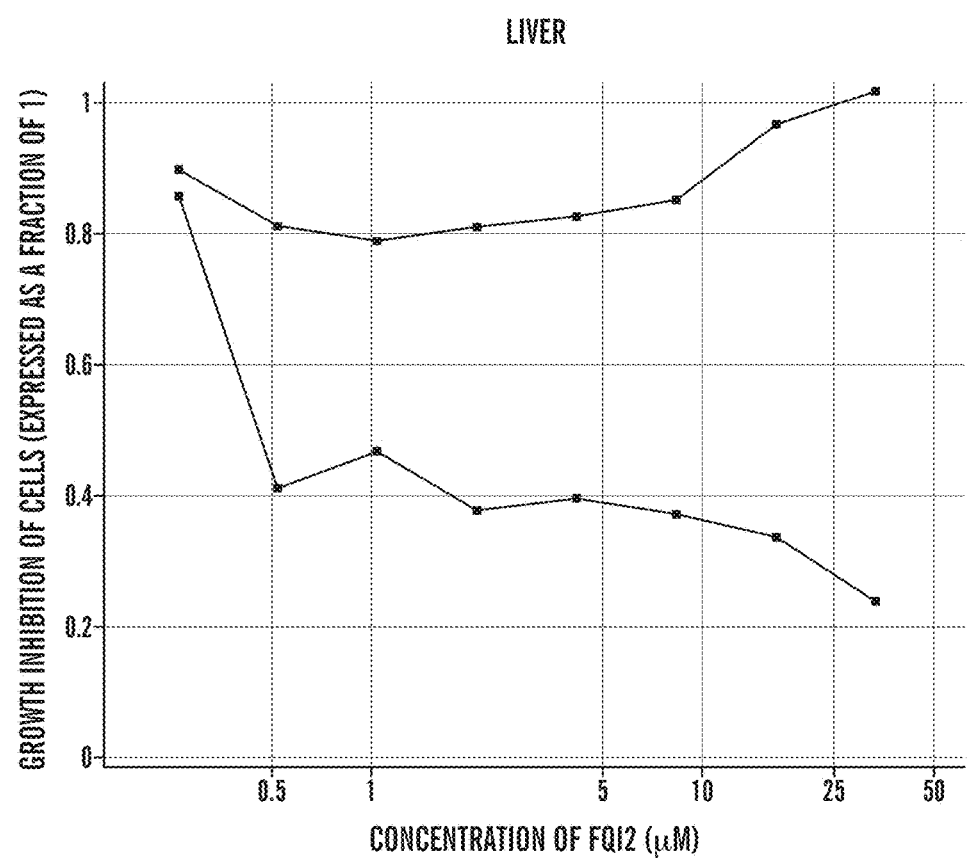
Figure 10E:
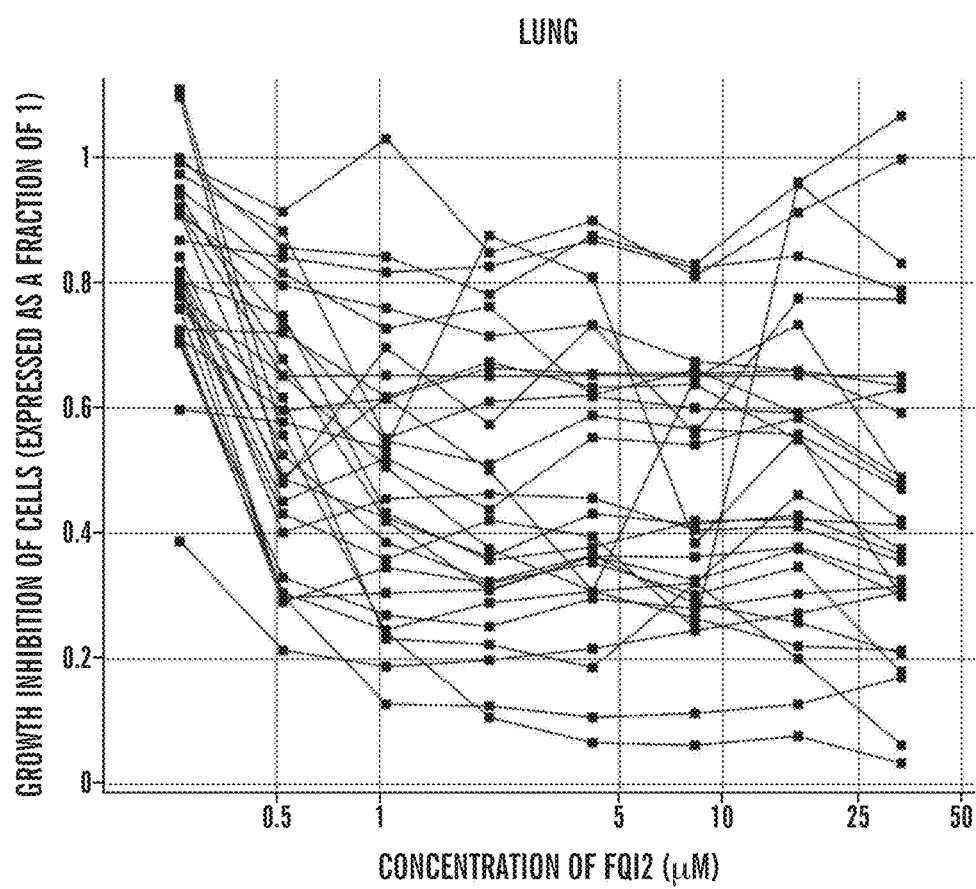
Figure 10F:
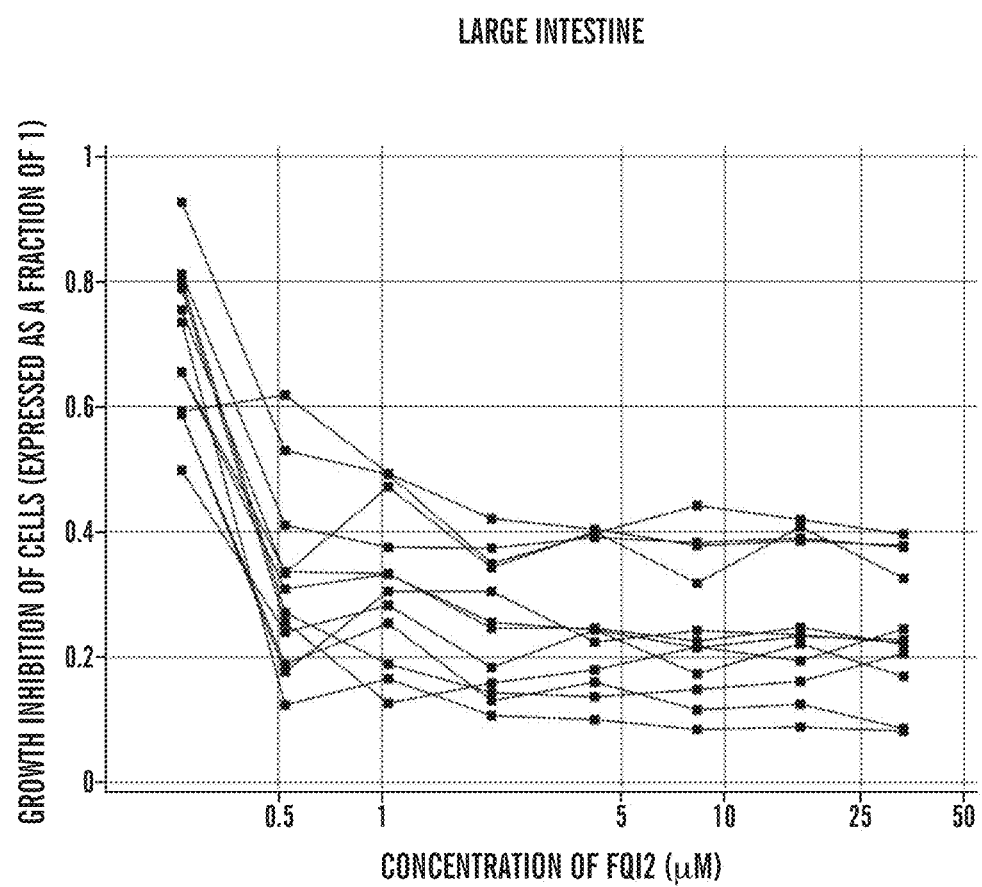
Figure 10G:
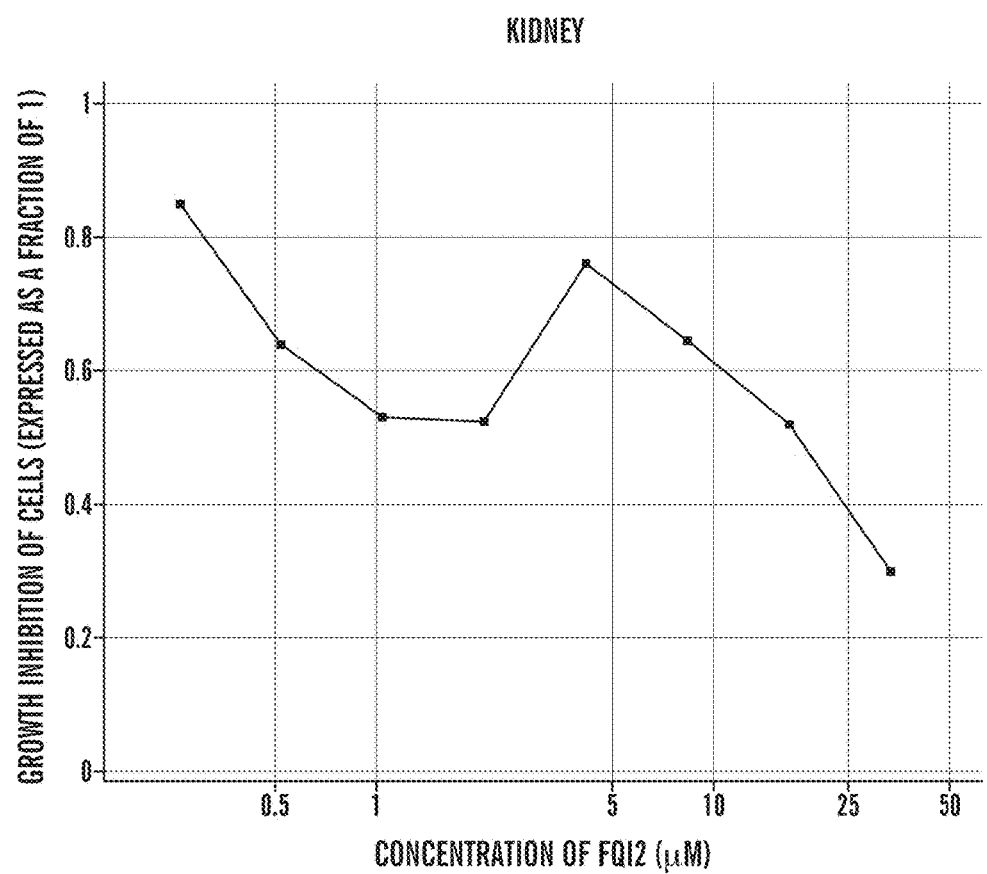
Figure 10H:
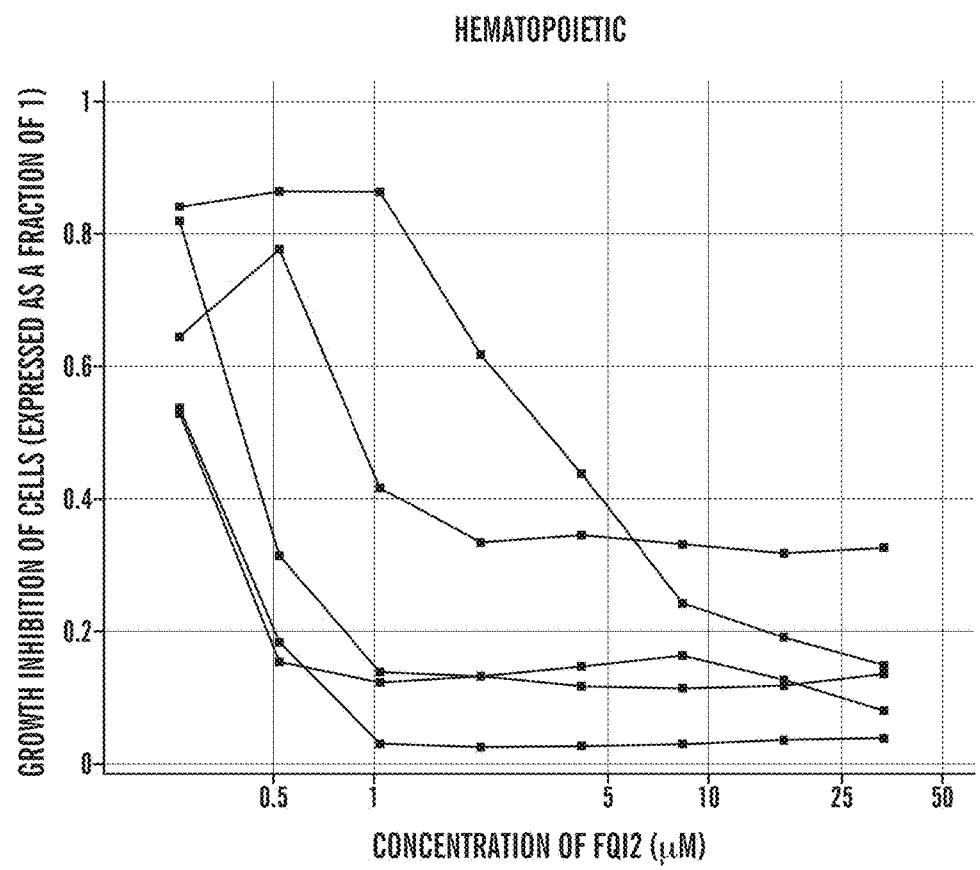
Figure 10I:
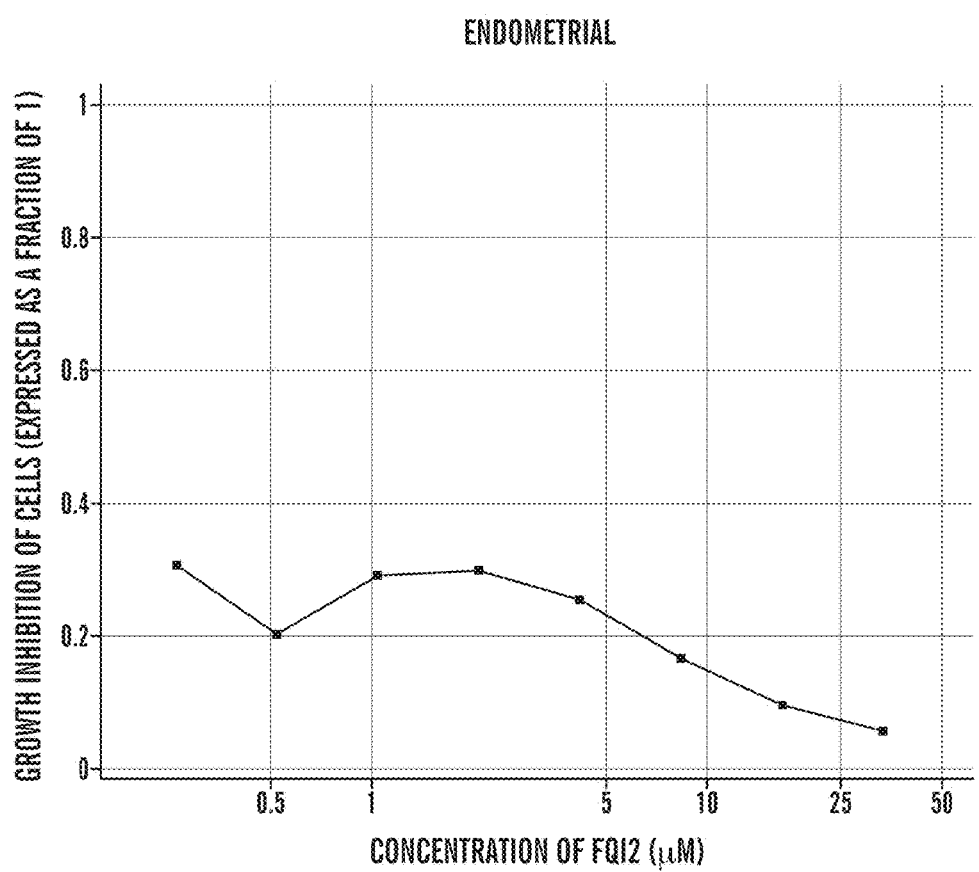
Figure 10J:
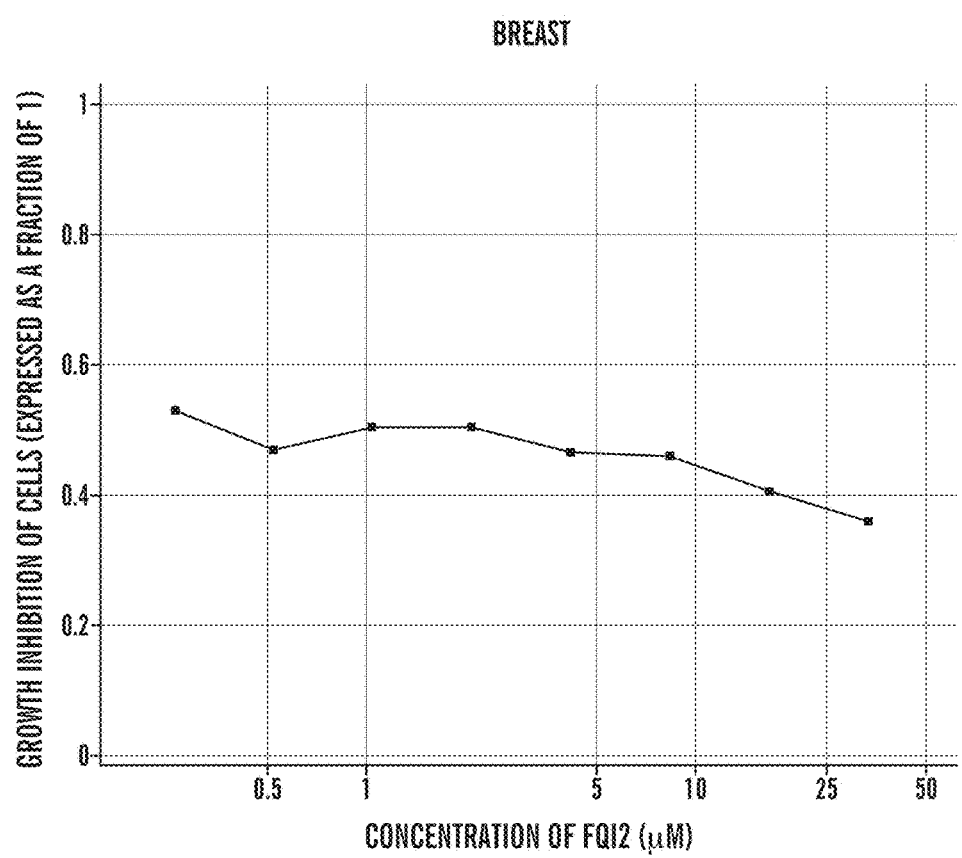
Figure 10K:
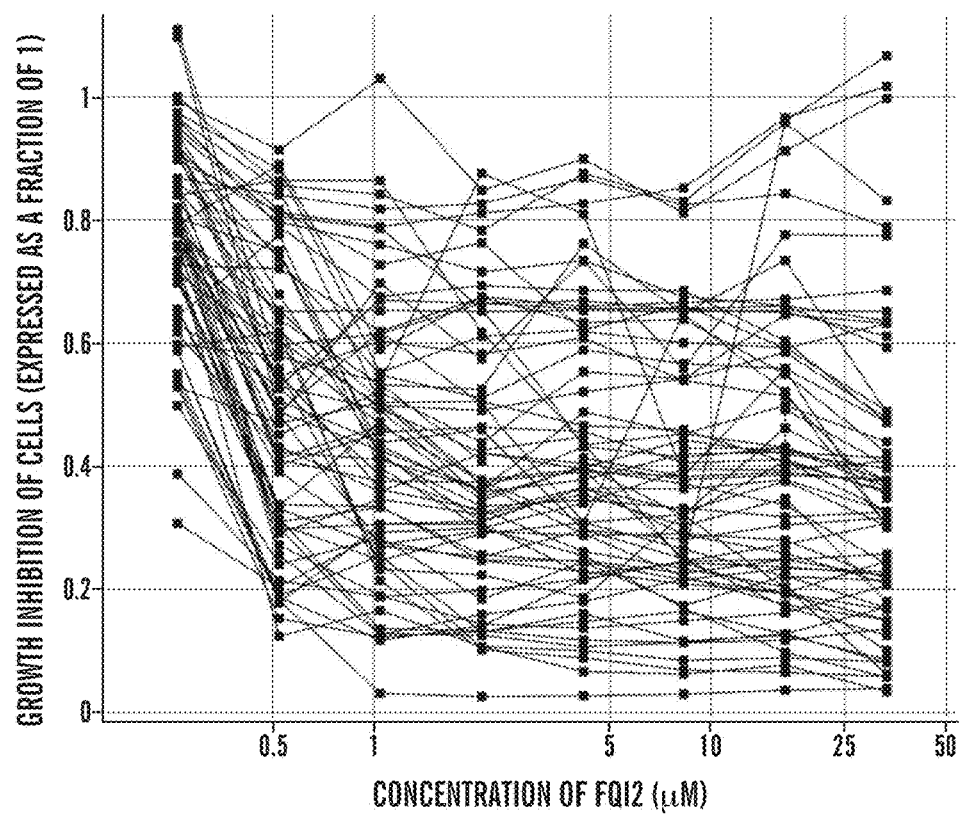

FIGS. 8A-8Q show the growth inhibition (as % control) versus concentrations of different FQI (log$_{10}$) was plotted to determine GI$_{50}$(IC$_{50}$) values of inhibitors. All data are reported in micromolar (μM) concentrations.

For FQI1 (Formula IV), growth inhibition of NIH/3T3 Cell Line IC50=3.0±0.85, HeLa Cell Line IC50=0.79±0.035; A549 Cell Line IC50=6.3±1.1 (FIG. 8A). For (S)-FQI1, growth inhibition of NIH/3T3 Cell Line IC50=1.1±0.45, HeLa Cell Line IC50=0.3±0.025; A549 Cell Line IC50=3.0±1.3 (FIG. 8B). For (R)-FQI1 (Formula (R)-IV), growth inhibition of NIH/3T3 Cell Line IC50=45±6.9, HeLa Cell Line IC50=8.0±1.0; A549 Cell Line IC50=18±3.2 (FIG. 8C).

The growth inhibition for other compounds as shown in FIGS. 8A-8Q. Growth curve data is not shown for FQI9, where the growth inhibition of NIH/3T3 Cell Line IC50=30±3.5, HeLa Cell Line IC50=6.6±1.2; A549 Cell Line IC50=>300. Growth curve data is not shown for FQI11 (Formula XXIII), where the growth inhibition of NIH/3T3 Cell Line IC50=>200, HeLa Cell Line IC50=>200; A549 Cell Line IC50=>200. Growth curve data is not shown for FQI13 (Formula XXI), where the growth inhibition of NIH/3T3 Cell Line NIH/3T3 Cell Line IC50=72±9.8, HeLa Cell Line IC50=8.8±1.4; A549 Cell Line IC50=>300. Growth curve data is not shown for FQI14 (Formula XI), where the growth inhibition of the A549 Cell Line IC50=>100 μM. Growth curve data is not shown for FQI15 (Formula XXIV), where the growth inhibition of NIH/3T3

Cell Line NIH/3T3 Cell Line IC50=>200, HeLa Cell Line IC50=>200; A549 Cell Line IC50=>200. Growth curve data is not shown for FQI19 (Formula XX), where the growth inhibition of NIH/3T3 Cell Line NIH/3T3 Cell Line IC50=>200, HeLa Cell Line IC50=>200; A549 Cell Line IC50=>200. Growth curve data is not shown for FQI21 (Formula XVII), where the growth inhibition of NIH/3T3 Cell Line NIH/3T3 Cell Line IC50=>200, HeLa Cell Line IC50=67±9.9; A549 Cell Line IC50=>200.

Example 8: Synthesis and Characterization of FQI-34

Synthesis of 4-(dimethylamino)-2-ethoxybenzaldehyde

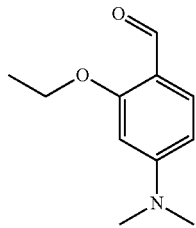

4-(dimethylamino)-2-ethoxybenzaldehyde

In a flame dried 500 mL round bottom flask was prepared a solution of 4-(dimethylamino)-2-hydroxy-benzaldehyde (3.00 g, 18.16 mmol) in Acetone (181.60 mL) followed by addition of bromoethane (9.89 g, 90.80 mmol, 6.78 mL), anhydrous potassium carbonate (3.76 g, 27.24 mmol) and 18-crown-6 (96.01 mg, 363.20 umol). The reaction mixture was fitted with a reflux condenser and heated at 40 C for 16 hr, and then cooled to room temperature. The reaction was filtered and filtered solid washed with acetone. The filtrate was evaporated to dryness to give 4-(dimethylamino)-2-ethoxy-benzaldehyde (3.51 g, reddish solid) in quantitative yield.

$^1$H NMR (400 MHz, Chloroform-d) δ 10.20 (s, 1H), 7.73 (d, J=9.0 Hz, 1H), 6.29 (d, J=9.0 Hz, 1H), 6.02 (s, 2H), 4.12 (q, J=7.0 Hz, 2H), 3.07 (s, 3H), 1.47 (t, J=7.0 Hz, 3H). $^{13}$C NMR (126 MHz, Chloroform-d) δ 187.60, 163.45, 155.99, 129.92, 114.65, 104.53, 93.76, 70.10, 63.79, 40.21, 14.72. IR (KBr): ν (max) 2979, 2905, 2763, 1659, 1587, 1553, 1526, 1440, 1372, 1360, 1287, 1241, 1108, 806 cm$^{-1}$. Melting point: 59° C. UV: λ (max) 351.888 nm. MS (UPLC): Calcd requires m/z [M+H]$^+$ 194.110; found 193.802.

Synthesis of (2-(benzo[d][1,3]dioxol-5-ylamino)-2-oxoethyl)triphenylphosphonium bromide

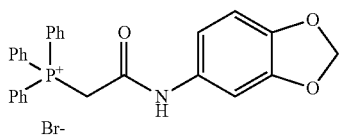 [SMILES: O=C(C[P+](c1ccccc1)(c1ccccc1)c1ccccc1)Nc1ccc2c(c1)OCO2 ; [Br-]]

(2-(benzo[d][1,3]dioxol-5-ylamino)-2-oxoethyl)triphenylphosphonium bromide

A solution of triphenylphosphine (20.70 g, 78.93 mmol) dissolved in Toluene (250.57 mL) was prepared in a 500 mL RBF. To the solution was added N-(1,3-benzodioxol-5-yl)-2-bromo-acetamide (19.40 g, 75.17 mmol) in one portion. The resulting slurry was heated to reflux and stirred for 16 h. The resulting grey precipitate was filtered, rinsed with toluene, and dried in vacuo to afford (2-(benzo[d][1,3]dioxol-5-ylamino)-2-oxoethyl)triphenylphosphonium bromide (29.80 g, 57.27 mmol, 76.19% yield) as a grey powder. Crude product was used in subsequent steps without further purification.

$^1$H NMR (500 MHz, DMSO-d6) δ 11.01 (s, 1H), 7.89-7.78 (overlap, 9H), 7.77-7.70 (overlap, 6H), 7.06 (d, J=2.0 Hz, 1H), 6.84 (dd, J=8.4, 2.0 Hz, 1H), 6.79 (d, J=8.4 Hz, 1H), 5.95 (s, 2H), 5.30 (d, J=14.9 Hz, 2H). 13C NMR (126 MHz, DMSO-d6) δ 161.16, 147.03, 143.68, 134.93, 133.88, 133.79, 132.16, 130.08, 129.98, 119.01, 118.31, 112.52, 108.08, 101.45, 101.18. IR (KBr): ν (max) 3155, 2907, 1665, 1486, 1502, 1436, 1245, 1114, 1035, 929, 737, 690 cm$^{-1}$. Melting Point: 225° C. UV: λ (max) 219.888. MS (UPLC): Calcd requires m/z [M-Br$^-$]$^+$440.141; found 440.124.

Synthesis of N-(benzo[d][1,3]dioxol-5-yl)-3-(4-(dimethylamino)-2-ethoxyphenyl)acrylamide

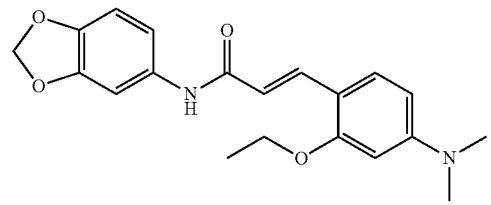 [SMILES: CCOc1cc(N(C)C)ccc1/C=C/C(=O)Nc1ccc2c(c1)OCO2]

N-(benzo[d][1,3]dioxol-5-yl)-3-(4-(dimethylamino)-2-ethoxyphenyl)acrylamide

In an 250 mL flask equipped with a stirbar and fitted with an argon balloon, Butyllithium (1.6 M, 13.58 mL) was slowly added to a mixture of (2-(benzo[d][1,3]dioxol-5-ylamino)-2-oxoethyl)triphenylphosphonium bromide (10.77 g, 20.70 mmol) in Tetrahydrofuran (69.00 mL). The resulting slurry was stirred for 30 minutes during which time the mixture was slowly warmed to room temperature. 4-(dimethylamino)-2-ethoxy-benzaldehyde (2.00 g, 10.35 mmol) was added as a single portion, and the reaction was fitted with condenser and stirred at reflux for 16 h. The reaction mixture was quenched by addition of saturated aq. ammonium chloride (150 mL), and extracted 3×50 mL DCM. The combined organics were washed with brine, dried over sodium sulfate, and concentrated in vacuo. The residue was dissolved in a minimal amount of DCM, and rinsed through a short silica plug to afford N-(benzo[d][1,3]dioxol-5-yl)-3-(4-(dimethylamino)-2-ethoxyphenyl)acrylamide (3.57 g, 10.07 mmol, 97.33% yield) as a mixture of E/Z isomers (~3:1). Notes: yellow solid.

$^1$H NMR (500 MHz, Chloroform-d) δ 7.93 (d, J=15.4 Hz, 1H), 7.36 (d, J=8.8 Hz, 1H), 7.20 (s, 1H), 6.86 (d, J=8.3 Hz, 1H), 6.74 (d, J=8.2 Hz, 1H), 6.45 (d, J=15.4 Hz, 1H), 6.27 (dd, J=8.7, 2.4 Hz, 1H), 6.14 (d, J=2.4 Hz, 1H), 5.94 (s, 2H), 4.09 (q, J=6.8 Hz, 2H), 3.00 (s, 6H), 1.48 (d, J=6.8 Hz, 3H). $^{13}$C NMR (126 MHz, cdcl$_3$) δ 165.71, 159.43, 158.29, 152.87, 147.77, 138.22, 133.79, 133.19, 131.42, 130.52, 115.91, 112.95, 112.27, 108.07, 104.72, 102.77, 101.22, 95.63, 77.41, 63.86, 40.33, 14.97. IR (KBr): ν (max) 3267, 2898, 1650, 1591, 1549, 1488, 1352, 1240, 1196, 1039, 806 cm$^{-1}$. Melting Point: 107° C. UV: λ (max) 371.888. MS (UPLC): calc'd requires m/z [M+H]$^+$: 355.166; found: 355.211.

Synthesis of 8-(4-(dimethylamino)-2-ethoxyphenyl)-7,8-dihydro-[1,3]dioxolo[4,5-g]quinolin-6(5H)-one (FQI-34)

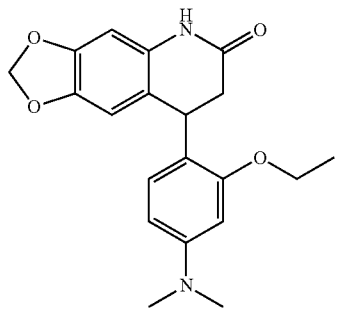 [SMILES: CCOc1cc(N(C)C)ccc1C1CC(=O)Nc2cc3c(cc21)OCO3]

8-(4-(dimethylamino)-2-ethoxyphenyl)-7,8-dihydro-[1,3]dioxolo[4,5-g]quinolin-6(5H)-one (FQI-34)

In a 250 mL round bottom flask, N-(1,3-benzodioxol-5-yl)-3-[4-(dimethylamino)-2-ethoxy-phenyl]prop-2-enamide (2.51 g, 7.08 mmol) was dissolved in trifluoroacetic acid (70.50 mL) and allowed to stir at room temperature for 2 days. Upon completion, the reaction was cooled to 0° C., and slowly neutralized by addition of saturated aqueous sodium bicarbonate then extracted 3×250 mL DCM. The combined organics were rinsed with brine, and dried over anhydrous sodium sulfate before concentration in vacuo. The crude solid was recrystallized in multiple batches from boiling DCM/hexanes to afford 8-[4-(dimethylamino)-2-ethoxyphenyl]-7,8-dihydro-5H-[1,3]dioxolo[4,5-g]quinolin-6-one (2.27 g, 6.41 mmol, 90.47% yield). Notes: Off-white powdery solid, slightly hygroscopic.

$^1$H NMR (500 MHz, Chloroform-d) δ 7.79 (s, 1H), 6.73 (d, J=8.4 Hz, 1H), 6.47 (s, 1H), 6.35 (s, 1H), 6.27 (d, J=2.4 Hz, 1H), 6.22 (dd, J=8.4, 2.4 Hz, 1H), 5.88 (m, 2H), 4.49 (t, J=7.1 Hz, 1H), 4.11-3.99 (m, 2H), 2.94-2.75 (overlap, 7H), 2.77 (dd, J=16.2, 6.4 Hz, 1H), 1.39 (t, J=7.0 Hz, 3H). $^{13}$C NMR (126 MHz, Chloroform-d) δ 171.25, 157.27, 151.25, 146.84, 143.62, 131.47, 128.77, 120.22, 117.83, 108.73, 104.88, 101.26, 97.40, 97.38, 97.25, 77.42, 77.16, 76.91, 63.56, 40.86, 37.22, 35.35, 15.09. IR (KBr): ν (max) 3194, 3107, 2977, 2896, 1672, 1617, 1478, 1236, 1041, 939, 798 cm$^{-1}$. HRMS: Exact mass calc'd for $C_{20}H_{22}N_2O_4$ requires m/z [M+H]$^+$: 355.1658. Found: 355.1668. UV: λ (max) 219.888 nm. Melting point: N/A. Decomposes at 193° C.

Example 9: Biochemical Characterization of the Compound FQI-34

Analysis of Cell Viability—Cell Line GI$_{50}$.

Figure 11A:
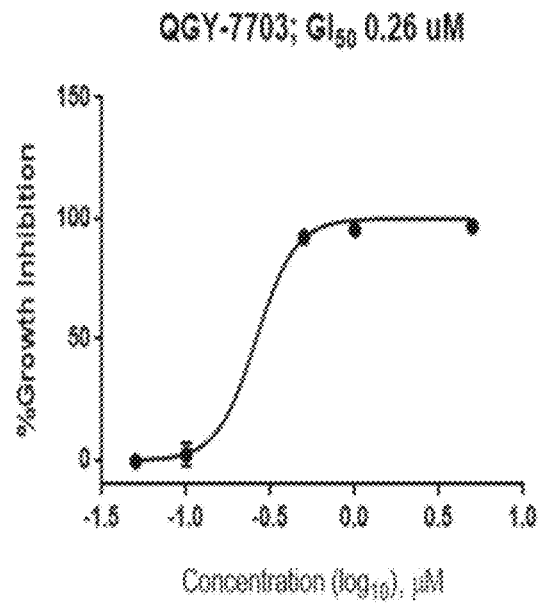
FIGS. 11A-11C show growth inhibition (as % control) versus FQI-34 concentration.
Figure 11B:
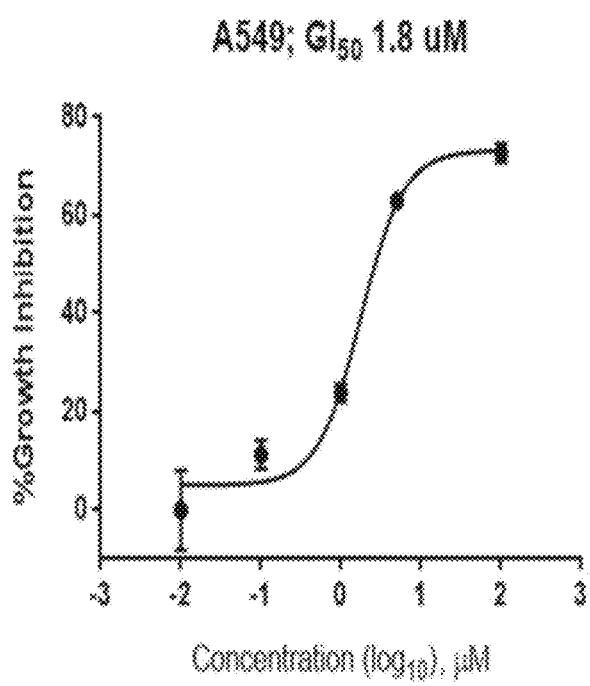
Figure 11:
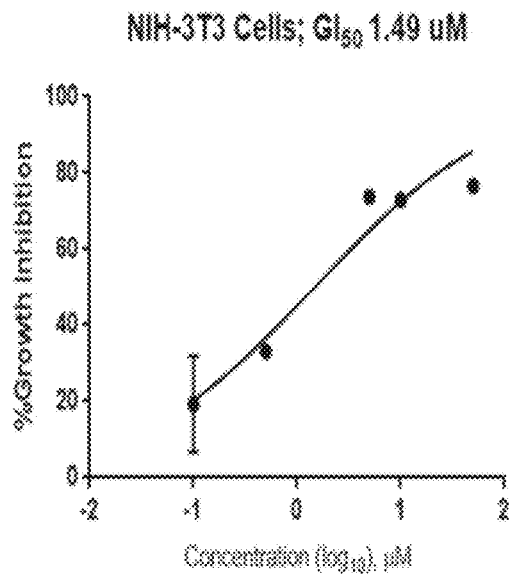

QGY-7703 and A549 cells were cultured at 37° C. in 5% CO$_2$ in DMEM (Dulbecco's modification of Eagle's Medium; Corning) supplemented with 10% Fetal Bovine Serum (FBS; Invitrogen). NIH-3T3 cells were cultured at 37° C. in 5% CO$_2$ in DMEM supplemented with 10% Fetal Calf Serum (FCS; Atlanta Biologicals). For cell viability assays, 1,500 cells were seeded in 96-well plates and treated with FQI-34 or vehicle (DMSO) at appropriate concentrations (DMSO at 1%) after 20 hours. After 72-hour incubation with compound or vehicle, cell growth was assessed via the Promega CellTiter 96® AQ$_{ueous}$ One Solution Cell Proliferation Assay, a colorimetric method to determine the number of viable cells. 20 µL of the CellTiter 96® AQ$_{ueous}$ One Solution Reagent was added directly into cultured wells and incubated for one hour, after which the absorbance at 490 nm was read with a 96-well plate reader (Opys MR Microplate Reader). The CellTiter 96® AQ$_{ueous}$ One Solution contains an MTS tetrazolium compound which is bioreduced by cells into a colored formazan product that is soluble in tissue culture medium. The quantity of formazan product as measured by absorbance is directly proportional to the number of living cells in culture. GI$_{50}$ values were determined from plots of the percentage of compound-treated cell growth to vehicle cell growth vs. compound concentration (GraphPad Prism; non-linear regression 4-parameter curve fit with variable slope). GI$_{50}$ values were 0.26 µM in QGY-7703 cells, 1.8 µM in A549 cells and 1.49 µM in NIH-3T3 cells (FIGS. 11A-11C)

Figure 12:
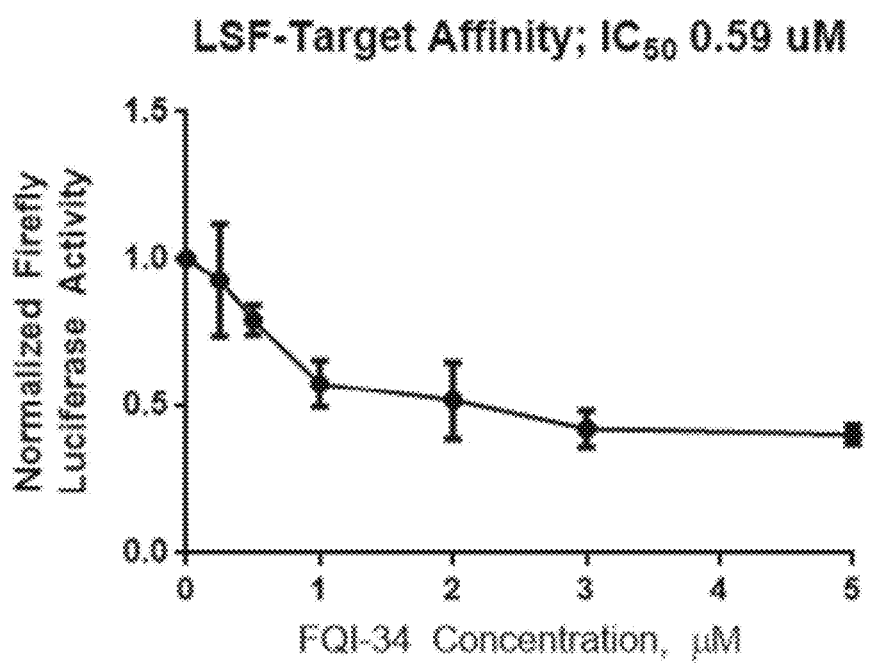
FIG. 12 shows LSF-dependent firefly luciferase reporter activity in NIH-3T3 cells from transfection using an LSF expression construct, and an internal control.
Figure 13A:
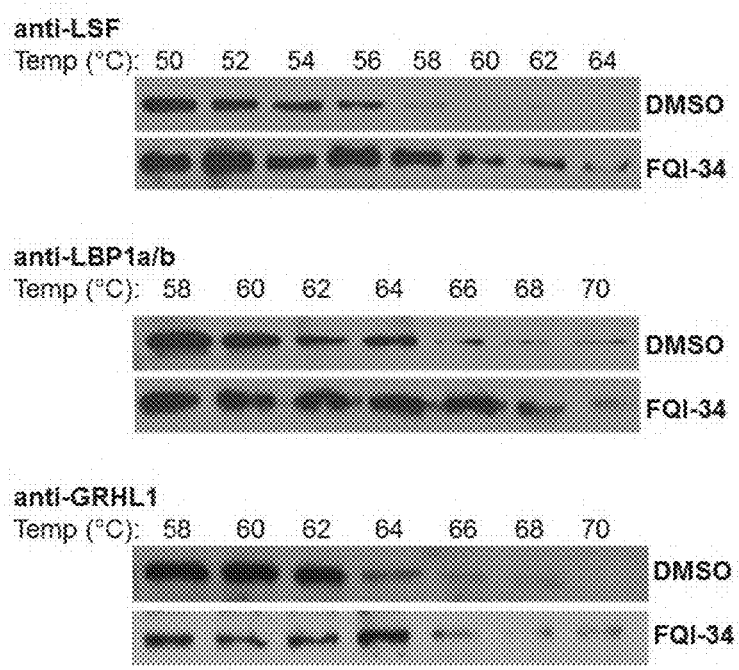
FIGS. 13A and 13B show target binding assessment by Cellular Thermal Shift Assay (CETSA).
Figure 13B:
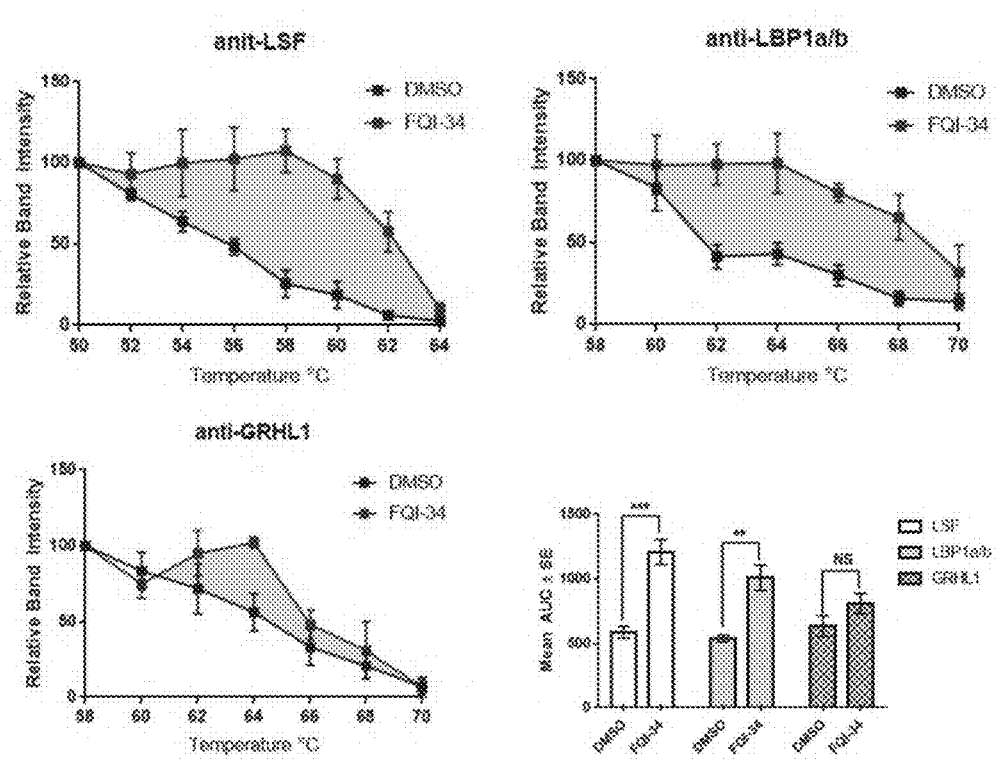

Target Affinity Measured by Dual-Luciferase Reporter Assay; LSF IC$_{50}$:

NIH-3T3 cells were cultured at 37° C. in 5% CO$_2$ in DMEM (Dulbecco's modification of Eagle's Medium; Corning) supplemented with 10% FCS (FCS; Atlanta Biologicals). Approximately 24 hours prior to transfection, 200,000 cells were plated in 35 mm dishes. After 24 hours, cells were ~70% confluent, and were transfected for 5 hours with pEF1α-LSF, the reporter construct pGL3B-WT4E1b, phRLTK, and pEFGP (Grant, T. J. et al. Antiproliferative small-molecule inhibitors of transcription factor LSF reveal oncogene addiction to LSF in hepatocellular carcinoma. PNAS (2012), 109, 1-6). Vehicle (DMSO) or FQI-34 was then added, keeping the DMSO at 0.5%. Cell extracts were harvested 36 h post-transfection, and firefly and renilla luciferase activities were measured via a dual luciferase assay (Promega Dual-Luciferase Reporter Assay System). Relative luciferase activity represents firefly luciferase activity normalized to that of renilla luciferase in each extract. IC$_{50}$ values were determined from plots of normalized luciferase activity vs. compound concentration (Prism GraphPad; non-linear regression 4-parameter curve fit with variable slope). LSF-Target affinity IC$_{50}$ was 0.59 µM (FIG. 12).

Target Binding Assessed by Cellular Thermal Shift Assay (CETSA):

Drug-target engagement was assessed using CETSA as described by Molina et al. (Monitoring Drug-Target Engagement in Cells and Tissues Using Cellular Thermal Shift Assay. Science (2013) 341, 84-87). QGY-7703 cells were cultured at 37° C. in 5% CO$_2$ in DMEM (Dulbecco's modification of Eagle's Medium; Corning) supplemented with 10% Fetal Bovine Serum (FBS; Invitrogen). Cells were seeded into 10 cm plates and allowed to reach 60-80% confluency. After trypsinization (0.05% Trypsin-EDTA, Invitrogen), cell pellet was washed twice with ice-cold 1×PBS (137 mM NaCl, 2.7 mM KCl, 10 mM Na$_2$HPO$_4$, 2 mM KH$_2$PO$_4$, pH 7.2). Cell pellet was lysed by addition of 200 µL freshly prepared ice-cold RIPA buffer (10 mM Tris-Cl pH 8.0, 1 mM EDTA, 0.5 mM EGTA, 1% Triton X-100, 0.1% sodium deoxycholate, 0.1% SDS, 140 mM NaCl) supplemented with 1 mM Pefabloc (Sigma-Aldrich), and flash frozen in liquid nitrogen and thawed for a total of three cycles. Cell lysate was centrifuged at 20,000×g for 20 minutes to clarify. Supernatant was either treated immediately or saved at −80° C. for future use. 200 µL of the lysate was treated with FQI-34 (addition of 2 µL 50 mM Stock; 500 µM final in 1% DMSO) or vehicle (DMSO) for 30 minutes at room temperature. After treatment, the lysate was separated into 20 µL aliquots for thermal denaturation. Lysate was heated at the given temperature for 5 minutes, then placed on ice for 5 minutes, and subsequently centrifuged at 20,000×g for 10 minutes to separate soluble protein from aggregates. 10 µL of the supernatant containing the soluble protein was saved at −20° C. for immunoblot analysis (anti-LSF and anti-LBP1a/b (Millipore); anti-GRHL1 (Sierra Sciences)).

Immunoblots were quantified using Image J and graphed using GraphPad PRISM. Area-under-the-curve (AUC) for the quantified western blots were calculated with GraphPad PRISM and non-parametric t-test was calculated to determine statistical significance between the curves. LSF is a member of a highly conserved family of transcription factors consisting of two branches: The LSF subfamily and the Grainyhead (GRH) subfamily. Despite a high degree of conservation in their DNA binding domains, and recognition of similar DNA motifs, the subfamilies target distinct sets of genes. CETSA results indicate FQI-34 directly binds the LSF subfamily members LSF and LBP1a/b, however does not bind the related GRHL1 subfamily member (FIGS. 13A, 13B, 16A and 16B).

TABLE 5

| ID | QGY-7703 GI50 (uM) | LSF-reporter assay IC50 (uM) | LSF CETSA |
|---|---|---|---|
| FQI-Br | 0.65 | 1.823 | YES |
| FQI-F | 1.50 | NA | NO |
| FQI-Cl | 0.31 | 1.732 | YES |
| FQI32 | 5.49 | Not tested | NO |
| FQI33 | No inhibition >10 uM | Not tested | NO |
| PEG-FQI | No inhibition >10 uM | Not tested | NO |
| FQI34 | 0.26 | 0.7257 | YES |

Figure 14:
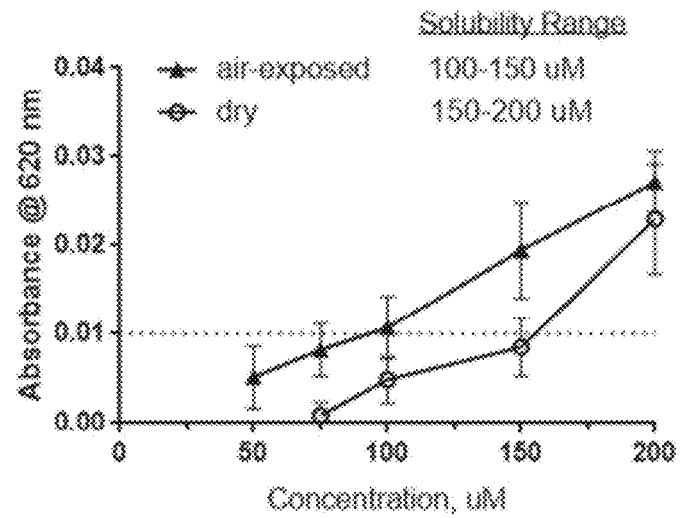
FIG. 14 shows mean absorbance readings at 620 nm±S.D for air-exposed and dry FQI-34. Dashed line at Y=0.01 represents the precipitation point.

Kinetic Solubility:

Kinetic solubility was measured via a turbidity based assay method (Kerns, E. et al. Automation in Pharmaceutical Profiling. *Journal of Laboratory Automation* (2005) 10, 114-123). 198 µL of 1×PBS (137 mM NaCl, 2.7 mM KCl, 10 mM $Na_2HPO_4$, 2 mM $KH_2PO_4$, pH 7.2) was added to the wells of a 96-well plate. FQI-34 (either dried or air-exposed (9% water as determined by NMR)) was dissolved in DMSO for 30 mM final concentration immediately before testing. The 30 mM stock was further diluted in DMSO appropriately for the desired final concentration to be tested in the solubility assay. 2 µL of the DMSO solutions were added to the 96-well plate such that DMSO was kept to 1%. The plate was sealed and gently shaken, and allowed to incubate at 37° C. for 2 hours, after which the absorbance at 620 nm was taken. The concentration at which the absorbance was greater than or equal to 0.01 absorbance units was taken as the precipitation point. Air-exposed FQI-34 first showed precipitates at 100 uM while dry FQI-34 first showed precipitates at 150 uM (FIG. 14)

Example 10: In Vivo Bio-Analysis

Pharmacokinetic Analysis in Rat Plasma:

Studies were conducted at Cyprotex (Watertown Mass., www.cyprotex.com). The purpose of the study was to measure the concentration of FQI-34 in rat plasma samples. The study was performed under non-GLP conditions. All work was performed with appropriate local health regulation and ethical approval. Plasma samples were taken at 0.08, 0.25, 0.5, 1, 2, 4, 8, and 24 hours. Plasma samples were crashed with three volumes of methanol containing an analytical internal standard (propranolol/bucetin/diclofenac). Samples were then centrifuged to remove precipitated protein, and the supernatant was analyzed by LC-MS/MS using a Waters Xevo TQ mass spectrometer coupled with an Acuity HPLC and a CTC PAL chilled autosampler, all controlled by MassLynx software (Waters). The analyte signal was optimized prior to analysis. After separation on a C18 reverse phase HPLC column (Waters Acquity HSS T3 2.1×50 mm 1.8 µM) using an acetonitrile-water gradient system, peaks were analyzed by mass spectrometry (MS) using ESI ionization in MRM mode. All plasma samples were compared to a calibration curve prepared in rat blank plasma.

Male Sprague-Dawley rats were obtained from a commercial source and housed in an AAALAC-approved facility until dosing. For IV dosing, FQI-34 was dissolved in 10% ethanol/16% PEG-400/74% saline at 0.4 mg/mL and in a 1% methylcellulose/0.5% Tween-80 suspension at 10 mg/mL for PO dosing. Three rats per group were dosed by a single IV bolus (10 mL/kg) or PO (10 mL/kg). The rodent dosing scheme used is shown in Table 6.

TABLE 6

Dosing scheme for FQI-34
Pharmacokinetics of FQI-34-01 After IV or PO Dose in Rat
Study#: NLS016-052516-01
Compound: FQI-34-01 Dose Route: PO or IV
Dose: 4 mg/kg IV; 100 mg/kg PO Date: May 25, 2016

| Dose Group | Rat ID | B.W. (g) | Dose voL. (mL) | time | 5 min | 15 min | 30 min | 1 hour | 2 hour | 4 hour | 8 hour | 24 hour | Drug Delivery |
|---|---|---|---|---|---|---|---|---|---|---|---|---|---|
| 1 IV | A | 242 | 2.4 | 8:11 | 8:16 | 8:26 | 8:41 | 9:11 | 10:11 | 12:11 | 4:11 | 8:11 | 4 mg/kg |
| | B | 252 | 2.5 | 8:13 | 8:18 | 8:28 | 8:43 | 9:13 | 10:13 | 12:13 | 4:13 | 8:13 | 0.4 mg/mL |
| | C | 223 | 2.2 | 8:15 | 8:20 | 8:30 | 8:45 | 9:15 | 10:15 | 12:15 | 4:15 | 8:15 | 10 mL/kg |
| 2 PO | A | 240 | 2.4 | 8:17 | 8:22 | 8:32 | 8:47 | 9:17 | 10:17 | 12:17 | 4:17 | 8:17 | 100 mg/kg |
| | B | 266 | 2.7 | 8:19 | 8:24 | 8:34 | 8:49 | 9:19 | 10:19 | 12:19 | 4:19 | 8:19 | 10 mg/mL |
| | C | 235 | 2.4 | 8:21 | 8:26 | 8:36 | 8:51 | 9:21 | 10:21 | 12:21 | 4:21 | 8:21 | 10 mL/kg |

Figure 15A:
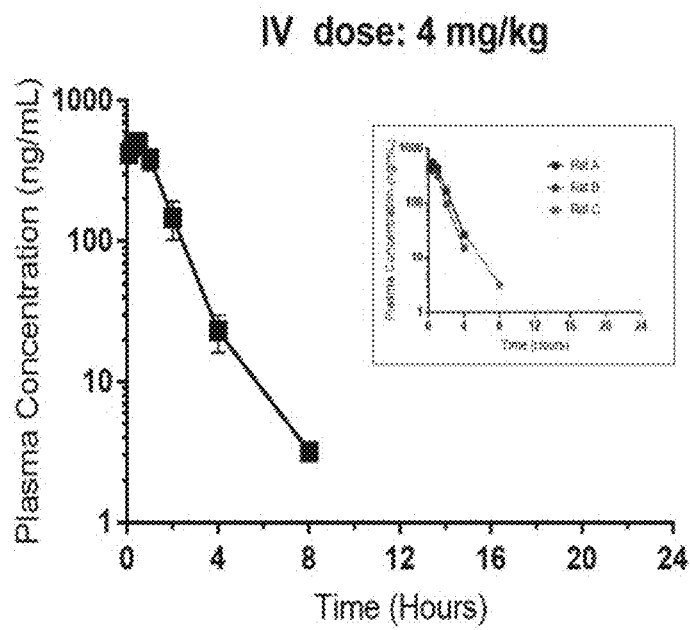
FIGS. 15A and 15B show average plasma concentration (ng/mL) vs time (hour) for IV dosing (FIG. 15A) and for PO dosing (FIG. 15B). Insets show individual rat values.
Figure 15B:
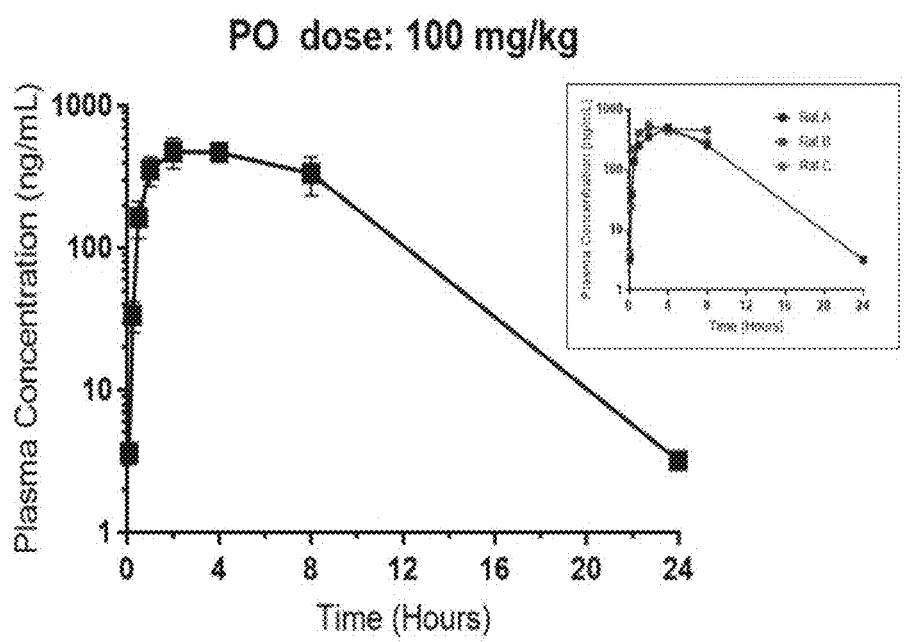
Figure 16:
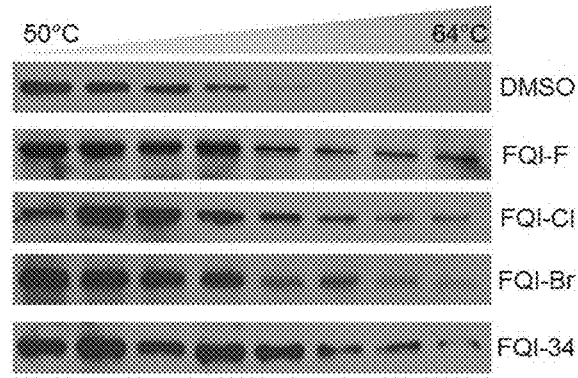
FIGS. 16A and 16B show target binding assessment by Cellular Thermal Shift Assay for compounds FQI-34, FQI-Br and FQI-Cl.
Figure 16:
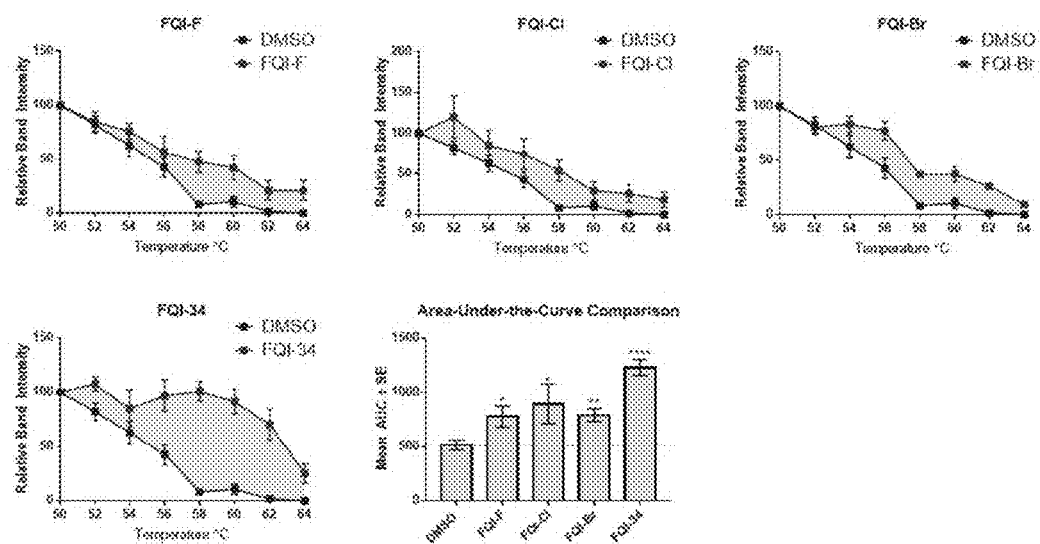

Plasma PK-parameters were independently verified and interpreted using PK-solver: An Excel add-In (Zhang, Y. et al. PKSolver: An add-in program for pharmacokinetic and pharmacodynamic data analysis in Microsoft Excel. *Comput. Methods Programs Biomed.* (2010) 99, 306-314), via a non-compartmental analysis using the linear-trapezoidal method (Fan, J. Pharmacokinetics. *Biochemical Pharmacology* (2014) 87, 93-120). The plasma concentration-vs time curves are shown in FIGS. 15A and 15B and PK parameters are summarized in Table 7.

TABLE 7

Plasma PK Parameters.
Rat Plasma PK Parameters

| | IV: 4 mg/kg | | | | PO: 100 mg/kg | | | |
|---|---|---|---|---|---|---|---|---|
| | RAT A | RAT B | RAT C | AVERAGE | RAT A | RAT B | RAT C | AVERAGE |
| Body weight (g) | 242 | 252 | 223 | | 240 | 266 | 235 | |
| $C_0$ (ng/mL) | 434 | 446 | 390 | 423 | | | | |
| $C_{max}$ (ng/mL) | 545 | 548 | 564 | 552 | 500 | 501 | 577 | 526 |
| $T_{max}$ (hour) | 0.5 | 0.25 | 0.5 | 0.42 | 4.0 | 2.0 | 2.0 | 2.7 |
| $AUC_{(0-\infty)}$ (ng/mL * hr) | 1019 | 759 | 2028 | 935 | 4902 | 4026 | 5936 | 4955 |
| $T_{1/2}$ (hour) | 0.73 | 0.72 | 0.99 | 0.81 | | | | |
| CL (mL/min/kg) | 65 | 88 | 65 | 73 | | | | |
| $V_{Dss}$ (L/kg) | 4.6 | 5.4 | 5.3 | 5.1 | | | | |
| % Bioavailability F | | | | | 21% | 17% | 25% | 21% |

Rat Tolerability:

Studies were conducted at Cyprotex (Watertown Mass., www.cyprotex.com). The purpose of the study was to determine the tolerability of FQI-34 in rats as administered by IV at 3 dose levels—5, 15, and 50 mg/kg. FQI-34 was formulated in 20% DMSO/50% PEG-400/30% saline, and administered by IV at 5 mL/kg for compound or 10 mL/kg for vehicle alone. 6 rats per dose arm were used (3 male and 3 female), with single dose administration with monitoring over 14 days. Gross necropsy was performed at the end of the study.

Observations:

Upon dosing, all rats receiving 50 mg/mL dose level experienced pronation, increased respiratory rate, and decreased activity. However, within 30 minutes the rats returned to normal and experienced no abnormal behavior for the remainder of the study. Male Rat B died upon receiving the 15 mg/mL dose, however this was believed to be due to stress and not compound related. All other rats at this dose level remained normal throughout the study. Excluding the male rat B, all rats stayed within normal limits for duration of study. Gross necropsy showed no abnormal findings.

TABLE 8

Summary of activity data

| Compound | QGY-7703 GI50 (µM) | LSF-reporter assay IC50 (µM) | Was CETSA performed? |
|---|---|---|---|
| FQI-Br | 0.65 | 1.823 | YES |
| FQI-F | 1.50 | 2.905 | YES |
| FQI-Cl | 0.31 | 1.732 | YES |
| FQI-32 | 5.49 | Not tested | Not tested |
| FQI-33 | >10 µM | Not tested | Not tested |
| PEG-FQI | >10 µM | Not tested | Not tested |
| FQI-34 | 0.26 | 0.7257 | YES |

REFERENCES

All references cited herein, in the specification and Examples are incorporated in their entirety by reference. References indicated by the bracketed numbers [e.g., (#)] in the Examples, are incorporated in their entirety by reference and are listed below.

1. El-Serag H B, Rudolph K L (2007) Hepatocellular carcinoma: Epidemiology and molecular carcinogenesis. Gastroenterology 132:2557-2576.
2. Jemal A, et al. (2008) Cancer statistics, 2008. CA Cancer J Clin 58:71-96.
3. Parkin D M, Bray F, Ferlay J, Pisani P (2005) Global cancer statistics, 2002. CA Cancer J Clin 55:74-108.
4. Bruix J, Sherman M; Practice Guidelines Committee, American Association for the Study of Liver Diseases (2005) Management of hepatocellular carcinoma. Hepatology 42:1208-1236.
5. Yoo B K, et al. (2009) Astrocyte elevated gene-1 regulates hepatocellular carcinoma development and progression. J Clin Invest 119:465-477.
6. Yoo B K, et al. (2009) Identification of genes conferring resistance to 5-fluorouracil. Proc Natl Acad Sci USA 106:12938-12943.
7. Veljkovic J, Hansen U (2004) Lineage-specific and ubiquitous biological roles of the mammalian transcription factor LSF. Gene 343:23-40.
8. Hansen U, Owens L, Saxena U H (2009) Transcription factors LSF and E2Fs: Tandem cyclists driving G0 to S? Cell Cycle 8:2146-2151.
9. Powell C M, Rudge T L, Zhu Q, Johnson L F, Hansen U (2000) Inhibition of the mammalian transcription factor LSF induces S-phase-dependent apoptosis by downregulating thymidylate synthase expression. EMBO J 19:4665-4675.
10. Huang J H, Liao W S (1999) Synergistic induction of mouse serum amyloid A3 promoter by the inflammatory mediators IL-1 and IL-6. J Interferon Cytokine Res 19:1403-1411.
11. Bing Z, Huang J H, Liao W S (2000) NFkappa B interacts with serum amyloid A3 enhancer factor to synergistically activate mouse serum amyloid A3 gene transcription. J Biol Chem 275:31616-31623.
12. Llovet J M, Brú C, Bruix J (1999) Prognosis of hepatocellular carcinoma: The BCLC staging classification. Semin Liver Dis 19:329-338.
13. Zondervan P E, et al. (2000) Molecular cytogenetic evaluation of virus-associated and non-viral hepatocellu- 14. Wilkens L, et al. (2000) Cytogenetic aberrations in primary and recurrent fibrolamellar hepatocellular carcinoma detected by comparative genomic hybridization. Am J Clin Pathol 114:867-874.
15. Bellahcene A, Castronovo V, Ogbureke K U, Fisher L W, Fedarko N S (2008) Small integrin-binding ligand N-linked glycoproteins (SIBLINGs): Multifunctional proteins in cancer. Nat Rev Cancer 8:212-226.
16. Takami Y, et al. (2007) Sp1 regulates osteopontin expression in SW480 human colon adenocarcinoma cells. Surgery 142:163-169.
17. Pan H W, et al. (2003) Overexpression of osteopontin is associated with intrahepatic metastasis, early recurrence, and poorer prognosis of surgically resected hepatocellular carcinoma. Cancer 98:119-127.
18. Pikarsky E, et al. (2004) NF-kappaB functions as a tumour promoter in inflammation-associated cancer. Nature 431:461-466.
19. Bissell D M, Guzelian P S (1980) Phenotypic stability of adult rat hepatocytes in primary monolayer culture. Ann NY Acad Sci 349:85-98.
20. Su Z Z, Luo Z Y, Guo L P, Li J Z, Liu Y L (1988) Inhibitory effect of parvovirus H-1 on cultured human tumour cells or transformed cells. Sci Sin B 31:69-80.
21. Sarkar D, et al. (2008) Molecular basis of nuclear factor-kappaB activation by astrocyte elevated gene-1. Cancer Res 68:1478-1484.
22. Irizarry R A, et al. (2003) Summaries of Affymetrix GeneChip probe level data. Nucleic Acids Res 31:e15.
23. Fuller C E, Wang H, Zhang W, Fuller G N, Perry A (2002) High-throughput molecular profiling of high-grade astrocytomas: The utility of fluorescence in situ hybridization on tissue microarrays (TMA-FISH). J Neuropathol Exp Neurol 61:1078-1084.
24. Fenech M (2006) Cytokinesis-block micronucleus assay evolves into a "cytome" assay of chromosomal instability, mitotic dysfunction and cell death. Mutat Res 600:58-66.
25. Sarkar D, et al. (2007) Eradication of therapy-resistant human prostate tumors using a cancer terminator virus. Cancer Res 67:5434-5442.

All references cited herein, indicated by the superscript numbers (e.g., Ref[#]) in the Examples, are incorporated in their entirety by reference.

1. El-Serag, H. B. & Rudolph, K. L. Hepatocellular carcinoma: epidemiology and molecular carcinogenesis. *Gastroenterology* 132, 2557-2576 (2007).
2. Farazi, P. A. & DePinho, R. A. Hepatocellular carcinoma pathogenesis: from genes to environment. *Nat. Rev. Cancer* 6, 674-687 (2006).
3. Yau, T., Chan, P., Epstein, R. & Poon, R. T. Evolution of systemic therapy of advanced hepatocellular carcinoma. *World J Gastroenterol.* 14, 6437-6441 (2008).
4. Weinstein, I. B. & Joe, A. Oncogene addiction. *Cancer Res.* 68, 3077-3080 (2008).
5. Sharma, S. V. & Settleman, J. Exploiting the balance between life and death: targeted cancer therapy and "oncogenic shock". *Biochem. Pharmacol.* 80, 666-673 (2010).
6. Powell, C. M. H., et al. Inhibition of the mammalian transcription factor LSF induces S-phase-dependent apoptosis by downregulating thymidylate synthase expression. *EMBO J.* 19, 4665-4675 (2000).
7. Bruni, P., et al. Fe65, a ligand of the Alzheimer's β-amyloid precursor protein, blocks cell cycle progression by down-regulating thymidylate synthase expression. *J Biol Chem* 277, 35481-35488 (2002).
8. Yoo, B. K., et al. Transcription factor Late SV40 Factor (LSF) functions as an oncogene in hepatocellular carcinoma. *Proc. Natl. Acad. Sci. USA* 107, 8357-8362 (2010).
9. Traylor-Knowles, N., et al. The evolutionary diversification of LSF and Grainyhead transcription factors preceded the radiation of basal animal lineages. *BMC Evolutionary Biology* 10, 101 (2010).
10. Swendeman, S. L., et al. Characterization of the genomic structure, chromosomal location, promoter, and developmental expression of the α-globin transcription factor CP2. *J Biol Chem* 269, 11663-11671 (1994).
11. Hansen, U., Owens, L. & Saxena, U. H. Transcription factors LSF and E2Fs: Tandem cyclists driving G0 to S? *Cell Cycle* 8, 2146-2151 (2009).
12. Saxena, U. H., et al. Phosphorylation by cyclin C/cyclin-dependent kinase 2 following mitogenic stimulation of murine fibroblasts inhibits transcriptional activity of LSF during G1 progression. *Mol Cell Biol.* 29, 2335-2345 (2009).
13. Yoo, B. K., et al. Astrocyte elevated gene-1 regulates hepatocellular carcinoma development and progression. *J Clin. Invest.* 119, 465-477 (2009).
14. Koehler, A. N. A complex task? Direct modulation of transcription factors with small molecules. *Curr. Opin. Chem. Biol.* 14, 331-340 (2010).
15. Zhong, F., et al. Evidence that levels of the dimeric cellular transcription factor CP2 play little role in the activation of the HIV-1 long terminal repeat in vivo or following superinfection with herpes simplex virus type 1. *J Biol Chem* 269, 21269-21276 (1994).
16. Shirra, M. K. & Hansen, U. LSF and NTF-1 share a conserved DNA-recognition motif yet require different oligomerization states to form a stable protein-DNA complex. *J Biol Chem* 273, 19260-19268 (1998).
17. Murata, T., Nitta, M. & Yasuda, K. Transcription factor CP2 is essential for lens-specific expression of the chicken αA-crystallin gene. *Genes to Cells* 3, 443-457 (1998).
18. Li, K., Foresee, L. N. & Tunge, J. A. Trifluoroacetic acid-mediated hydroarylation: synthesis of dihydrocoumarins and dihydroquinolones. *J. Org. Chem.* 70, 2881-2883 (2005).
19. Haigh, J. A., Pickup, B. T., Grant, J. A. & Nicholls, A. Small molecule shape-fingerprints. *J. Chem. Inf. Model.* 45, 673-684 (2005).
20. Drouin, E. E., Schrader, C. E., Stavnezer, J. & Hansen, U. The ubiquitously expressed DNA-binding protein Late SV40 Factor binds Ig switch regions and represses class switching to IgA. *J. Immunol* 168, 2847-2856 (2002).

SEQUENCE LISTING

```
                                                           SEQ ID NO: 1
   1  gacgtcatgt tcgccgggca ggcgaggaaa gaggacgcca tgattggttg gcgctggggc
  61  ggcggacggt ggaagggcct ggcgagtcta ggttttacgc ctgtgctgga ctttctcctt
 121  ccatgtttcc aggccgtggg gggctacaga gggcgagaag tcggctcagc ggaaacctgg
 181  atttggttct aagccgtggg gttgagaagg ggtgaccgga agtgatcgtg ggactgaccg
 241  gaagcgaggc ctggagggga aagagagagc gagacctggg agggaggggg cctccagcag
 301  aaaggggcgg gggaaaaggt gcaaaagcag cgtgggagcg ccgggctggc ttcctgcggc
 361  tgctgctggt ctgactggga agcagcaagc caccactacg aactctcaag aggagtggga
 421  gtgcgggagt ccagagctgc ctctgggaag tctgcagtag ttgagcaaag gggtcctcac
 481  gttcctgaga gctgggcagg ggggatttg gaacctgggg cagccaagaa cgagcagcca
 541  agggtacggg agattagttg tgcacagagc agtgctggtc gggcttgggg gtggctggtg
 601  ggcactgcgt gggaaacctt ggtttgtagt tttcttggtt tgcgttactc ctgttgggta
 661  gaattaccct ccgcgccttt gtacaagaca cggtgtctcc tggggcaagg aaggagccag
 721  gatggcctgg gctctgaagc tgcctctggc cgacgaagtg attgaatccg ggttggtgca
 781  ggactttgat gctagcctgt ccgggatcgg ccaggaactg ggtgctggtg cctatagcat
 841  gagtgatgtc cttgcattgc ccattttaa gcaagaagag tcgagtttgc ctcctgataa
 901  tgagaataaa atcctgcctt ttcaatatgt gctttgtgct gctacctctc cagcagtgaa
 961  actccatgat gaaaccctaa cgtatctcaa tcaaggacag tcttatgaaa ttcgaatgct
1021  agacaatagg aaacttggag aacttccaga aattaatggc aaattggtga agagtatatt
1081  ccgtgtggtg ttccatgaca aaaggcttca gtacactgag catcagcagc tagagggctg
1141  gaggtggaac cgacctggag acagaattct tgacatagat atcccgatgt ctgtgggtat
1201  aatcgatcct agggctaatc caactcaact aaatacagtg gagttcctgt gggaccctgc
1261  aaagaggaca tctgtgttta ttcaggtgca ctgtattagc acagagttca ctatgaggaa
1321  acatggtgga gaaaaggggg tgccattccg agtacaaata gataccttca aggagaatga
1381  aaacggggaa tatactgagc acttacactc ggccagctgc cagatcaaag ttttcaagcc
1441  caaaggtgca gacagaaagc aaaaaacgga tagggaaaaa atggagaaac gaacacctca
1501  tgaaaaggag aaatatcagc cttcctatga cacaaccata ctcacagagt gttctccatg
1561  gcccgagatc acgtatgtca ataactcccc atcacctggc ttcaacagtt cccatagcag
1621  ttttttctctt ggggaaggaa atggttcacc aaaccaccag ccagagccac cccctccagt
1681  cacagataac ctcttaccaa caaccacacc tcaggaagct cagcagtggt tgcatcgaaa
1741  tcgttttttct acattcacaa ggcttttcac aaacttctca ggggcagatt tattgaaatt
1801  aactagagat gatgtgatcc aaatctgtgg ccctgcagat ggaatcagac tttttaatgc
1861  attaaaaggc cggatggtgc gtccaaggtt aaccatttat gtttgtcagg aatcactgca
1921  gttgagggag cagcaacaac agcagcagca acagcagcag aagcatgagg atggagactc
1981  aaatggtact ttcttcgttt accatgctat ctatctagaa gaactaacag ctgttgaatt
2041  gacagaaaaa attgctcagc tttcagcat ttcccttgc cagatcagcc agatttacaa
2101  gcaggggcca acaggaattc atgtgctcat cagtgatgag atgatacaga ctttcagga
2161  agaagcatgt tttattctgg acacaatgaa agcagaaacc aatgatagct atcatatcat
2221  actgaagtag gagtgcggcg tttcgtgccc agtggctgct ccttccttca cctctgaaaa
2281  cggccctctt gaagggggat atgaatggag atttgaaggt ctgcaagaac ctgactcgtc
```

```
2341  tgactgtgtg tggaggagtc caggccatgg aggcagaatc ctggccctct gtgttggccc
2401  aagctcttgt ggtacacaca gattactgcc caatatgcag ttctgcagct gttttagtta
2461  aatttctgga ccttgttgtt gttaaatatc agtagaaact ctacataatt tagagtgtat
2521  gtagggcata atgatgatgg gaattgtgtg atgtttaaca ggaagatctt aaattttgtg
2581  atatggagcc ctgtaatttt tttcttatat aaaaatgggt atctatattc ataagactag
2641  gtcttcaatc tctttgtact ggtctcaaat gtactggtat ctctgctttt tgccacagtt
2701  tgtccctgaa aactttatca gtgaggagaa atacagaatt ttccttttgg ttcccctgta
2761  ataccacaac taatagtatt ttcagctaac atttattgac caggcagtgt gataaatttt
2821  ttgaatgacc atcttgttta accccctaat cacactatct gaagtaggtg ctatagtgac
2881  ccccaaccga agatgaggaa atggagacac acagtggcta agtagcttgc taggtgccag
2941  gagctggcag gcagtgatgc tgaaatccaa accaggcaat ctggccctcc ttattcaccc
3001  tctcatacca ccagtgctac ccattataac ctgtgttcac ttcgcttatt actgtggccc
3061  ttctggtgac tacaacataa cactgagtat gaactgagga attaaccact gaaagagaca
3121  aagcacacct aaataatgat gaacaaatca agacctacaa gaatgaaca catagatgct
3181  ttttaagtgt cattagttat cggaatcaaa gaatttgagg tggtgacaac tggggattat
3241  ctgtaactcc ccaaatttac tgttcttgaa tgacattctc aaactattta ttaatgagtt
3301  agtctcatcc ctgctttctg tttcctctct ctgcatcttc tcttggcata ggaagttatt
3361  ttactcatgc tatgtttttt aatagaagct ttacaaaaaa agatgcattc ccttcctgtt
3421  cacactctta ccatgttttt gttcttcctt aagaatgatt gtgtgtgtgt gtgtgtgtgt
3481  gtgtaagtgt gtaagtgtaa catcatgggt tttctttctt cacttgtaaa gttttatcta
3541  gaaatacttt tacaggttat gttgaggtac acaaagataa tgttctaaga ttgtgtattg
3601  gatttggatt tgtgtgtgtg tgtgtgtgtg tgtgtgttta aagcatttga taaggtttaa
3661  atgtttttta tacagagatt tttgttcatt aaactcaatc tgcatcatgg tctaa
```

SEQ ID NO: 2
```
  1  mawalklpla deviesglvq dfdaslsgig qelgagaysm sdvlalpifk qeesslppdn
 61  enkilpfqyv lcaatspavk lhdetltyln qgqsyeirml dnrklgelpe ingklvksif
121  rvvfhdrrlq ytehqqlegw rwnrpgdril didipmsvgi idpranptql ntveflwdpa
181  krtsvfiqvh cisteftmrk hggekgvpfr vqidtfkene ngeytehlhs ascqikvfkp
241  kgadrkqktd rekmekrtph ekekyqpsye ttiltecspw peityvnnsp spgfnsshss
301  fslgegngsp nhqpepppv tdnllptttp qeaqqwlhrn rfstftrlft nfsgadllkl
361  trddviqicg padgirlfna lkgrmvrprl tiyvcqeslq lreqqqqqq qqqkhedgds
421  ngtffvyhai yleeltavel tekiaqlfsi spcqisqiyk qgptgihvli sdemiqnfqe
481  eacfildtmk aetndsyhii lk
```

SEQ ID NO: 3
5'-ACACGCTTATGCGGGTATGT-3'

SEQ ID NO: 4
5'-GAACATTTGGTAGGGGAAA-3'

SEQ ID NO: 5
TGGCTGGTTATGGCTGGTCAGACTAG

What is claimed is:

1. A compound of formula (III'), wherein the Formula (III') has the structure:

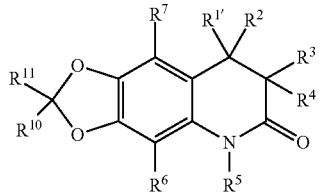

wherein:

$R^{1'}$ is an aryl substituted with at least one $C_1$-$C_6$ alkoxyl and at least one di($C_1$-$C_{24}$alkyl)amino, halogen or $C_2$-$C_8$alkenyl, wherein the substituted aryl can be optionally further substituted with halogen, $C_1$-$C_4$ alkyl, $C_1$-$C_4$haloalkyl, $C_1$-$C_4$ heteroalkyl, di($C_1$-$C_{24}$alkyl)amino or combinations thereof;

$R^2$ and $R^3$ are hydrogen or $R^2$ and $R^3$ together form a second bond between the carbons to which they are attached;

$R^4$ is hydrogen;

$R^5$ is selected from the group consisting of hydrogen and $C_1$-$C_6$ alkyl;

$R^6$ and $R^7$ are each independently selected from the group consisting of hydrogen, F, Br, Cl and I;

$R^{10}$ and $R^{11}$ are each independently selected from the group consisting of hydrogen, F, Br, Cl, and I;

or enantiomers, prodrugs, derivatives, and pharmaceutically acceptable salts thereof, and wherein the compound is capable of inhibiting late SV40 factor (LSF).

2. The compound of claim 1, wherein $R^{1'}$ is a phenyl substituted with at least one $C_1$-$C_6$ alkoxyl and at least one di($C_1$-$C_{24}$alkyl)amino, halogen or $C_2$-$C_8$alkenyl.

3. The compound of claim 2, wherein $R^{1'}$ is

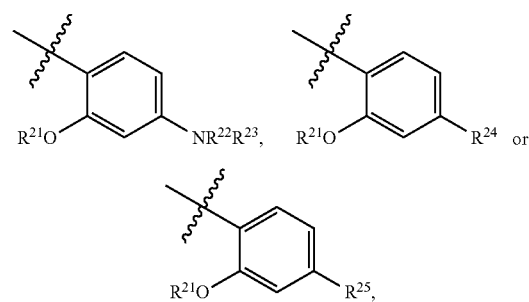

wherein $R^{21}$ is $C_1$-$C_6$alkyl; $R^{22}$ and $R^{23}$ are independently selected $C_1$-$C_{24}$alkyl; $R^{24}$ is halogen; and $R^{25}$ is $C_2$-$C_8$alkenyl.

4. The compound of claim 3, wherein $R^{1'}$ is

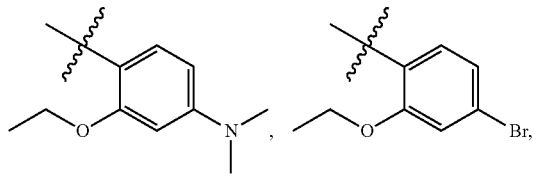

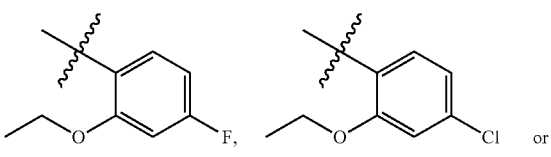

-continued
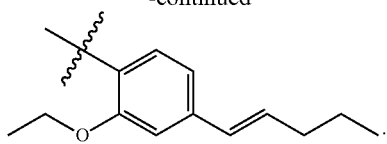
5. The compound of claim 1, wherein the compound is selected from the groups consisting of
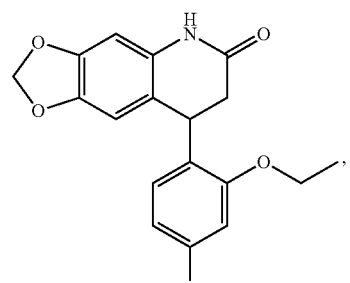
(FQI-34)
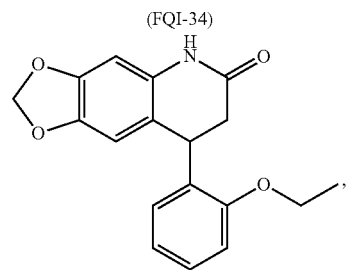
(FQI-Br)
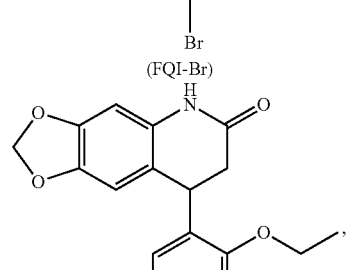
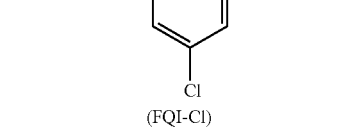
(FQI-Cl)
-continued
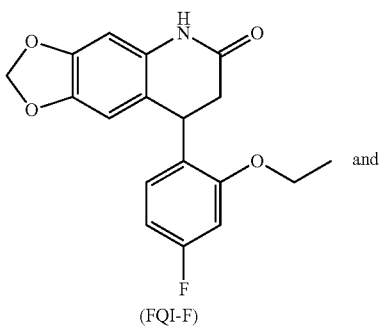
(FQI-F)
and
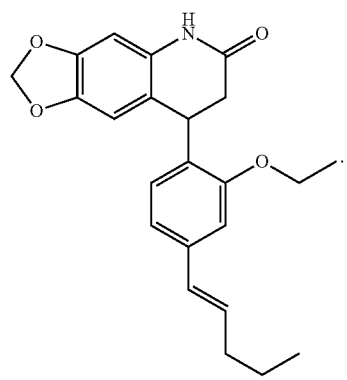
(FQI32)
6. The compound of claim 1, wherein the compound is FQI-34.
7. A pharmaceutical composition comprising a compound of claim 1 and a pharmaceutically acceptable excipient or carrier.
\* \* \* \* \*

SEQUENCE LISTING

<160> NUMBER OF SEQ ID NOS: 5

<210> SEQ ID NO 1
<211> LENGTH: 3715
<212> TYPE: DNA
<213> ORGANISM: Homo sapiens

<400> SEQUENCE: 1

| | | | | | |
|---|---|---|---|---|---|
| gacgtcatgt | tcgccgggca | ggcgaggaaa | gaggacgcca | tgattggttg gcgctggggc | 60 |
| ggcggacggt | ggaagggcct | ggcgagtcta | ggttttacgc | ctgtgctgga ctttctcctt | 120 |
| ccatgtttcc | aggccgtggg | gggctacaga | gggcgagaag | tcggctcagc ggaaacctgg | 180 |
| atttggttct | aagccgtggg | gttgagaagg | ggtgaccgga | agtgatcgtg ggactgaccg | 240 |
| gaagcgaggc | ctggagggga | aagagagagc | gagacctggg | agggaggggg cctccagcag | 300 |
| aaagggcgg | gggaaaaggt | gcaaaagcag | cgtgggagcg | ccgggctggc ttcctgcggc | 360 |
| tgctgctggt | ctgactggga | agcagcaagc | caccactacg | aactctcaag gagagtggga | 420 |
| gtgcgggagt | ccagagctgc | ctctgggaag | tctgcagtag | ttgagcaaag gggtcctcac | 480 |
| gttcctgaga | gctgggcagg | ggggattttg | gaacctgggg | cagccaagaa cgagcagcca | 540 |
| agggtacggg | agattagttg | tgcacagagc | agtgctggtc | gggcttgggg gtggctggtg | 600 |
| ggcactgcgt | gggaaacctt | ggtttgtagt | tttcttggtt | tgcgttactc ctgttgggta | 660 |
| gaattaccct | ccgcgccttt | gtacaagaca | cggtgtctcc | tggggcaagg aaggagccag | 720 |
| gatggcctgg | gctctgaagc | tgcctctggc | cgacgaagtg | attgaatccg ggttggtgca | 780 |
| ggactttgat | gctagcctgt | ccgggatcgg | ccaggaactg | ggtgctggtg cctatagcat | 840 |
| gagtgatgtc | cttgcattgc | ccattttta | gcaagaagag | tcgagtttgc ctcctgataa | 900 |
| tgagaataaa | atcctgcctt | ttcaatatgt | gctttgtgct | gctacctctc cagcagtgaa | 960 |
| actccatgat | gaaaccctaa | cgtatctcaa | tcaaggacga | tcttatgaaa ttcgaatgct | 1020 |
| agacaatagg | aaacttggag | aacttccaga | aattaatggc | aaattggtga gagtatatt | 1080 |
| ccgtgtggtg | ttccatgaca | gaaggcttca | gtacactgag | catcagcagc tagagggctg | 1140 |
| gaggtggaac | cgacctggag | acagaattct | tgacatagat | atcccgatgt ctgtgggtat | 1200 |
| aatcgatcct | agggctaatc | caactcaact | aaatacagtg | gagttcctgt gggaccctgc | 1260 |
| aaagaggaca | tctgtgttta | ttcaggtgca | ctgtattagc | acagagttca ctatgaggaa | 1320 |
| acatggtgga | gaaaaggggg | tgccattccg | agtacaaata | gataccttca aggagaatga | 1380 |
| aaacggggaa | tatactgagc | acttacactc | ggccagctgc | cagatcaaag tttttcaagcc | 1440 |
| caaaggtgca | gacagaaagc | aaaaaacgga | tagggaaaaa | atggagaaac gaacacctca | 1500 |
| tgaaaaggag | aaatatcagc | cttcctatga | gacaaccata | ctcacagagt gttctccatg | 1560 |
| gcccgagatc | acgtatgtca | ataactcccc | atcacctggc | ttcaacagtt cccatagcag | 1620 |
| tttttctctt | ggggaaggaa | atggttcacc | aaaccaccag | ccagagccac cccctccagt | 1680 |
| cacagataac | ctcttaccaa | caaccacacc | tcaggaagct | cagcagtggt tgcatcgaaa | 1740 |
| tcgttttct | acattcacaa | ggcttttcac | aaacttctca | ggggcagatt tattgaaatt | 1800 |
| aactagagat | gatgtgatcc | aaatctgtgg | ccctgcagat | ggaatcagac tttttaatgc | 1860 |
| attaaaaggc | cggatggtgc | gtccaaggtt | aaccatttat | gtttgtcagg aatcactgca | 1920 |
| gttgagggag | cagcaacaac | agcagcagca | acagcagcag | aagcatgagg atggagactc | 1980 |
| aaatggtact | ttcttcgttt | accatgctat | ctatctagaa | gaactaacag ctgttgaatt | 2040 |
| gacagaaaaa | attgctcagc | ttttcagcat | ttccccttgc | cagatcagcc agatttacaa | 2100 |

-continued

```
gcaggggcca acaggaattc atgtgctcat cagtgatgag atgatacaga actttcagga    2160
agaagcatgt tttattctgg acacaatgaa agcagaaacc aatgatagct atcatatcat    2220
actgaagtag gagtgcggcg tttcgtgccc agtggctgct ccttccttca cctctgaaaa    2280
cggccctctt gaaggggat atgaatgag atttgaaggt ctgcaagaac ctgactcgtc     2340
tgactgtgtg tggaggagtc caggccatgg aggcagaatc ctggccctct gtgttggccc    2400
aagctcttgt ggtacacaca gattactgcc caatatgcag ttctgcagct gttttagtta    2460
aatttctgga ccttgttgtt gttaaatatc agtagaaact ctacataatt tagagtgtat    2520
gtagggcata atgatgatgg gaattgtgtg atgtttaaca ggaagatctt aaattttgtg    2580
atatggagcc ctgtaatttt tttcttatat aaaaatgggt atctatattc ataagactag    2640
gtcttcaatc tctttgtact ggtctcaaat gtactggtat ctctgctttt tgccacagtt    2700
tgtccctgaa aactttatca gtgaggagaa atacagaatt ttccttttgg ttcccctgta    2760
ataccacaac taatagtatt ttcagctaac atttattgac caggcagtgt gataaatttt    2820
ttgaatgacc atcttgttta acccctaat cacactatct gaagtaggtg ctatagtgac      2880
ccccaaccga agatgaggaa atggagacac acagtggcta agtagcttgc taggtgccag    2940
gagctggcag gcagtgatgc tgaaatccaa accaggcaat ctggccctcc ttattcaccc    3000
tctcatacca ccagtgctac ccattataac ctgtgttcac ttcgcttatt actgtggccc    3060
ttctggtgac tacaacataa cactgagtat gaactgagga attaaccact gaaagagaca    3120
aagcacacct aaataatgat gaacaaatca agacctacaa gaaatgaaca catagatgct    3180
ttttaagtgt cattagttat cggaatcaaa gaatttgagg tggtgacaac tggggattat    3240
ctgtaactcc ccaaatttac tgttcttgaa tgacattctc aaactattta ttaatgagtt    3300
agtctcatcc ctgctttctg tttcctctct ctgcatcttc tcttggcata ggaagttatt    3360
ttactcatgc tatgtttttt aatagaagct ttacaaaaaa agatgcattc ccttcctgtt    3420
cacactctta ccatgttttt gttcttcctt aagaatgatt gtgtgtgtgt gtgtgtgtgt    3480
gtgtaagtgt gtaagtgtaa catcatgggt tttctttctt cacttgtaaa gttttatcta    3540
gaaatacttt tacaggttat gttgaggtac acaaagataa tgttctaaga ttgtgtattg    3600
gatttggatt tgtgtgtgtg tgtgtgtgtg tgtgtgttta aagcatttga taaggtttaa    3660
atgtttttta tacagagatt tttgttcatt aaactcaatc tgcatcatgg tctaa          3715
```

<210> SEQ ID NO 2
<211> LENGTH: 502
<212> TYPE: PRT
<213> ORGANISM: Homo sapiens
<400> SEQUENCE: 2

```
Met Ala Trp Ala Leu Lys Leu Pro Leu Ala Asp Glu Val Ile Glu Ser
1               5                   10                  15

Gly Leu Val Gln Asp Phe Asp Ala Ser Leu Ser Gly Ile Gly Gln Glu
            20                  25                  30

Leu Gly Ala Gly Ala Tyr Ser Met Ser Asp Val Leu Ala Leu Pro Ile
        35                  40                  45

Phe Lys Gln Glu Glu Ser Ser Leu Pro Pro Asp Asn Glu Asn Lys Ile
    50                  55                  60

Leu Pro Phe Gln Tyr Val Leu Cys Ala Ala Thr Ser Pro Ala Val Lys
65                  70                  75                  80

Leu His Asp Glu Thr Leu Thr Tyr Leu Asn Gln Gly Gln Ser Tyr Glu
```

```
                         85                  90                  95
Ile Arg Met Leu Asp Asn Arg Lys Leu Gly Glu Leu Pro Glu Ile Asn
                100                 105                 110
Gly Lys Leu Val Lys Ser Ile Phe Arg Val Phe His Asp Arg Arg
            115                 120                 125
Leu Gln Tyr Thr Glu His Gln Leu Glu Gly Trp Arg Trp Asn Arg
        130                 135                 140
Pro Gly Asp Arg Ile Leu Asp Ile Asp Ile Pro Met Ser Val Gly Ile
145                 150                 155                 160
Ile Asp Pro Arg Ala Asn Pro Thr Gln Leu Asn Thr Val Glu Phe Leu
                165                 170                 175
Trp Asp Pro Ala Lys Arg Thr Ser Val Phe Ile Gln Val His Cys Ile
                180                 185                 190
Ser Thr Glu Phe Thr Met Arg Lys His Gly Gly Glu Lys Gly Val Pro
            195                 200                 205
Phe Arg Val Gln Ile Asp Thr Phe Lys Glu Asn Glu Asn Gly Glu Tyr
        210                 215                 220
Thr Glu His Leu His Ser Ala Ser Cys Gln Ile Lys Val Phe Lys Pro
225                 230                 235                 240
Lys Gly Ala Asp Arg Lys Gln Lys Thr Asp Arg Glu Lys Met Glu Lys
                245                 250                 255
Arg Thr Pro His Glu Lys Glu Lys Tyr Gln Pro Ser Tyr Glu Thr Thr
            260                 265                 270
Ile Leu Thr Glu Cys Ser Pro Trp Pro Glu Ile Thr Tyr Val Asn Asn
        275                 280                 285
Ser Pro Ser Pro Gly Phe Asn Ser Ser His Ser Ser Phe Ser Leu Gly
    290                 295                 300
Glu Gly Asn Gly Ser Pro Asn His Gln Pro Pro Pro Pro Val
305                 310                 315                 320
Thr Asp Asn Leu Leu Pro Thr Thr Thr Pro Gln Glu Ala Gln Gln Trp
                325                 330                 335
Leu His Arg Asn Arg Phe Ser Thr Phe Thr Arg Leu Phe Thr Asn Phe
            340                 345                 350
Ser Gly Ala Asp Leu Leu Lys Leu Thr Arg Asp Asp Val Ile Gln Ile
        355                 360                 365
Cys Gly Pro Ala Asp Gly Ile Arg Leu Phe Asn Ala Leu Lys Gly Arg
    370                 375                 380
Met Val Arg Pro Arg Leu Thr Ile Tyr Val Cys Gln Glu Ser Leu Gln
385                 390                 395                 400
Leu Arg Glu Gln Gln Gln Gln Gln Gln Gln Gln Lys His Glu
                405                 410                 415
Asp Gly Asp Ser Asn Gly Thr Phe Phe Val Tyr His Ala Ile Tyr Leu
            420                 425                 430
Glu Glu Leu Thr Ala Val Glu Leu Thr Glu Lys Ile Ala Gln Leu Phe
        435                 440                 445
Ser Ile Ser Pro Cys Gln Ile Ser Gln Ile Tyr Lys Gln Gly Pro Thr
    450                 455                 460
Gly Ile His Val Leu Ile Ser Asp Glu Met Ile Gln Asn Phe Gln Glu
465                 470                 475                 480
Glu Ala Cys Phe Ile Leu Asp Thr Met Lys Ala Glu Thr Asn Asp Ser
                485                 490                 495
Tyr His Ile Ile Leu Lys
            500
```

```
<210> SEQ ID NO 3
<211> LENGTH: 20
<212> TYPE: DNA
<213> ORGANISM: Homo sapiens

<400> SEQUENCE: 3
acacgcttat gcgggtatgt                                               20

<210> SEQ ID NO 4
<211> LENGTH: 20
<212> TYPE: DNA
<213> ORGANISM: Homo sapiens

<400> SEQUENCE: 4
gaacatttgg taggggaaa                                                20

<210> SEQ ID NO 5
<211> LENGTH: 26
<212> TYPE: DNA
<213> ORGANISM: Simian virus 40

<400> SEQUENCE: 5
tggctggtta tggctggtca gactag                                        26
```